United States Patent
Hatakeyama et al.

(10) Patent No.: US 12,036,025 B2
(45) Date of Patent: *Jul. 16, 2024

(54) BIO-ELECTRODE, METHOD FOR MANUFACTURING BIO-ELECTRODE, AND METHOD FOR MEASURING BIOLOGICAL SIGNAL

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Koji Hasegawa, Joetsu (JP); Joe Ikeda, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 718 days.

This patent is subject to a terminal disclaimer.

(21) Appl. No.: 17/193,445

(22) Filed: Mar. 5, 2021

(65) Prior Publication Data

US 2021/0307665 A1 Oct. 7, 2021

(30) Foreign Application Priority Data

Mar. 19, 2020 (JP) ................................ 2020-050087

(51) Int. Cl.
| | |
|---|---|
| A61B 5/265 | (2021.01) |
| A61B 5/268 | (2021.01) |
| A61B 5/28 | (2021.01) |
| A61N 1/04 | (2006.01) |

(52) U.S. Cl.
CPC .............. *A61B 5/265* (2021.01); *A61B 5/268* (2021.01); *A61B 5/28* (2021.01); *A61N 1/0496* (2013.01)

(58) Field of Classification Search
USPC ......................................................... 528/28
See application file for complete search history.

(56) References Cited

U.S. PATENT DOCUMENTS

| | | |
|---|---|---|
| 5,981,680 A | 11/1999 | Petroff et al. |
| 2002/0188069 A1 | 12/2002 | Sugo et al. |
| 2009/0061358 A1 | 3/2009 | Ohashi et al. |
| 2015/0275060 A1 | 10/2015 | Kuroda et al. |
| 2016/0155530 A1 | 6/2016 | Someya et al. |
| 2017/0275510 A1 | 9/2017 | Quan et al. |
| 2018/0072930 A1 | 3/2018 | Hatakeyama et al. |
| 2018/0085019 A1 | 3/2018 | Hatakeyama et al. |
| 2018/0086948 A1 | 3/2018 | Hatakeyama et al. |
| 2018/0168470 A1 | 6/2018 | Hatakeyama et al. |
| 2018/0215876 A1 | 8/2018 | Hatakeyama et al. |
| 2018/0223133 A1 | 8/2018 | Hatakeyama et al. |
| 2018/0229023 A1 | 8/2018 | Hatakeyama et al. |
| 2018/0229024 A1 | 8/2018 | Hatakeyama et al. |
| 2018/0273811 A1 | 9/2018 | Cura et al. |
| 2019/0106528 A1 | 4/2019 | Hatakeyama et al. |
| 2019/0159978 A1 | 5/2019 | Sakuta et al. |
| 2020/0008695 A1 | 1/2020 | Hatakeyama et al. |
| 2020/0275853 A1 | 9/2020 | Futashima et al. |

FOREIGN PATENT DOCUMENTS

| | | | |
|---|---|---|---|
| JP | H05-095924 A | 4/1993 | |
| JP | 2001181597 A | * 7/2001 | ......... A61B 5/04087 |
| JP | 2002-332305 A | 11/2002 | |
| JP | 2003-225217 A | 8/2003 | |
| JP | 2004-033468 A | 2/2004 | |
| JP | 2005-320418 A | 11/2005 | |
| JP | 2008-111103 A | 5/2008 | |
| JP | 2009-080474 A | 4/2009 | |
| JP | 2011-079946 A | 4/2011 | |
| JP | 2015-019806 A | 2/2015 | |
| JP | 2015-100673 A | 6/2015 | |
| JP | 2015-193803 A | 11/2015 | |
| JP | 2016-011338 A | 1/2016 | |
| JP | 2016-047194 A | 4/2016 | |
| JP | 2016-065238 A | 4/2016 | |
| JP | 2018-044147 A | 3/2018 | |
| JP | 2018-059050 A | 4/2018 | |
| JP | 2018-059052 A | 4/2018 | |
| JP | 2018-099504 A | 6/2018 | |
| JP | 2018-123304 A | 8/2018 | |
| JP | 2018-126496 A | 8/2018 | |

(Continued)

OTHER PUBLICATIONS

WO2013073673A1 Machine Translation (Year: 2013).*
JP 2012205884 Machine Translation (Year: 2012).*
JP 2001181597 Machine Translation (Year: 2001).*
Aug. 16, 2021 Extended Search Report issued in European Patent Application No. 21162152.9.
Aug. 29, 2023 Office Action Issued in Japanese Patent Application No. 2021-018402.
Nov. 23, 2022 Office Action issued in Korean Patent Application No. 10-2021-0033474.

*Primary Examiner* — Terressa Boykin
(74) *Attorney, Agent, or Firm* — Oliff PLC

(57) ABSTRACT

A bio-electrode includes an electro-conductive base material and a living body contact layer. The living body contact layer includes a water-free resin layer and a permeation layer on a surface side of the resin layer where a living body comes into contact. The permeation layer is permeated with water and a water-soluble salt selected from the group consisting of sodium salts, potassium salts, calcium salts, magnesium salts, and betaines. This aims to provide: a dry-type bio-electrode that enables quick signal collection after attachment to skin, the bio-electrode being excellent in electric conductivity and biocompatibility, light-weight, and manufacturable at low cost, and capable of preventing significant reduction in the electric conductivity even when wetted with water or dried; a method for manufacturing the bio-electrode; and a method for measuring a biological signal.

19 Claims, 3 Drawing Sheets

(56) References Cited

FOREIGN PATENT DOCUMENTS

| | | |
|---|---|---|
| JP | 2018-130533 A | 8/2018 |
| JP | 2018-130534 A | 8/2018 |
| JP | 2019-503406 A | 2/2019 |
| JP | 2019-070109 A | 5/2019 |
| JP | 2019-099469 A | 6/2019 |
| KR | 10-2003-0045730 A | 6/2003 |
| KR | 10-2018-0091749 A | 8/2018 |
| WO | 2013/039151 A1 | 3/2013 |
| WO | WO-2013073673 A1 * | 5/2013 ............... A61B 5/25 |
| WO | 2019/139164 A1 | 7/2019 |

* cited by examiner

[FIG. 1]
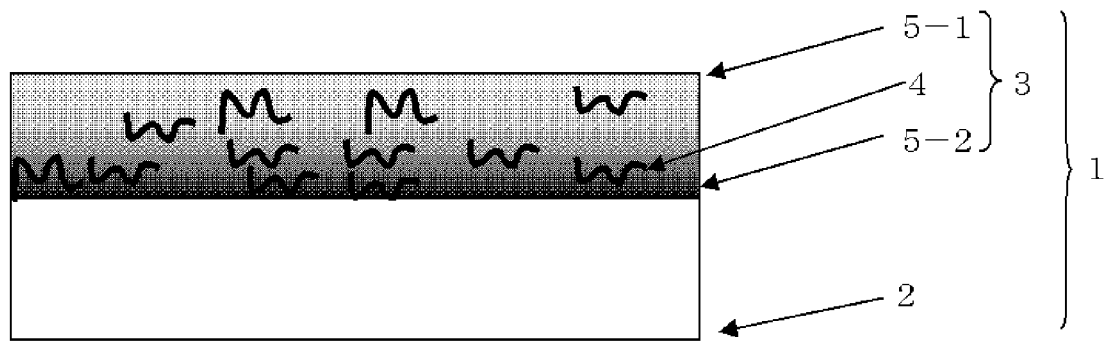
[FIG. 2]
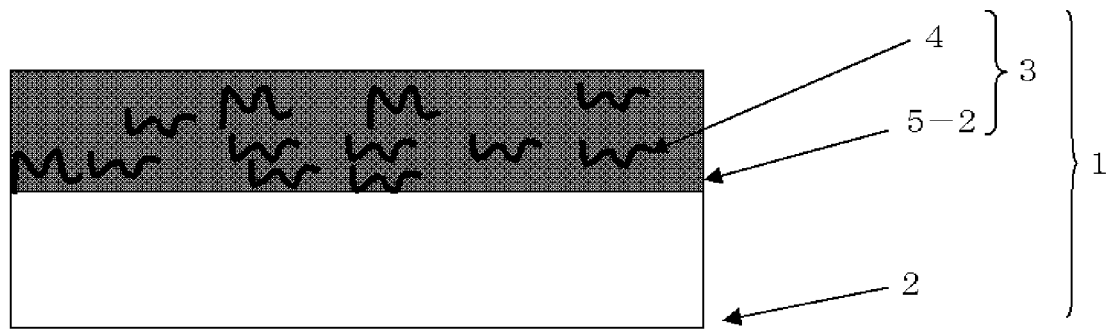
[FIG. 3]
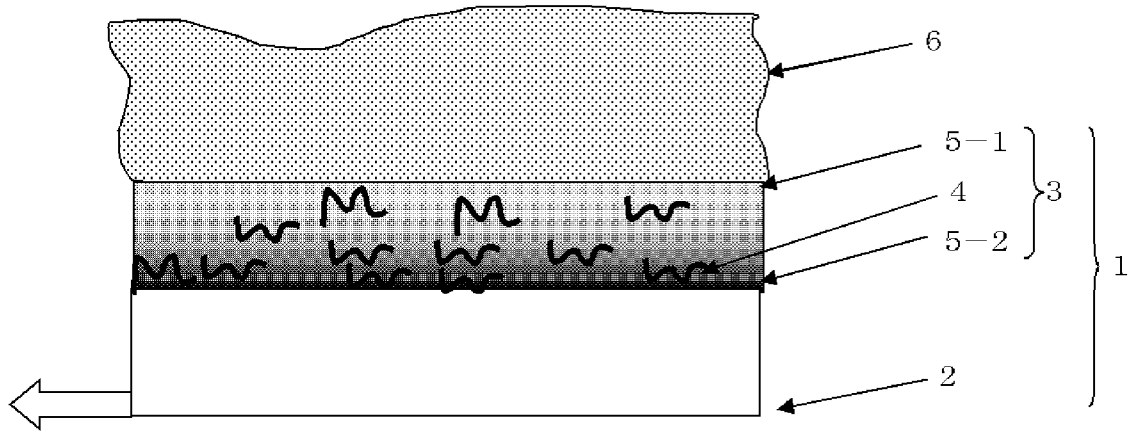
Connected to a biological sensor

[FIG. 4]
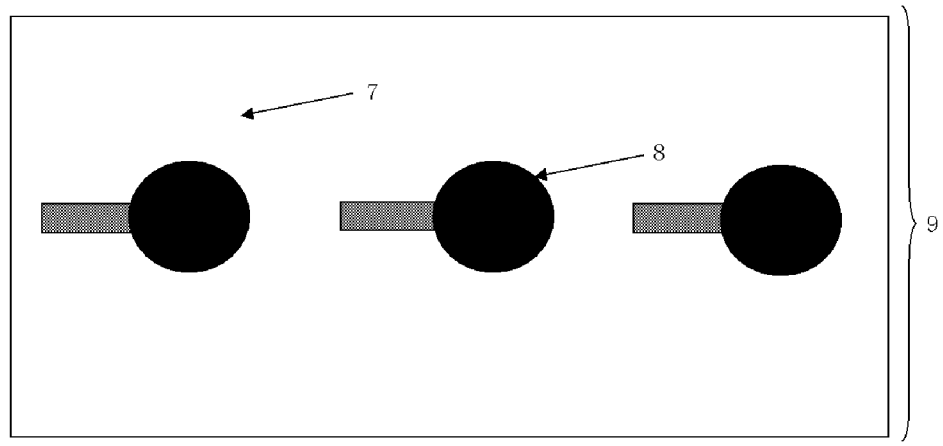
[FIG. 5]
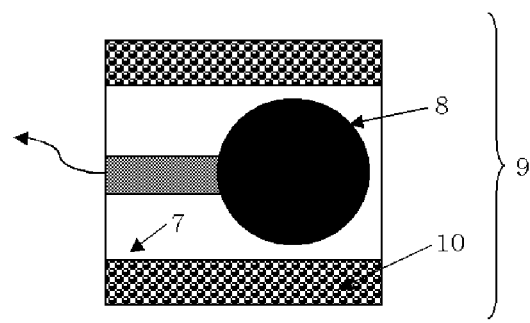
[FIG. 6]
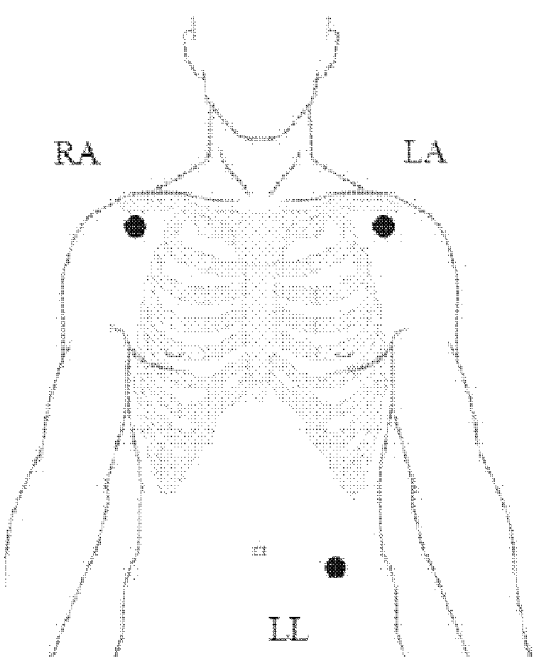

[FIG. 7]
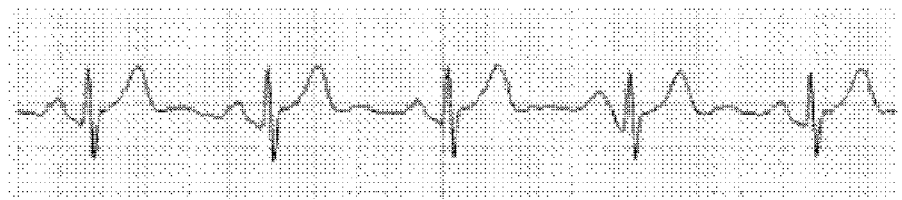

BIO-ELECTRODE, METHOD FOR MANUFACTURING BIO-ELECTRODE, AND METHOD FOR MEASURING BIOLOGICAL SIGNAL

TECHNICAL FIELD

The present invention relates to a bio-electrode that is used in contact with the skin of a living body and capable of detecting physical conditions such as heart rate by an electric signal transmitted from the skin, a method for manufacturing the bio-electrode, and a method for measuring a biological signal by using the bio-electrode.

BACKGROUND ART

A recent growing popularity of Internet of Things (IoT) has accelerated the development of such major wearable devices as watches and eye-glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by sensing extremely weak current has been examined. The electrocardiogram measurement is conducted by attaching an electrode coated with an electro-conductive paste to a body, but this is a single (not continuous), short-time measurement. On the other hand, the above medical wearable device is aimed at continuously monitoring the state of physical conditions for a few weeks.

Accordingly, a bio-electrode used in a medical wearable device is required to make no changes in electric conductivity even in long-time use and cause no skin allergy. In addition to these, bio-electrodes must be light-weight and produced at low cost.

Medical wearable devices are classified into two types: direct body attachment and clothing attachment. As one typical body attachment device, a bio-electrode is proposed which is formed of a hydrophilic gel containing water and electrolytes as ingredients of the above electro-conductive paste (Patent Document 1). The hydrophilic gel, containing sodium, potassium, and calcium electrolytes in a hydrophilic polymer for retaining water, detects changes in ion concentration from the skin to convert the data into electricity. Meanwhile, one typical clothing attachment device is proposed which is characterized by a method for using as an electrode a fabric including an electro-conductive polymer, such as PEDOT-PSS (Poly-3,4-ethylenedioxythiophene-Polystyrenesulfonate), and a silver paste incorporated into the fiber (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. Nevertheless, metal nanowires, formed of a pointed thin material, may cause skin allergy. Likewise, carbon nanotubes can stimulate (irritate) a living body. Although the carbon black is not as poisonous as carbon nanotube, it also stimulates the skin to a certain degree. Accordingly, even if these electrode materials themselves cause no allergic reaction, the biocompatibility may be degraded depending on the shape of a material and its inherent stimulation, thereby making it hard to satisfy both electric conductivity and biocompatibility.

Although metal films seem to function as an excellent bio-electrode thanks to extremely high electric conductivity, this is not always the case. Upon heartbeat, the human skin releases not only extremely weak current, but also a sodium ion, a potassium ion, and a calcium ion. It is thus necessary to convert changes in ion concentration into current, but less ionized precious metals unfortunately fail to do efficiently. The resulting bio-electrode using the precious metal is characterized by high impedance and high resistance to the skin during electrical conduction.

There have been proposed bio-electrodes in each of which an ionic polymer is added (Patent Documents 6, 7, 8). A bio-electrode obtained by mixing a silicone adhesive with an ion polymer and a carbon powder added thereto has adhesion and high water repellency so that biological signals can be stably collected even when the bio-electrode is attached to the skin for a long time in a wet state by shower or sweat. Ion polymers do not permeate to the skin and hence do not stimulate the skin, and the biocompatibility is high. From these aspects, the bio-electrode enables long-time attachment.

Although silicones are inherently insulators, the ionic conductivity is improved by the combination with an ion polymer and a carbon powder, and thus the function as a bio-electrode is obtained. Nevertheless, it has been desired to improve the performance by further improving the ionic conductivity.

Patent Documents 6, 7, and 8 mentioned above state that a silicone compound having a polyether chain as an additive is effective to improve the ionic conductivity. Polyether chains are also used to improve the ionic conductivity of lithium ion polymer batteries, and are effective to improve the conductivity of ions. However, the ionic conductivity by such polyether chain is lower than that in a water-containing gel of a hydrophilic gel, and further improvement of the ionic conductivity is demanded.

Bio-electrodes are required to collect signals immediately after attached to skin. A gel electrode has ion concentrations equivalent to those of skin, and ions move in and out smoothly. In a water-containing gel, ions move so fast that signals can be detected immediately after attachment to the skin. Meanwhile, it takes long time for a dry electrode to detect signals after attachment to skin, presumably for the following reason. Specifically, although ions are released from skin, no signal is found until the dry electrode surface is saturated with the ions.

CITATION LIST

Patent Literature

Patent Document 1: WO 2013-039151 A1
Patent Document 2: JP 2015-100673 A
Patent Document 3: JP H05-095924 A
Patent Document 4: JP 2003-225217 A
Patent Document 5: JP 2015-019806 A Patent Document 6: JP 2018-099504 A
Patent Document 7: JP 2018-126496 A
Patent Document 8: JP 2018-130533 A

SUMMARY OF INVENTION

Technical Problem

The present invention has been made to solve the above problems and has an object to provide: a dry-type bio-electrode that enables quick signal collection after attachment to skin, the bio-electrode being excellent in electric conductivity and biocompatibility, light-weight, and manufacturable at low cost, and capable of preventing significant reduction in the electric conductivity even when wetted with water or dried; and a method for manufacturing the bio-electrode.

Solution to Problem

To achieve the object, the present invention provides a bio-electrode, a method for manufacturing the bio-electrode, and a method for measuring a biological signal, which are described below.

The present invention provides a bio-electrode comprising an electro-conductive base material and a living body contact layer, wherein the living body contact layer comprises a water-free resin layer and a permeation layer on a surface side of the resin layer where a living body comes into contact, and the permeation layer comprises water and a water-soluble salt selected from the group consisting of sodium salts, potassium salts, calcium salts, magnesium salts, and betaines.

Such a bio-electrode is a dry-type bio-electrode that enables quick signal collection after attachment to skin, the bio-electrode being excellent in electric conductivity and biocompatibility, light-weight, and manufacturable at low cost, and capable of preventing significant reduction in the electric conductivity even when wetted with water or dried.

Moreover, the present invention provides the bio-electrode, wherein the water-soluble salt is a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines.

Such a bio-electrode can improve the ionic conductivity.

Further, the present invention provides the bio-electrode, wherein the resin layer comprises a polymer compound (A) comprising a repeating unit having a salt structure selected from the group consisting of salts of ammonium, sodium, potassium, and silver formed with any of fluorosulfonic acid, fluorosulfonimide, and N-carbonyl-fluorosulfonamide.

Such a bio-electrode can improve the effects of the present invention.

Further, the present invention provides the bio-electrode, wherein the salt structure is shown by any of the following general formulae (1)-1 to (1)-4,

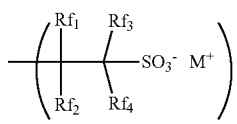
(1)-1

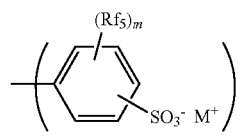
(1)-2

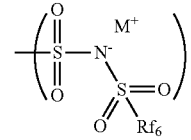
(1)-3

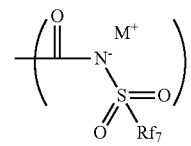
(1)-4 wherein at least one of $Rf_1$ to $Rf_4$ is a fluorine atom or a trifluoromethyl group, and $Rf_1$ and $Rf_2$ optionally bond to a carbon atom bonded therewith to form a carbonyl group; $Rf_5$, $Rf_6$, and $Rf_7$ each represent a fluorine atom, a linear alkyl group having 1 to 4 carbon atoms, or a branched alkyl group having 3 or 4 carbon atoms, and have at least one or more fluorine atoms; "m" represents an integer of 1 to 4; and M represents ammonium, sodium, potassium, or silver.

Such a bio-electrode can further improve the effects of the present invention.

Further, the present invention provides the bio-electrode, wherein one or more repeating units selected from the group consisting of salts of ammonium, sodium, potassium, and silver formed with any of fluorosulfonic acid as shown by the general formula (1)-1 or (1)-2, sulfonimide as shown by the general formula (1)-3, and sulfonamide as shown by the general formula (1)-4 comprise at least one repeating unit selected from the group consisting of repeating units A1 to A7 shown by the following general formula (1'), (1')

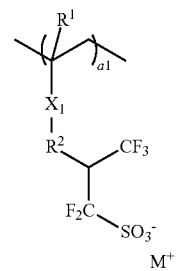
(A1)

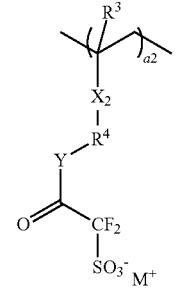
(A2)

(A3) 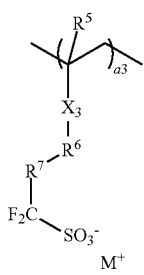

(A4) 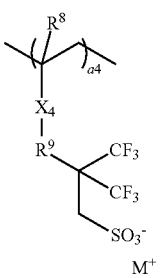

(A5) 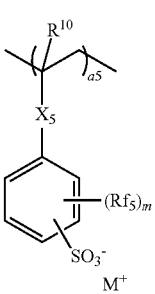

(A6) 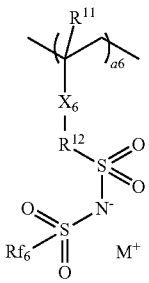

(A7) 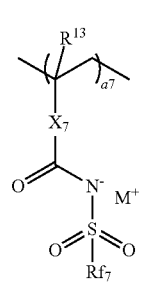

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, a linear hydrocarbon group having 1 to 12 carbon atoms, and a branched or cyclic hydrocarbon group having 3 to 12 carbon atoms, the hydrocarbon groups optionally having either or both of an ester group and an ether group; $R^7$ represents a linear alkylene group having 1 to 4 carbon atoms, or a branched alkylene group having 3 or 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{14}$— group; $R^{14}$ represents a hydrogen atom, a linear alkyl group having 1 to 4 carbon atoms, or a branched alkyl group having 3 or 4 carbon atoms, and optionally forms a ring together with $R^4$; "m" represents an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 < 1.0$; and M, $Rf_5$, $Rf_6$, and $Rf_7$ are as defined above.

Such a bio-electrode can further improve the effects of the present invention.

Further, the present invention provides the bio-electrode, wherein the salt structure shown by any of the general formulae (1)-1 to (1)-4 comprises an ammonium ion shown by the following general formula (2) as $M^+$,

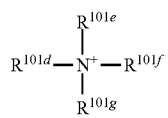 (2)

wherein $R^{101d}$, $R^{101e}$, $R^{101f}$, and $R^{101g}$ each represent a hydrogen atom, a linear alkyl group having 1 to 12 carbon atoms, a branched or cyclic alkyl group having 3 to 12 carbon atoms, a linear alkenyl group or alkynyl group having 2 to 12 carbon atoms, a branched or cyclic alkenyl group or alkynyl group having 3 to 12 carbon atoms, or an aromatic group having 4 to 20 carbon atoms, and optionally have at least one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

In the bio-electrode as described above, such an ammonium ion is suitable.

Further, the present invention provides the bio-electrode, wherein the permeation layer further comprises a monohydric alcohol or polyhydric alcohol having 1 to 4 carbon atoms.

In the bio-electrode as above, such alcohols are suitable.

Further, the present invention provides the bio-electrode, wherein the polyhydric alcohol is selected from the group consisting of glycerin, pentaerythritol, sorbitan, sorbitol, polyethylene glycol, polypropylene glycol, diglycerin, polyglycerin, a silicone compound having a polyglycerin structure, monosaccharide, polysaccharide, and products obtained from any preceding materials by substituting hydroxy groups thereof.

In the bio-electrode as above, such alcohols are more suitable.

Further, the present invention provides the bio-electrode, wherein the silicone compound having a polyglycerin structure is shown by the following general formula (3) or (4),

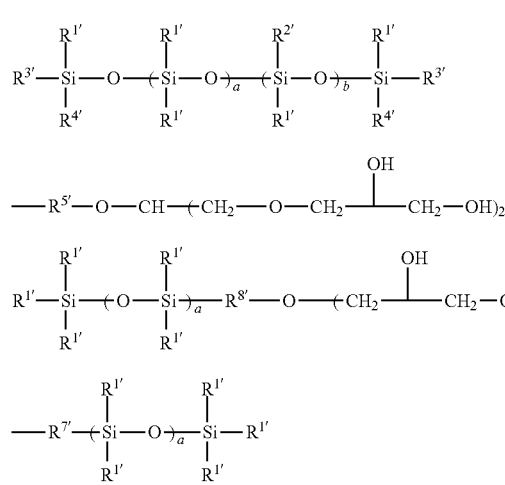
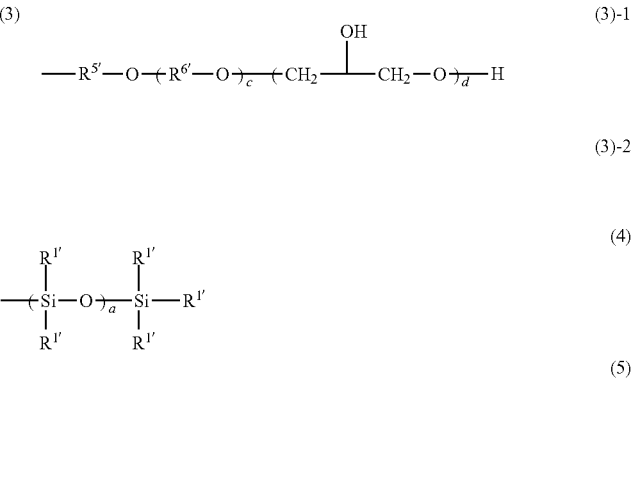

wherein each $R^{1\prime}$ is identical to or different from each other and independently represents a linear alkyl group having 1 to 50 carbon atoms, a branched alkyl group having 3 to 50 carbon atoms, a phenyl group, or a silicone chain shown by a general formula (5), and optionally contains an ether group; $R^{2\prime}$ represents a group having a polyglycerin group structure shown by a general formula (3)-1 or (3)-2; each $R^{3\prime}$ is identical to or different from each other and independently represents the $R^{1\prime}$ group or the $R^{2\prime}$ group; each $R^{4\prime}$ is identical to or different from each other and independently represents the $R^{1\prime}$ group, the $R^{2\prime}$ group, or an oxygen atom, provided that when $R^{4\prime}$ represents an oxygen atom, the two $R^{4\prime}$ moieties are integrated with each other and optionally constitute an ether group to form a ring together with silicon atoms; and each "a" is identical to or different from each other and represents 0 to 100, "b" represents 0 to 100, and a+b is 0 to 200, provided that when "b" is 0, at least one $R^{3\prime}$ is the $R^{2\prime}$ group; and $R^{5\prime}$ represents an alkylene group having 2 to 10 carbon atoms or an aralkylene group having 7 to 10 carbon atoms; $R^{6\prime}$, $R^{7\prime}$, and $R^{8\prime}$ each represent an alkylene group having 2 to 6 carbon atoms; "c" represents 0 to 20; and "d" represents 1 to 20.

Such a bio-electrode can further improve the effects of the present invention.

Further, the present invention provides the bio-electrode, wherein the resin layer further comprises a component (B) which is one or more selected from the group consisting of silicone based, acrylic based, and urethane based resins.

In such a bio-electrode, the resin component (B) is compatibilized with the ionic material (salt) of the polymer compound (A), thereby making it possible to prevent elution of the salt, hold an electric conductivity improver such as a metal powder, a carbon material, a silicon powder, or a lithium titanate powder, and exhibit adhesion.

Further, the present invention provides the bio-electrode, wherein the silicone type resin of the component (B) comprises:
  a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" is a number in a range of 2.5 to 3.5;
  diorganosiloxane having an alkenyl group; and
  organohydrogenpolysiloxane having an SiH group.

Such a bio-electrode can improve the dispersibility of the polymer compound as the component (A) in the silicone resin.

Further, the present invention provides the bio-electrode, wherein the resin layer comprises a carbon material, a silver powder, a silicon powder, or a lithium titanate powder.

Such a bio-electrode can improve the electric conductivity.

Further, the present invention provides the bio-electrode, wherein the carbon material is one or both of carbon black and carbon nanotube.

Such a bio-electrode can further improve the electric conductivity.

Further, the present invention provides the bio-electrode, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

In the bio-electrode as above, such an electro-conductive base material is suitable.

Further, the present invention provides the bio-electrode, further comprising a protective film on the permeation layer.

Such a bio-electrode can prevent the permeation layer from drying.

Further, the present invention provides a method for manufacturing a bio-electrode, comprising:
  coating an electro-conductive base material with a bio-electrode composition comprising a polymer compound (A) containing a repeating unit having a salt structure selected from the group consisting of salts of ammonium, sodium, potassium, and silver formed with any of fluorosulfonic acid, fluorosulfonimide, and N-carbonyl-fluorosulfonamide;
  curing the bio-electrode composition to form a living body contact layer; and
  bringing an aqueous solution containing a water-soluble salt selected from the group consisting of sodium salts, potassium salts, calcium salts, magnesium salts, and betaines into contact with a surface of the living body contact layer where a living body comes into contact to form a permeation layer in the surface of the living body contact layer where a living body comes into contact, the permeation layer being permeated with the aqueous solution containing the water-soluble salt.

Such a method for manufacturing a bio-electrode makes it possible to efficiently manufacture a dry-type bio-electrode that enables quick signal collection after attachment to skin, the bio-electrode being excellent in electric conductivity and biocompatibility, light-weight, and manufacturable at low cost, and capable of preventing significant reduction in the electric conductivity even when wetted with water or dried.

Furthermore, the present invention provides a method for manufacturing a bio-electrode, wherein a solution containing the water-soluble salt, a monohydric alcohol or polyhydric alcohol having 1 to 4 carbon atoms, and water is brought, by a spraying method, into contact with the surface of the living body contact layer where a living body comes into contact.

Such a method for manufacturing a bio-electrode allows more efficient manufacturing of the inventive bio-electrode.

Further, the present invention provides the method for manufacturing a bio-electrode, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

Such a method for manufacturing a bio-electrode allows more efficient manufacturing of the inventive bio-electrode.

Further, the present invention provides the method for manufacturing a bio-electrode, further comprising stacking a protective film on the permeation layer.

Such a method for manufacturing a bio-electrode enables more efficient manufacturing of the inventive bio-electrode, while preventing the permeation layer from drying.

Furthermore, the present invention provides a method for measuring a biological signal, comprising:
treating a portion of skin with a solution containing water; and
attaching the bio-electrode to the treated portion to measure a biological signal.

Such a method for measuring a biological signal has effects of not only moisturizing skin but also removing the fat/oil content on the skin surface, thereby improving the sensitivity to biological signals, and enabling efficient biological signal measurement.

Advantageous Effects of Invention

As described above, the inventive bio-electrode and method for manufacturing the bio-electrode make it possible to provide: a dry-type bio-electrode that is excellent in electric conductivity and biocompatibility, light-weight, and manufacturable at low cost, and prevents significant reduction in the electric conductivity even when wetted with water or dried to enable quick signal collection after attachment to skin; a method for manufacturing the bio-electrode; and a method for measuring a biological signal.

BRIEF DESCRIPTION OF DRAWINGS

FIG. 1 is a schematic sectional view showing an example of the inventive bio-electrode;

FIG. 2 is a schematic sectional view showing an example of the bio-electrode before salt solution treatment;

FIG. 3 is a schematic sectional view showing an example of the inventive bio-electrode worn on a living body;

FIG. 4 is a schematic view of bio-electrodes prepared in Examples of the present invention;

FIG. 5 is a schematic view of one of the bio-electrodes prepared in Examples of the present invention, the bio-electrode being cut out and provided with an adhesive layer and an electric wire;

FIG. 6 is a schematic view of a human body showing locations where electrodes and earth of an electrocardiograph are attached; and FIG. 7 is a graph showing an electrocardiogram waveform including P, Q, R, S, and T waves.

DESCRIPTION OF EMBODIMENTS

As described above, it has been desired to develop: a bio-electrode composition capable of forming a living body contact layer for a bio-electrode which enables quick signal collection after attachment to skin, and which is excellent in electric conductivity and biocompatibility, light-weight, and manufacturable at low cost; a bio-electrode including a living body contact layer formed from the bio-electrode composition; and a method for manufacturing the bio-electrode.

The surface of skin releases ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions.

In neutralized salts formed from highly acidic acids, the ions are strongly polarized, so that the ionic conductivity is improved. This is why lithium salts of bis(trifluoromethanesulfonyl)imidic acid and tris(trifluoromethanesulfonyl)methide acid show high ionic conductivity as lithium ion batteries. On the other hand, before the formation of the neutralized salt, the higher acidity of the acid makes the salt have stronger irritation to a body. That is, ionic conductivity and irritation to a body are in relation of trade-off. Salts to be applied to a bio-electrode, however, have to achieve both higher ionic conductivity and lower irritation to a body.

As the molecular weight of ionic compound increases, the permeability and the stimulus to skin tend to decrease. Accordingly, the ionic compound is preferably a polymer type with higher molecular weight. Thus, the present inventors have synthesized such a polymer by polymerizing an ionic compound having a polymerizable double bond, and have found that adding this polymer enables formation of a bio-electrode sensitive to the increase and decrease of ions released from skin.

Patent Documents 6, 7, and 8 noted above disclose a copolymer of a strong acidic ionic repeating unit, a repeating unit having a silicone chain, and a hydrophilic repeating unit such as polyether. The ionic repeating unit and the hydrophilic repeating unit are units necessary to exhibit and enhance the ionic conductivity in accordance with the combination. However, these units alone make the hydrophilicity so high that when the resulting bio-electrode film comes into contact with water or sweat, the ion polymer is dissolved in water, and no biological signal is collected in some cases. Accordingly, the ion polymer needs to be insoluble in water. For this reason, the repeating unit having a silicone chain is also copolymerized.

When an ion polymer having all of an ionic repeating unit, a hydrophilic repeating unit, and a repeating unit with hydrophobic silicone is added to a silicone adhesive, ionic conductivity is exhibited, and biological signals can be obtained. The mechanism of ion conduction in the silicone adhesive, which is inherently an insulator, is conceivably attributable to the microphase separation structure of the ion polymer. Nafion which is excellent in ionic conductivity is described to exhibit high ionic conductivity by microphase separation of a hydrophilic sulfonate moiety and a hydrophobic fluoropolymer moiety thereof.

If an ionic polymer for bio-electrode can be formed to attain more prominent microphase separation, the ionic conductivity will be further improved, and it will be possible to form a dry electrode that can obtain biological signals in higher sensitivity.

The electric potential on the skin surface and the amount of sodium, potassium, and calcium ions released vary among people. If a person has low electric potential on the skin surface or releases a small amount of ions, no signal may be detected, or noise may appear more noticeably. Although such noise can be removed by means of software, it is most important to increase the sensitivity of the bio-electrode, which is the detection source.

The ionic conductivity in a bio-electrode film can be improved by adding a highly-polarized ion polymer or causing microphase separation as described above. Further, when sodium, potassium, and calcium ions are released from skin, it is necessary to conduct the ions smoothly in such a bio-electrode containing an ion polymer.

To smoothly introduce sodium, potassium, and calcium ions released from skin into an ion polymer, the surface state of the bio-electrode is preferably close to that of skin; in other words, water and ions of sodium, potassium, calcium, magnesium, or betaine should be present on the bio-electrode surface.

The present inventors have earnestly studied the problems as described above, and consequently arrived at a bio-electrode having the following configuration and a method for manufacturing the bio-electrode, thereby completing the present invention.

Specifically, the present invention provides: a bio-electrode comprising an electro-conductive base material and a living body contact layer, wherein the living body contact layer comprises a water-free resin layer and a permeation layer on a surface side of the resin layer where a living body comes into contact, and the permeation layer comprises water and a water-soluble salt selected from the group consisting of sodium salts, potassium salts, calcium salts, magnesium salts, and betaines; a method for manufacturing the bio-electrode; and a method for measuring a biological signal.

Hereinafter, the present invention will be described in detail, but the present invention is not limited thereto.

<Bio-Electrode>

The inventive bio-electrode includes an electro-conductive base material and a living body contact layer. The living body contact layer includes a water-free resin layer and has a permeation layer on a surface side of the resin layer where a living body comes into contact. The permeation layer contains water and a water-soluble salt selected from the group consisting of sodium salts, potassium salts, calcium salts, magnesium salts, and betaines.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is a layer including a permeation layer 5-1 and a water-free resin layer 5-2. Additionally, the living body contact layer 3 may contain the carbon material 4. FIG. 2 is a schematic sectional view showing an example of the bio-electrode before salt solution treatment.

The permeation layer is located on the surface side of the water-free resin layer toward which a living body is brought into contact, and is permeated with water and a water-soluble salt selected from the group consisting of sodium salts, potassium salts, calcium salts, magnesium salts, and betaines. The permeation layer can be formed, for example, by treatment with water containing a water-soluble salt as will be described later.

When the bio-electrode 1 as shown in FIG. 1 is used, the living body contact layer 3 (i.e., the layer including the carbon material 4, the permeation layer 5-1, and the water-free resin layer 5-2) is brought into contact with a living body 6 as shown in FIG. 3. Electric signals are picked from the living body 6 through the carbon material 4 and the permeation layer 5-1, and then conducted to a sensor device etc. (not shown) via the electro-conductive base material 2. As described above, the inventive bio-electrode is capable of coping with both electric conductivity and biocompatibility by using the ionic polymer (ionic material) to be described later, and capable of obtaining electric signals from skin stably in high sensitivity because the contact area with skin is kept constant due to the adhesion thereof. The inventive bio-electrode may further have a protective film placed on the permeation layer to prevent the permeation layer from drying.

Hereinafter, the configuration of the inventive bio-electrode will be described more specifically.

[Electro-Conductive Base Material]

The inventive bio-electrode has an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from the group consisting of gold, silver, silver chloride, platinum, aluminum, magnesium, tin, tungsten, iron, copper, nickel, stainless steel, chromium, titanium, and carbon, for example.

In the inventive bio-electrode, such electro-conductive base materials are suitable.

The electro-conductive base material is not particularly limited, and may be a hard electro-conductive substrate, an electro-conductive film having flexibility, a substrate having a stretchable film coated with electro-conductive paste, a cloth with the surface being coated with electro-conductive paste, a cloth into which electro-conductive polymer is kneaded, or the like. The electro-conductive base material may be flat, uneven, or mesh-form of woven metal wires, which can be appropriately selected in accordance with the use of the bio-electrode, and so forth. Among these, in consideration of the use of the bio-electrode that is attached onto skin, preferable is a substrate having a stretchable film or cloth coated with electro-conductive paste. Examples of the stretchable film include polyurethane and polyester. The electro-conductive paste to be used can be obtained by mixing an electro-conductive powder of carbon, silver, gold, copper, or the like with a solvent in a stretchable resin such as polyurethane, polyester, silicone, or nitrile resin.

[Living Body Contact Layer]

The inventive bio-electrode includes the electro-conductive base material and a living body contact layer. The living body contact layer includes a water-free resin layer, and has a permeation layer on a surface side of the resin layer where a living body comes into contact, the permeation layer being permeated with water and a water-soluble salt selected from the group consisting of sodium salts, potassium salts, calcium salts, magnesium salts, and betaines. This living body contact layer is formed on the electro-conductive base material, and is a part to be actually in contact with a living body when the bio-electrode is used. The living body contact layer has electric conductivity and adhesion. The living body contact layer is not particularly limited, as long as it includes the water-free resin layer and has the permeation layer in the surface side of the resin layer where a living body comes into contact with the living body contact layer. For example, the resin layer is formed from a cured material (cured product) of a bio-electrode composition to be described later; in other words, the resin layer is an adherent resin layer obtained by curing a composition containing (A) a polymer compound (ionic material (salt)) and an additive such as (B) a resin, which are described later. The resin layer may be permeated with an aqueous solution containing particular ion to form the permeation layer on the resin layer.

The living body contact layer preferably has adhesive strength in a range of 0.5 N/25 mm or more and 20 N/25 mm or less. The adhesive strength is commonly measured by the method shown in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and as low as that of Teflon (registered trade mark). Hence, human skin is hard to adhere.

The living body contact layer of the bio-electrode has a thickness of preferably 1 μm or more and 5 mm or less, more preferably 2 μm or more and 3 mm or less. As the living body contact layer is thinner, the adhesive strength lowers, but the flexibility is improved, and the weight decreases to improve the compatibility with skin. The thickness of the living body contact layer can be selected based on the balance of adhesion and texture to the skin.

The inventive bio-electrode may be provided with an adherent film separately on the living body contact layer as in conventional bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of: the high oxygen permeability, which enables dermal respiration while pasting the same; the high water repellency, which decreases lowering of adhesion due to perspiration; and the low irritation to skin. It is to be noted that the inventive bio-electrode does not necessarily require this adherent film that is prepared separately, because peeling off from a living body can be prevented by adding a tackifier to the bio-electrode composition or using a resin having good adhesion to a living body.

When the inventive bio-electrode is used as a wearable device, wiring between the bio-electrode and a sensor device, and other components are not limited to particular ones. For example, it is possible to employ the ones described in JP 2004-033468A.

[Water-Free Resin Layer]

In the inventive bio-electrode, the living body contact layer includes a resin layer containing no water. Hereinbelow, this water-free resin layer will be described.

[Bio-Electrode Composition]

A bio-electrode composition for forming the water-free resin layer of the inventive bio-electrode is not particularly limited. For example, a polymer having an ionic repeating unit can be incorporated as an ionic material of the polymer compound (A). Hereinafter, exemplary components of such a bio-electrode composition will be further described in detail.

[Ionic Material (Salt)]

A salt to be blended into the bio-electrode composition as the ionic material (conductive material) of the polymer compound (A) (component (A)) can be a polymer having a repeating unit with a salt structure selected from the group consisting of salts of ammonium, sodium, potassium, and silver formed with any of fluorosulfonic acid, fluorosulfonimide, and N-carbonyl-fluorosulfonamide.

Examples of the salts of ammonium, sodium, potassium, and silver selected from fluorosulfonate, fluorosulfonimide, and N-carbonyl-fluorosulfonamide (i.e., the aforementioned salt structure) include ones shown by the following general formulae (1)-1 to (1)-4.

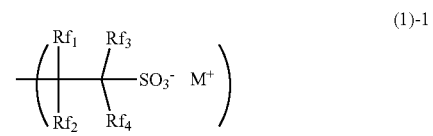

(1)-1

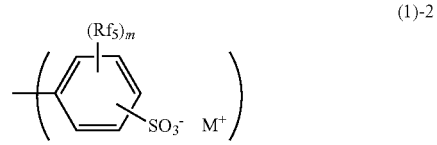

(1)-2

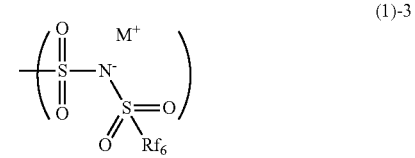

(1)-3

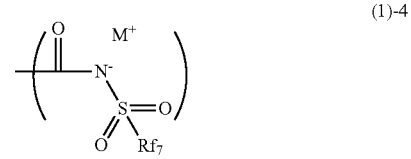

(1)-4

In the formulae, at least one of $Rf_2$ to $Rf_4$ is a fluorine atom or a trifluoromethyl group. $Rf_2$ and $Rf_2$ optionally bond to a carbon atom bonded therewith to form a carbonyl group. $Rf_5$, $Rf_6$, and $Rf_7$ each represent a fluorine atom, a linear alkyl group having 1 to 4 carbon atoms, or a branched alkyl group having 3 or 4 carbon atoms, and have at least one or more fluorine atoms. "m" represents an integer of 1 to 4. M represents ammonium, sodium, potassium, or silver.

One or more repeating units selected from the group consisting of salts of ammonium, sodium, potassium, and silver formed with any of fluorosulfonic acid as shown by the general formula (1)-1 or (1)-2, sulfonimide as shown by (1)-3, and N-carbonyl-sulfonamide as shown by (1)-4 are preferably at least one repeating unit selected from the group consisting of repeating units A1 to A7 shown by the following general formula (1').

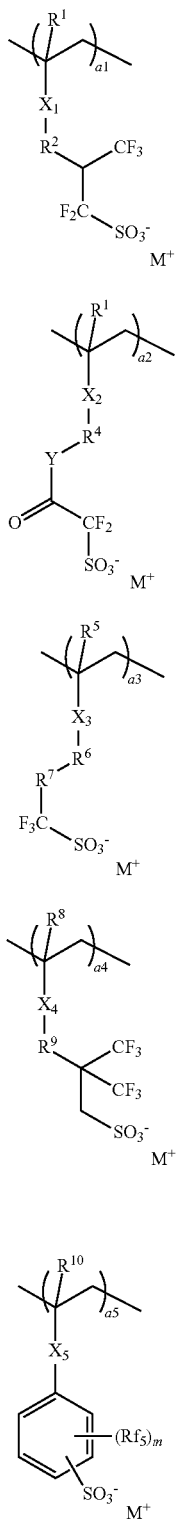

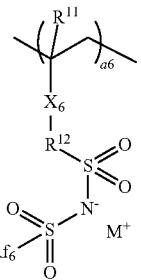

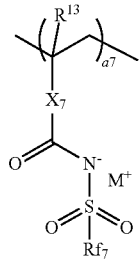

In the formula, $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent any of a single bond, a linear hydrocarbon group having 1 to 12 carbon atoms, and a branched or cyclic hydrocarbon group having 3 to 12 carbon atoms, the hydrocarbon groups optionally having either or both of an ester group and an ether group. $R^7$ represents a linear alkylene group having 1 to 4 carbon atoms, or a branched alkylene group having 3 or 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents an oxygen atom or a —$NR^{14}$— group. $R^{14}$ represents a hydrogen atom, a linear alkyl group having 1 to 4 carbon atoms, or a branched alkyl group having 3 or 4 carbon atoms, and optionally forms a ring together with $R^4$. "m" represents an integer of 1 to 4. a1, a2, a3, a4, a5, a6, and a7 satisfy 0≤a1≤1.0, 0≤a2≤1.0, 0≤a3≤1.0, 0≤a4≤1.0, 0≤a5≤1.0, 0≤a6≤1.0, 0≤a7≤1.0, and 0<a1+a2+a3+a4+a5+a6+a7<1.0. M, $Rf_5$, $Rf_6$, and $Rf_7$ are as defined above.

a1 to a7 shown in the general formula (1') represent the proportions of the respective repeating units A1 to A7. Among the repeating units A1 to A7, the repeating units A1 to A5 can be obtained from fluorosulfonic acid salt monomers specifically exemplified below.

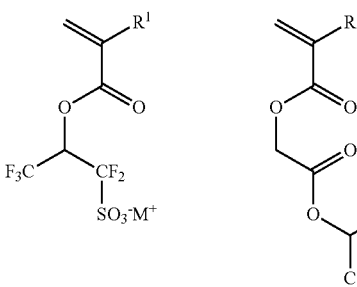

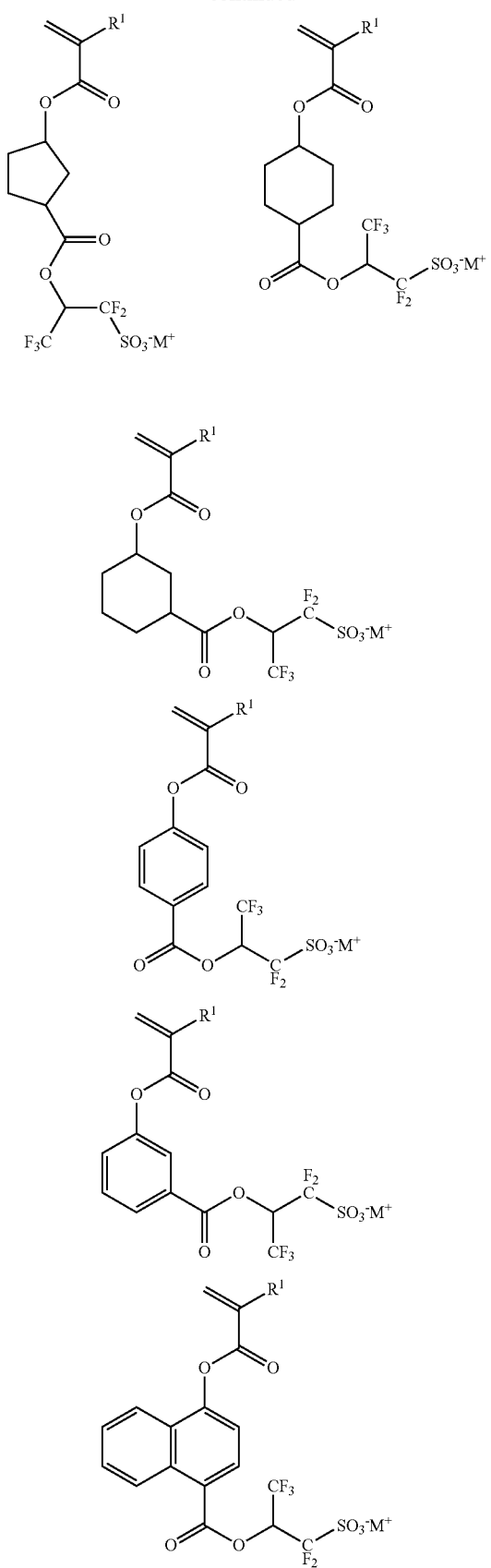
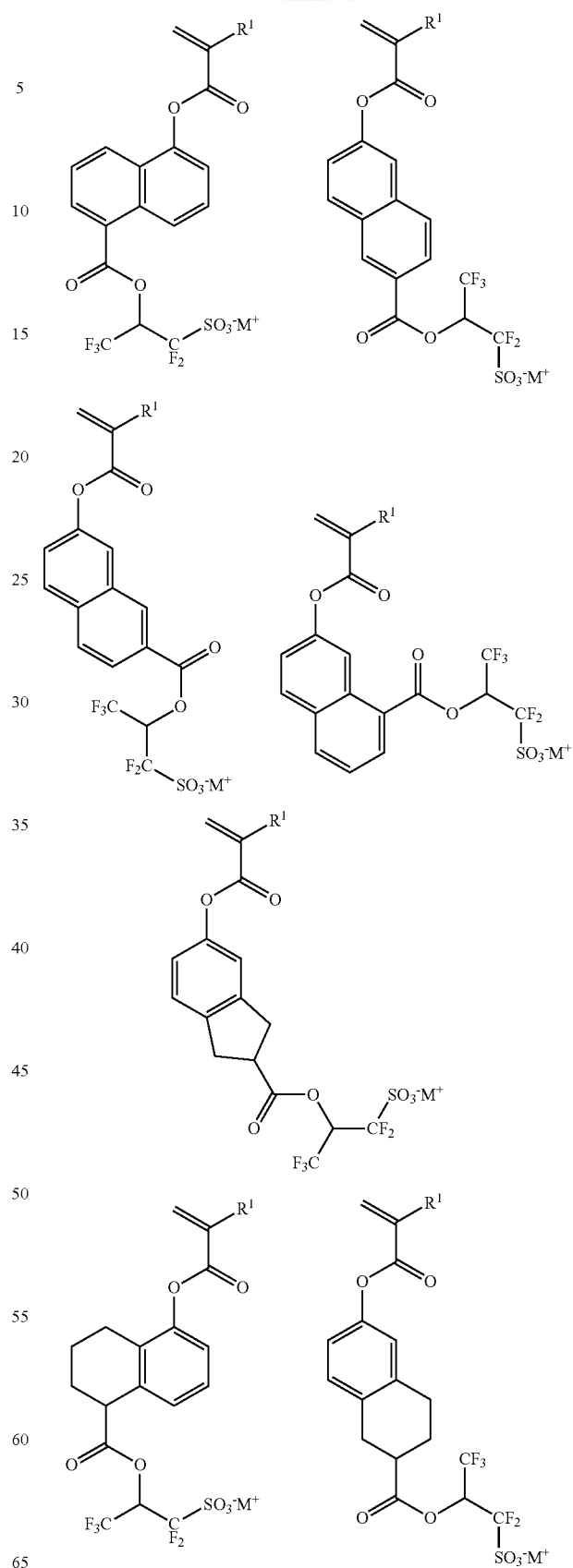

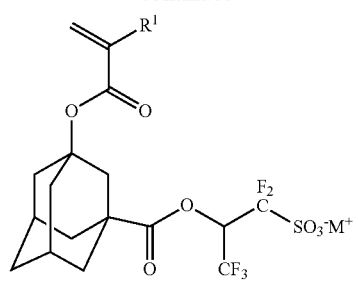
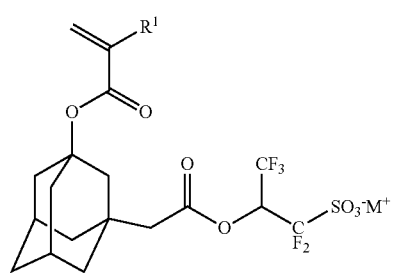
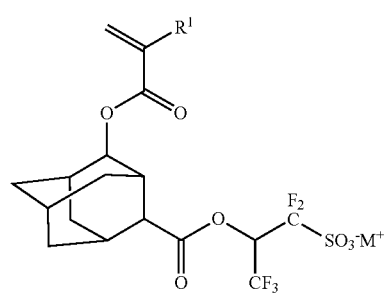
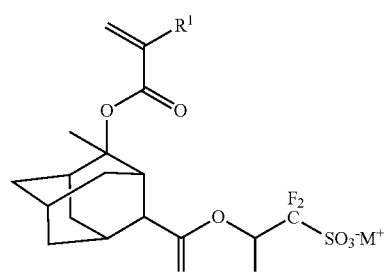
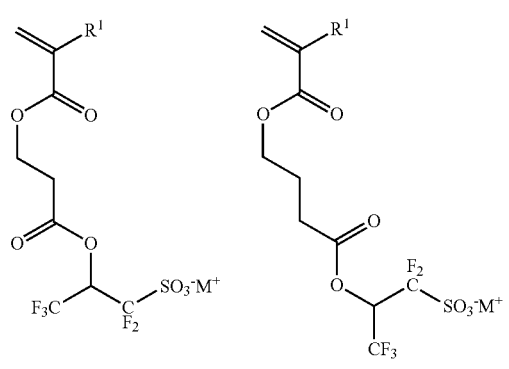
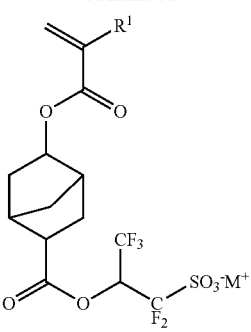
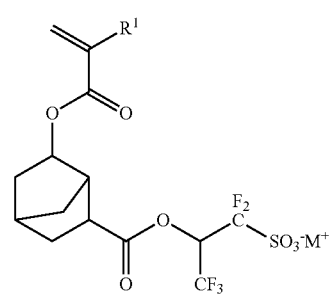
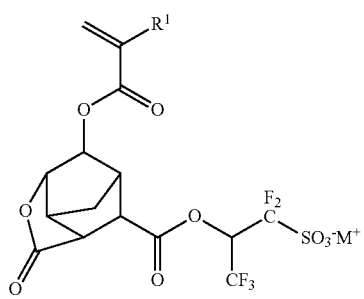
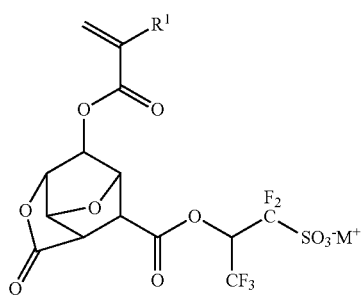
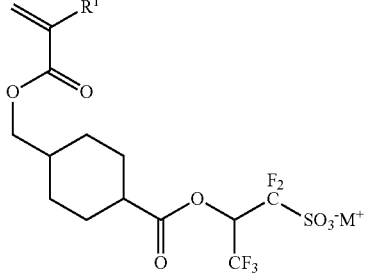

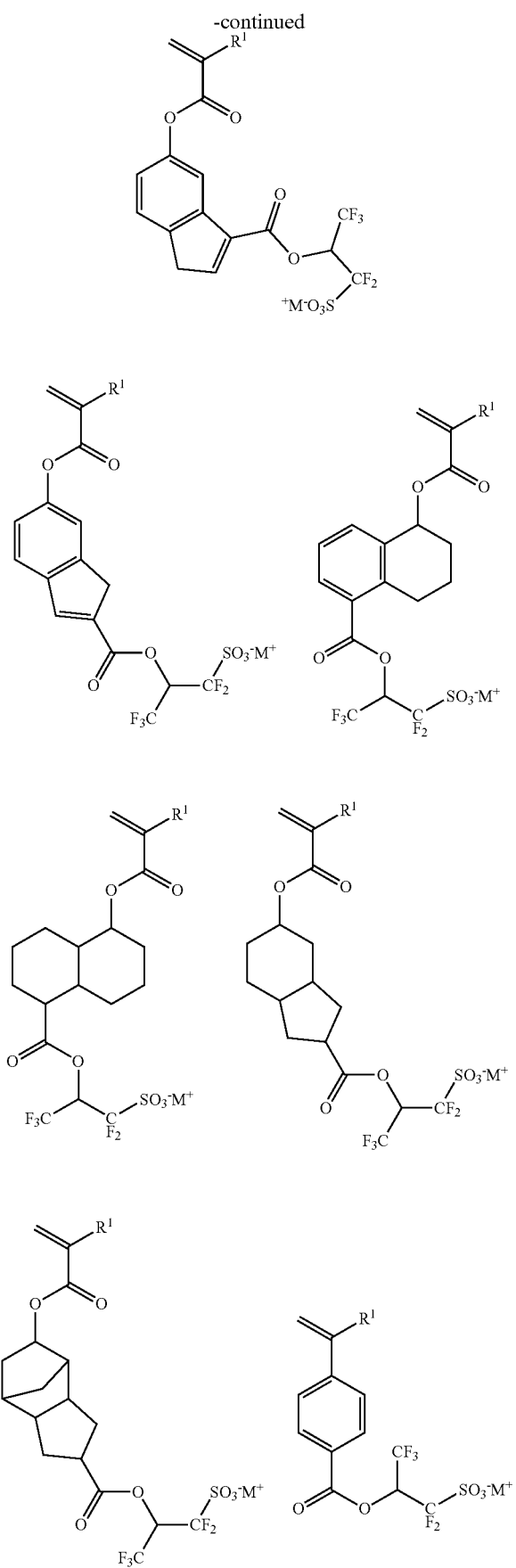
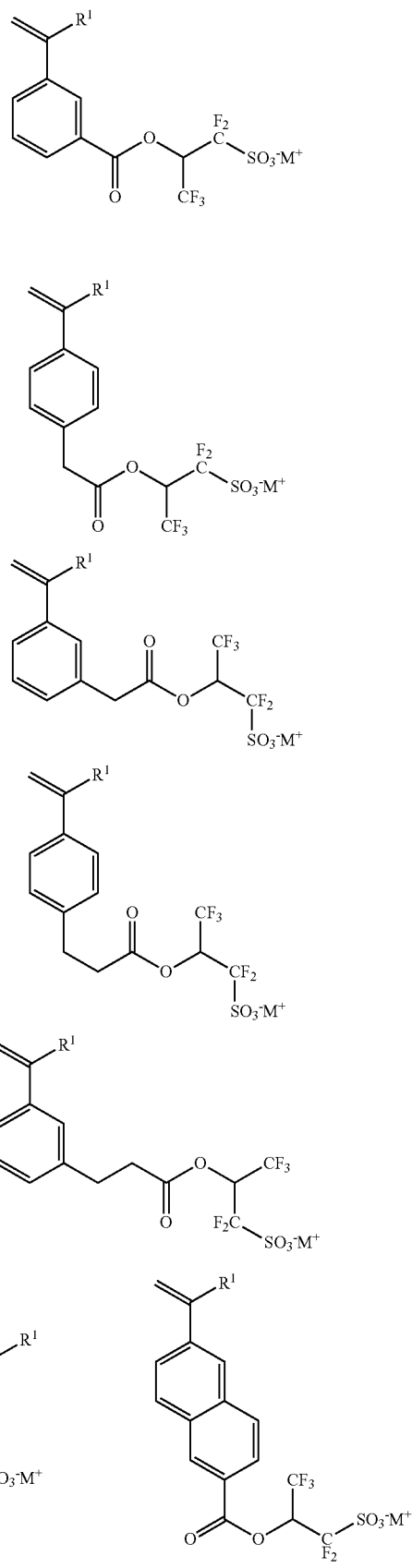

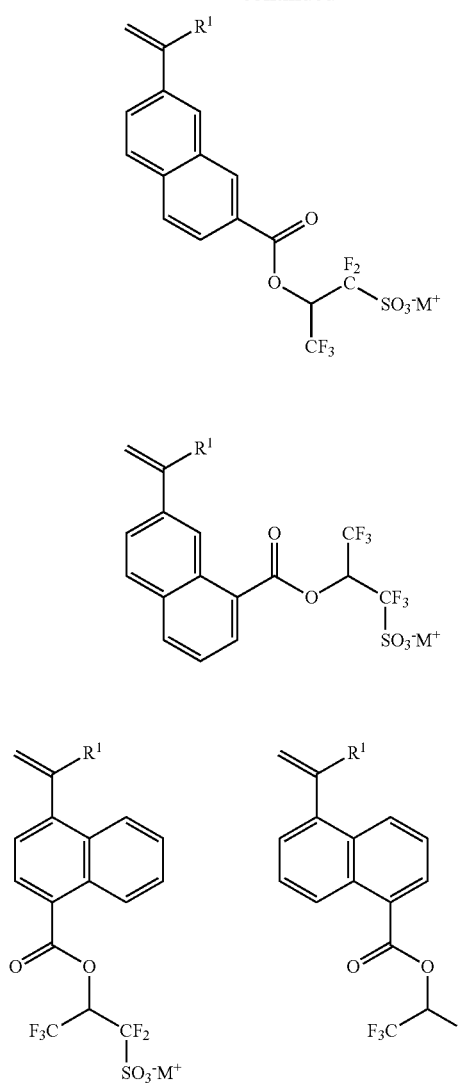
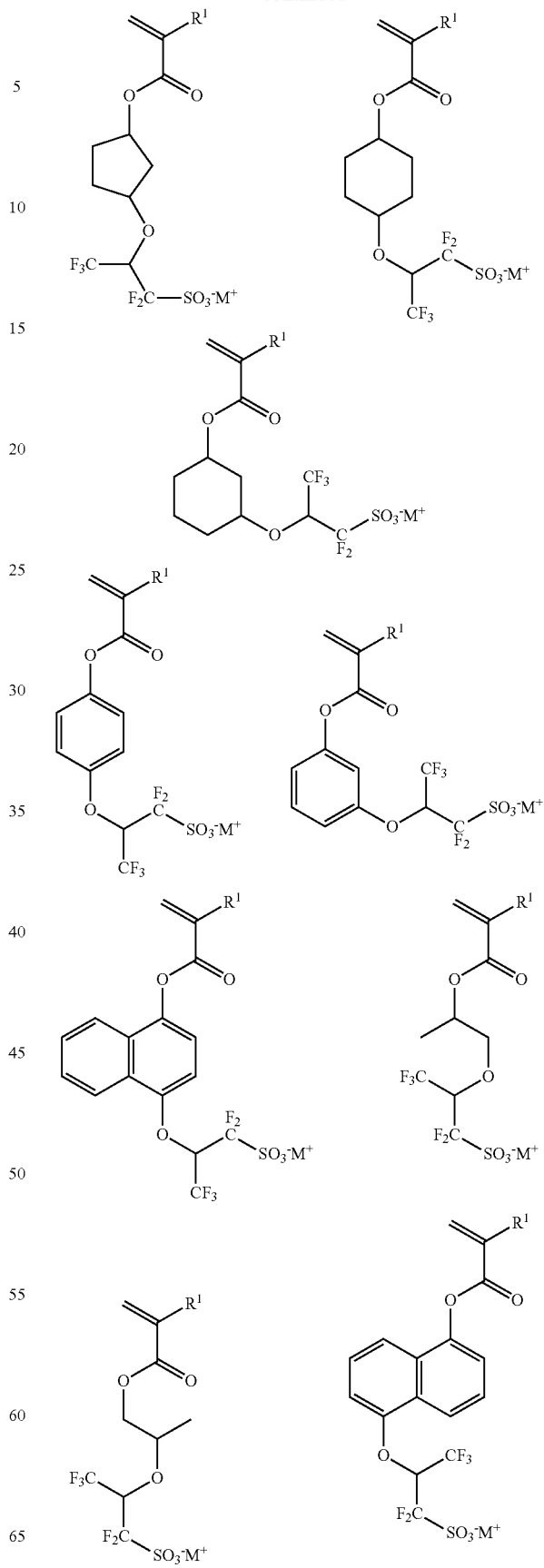

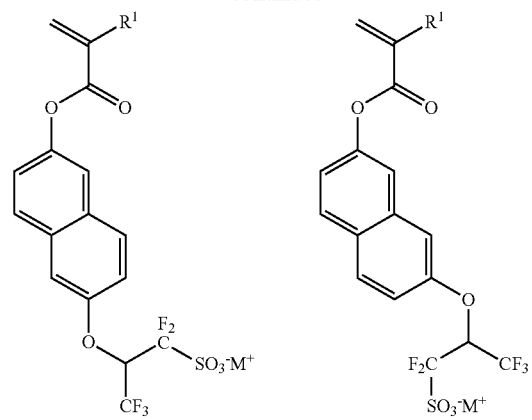
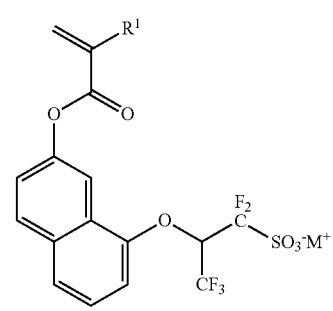
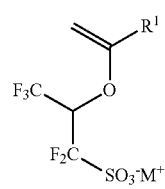
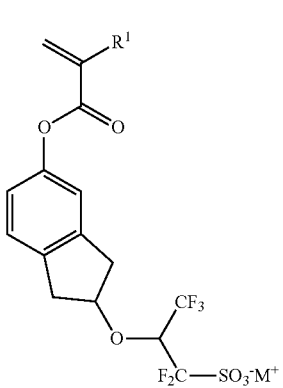
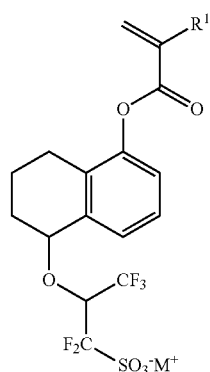
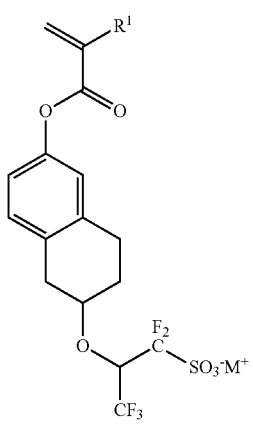
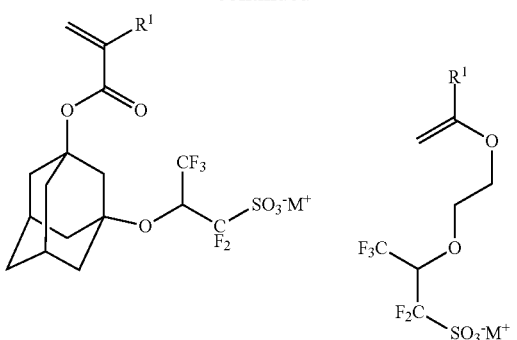
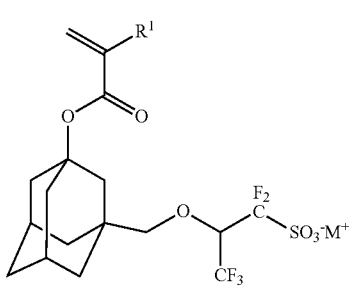
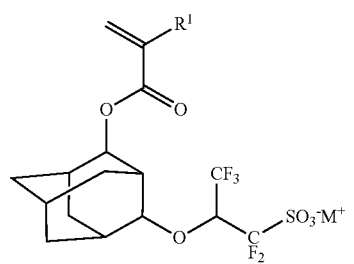
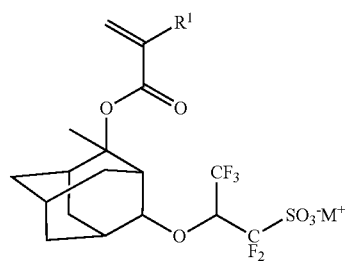
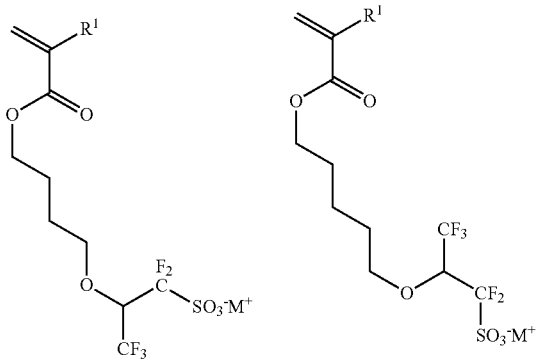

-continued
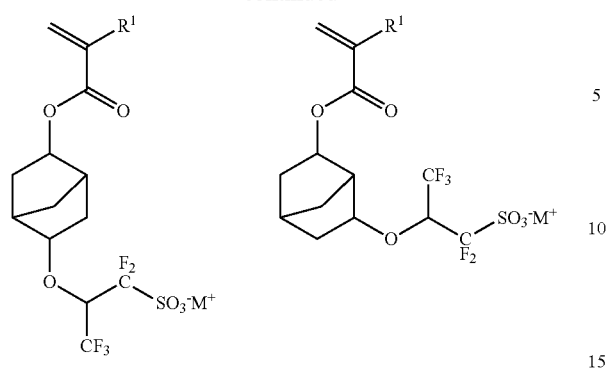
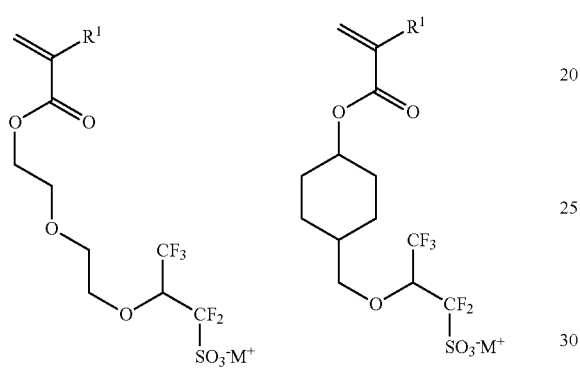
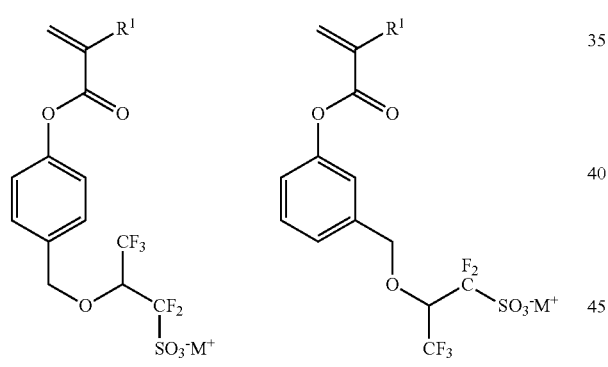
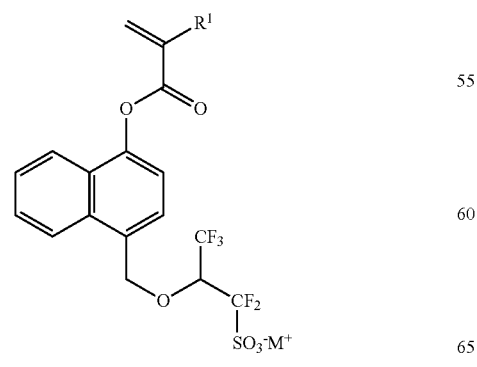
-continued
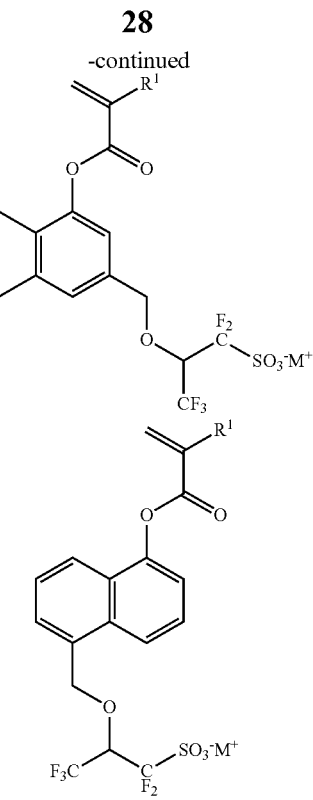
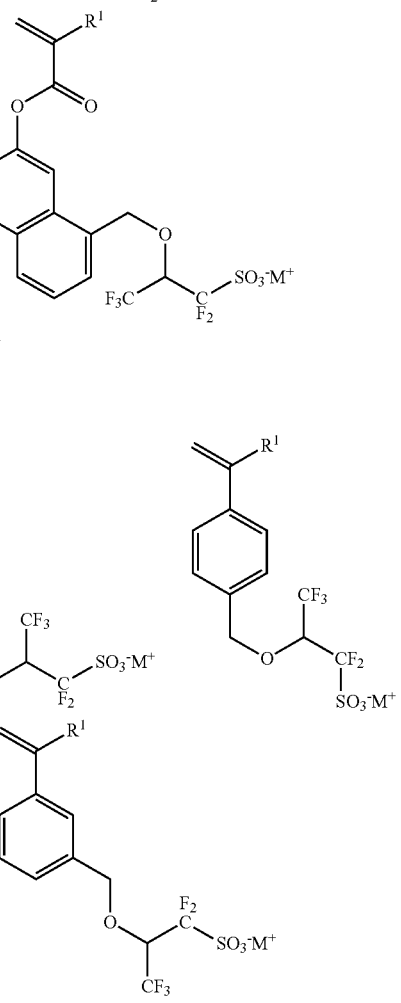

-continued
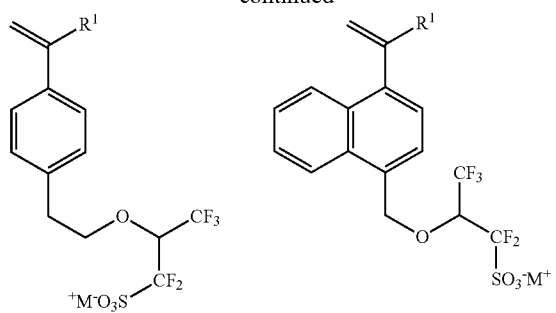
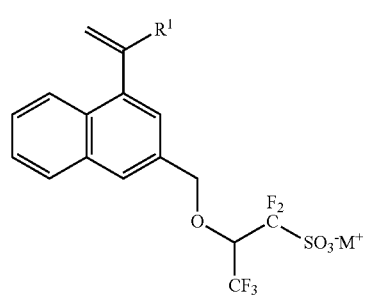
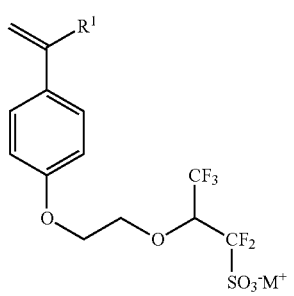
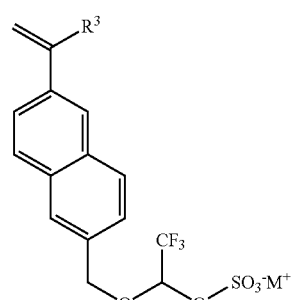
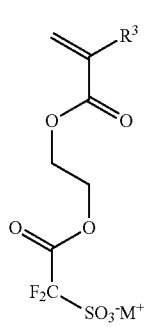
-continued
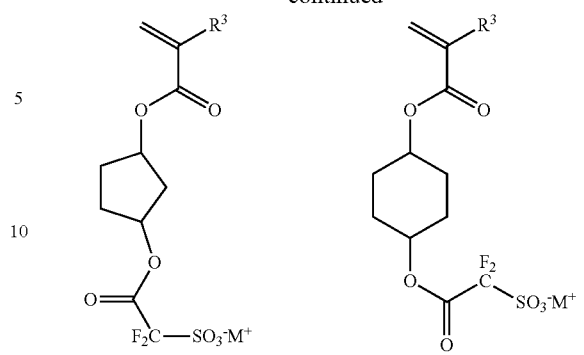
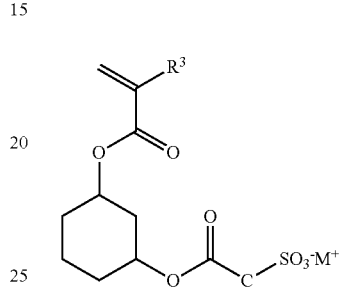
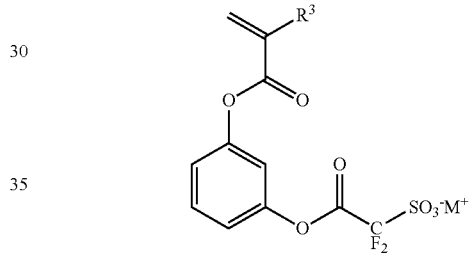
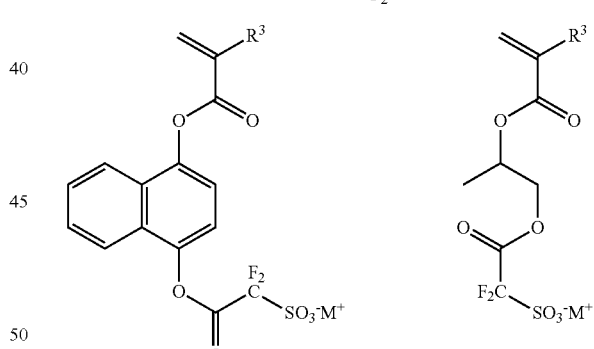
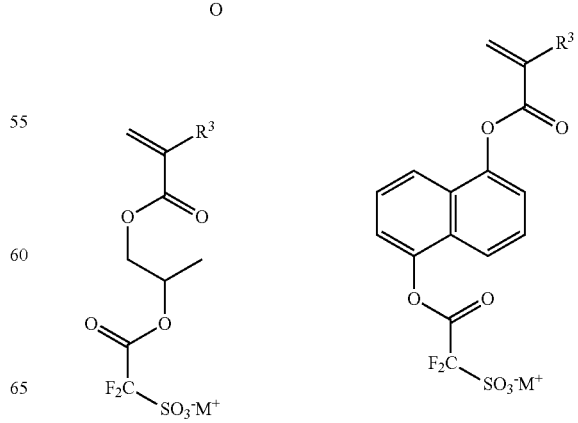

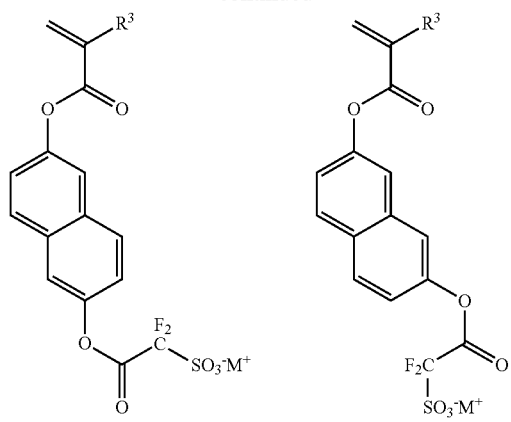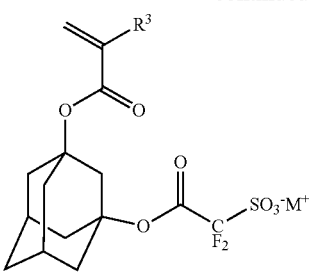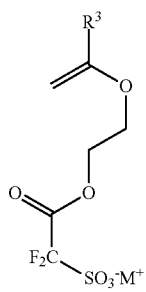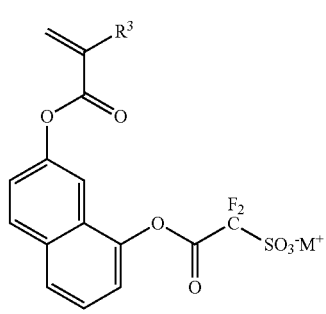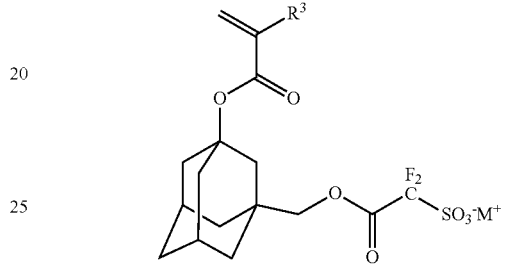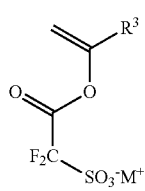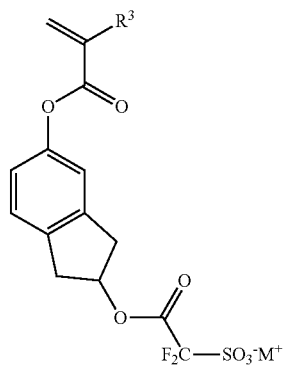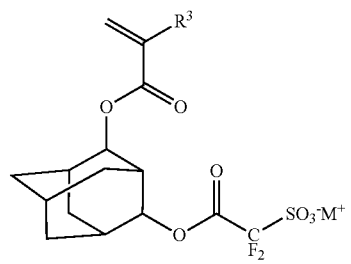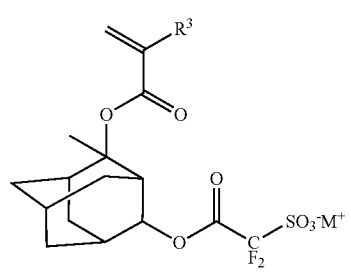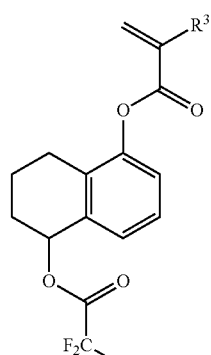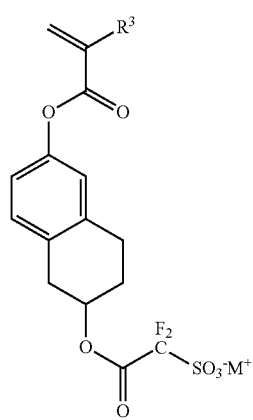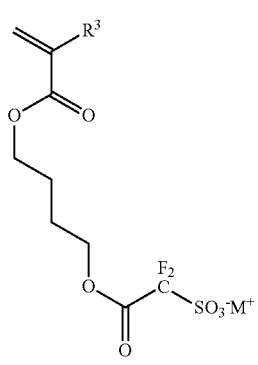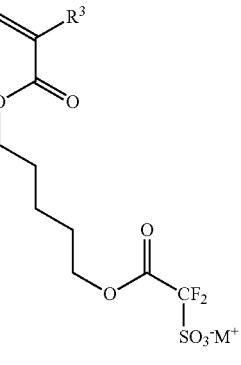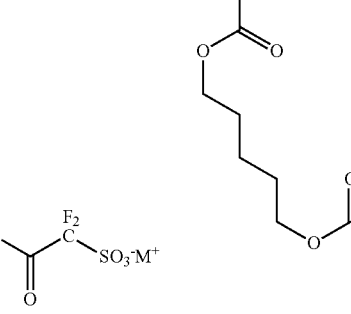

-continued
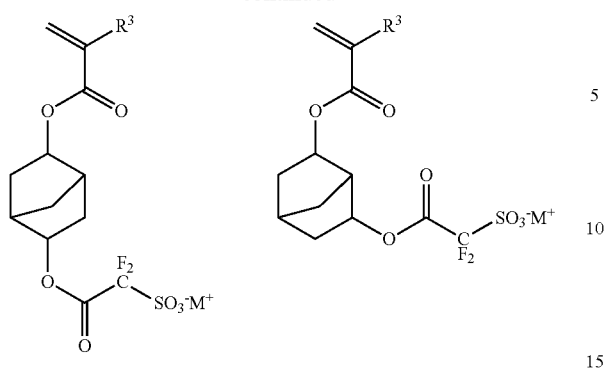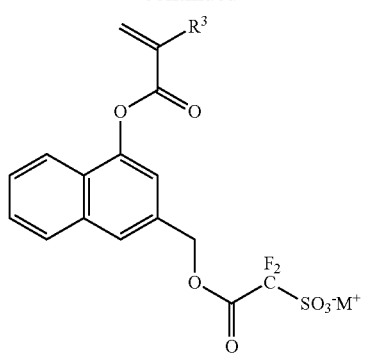
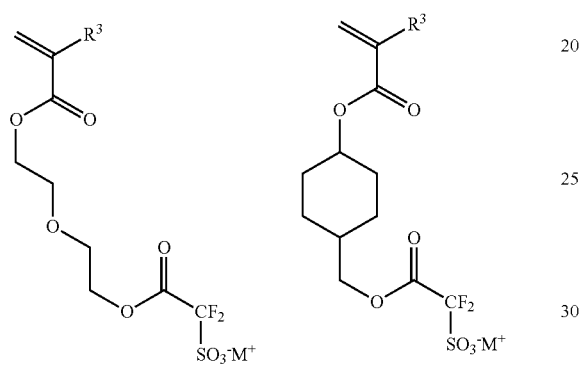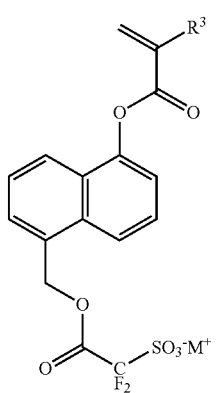
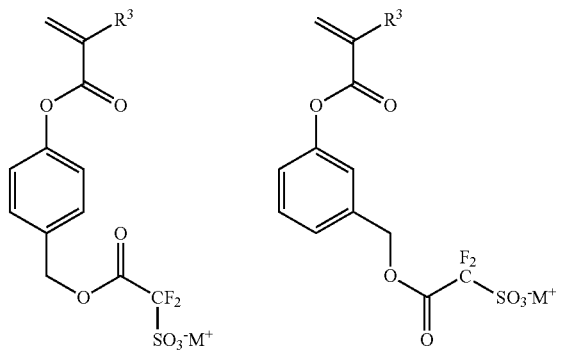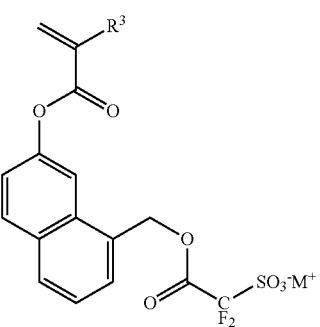
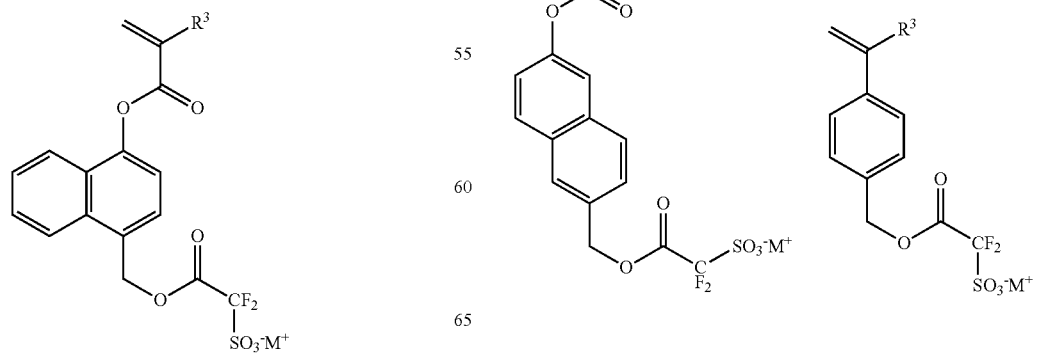

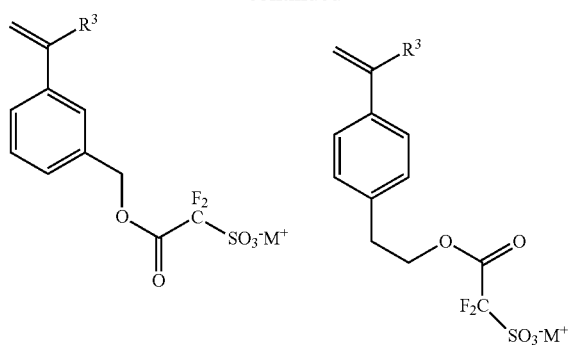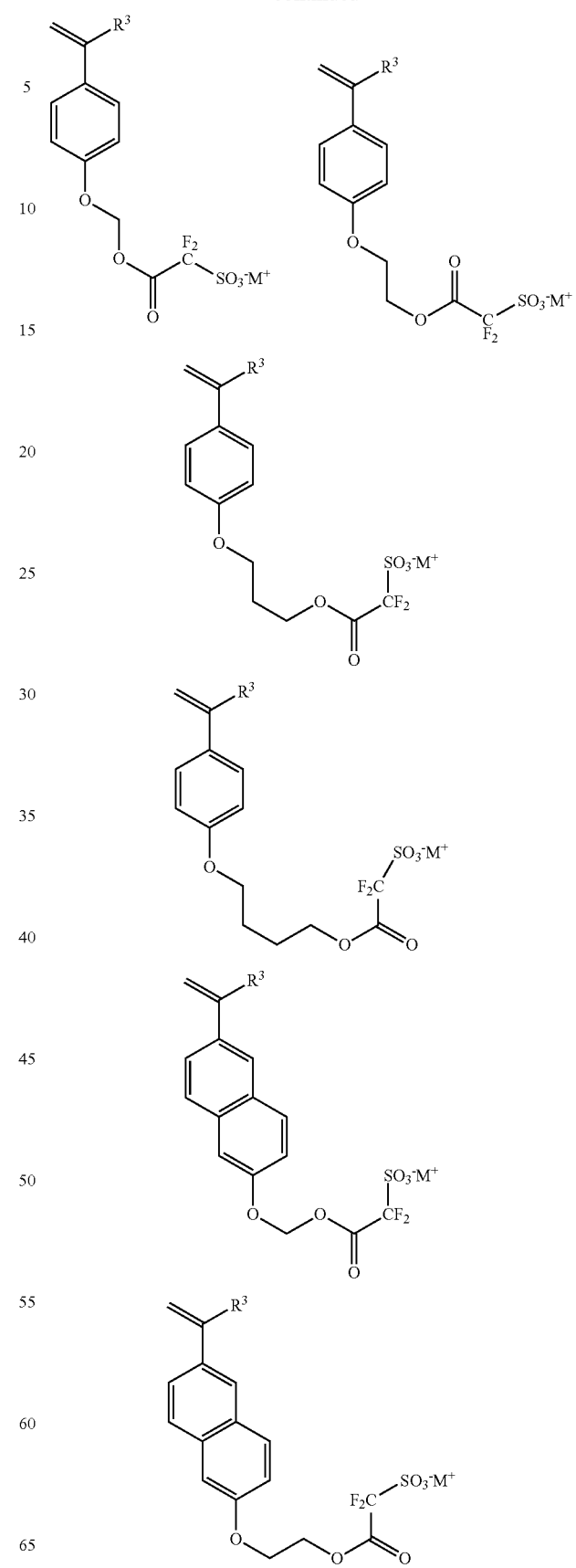

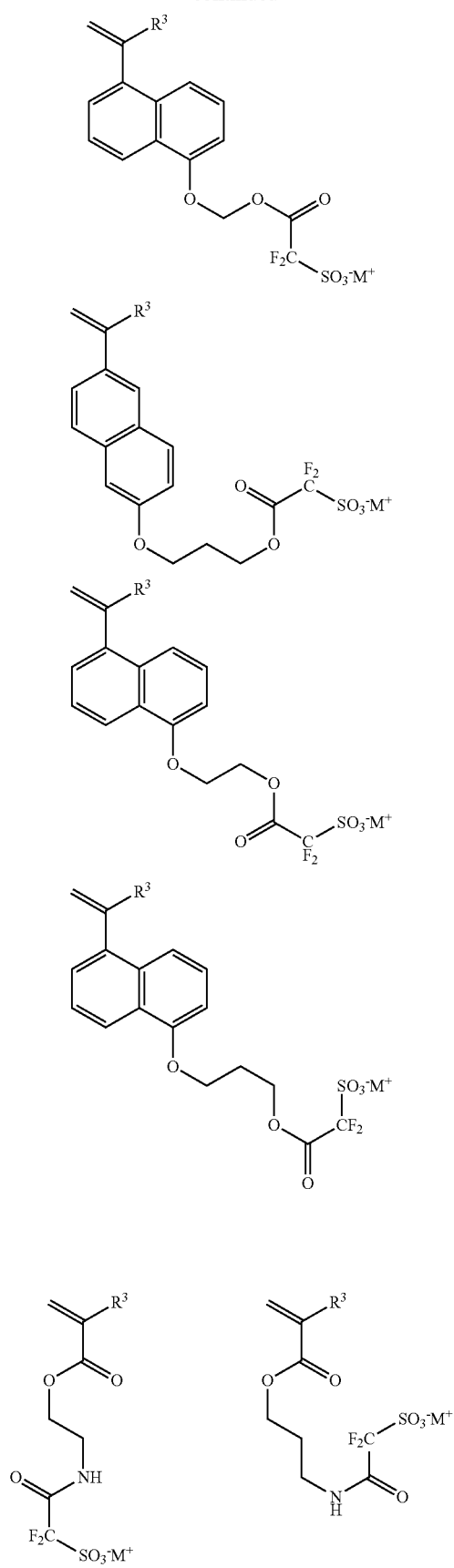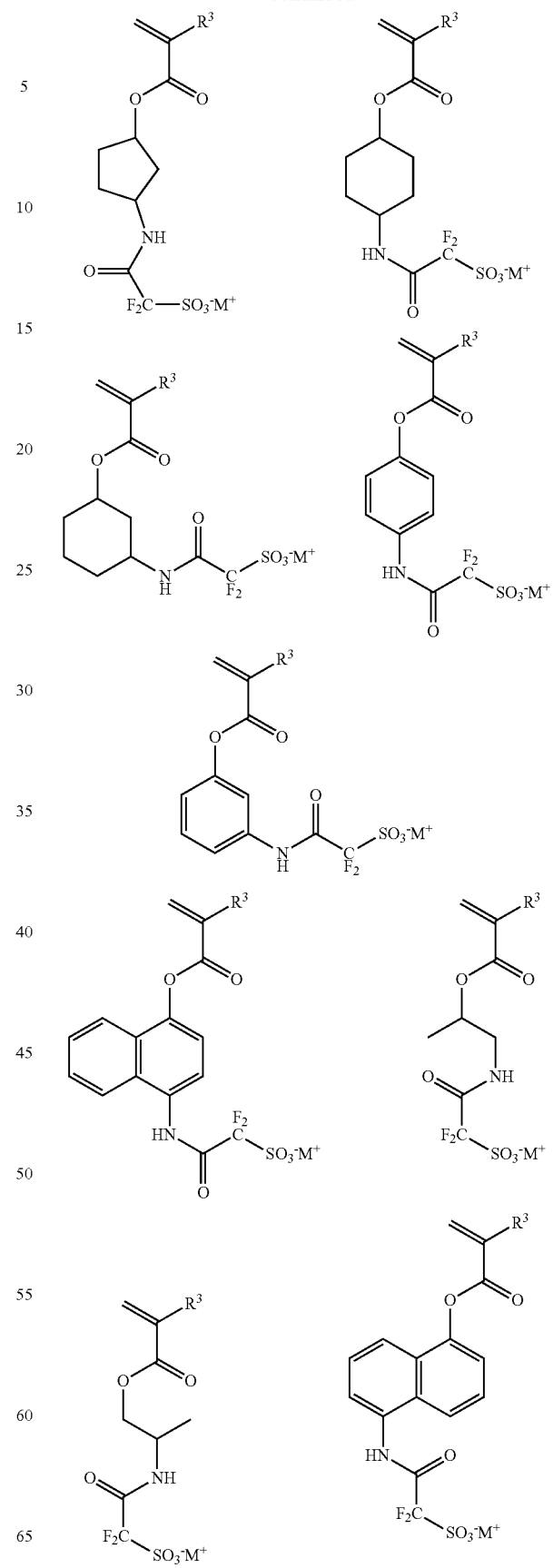

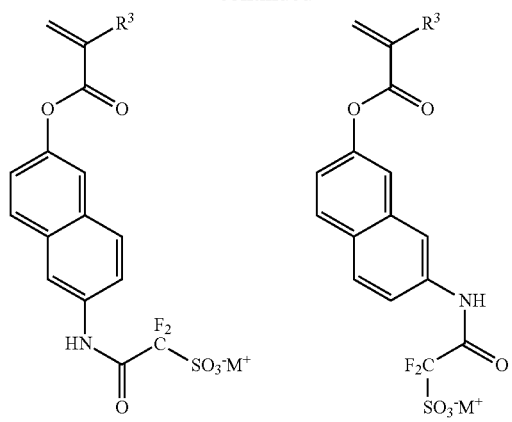
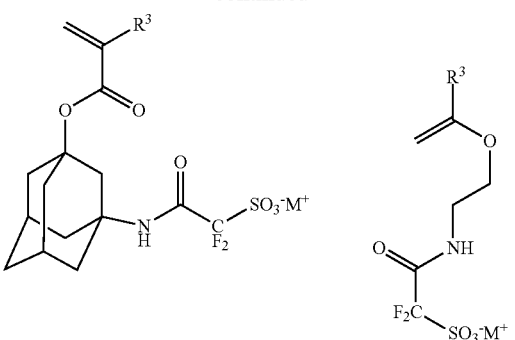
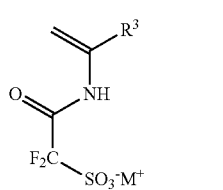
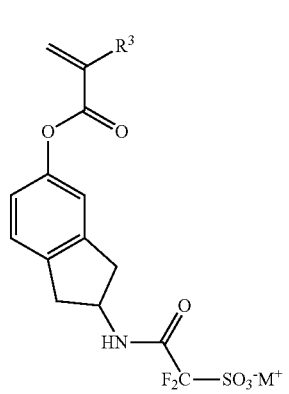
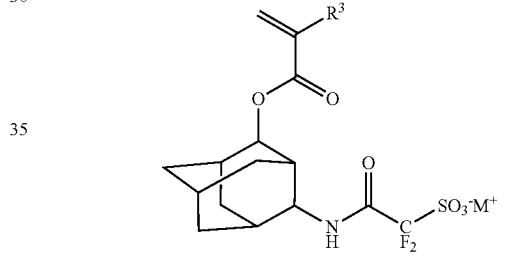
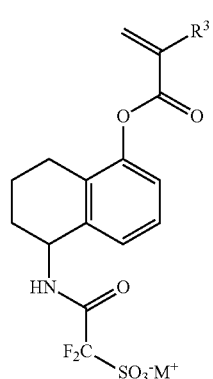
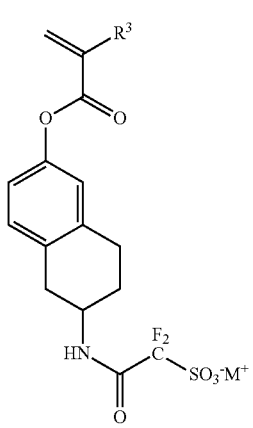
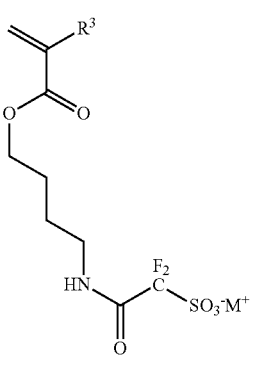

-continued
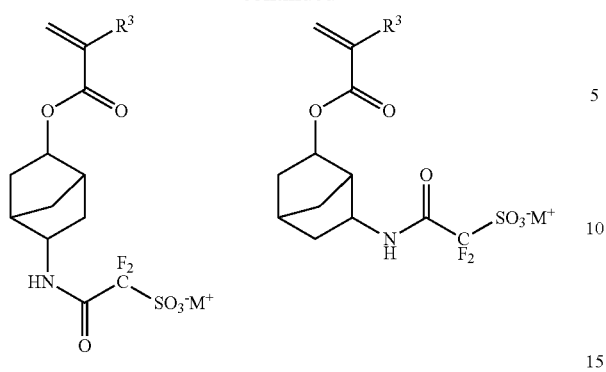
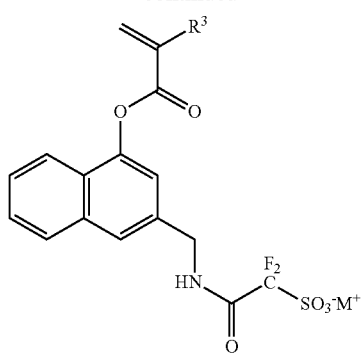
-continued
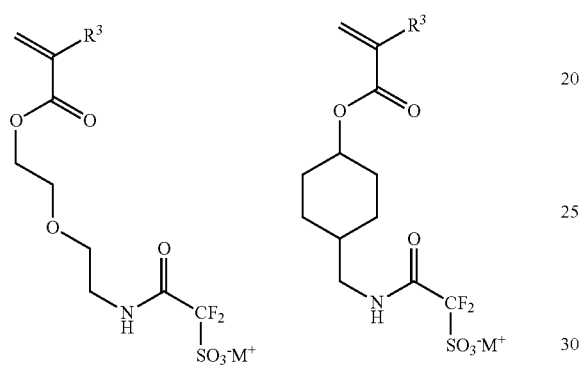
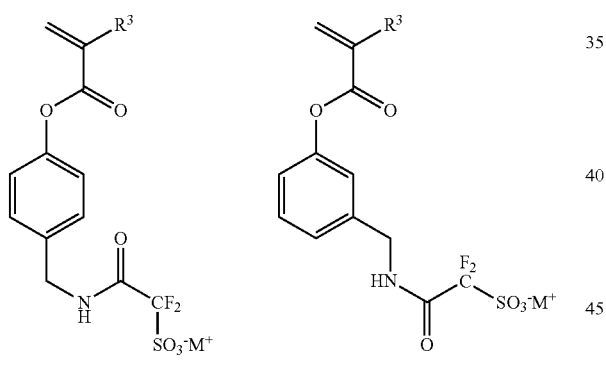
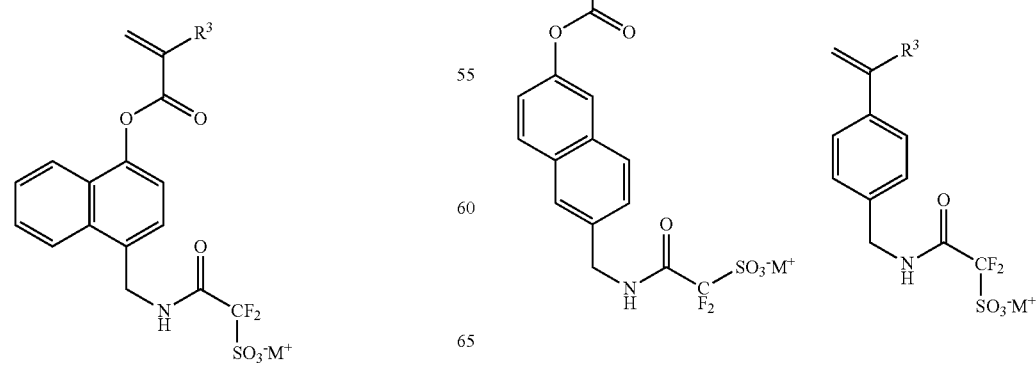

-continued
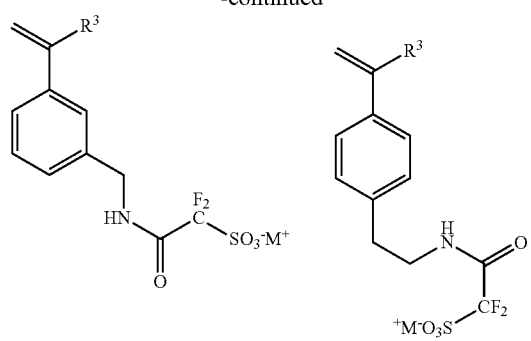
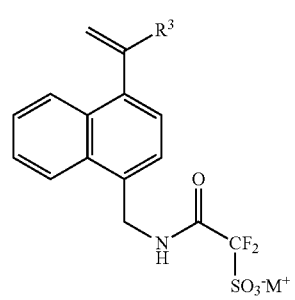
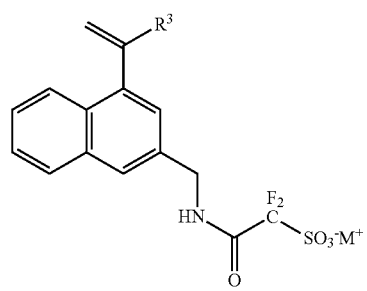
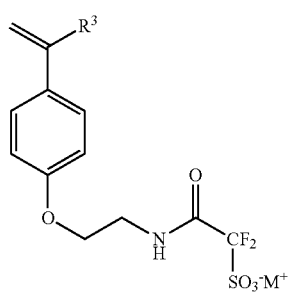
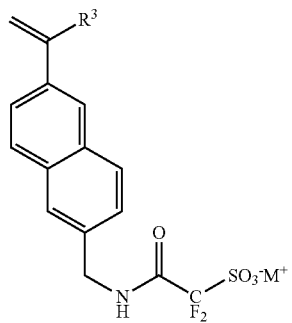
-continued
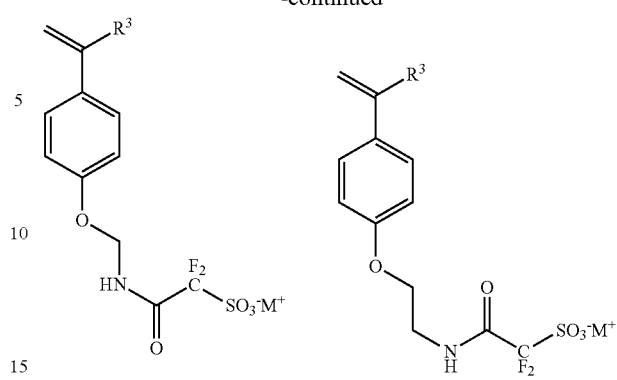
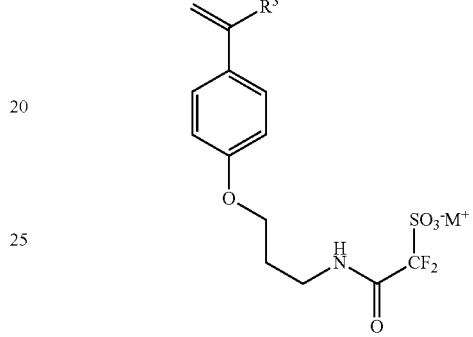
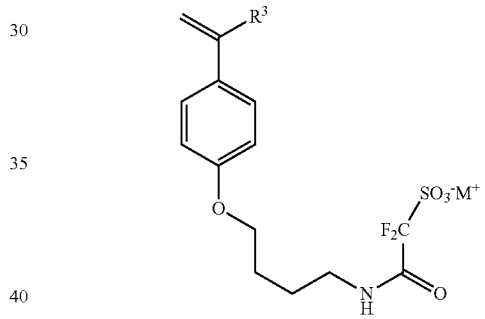
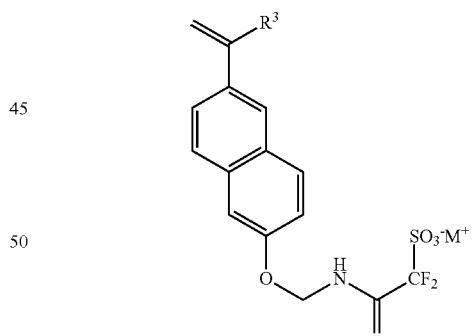
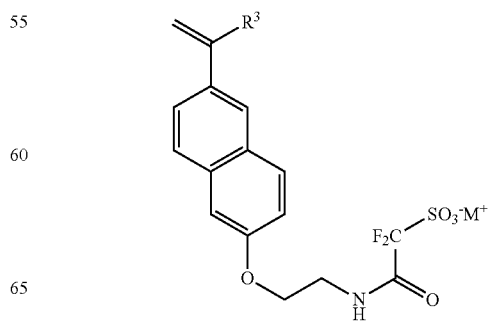

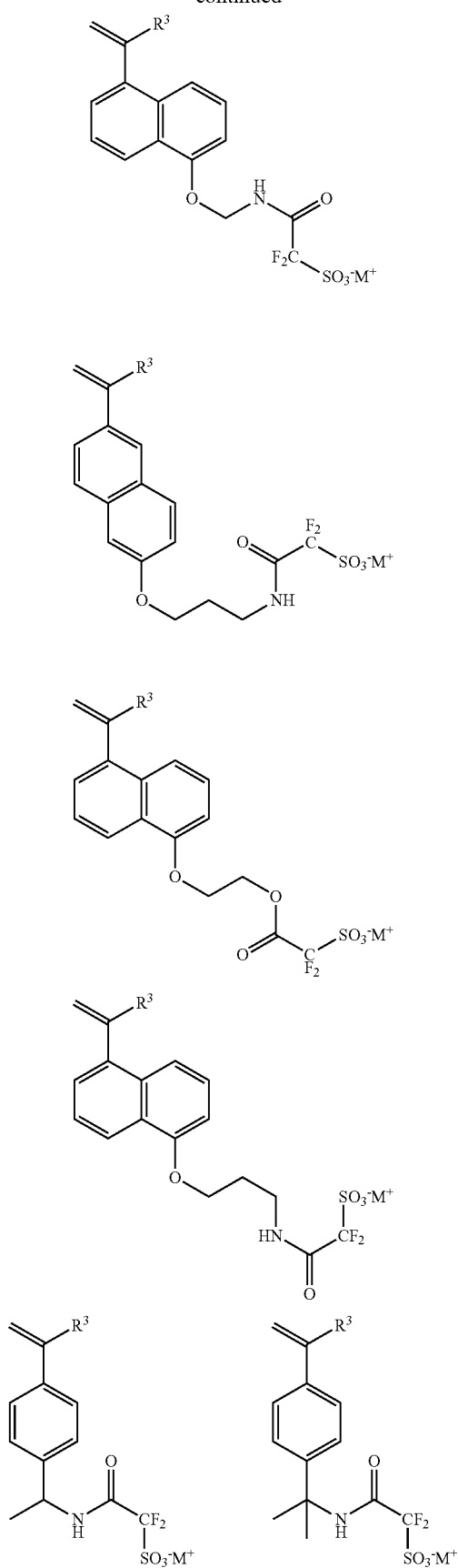

47
-continued
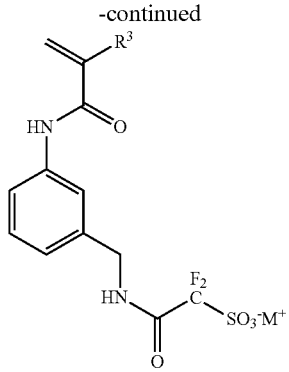
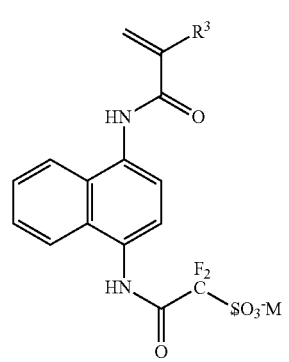
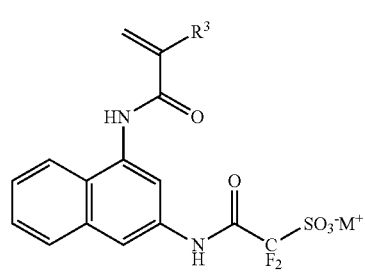
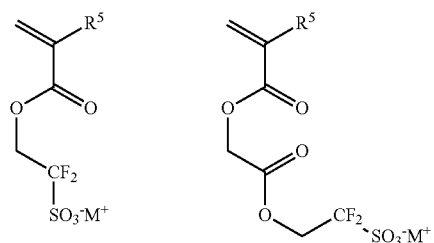
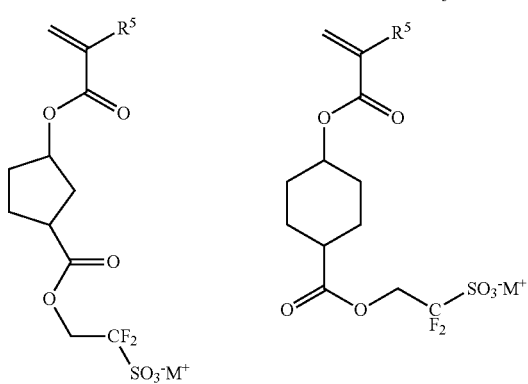
48
-continued
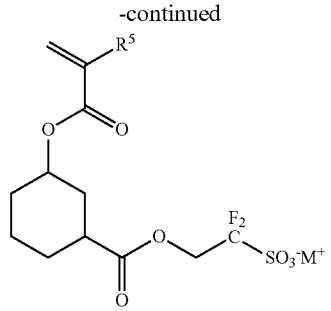
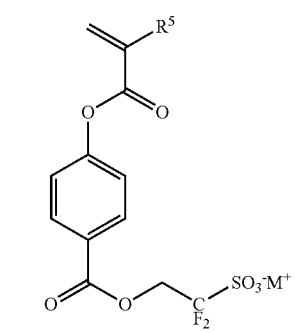
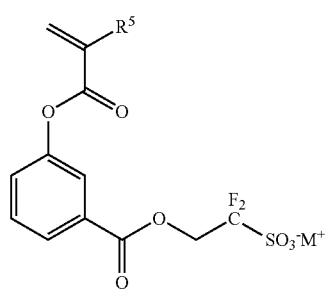
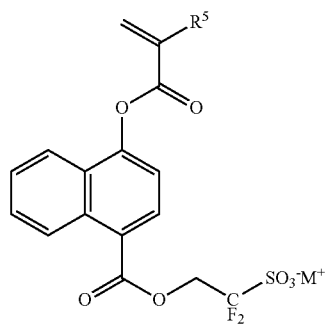
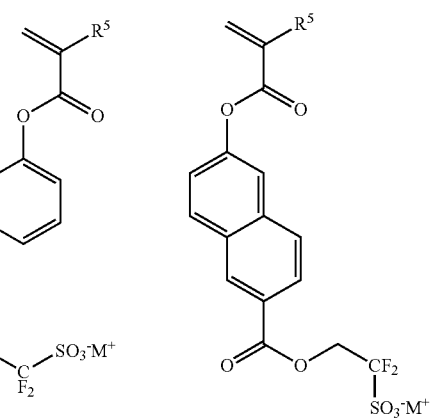

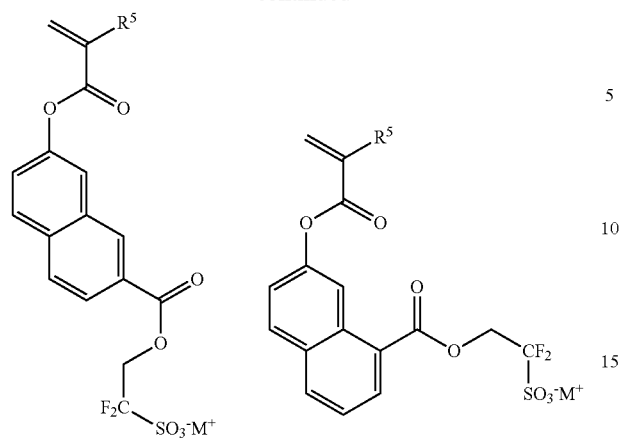
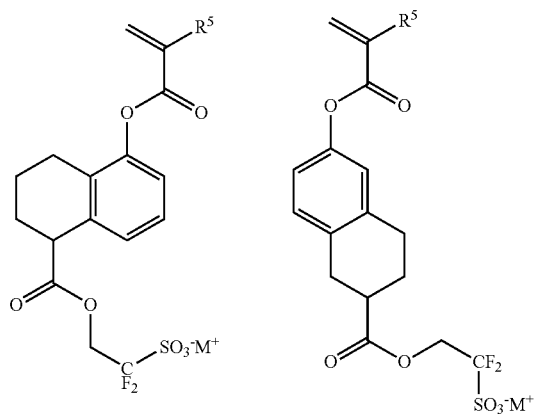
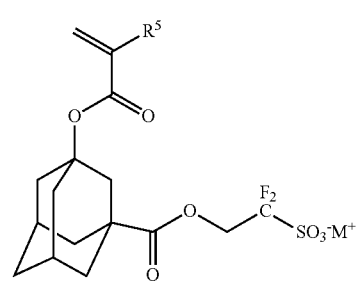
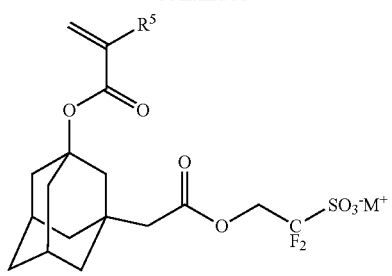
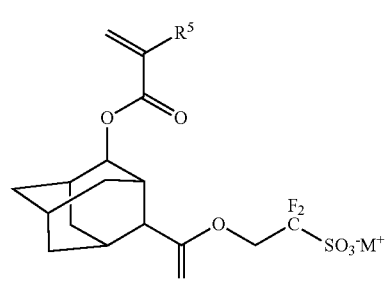
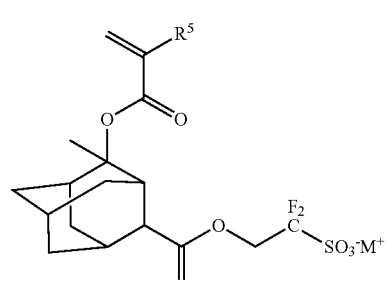
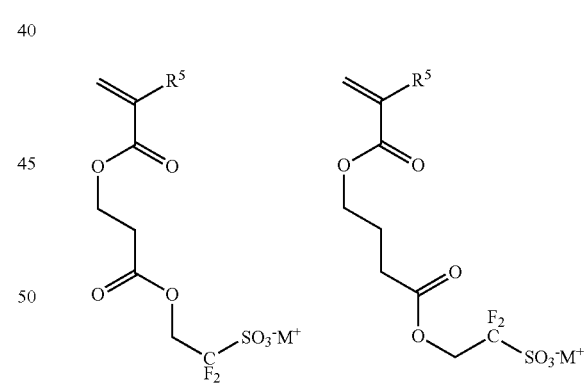

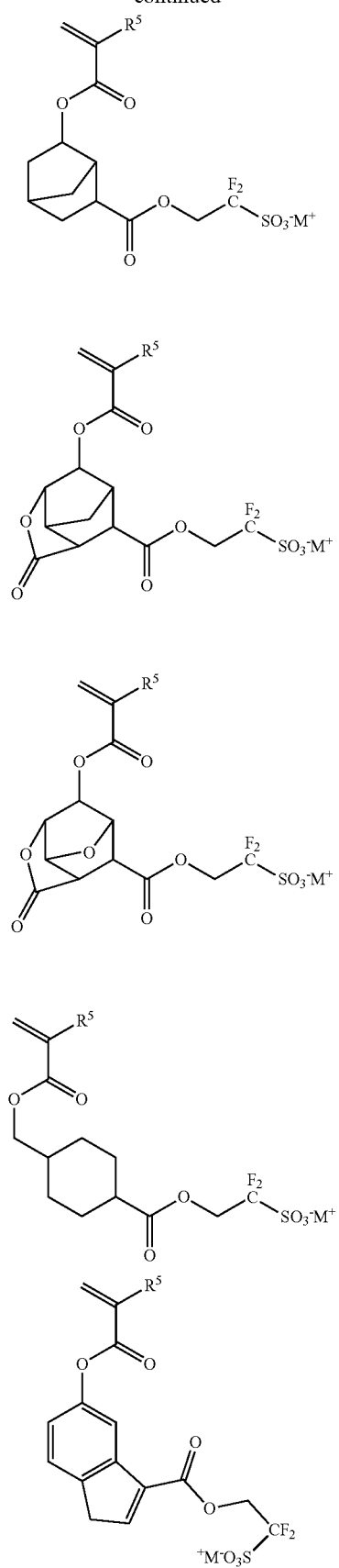
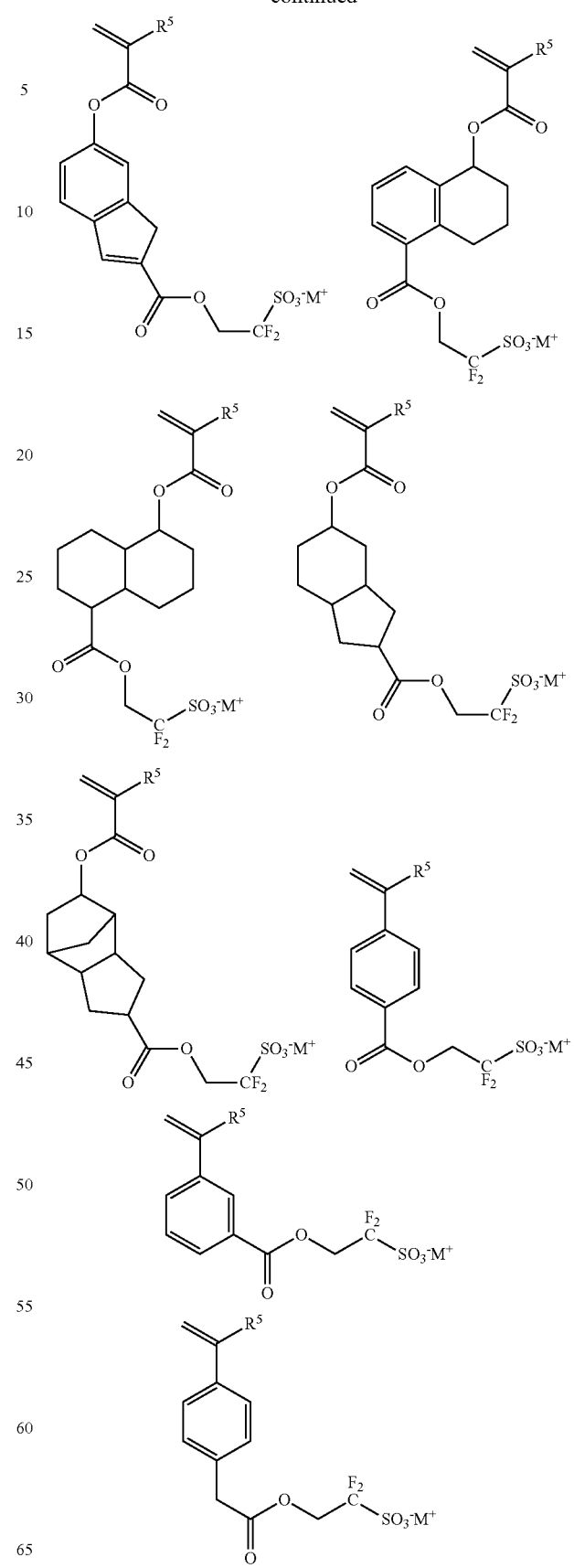

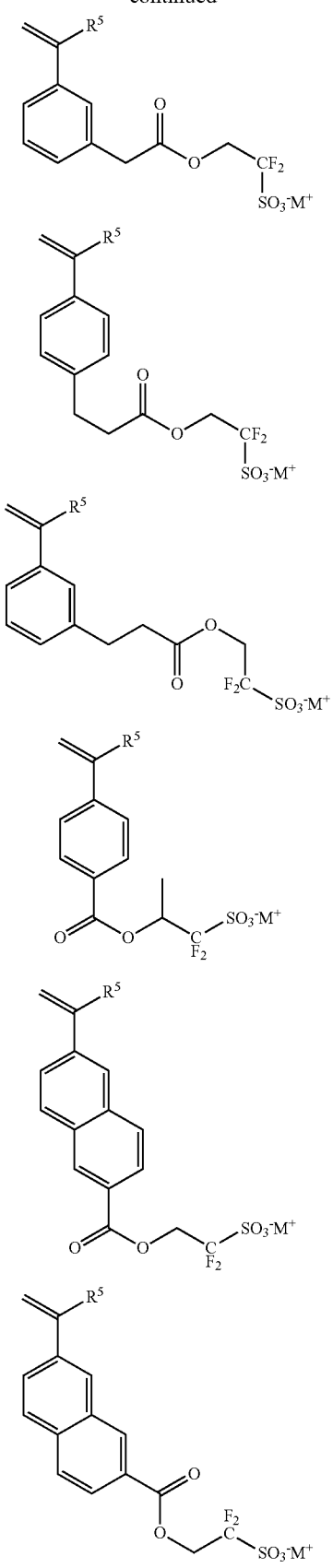
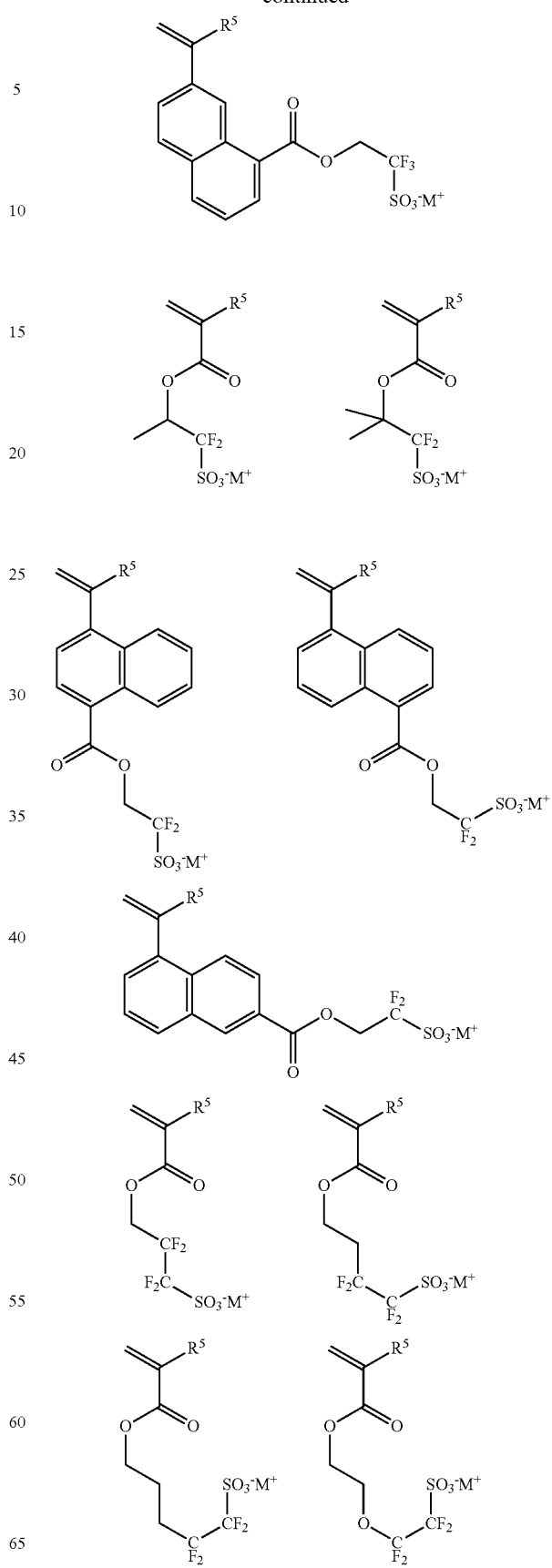

-continued
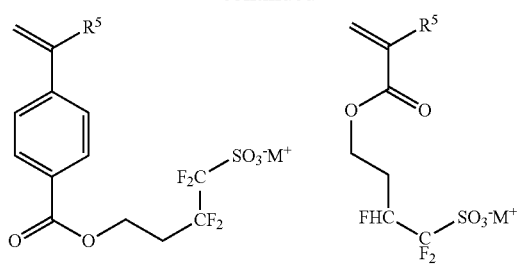
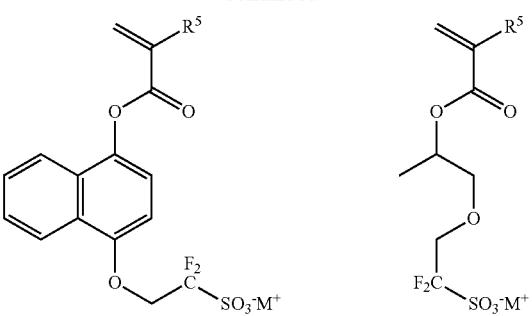
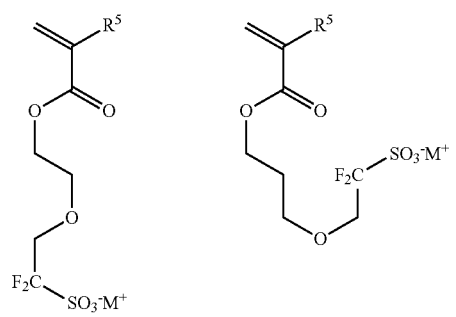
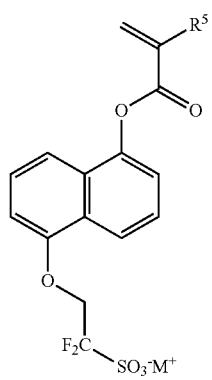
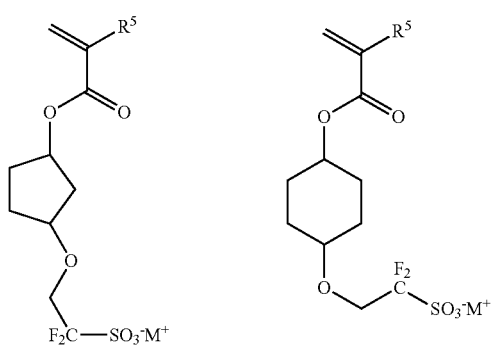
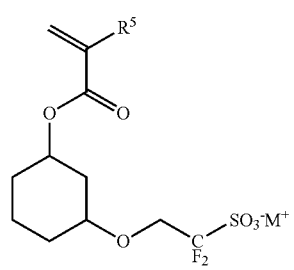
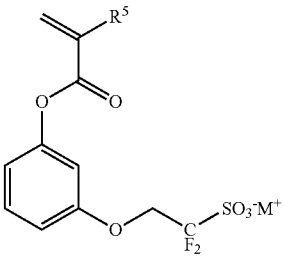
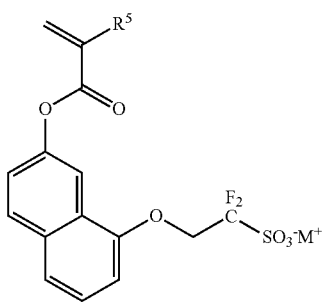

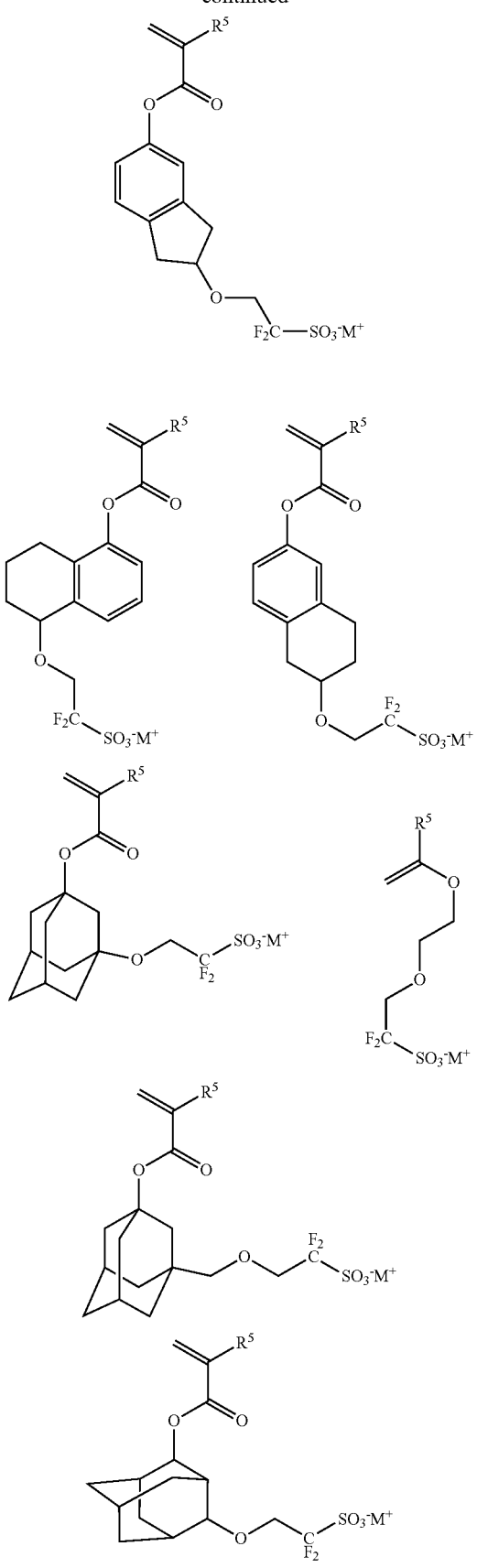
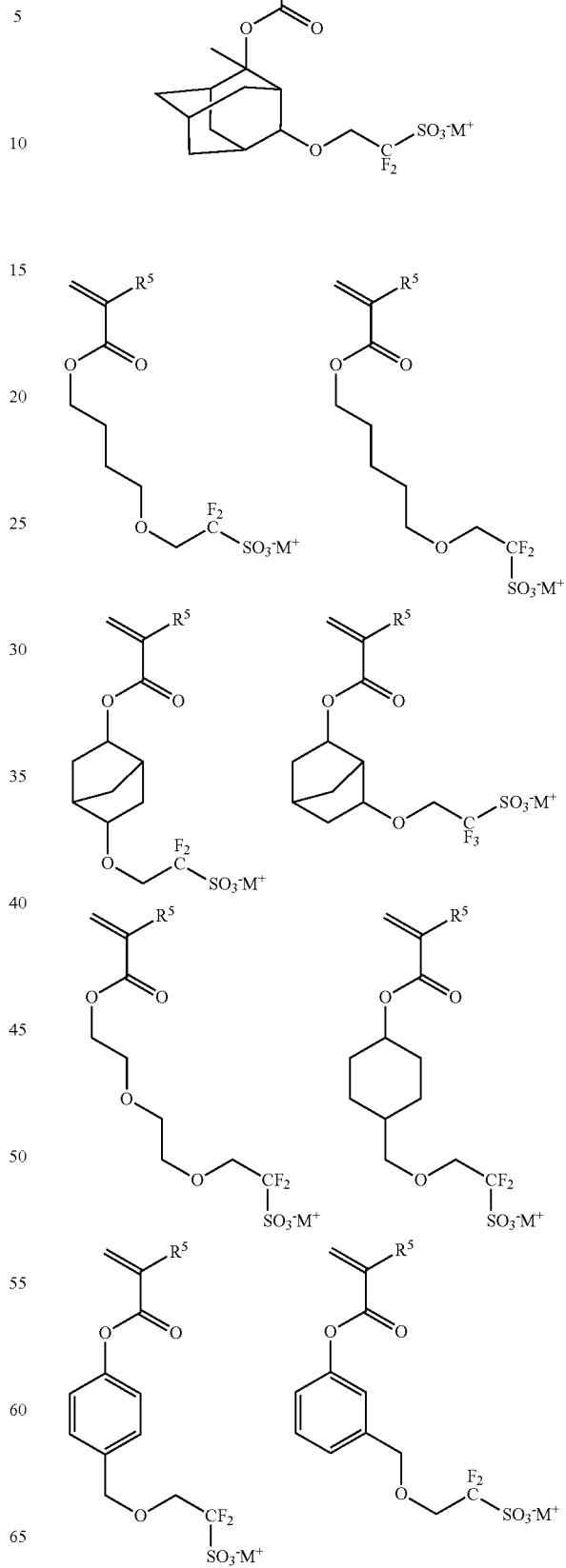

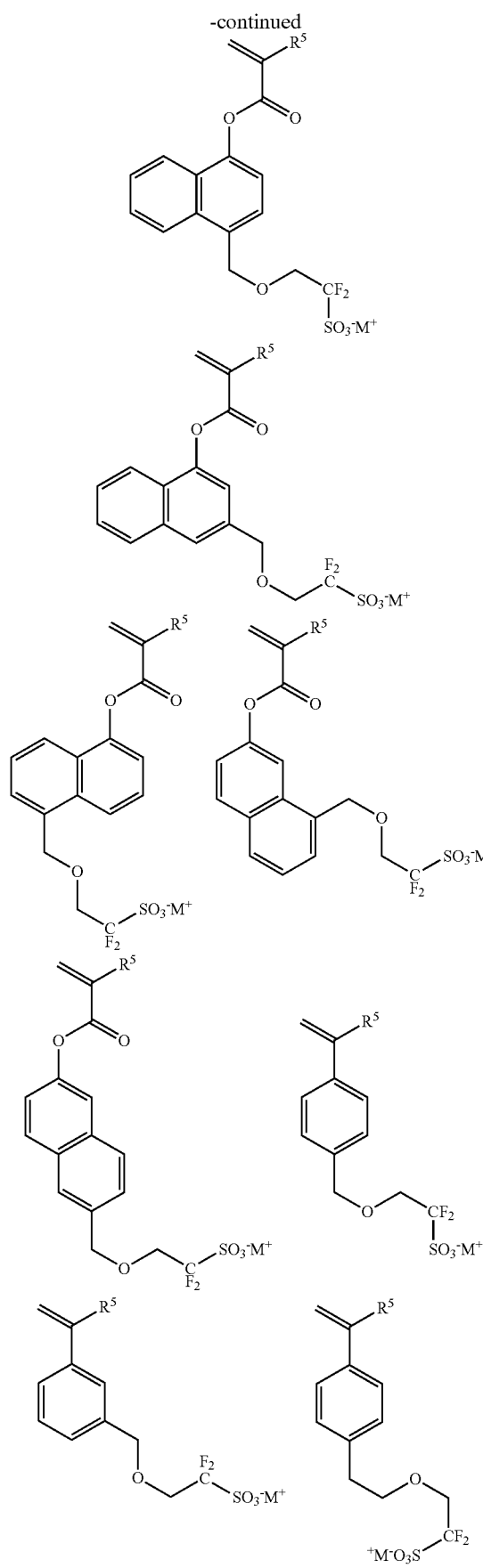

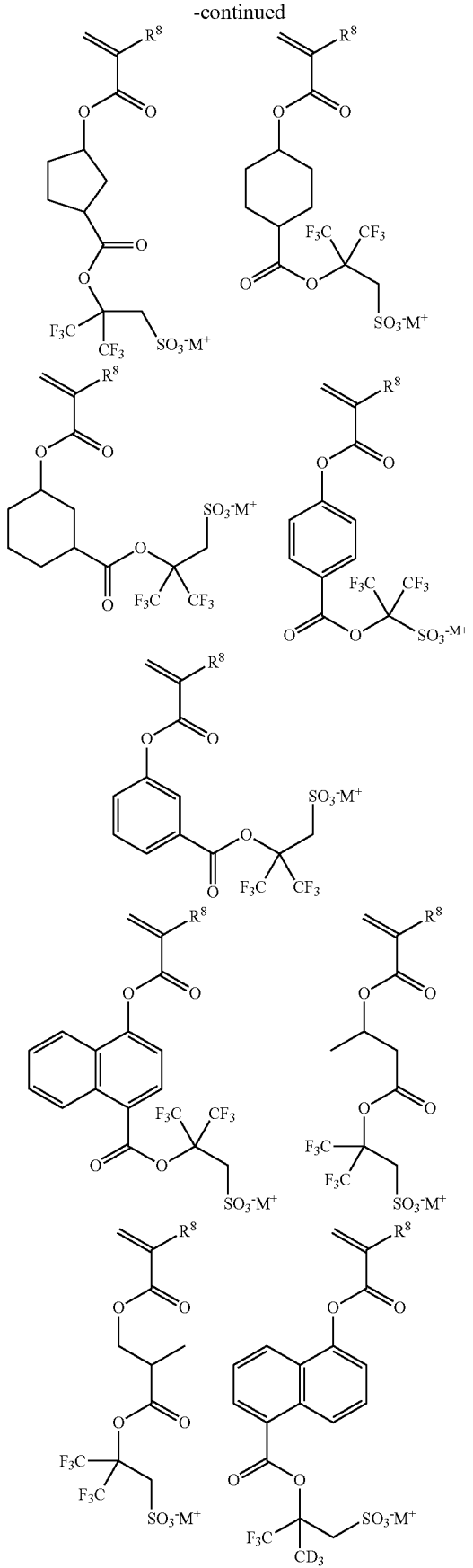
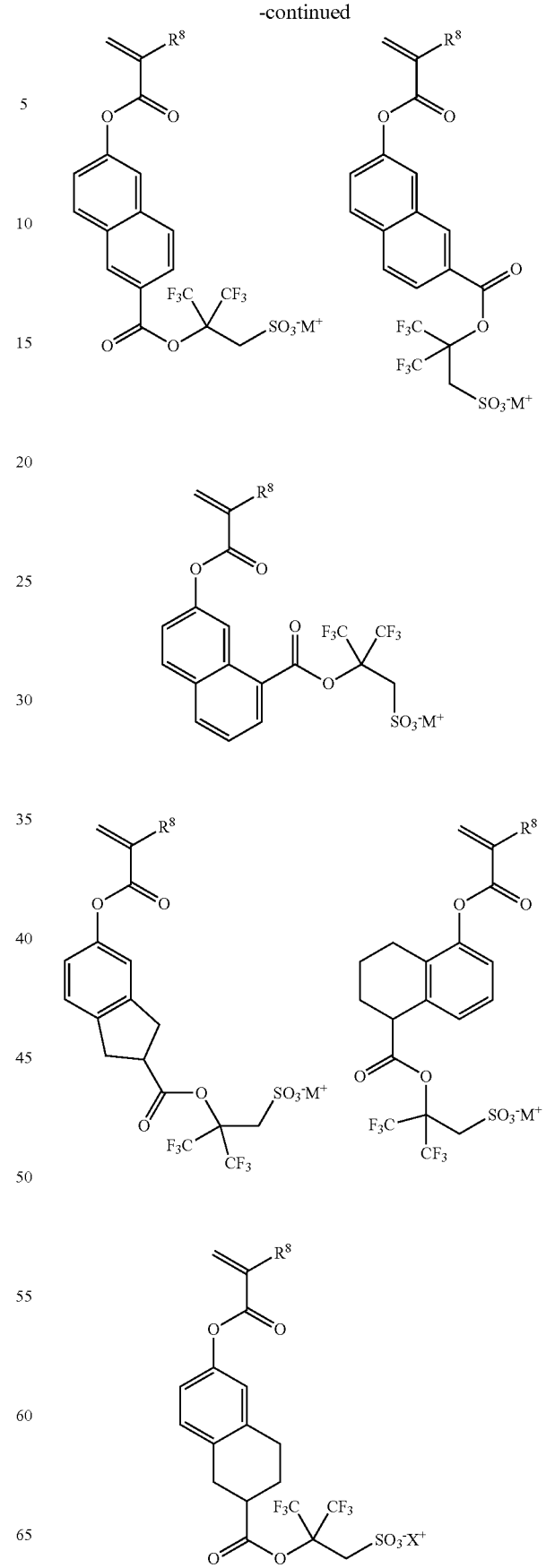

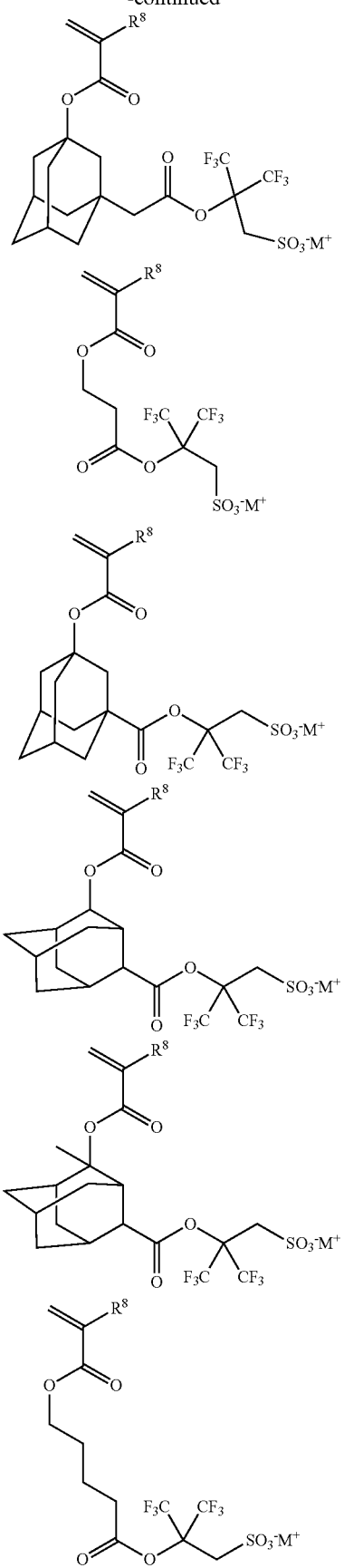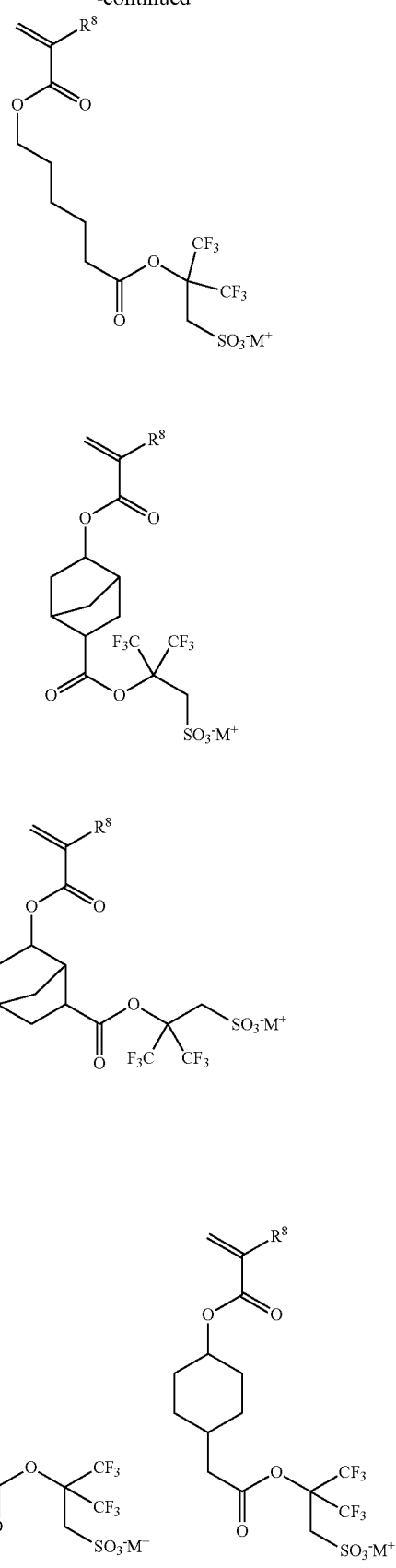

-continued
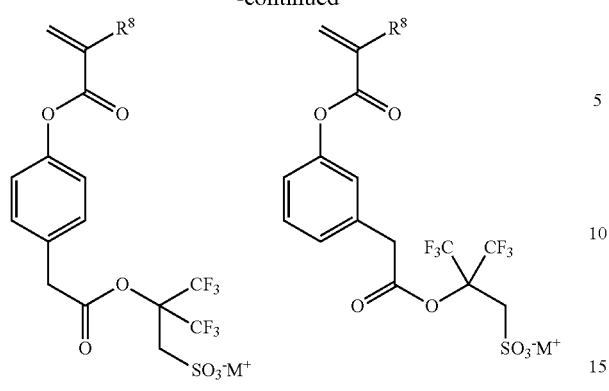
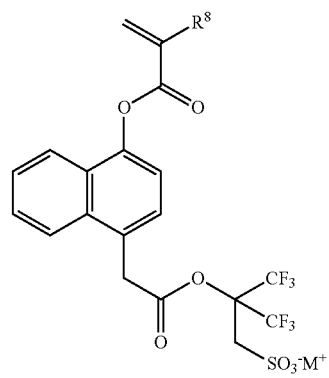
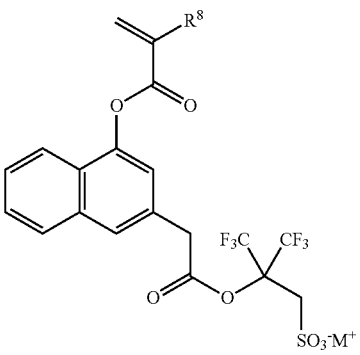
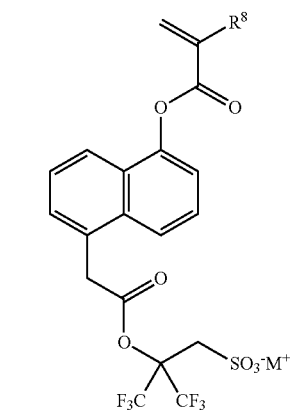
-continued
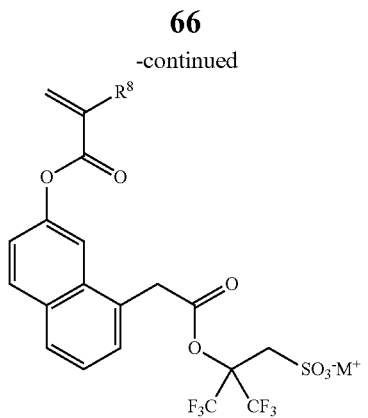
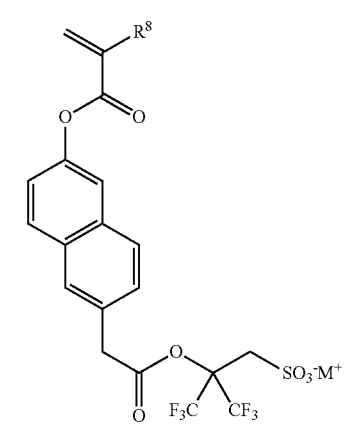
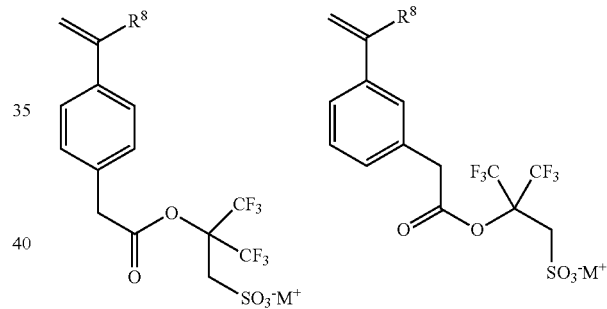
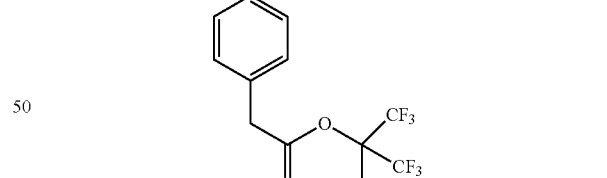
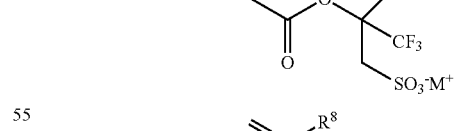
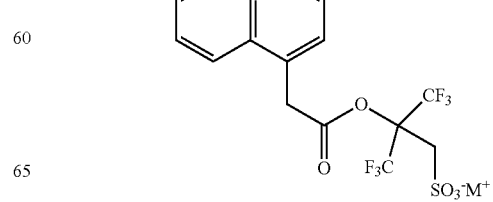

-continued
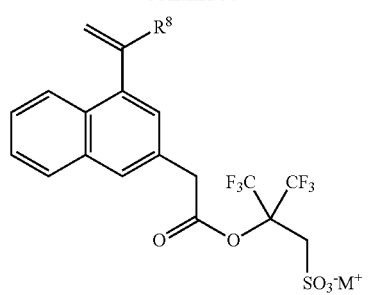
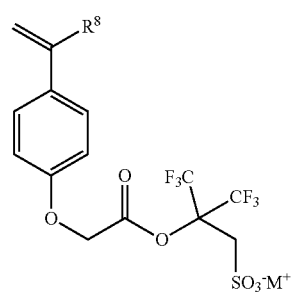
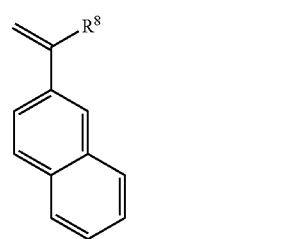
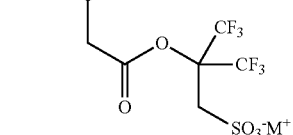
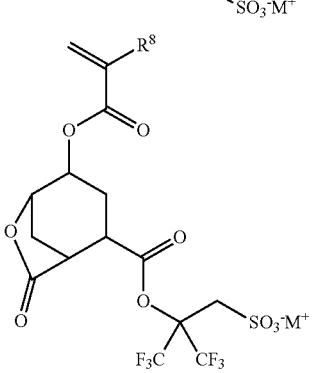
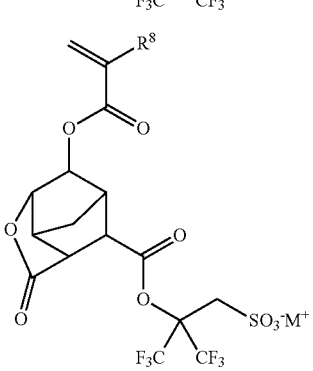
-continued
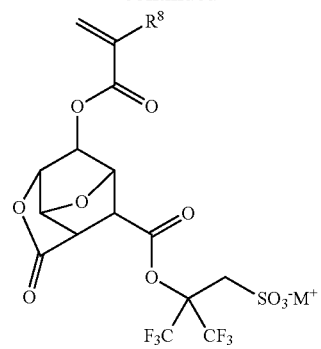
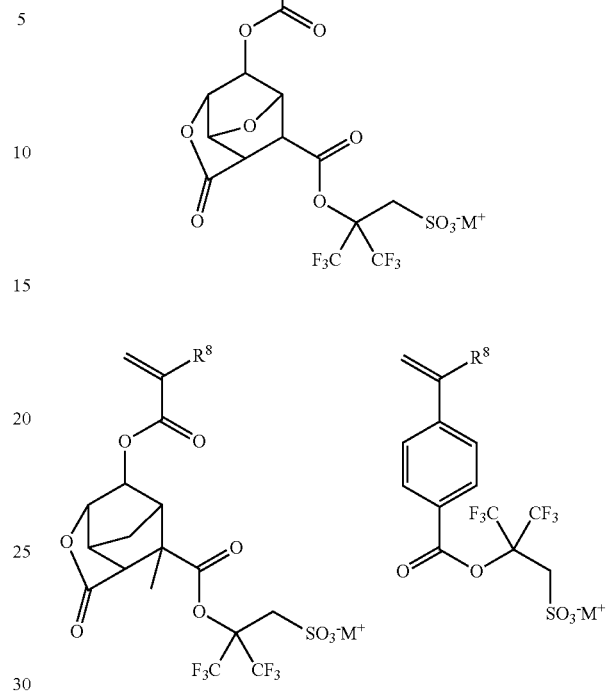
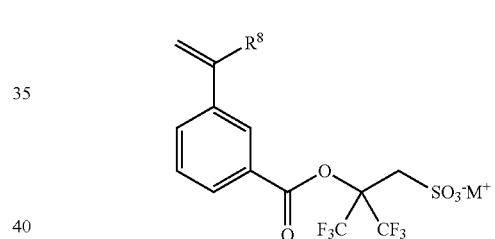
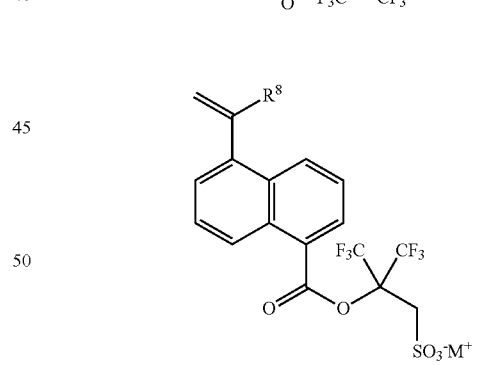
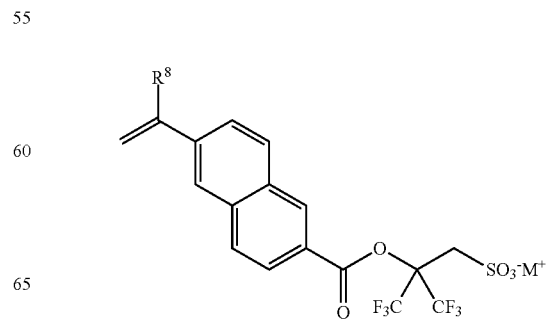

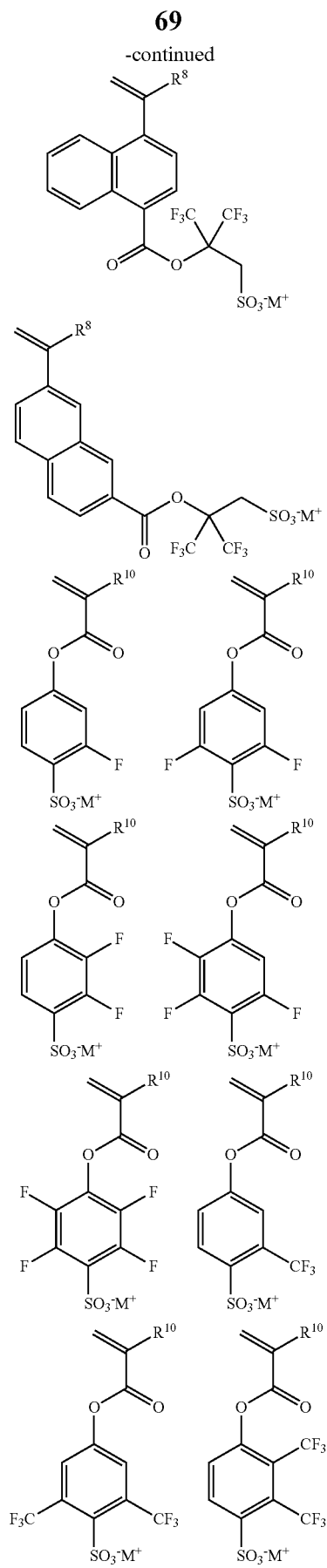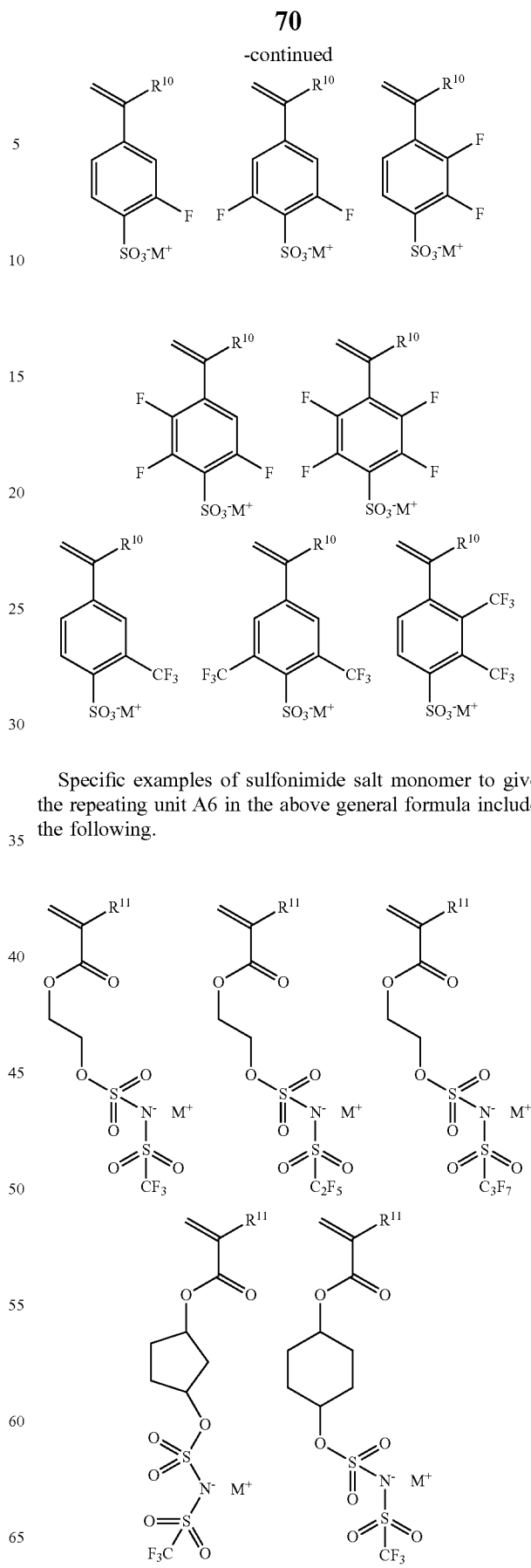
Specific examples of sulfonimide salt monomer to give the repeating unit A6 in the above general formula include the following.

-continued
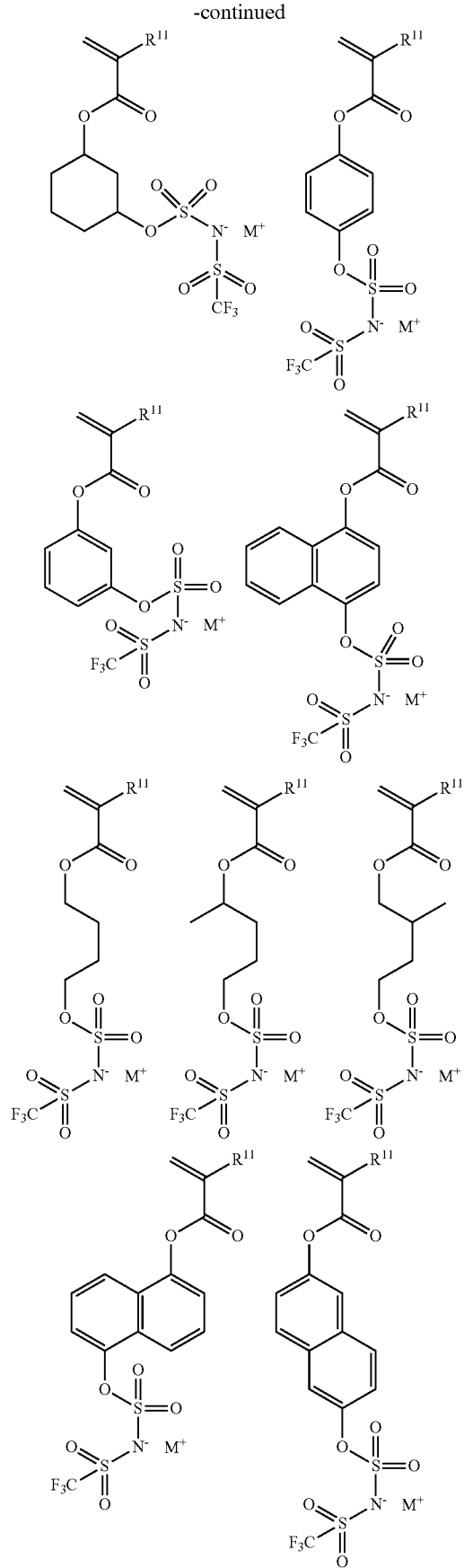
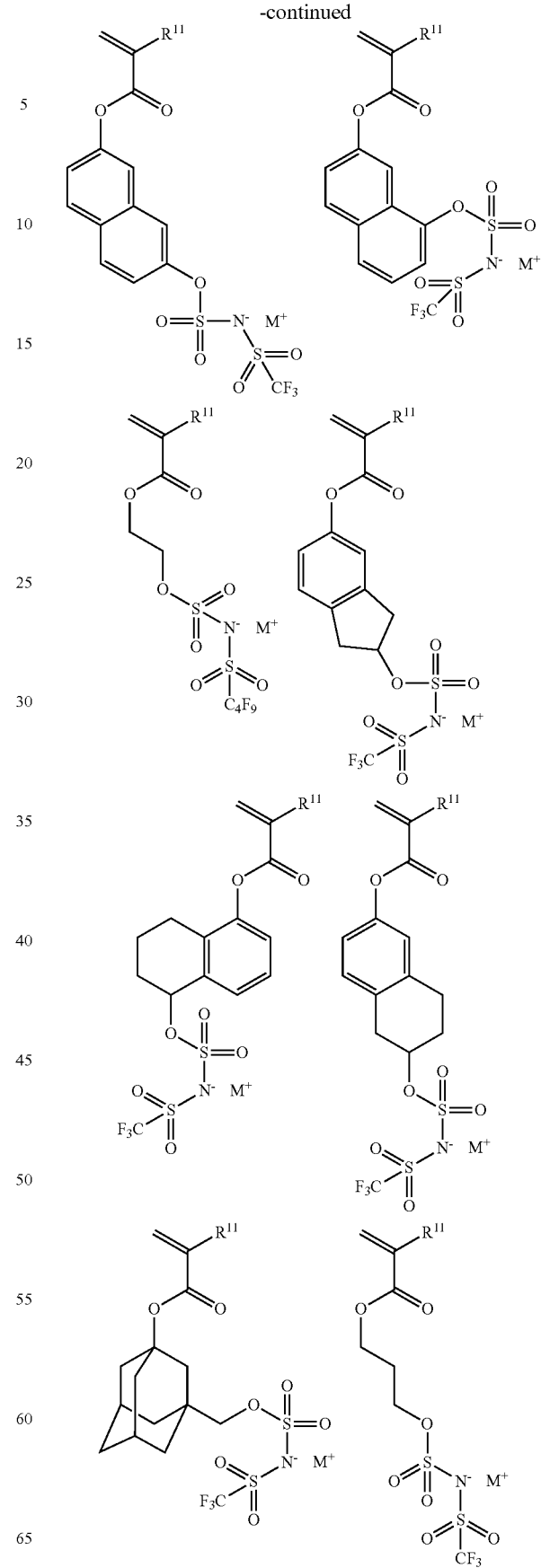

-continued
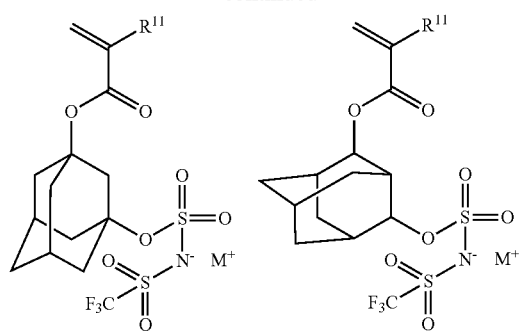
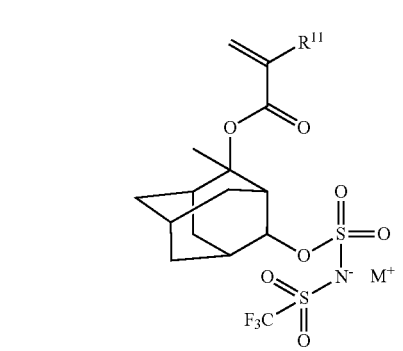
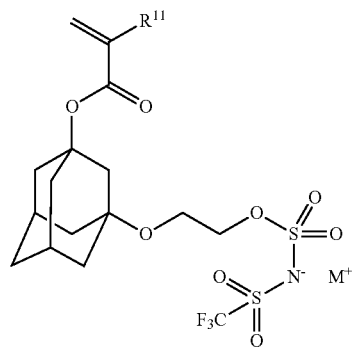
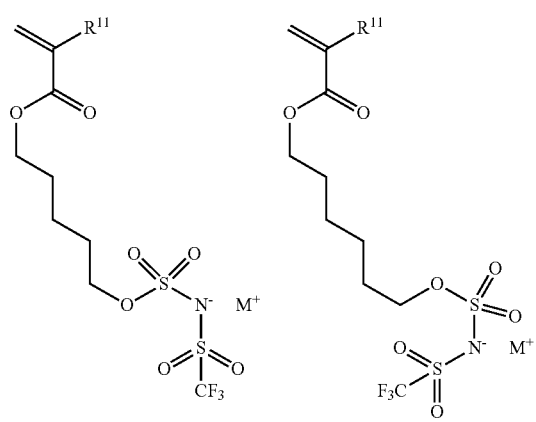
-continued
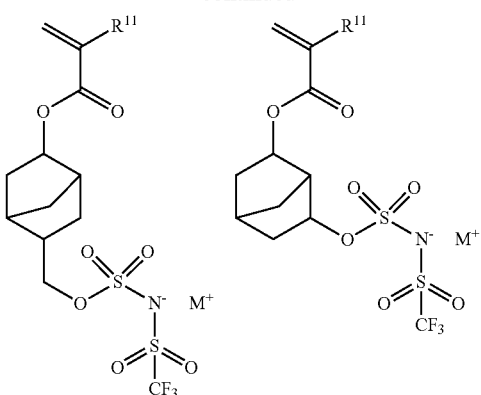
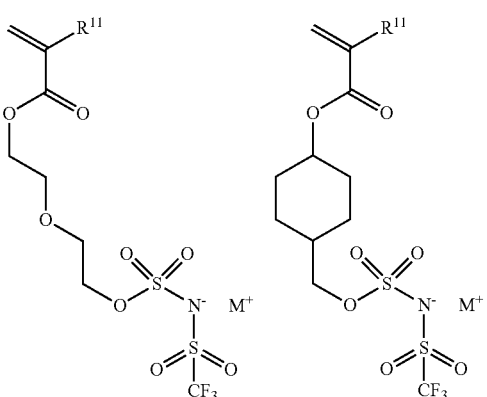
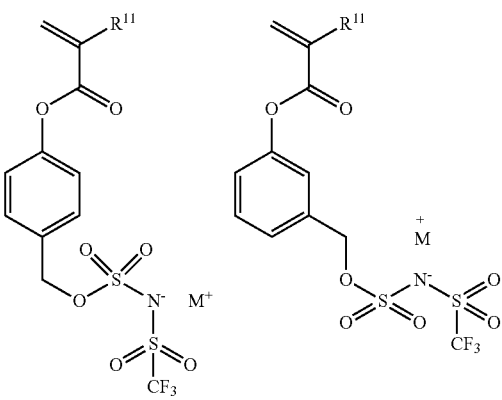
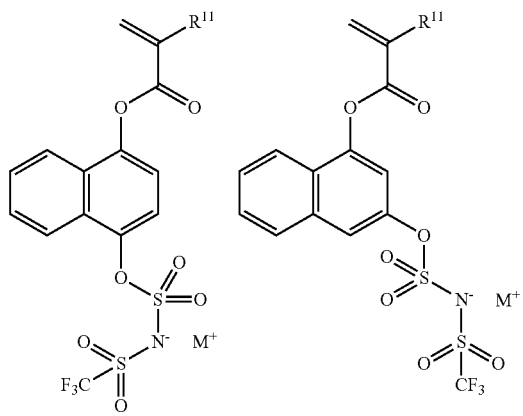

-continued
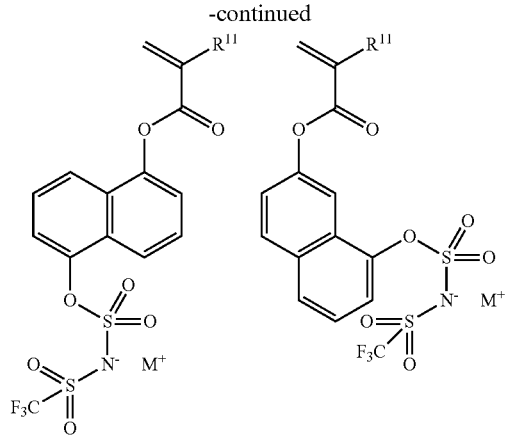
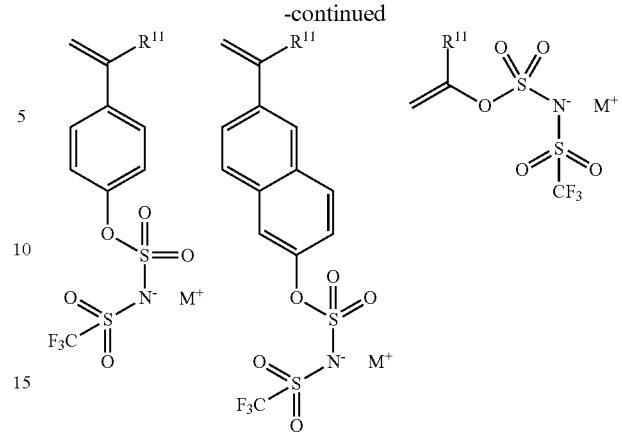
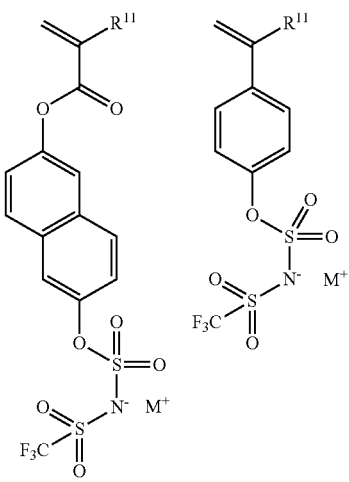
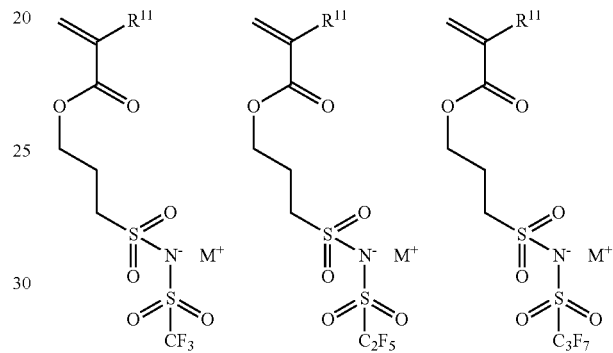
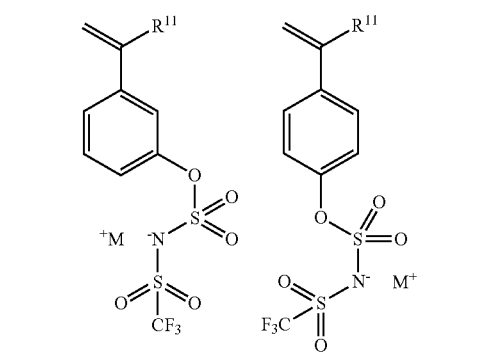
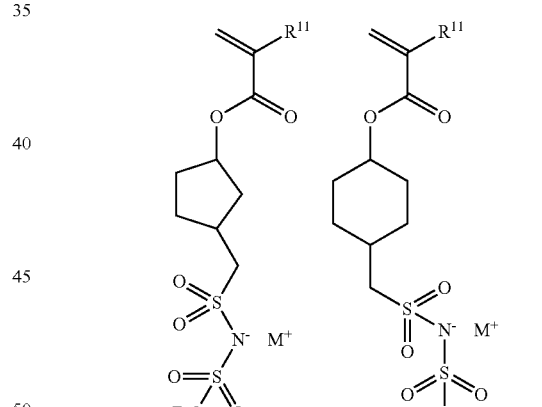
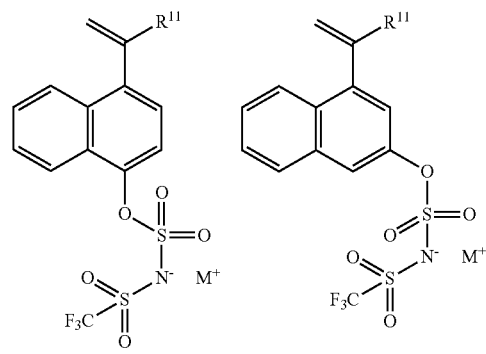
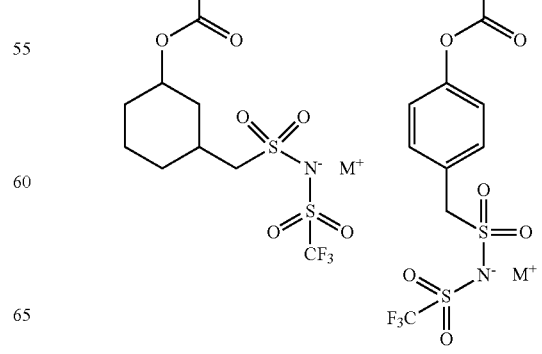

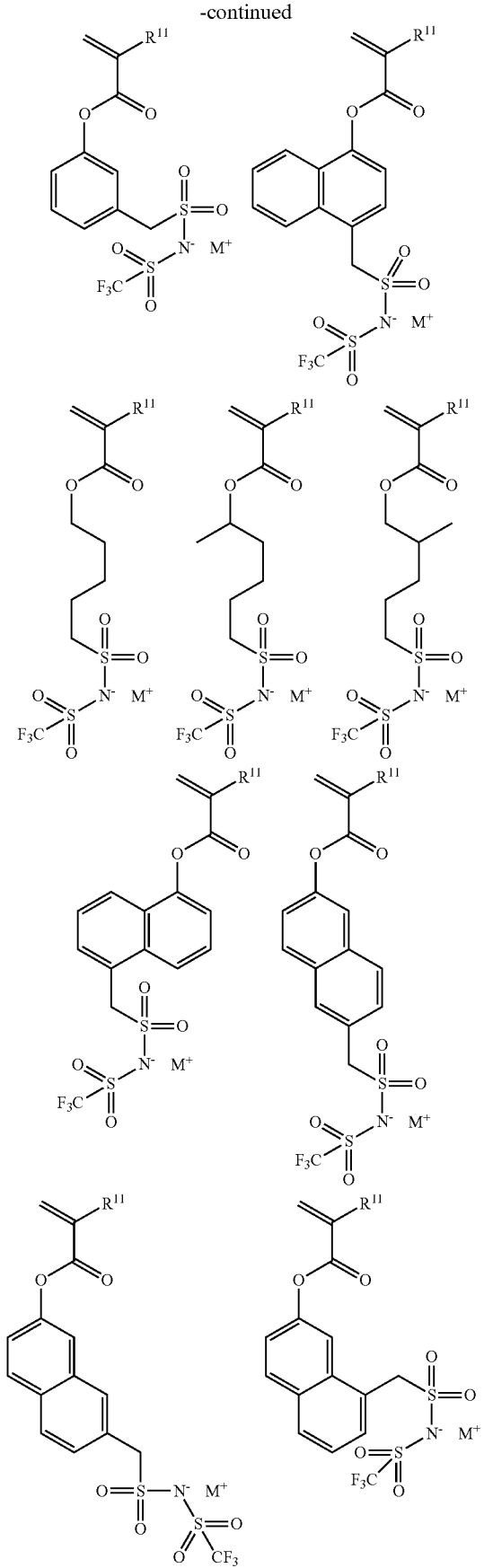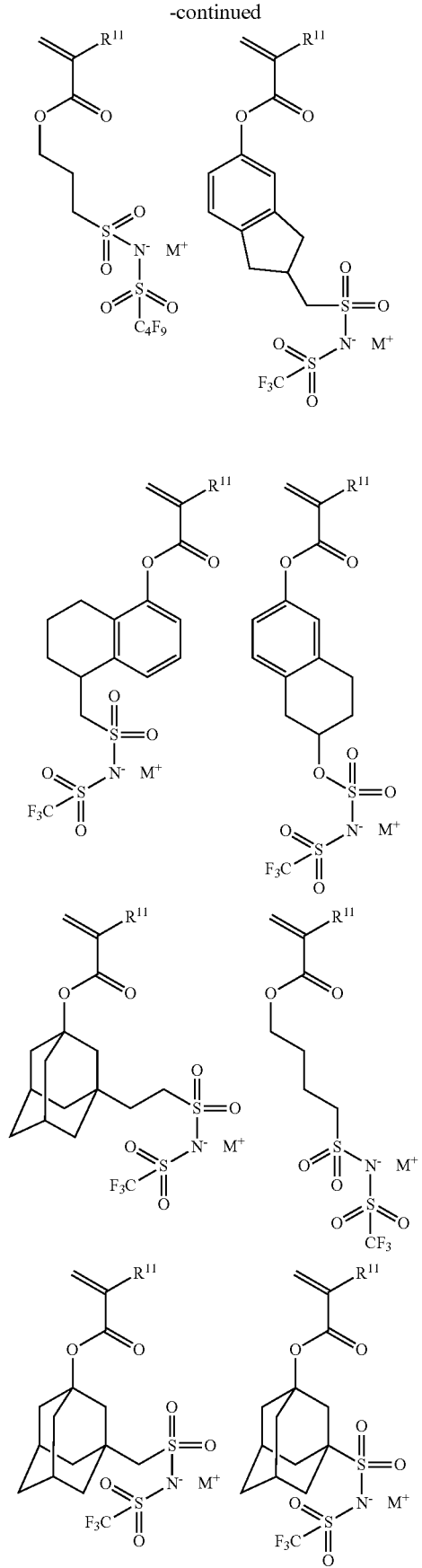

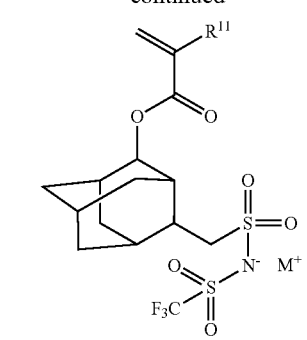
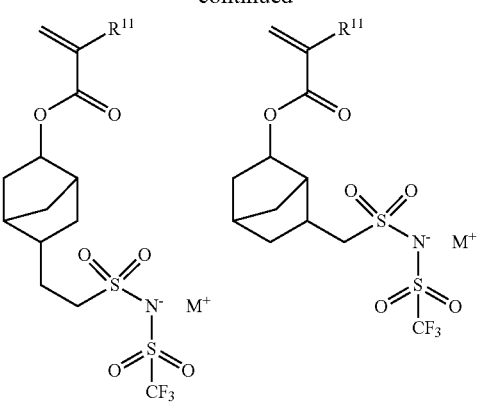
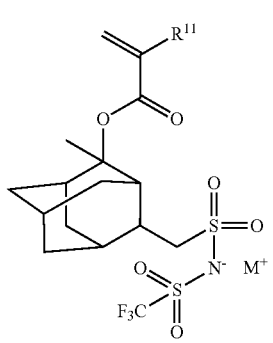
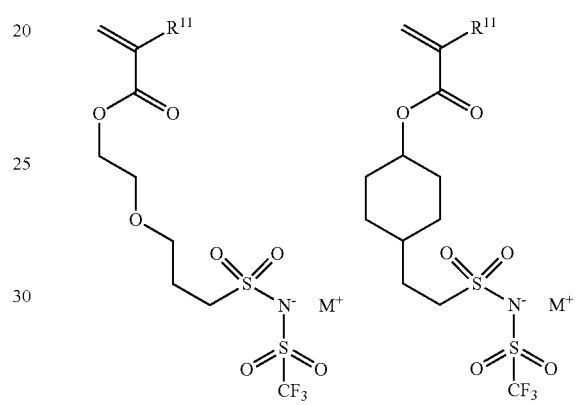
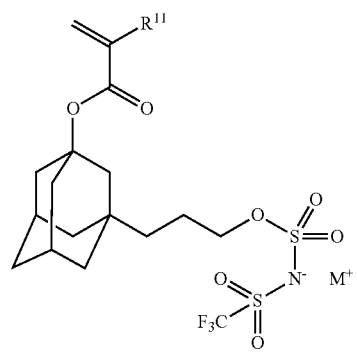
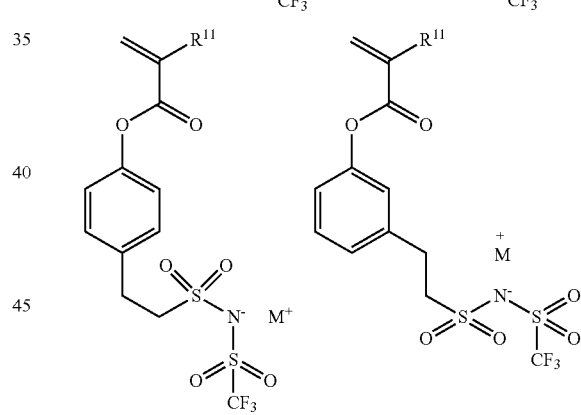
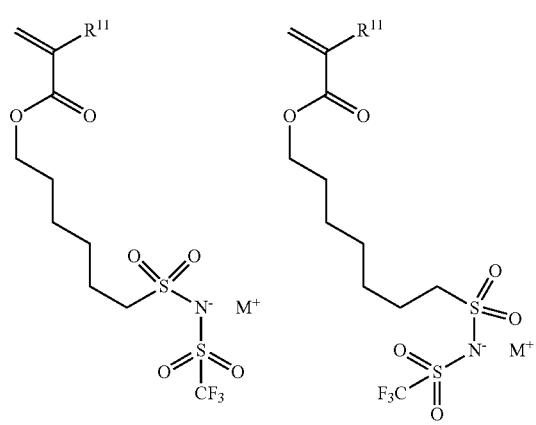
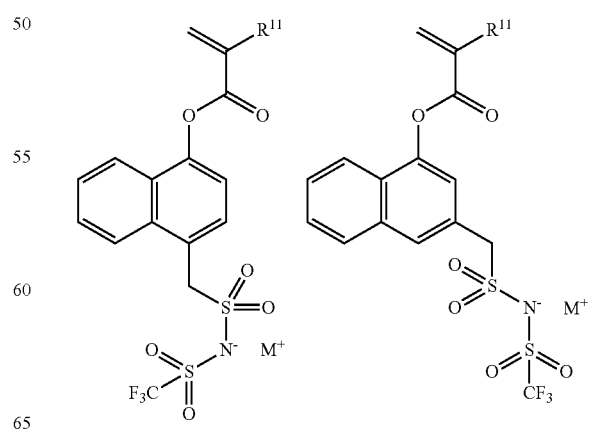

81
-continued
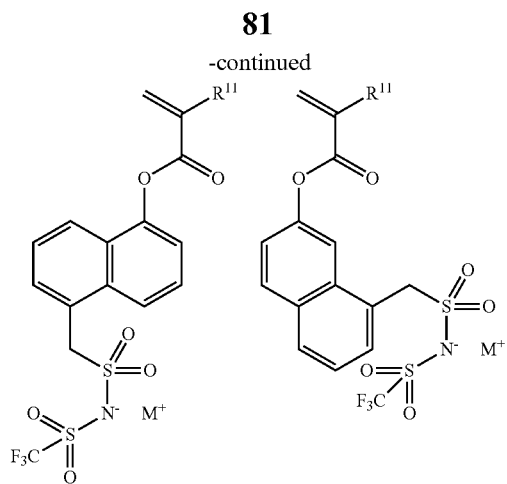
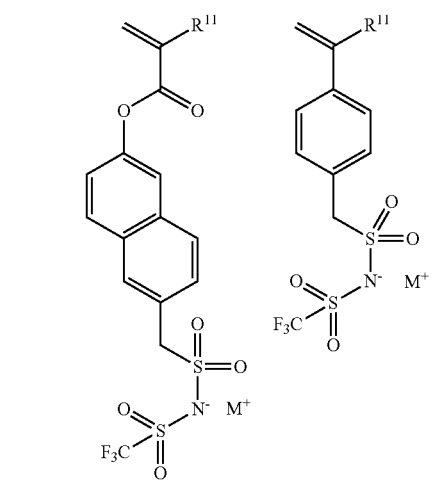
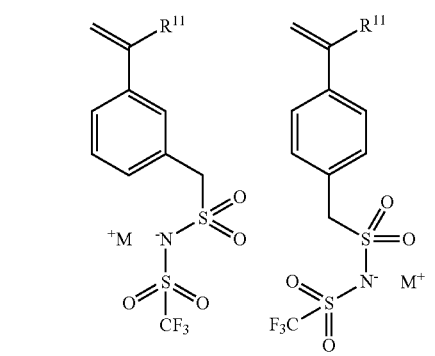
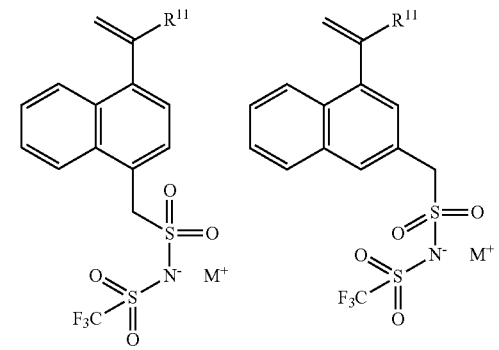
82
-continued
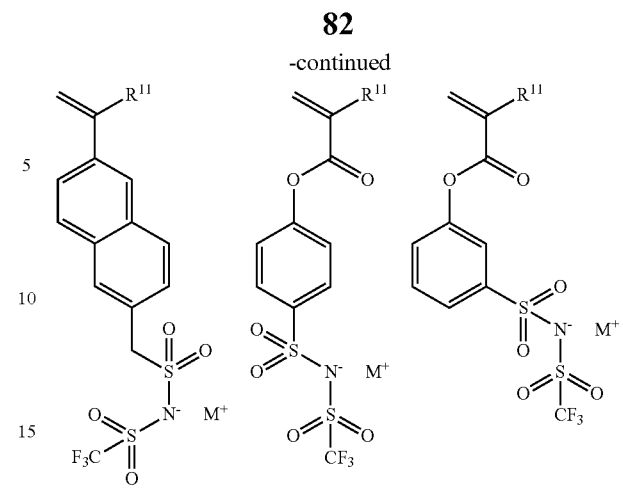
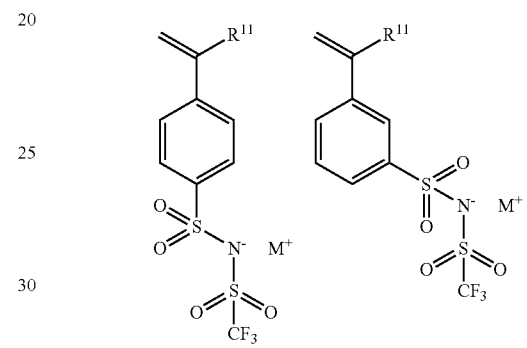
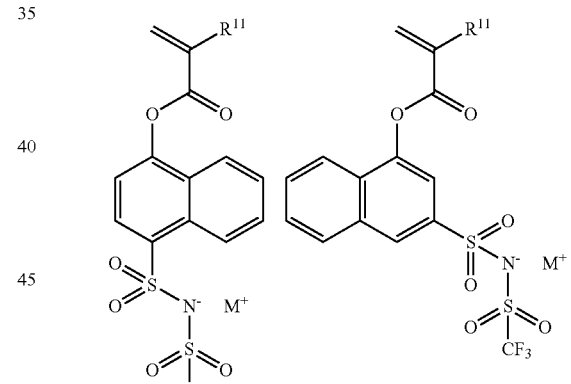
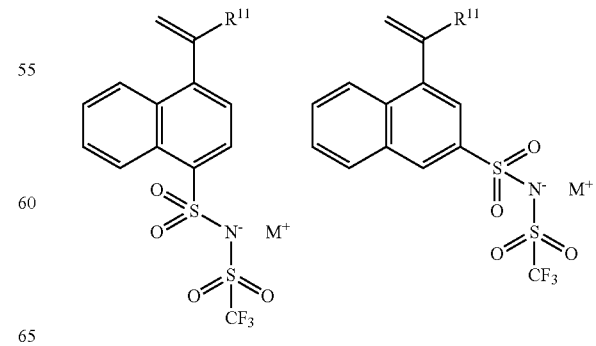

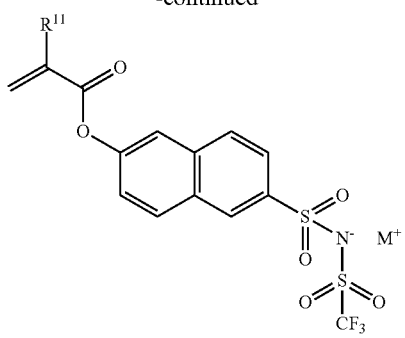
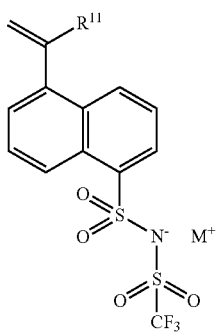
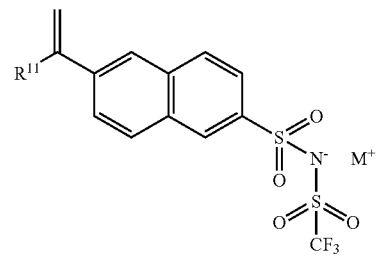
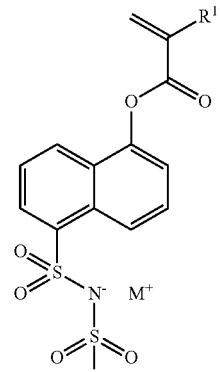
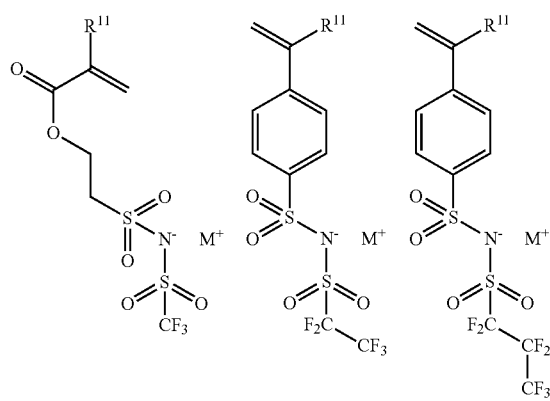
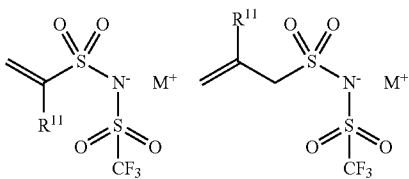
Specific examples of N-carbonylsulfonamide salt monomer to give the repeating unit A7 in the above general formula include the following.
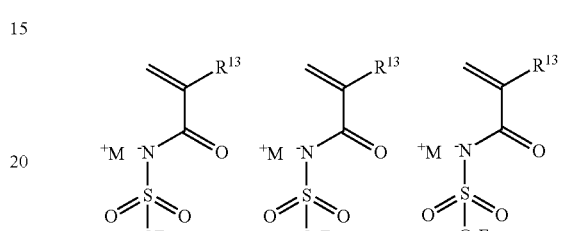
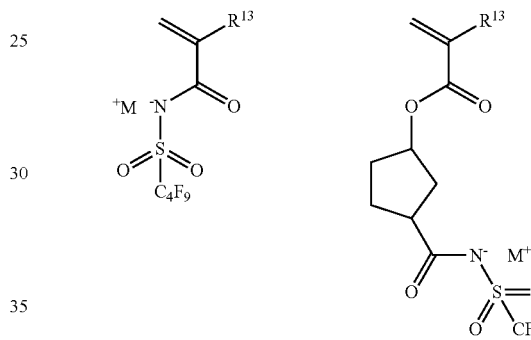
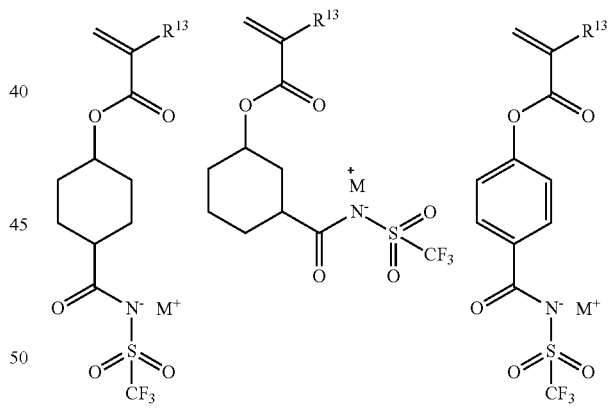
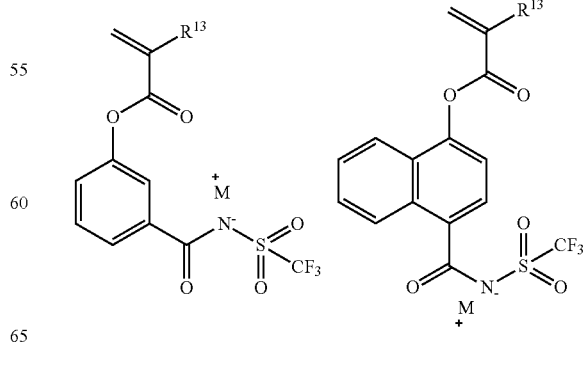

-continued
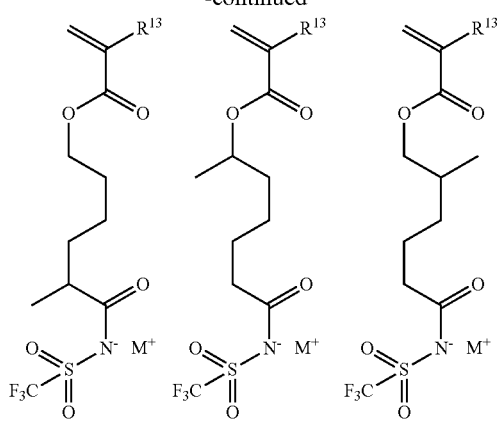
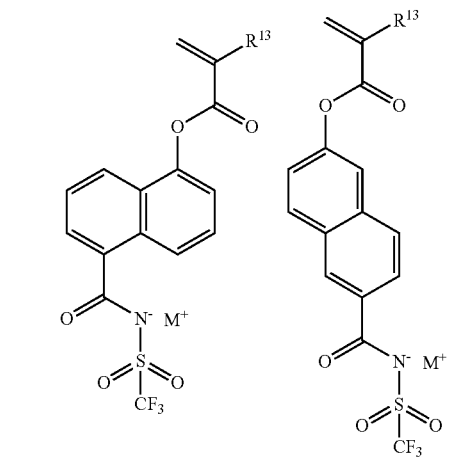
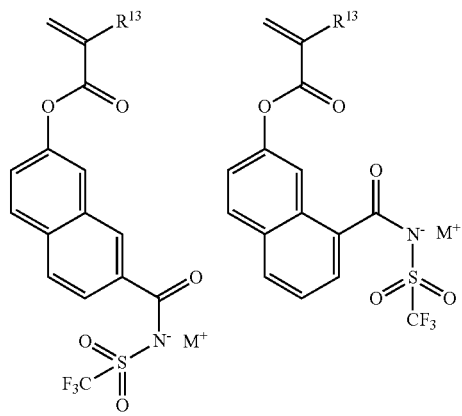
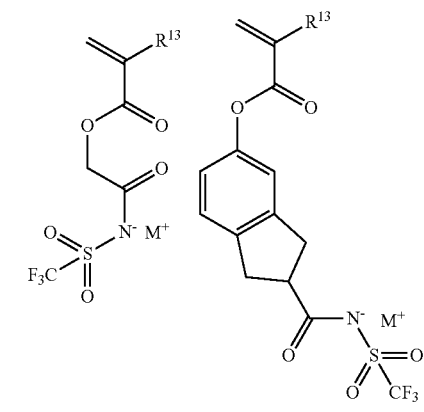
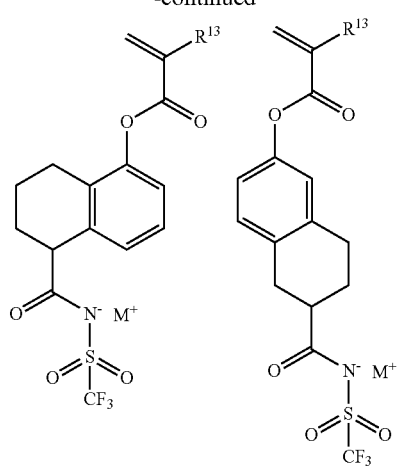
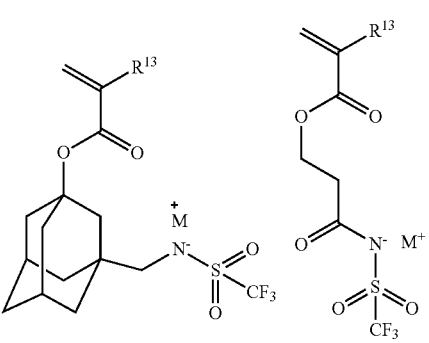
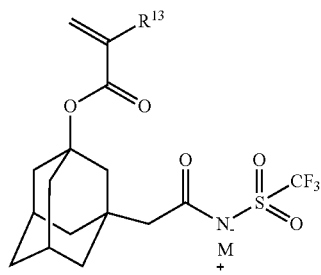
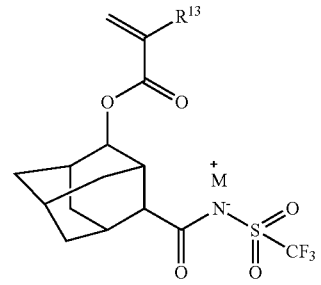
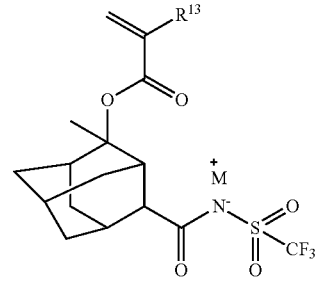

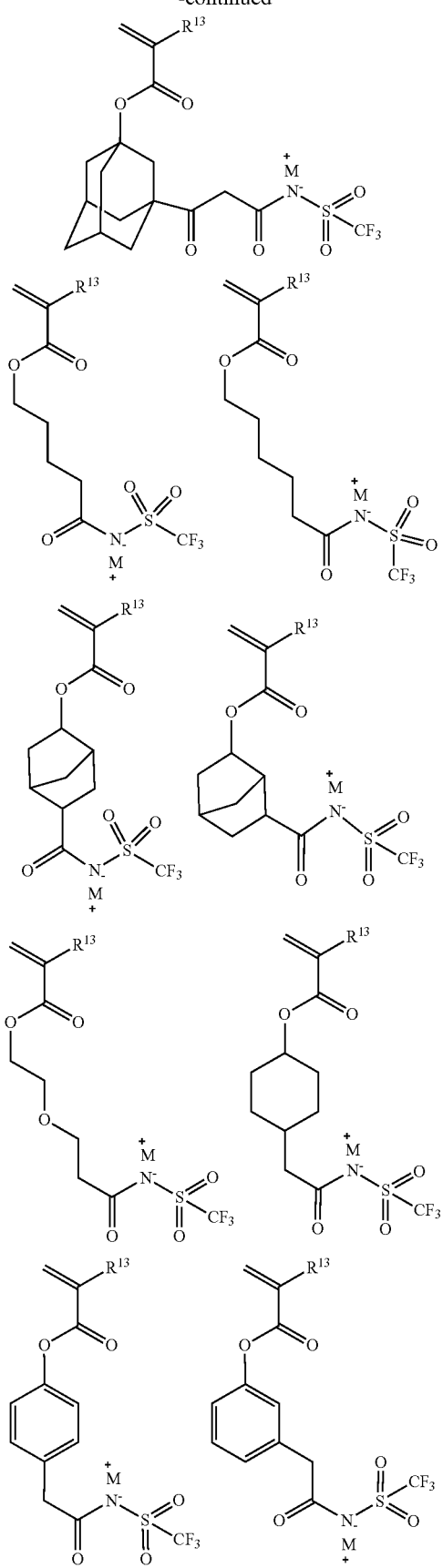
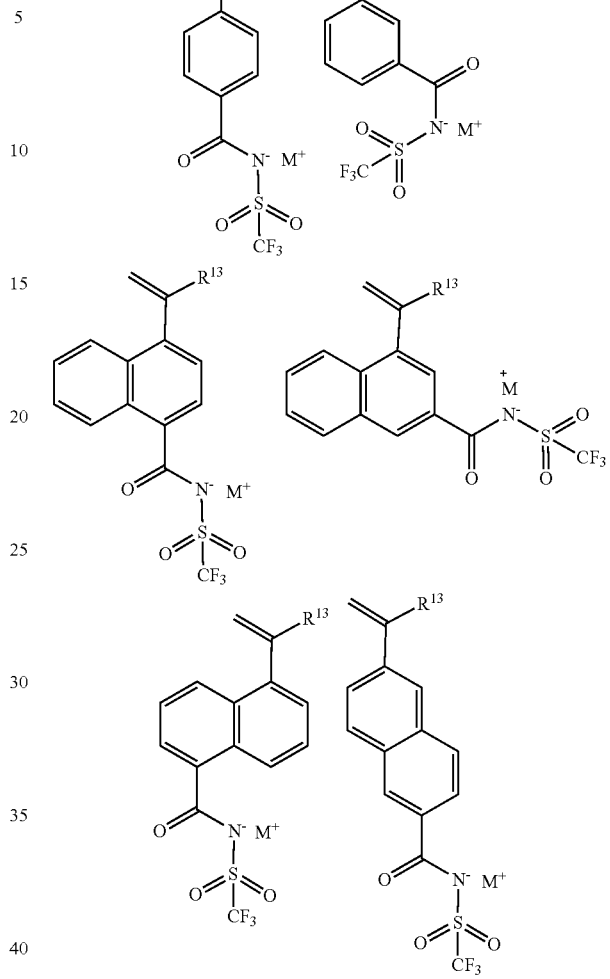

In the formulae, $R^1$, $R^3$, $R^5$, $R^8$, $R^{10}$, $R^{11}$, and $R^{13}$ are as defined above.

The polymer compound as the component (A) preferably contains an ammonium ion (ammonium cation) shown by the following general formula (2) as $M^+$ in the salt structure (e.g., repeating unit A (i.e., the repeating units A1 to A7)).

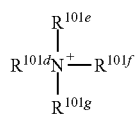

(2)

In the formula, $R^{101d}$, $R^{101e}$, $R^{101f}$, and $R^{101g}$ each represent a hydrogen atom, a linear alkyl group having 1 to 12 carbon atoms, a branched or cyclic alkyl group having 3 to 12 carbon atoms, a linear alkenyl group or alkynyl group having 2 to 12 carbon atoms, a branched or cyclic alkenyl group or alkynyl group having 3 to 12 carbon atoms, or an aromatic group having 4 to 20 carbon atoms, and optionally have at least one or more selected from the group consisting of an ether group, a carbonyl group, an ester group, a hydroxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

Specific examples of the ammonium ion shown by the general formula (2) include the following.

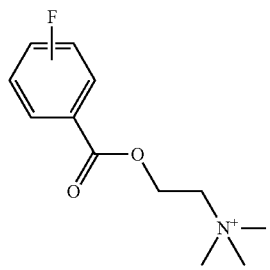
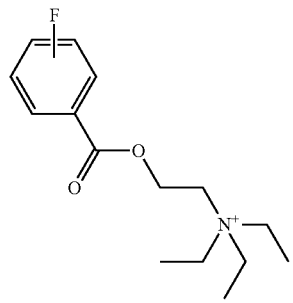
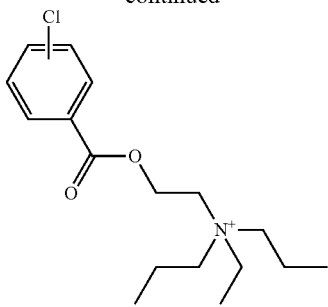

-continued

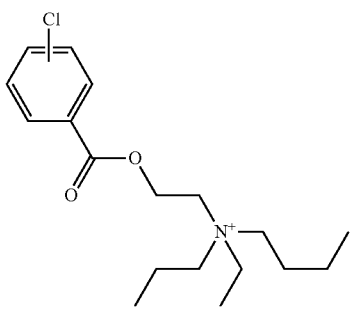

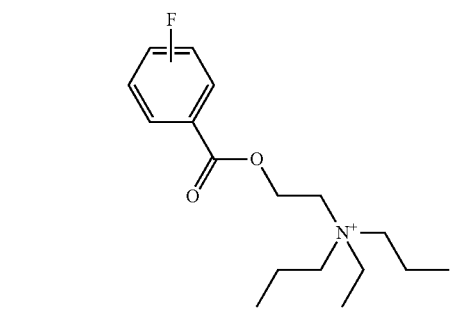
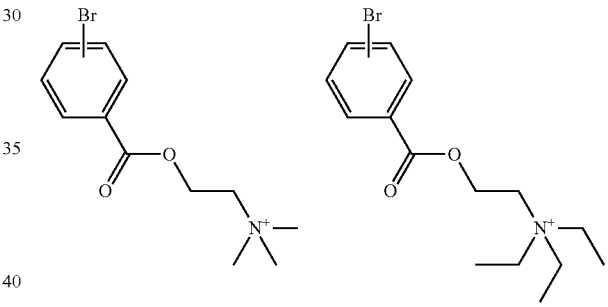

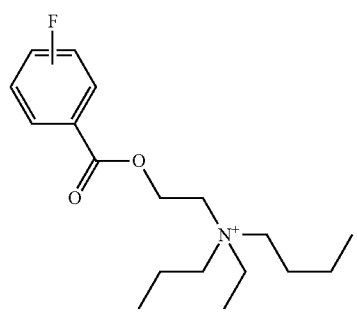
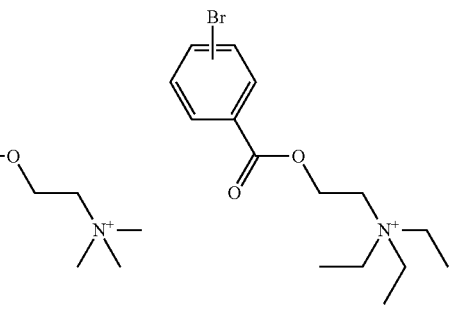

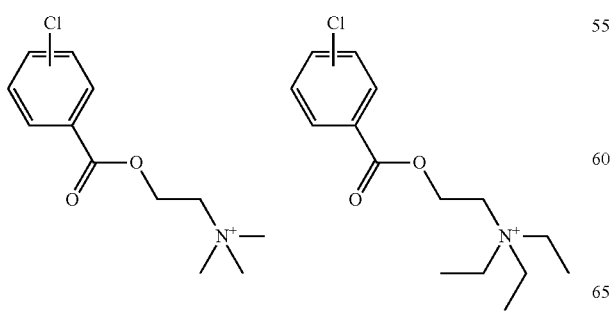
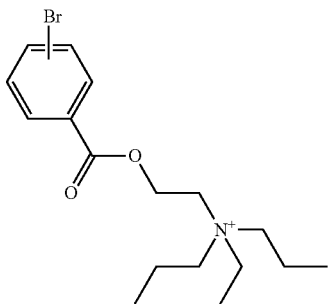

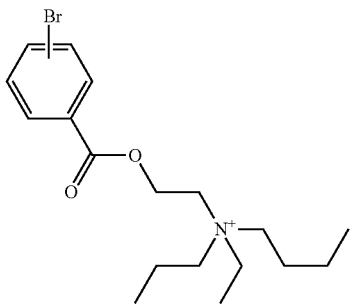

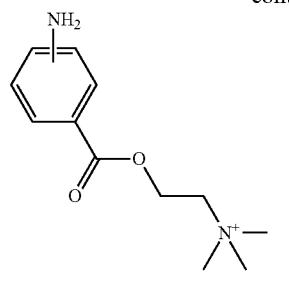
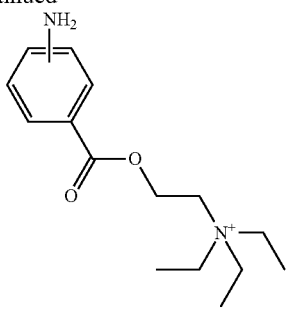
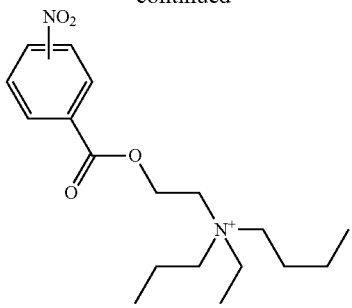
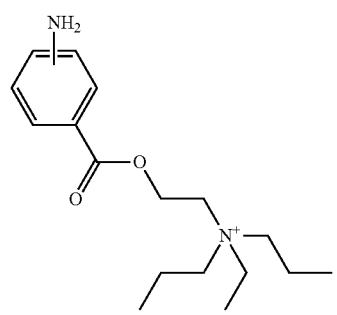
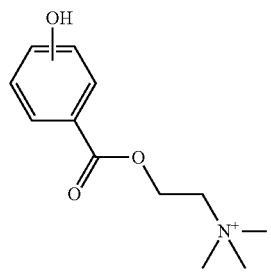
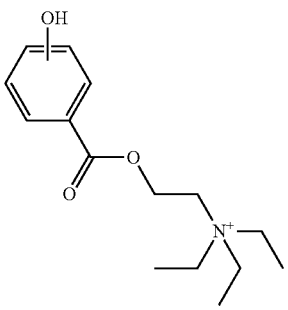
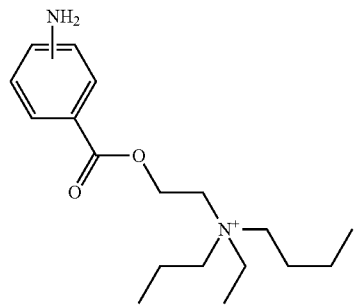
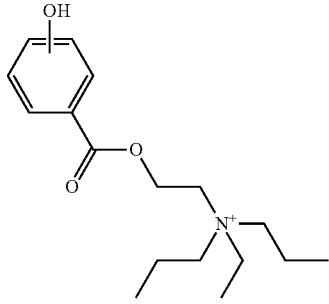
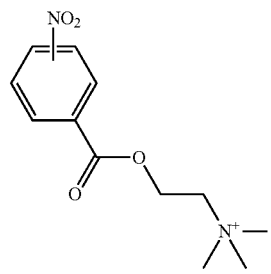
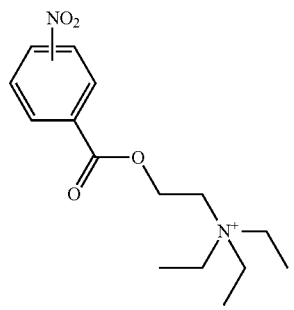
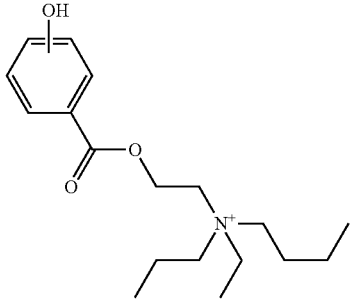
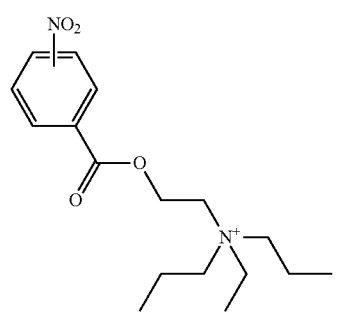
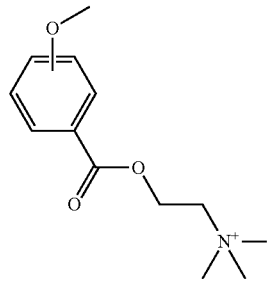

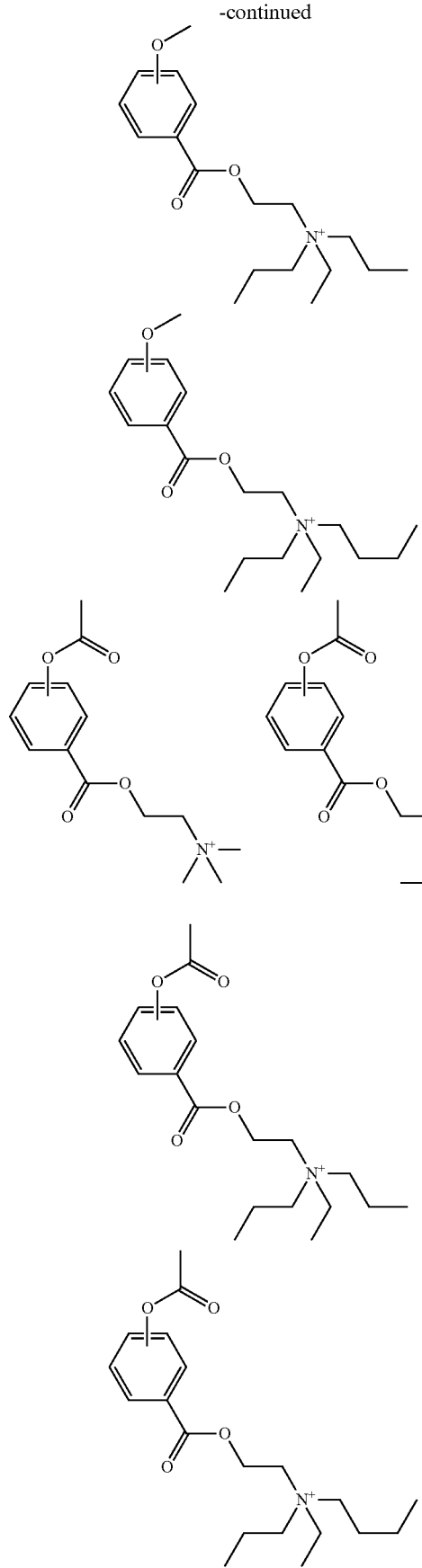
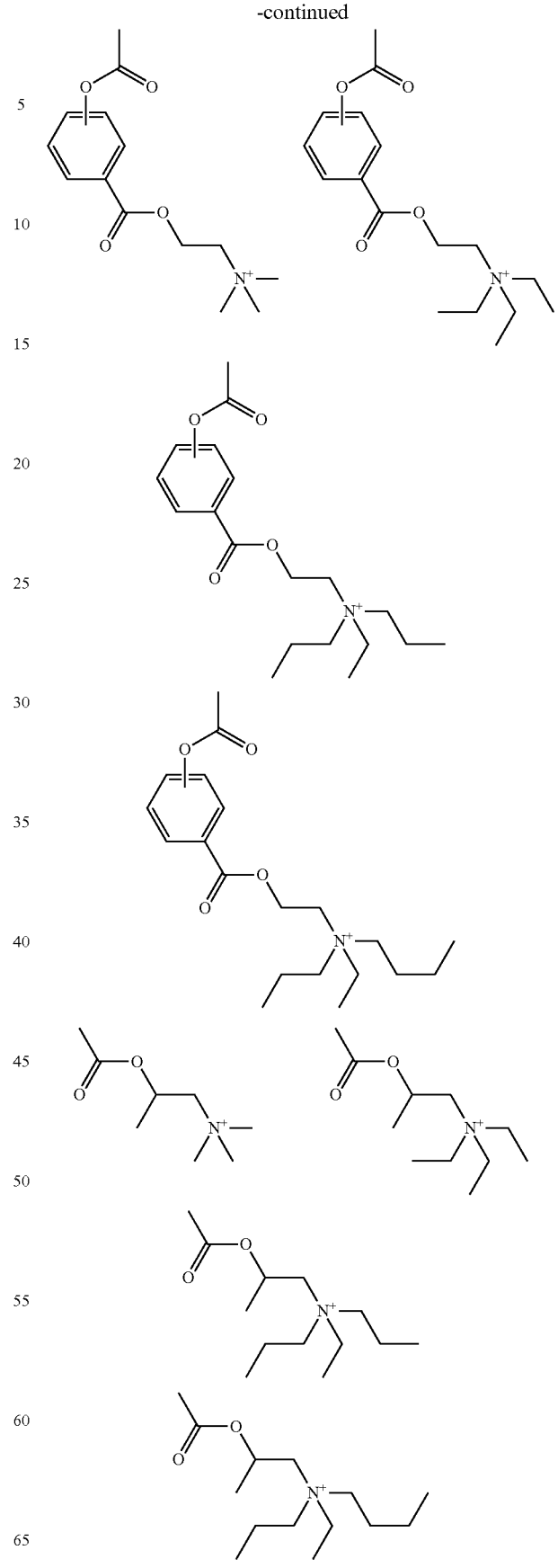

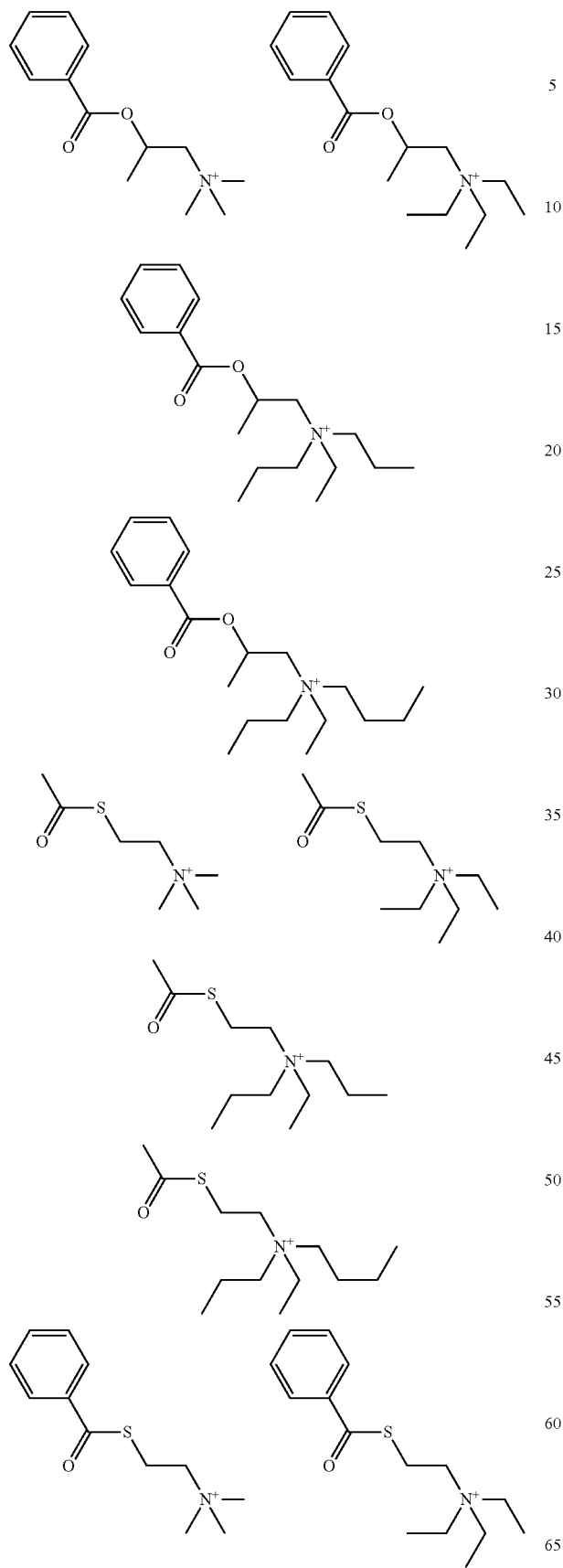

97
-continued
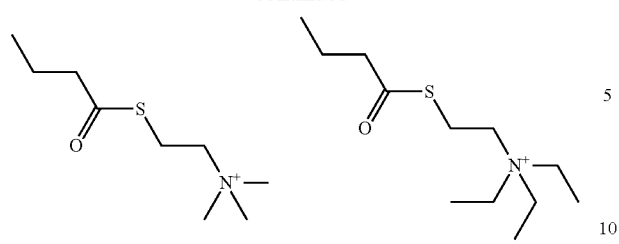
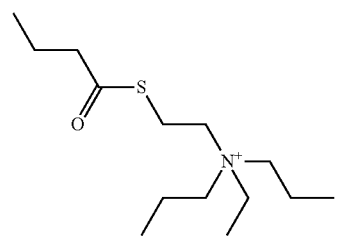
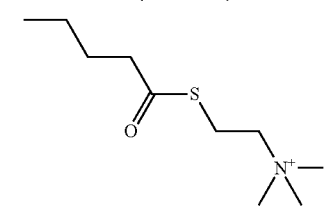
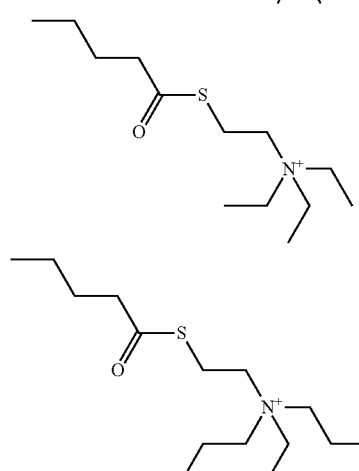
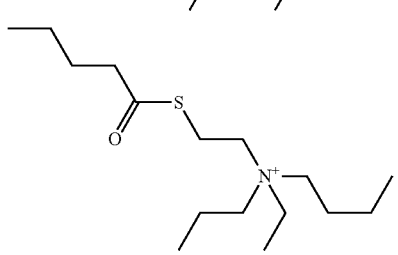
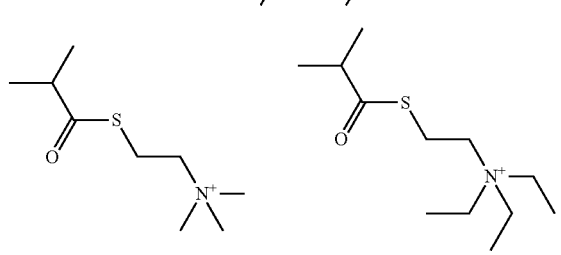
98
-continued
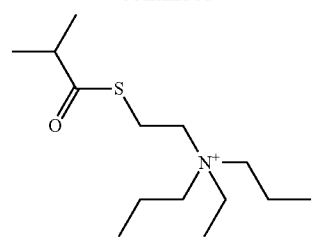
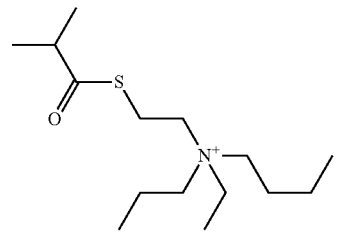
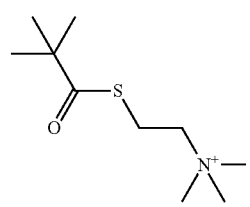
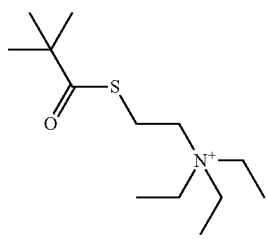
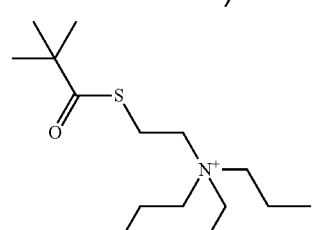
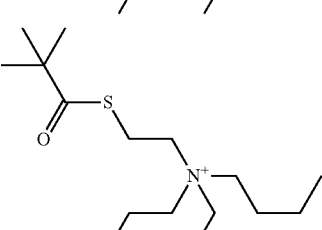
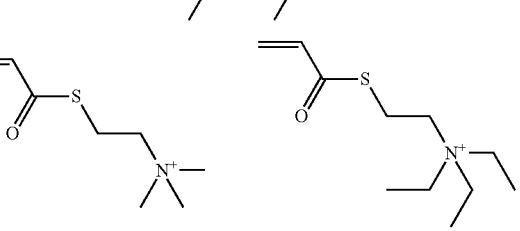

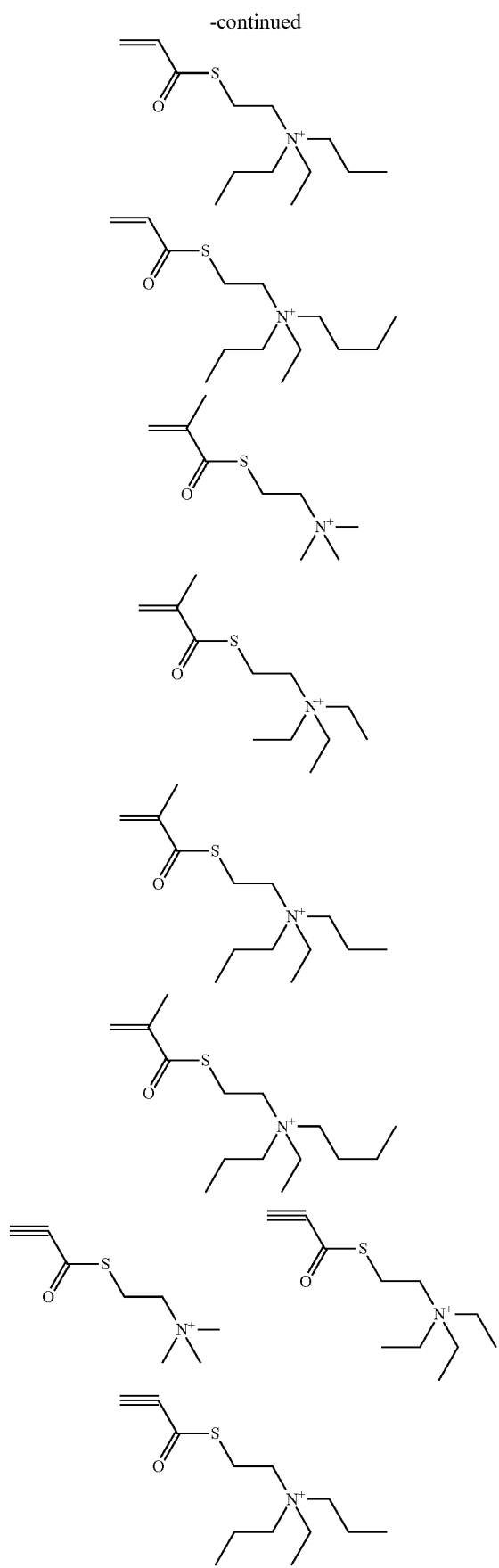

101
-continued
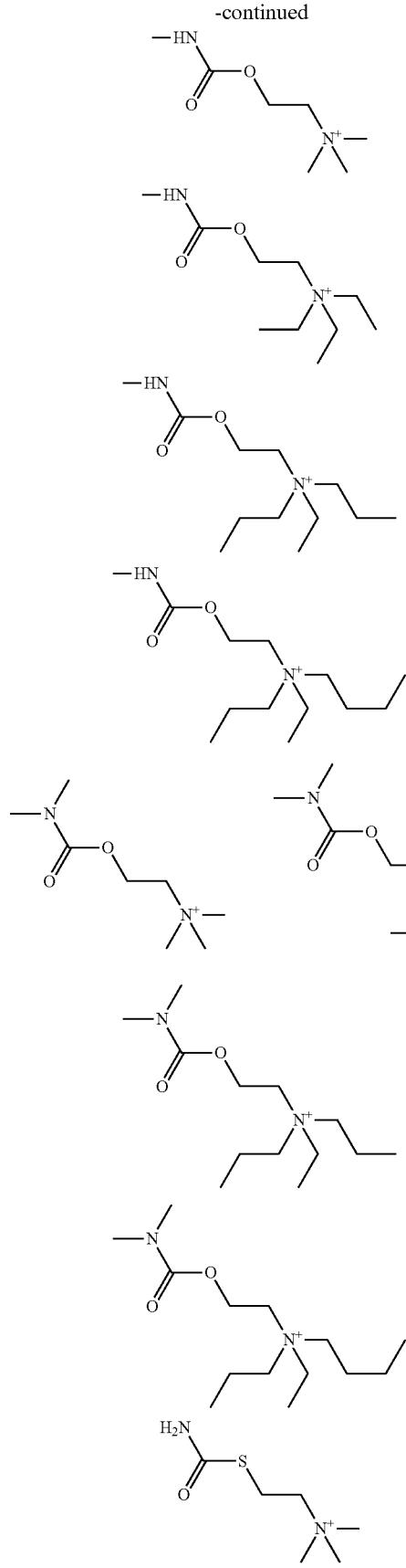
102
-continued
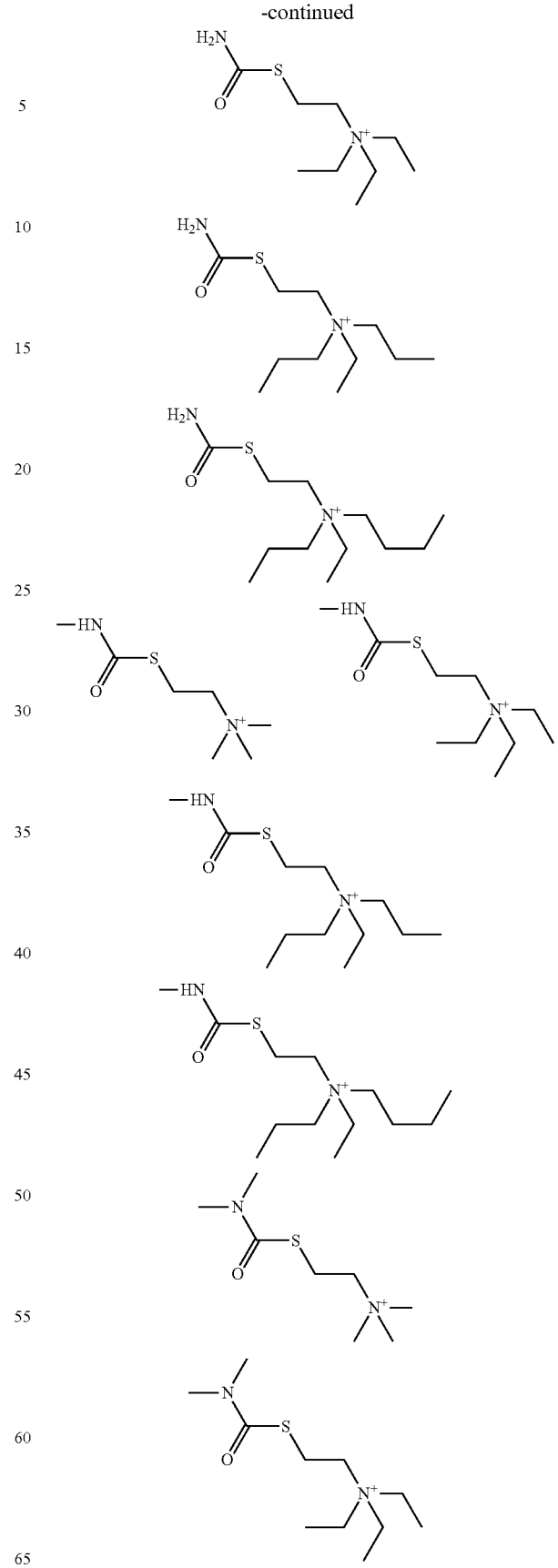

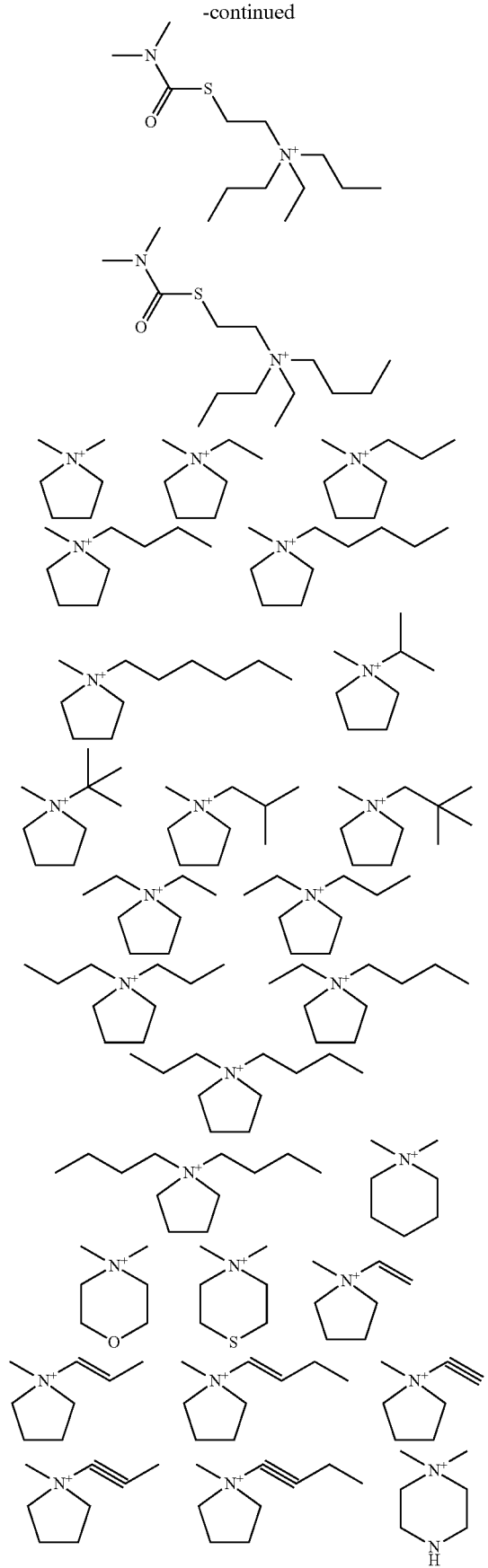
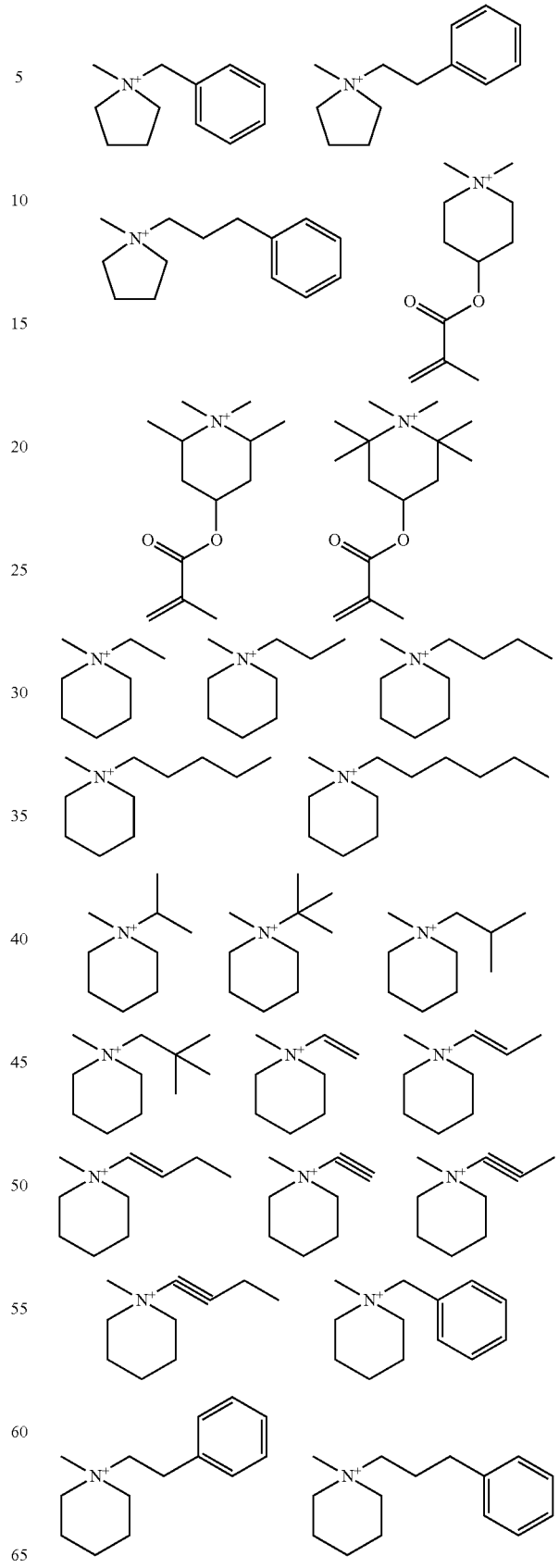

105
-continued
106
-continued
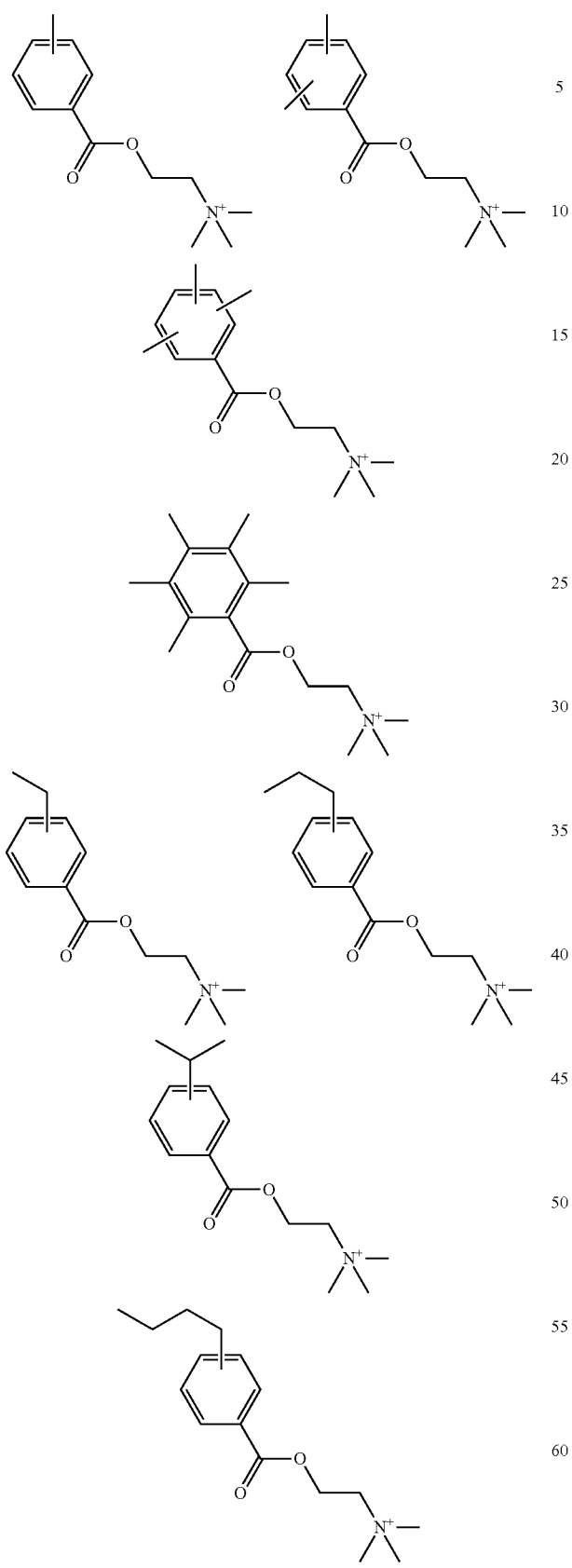
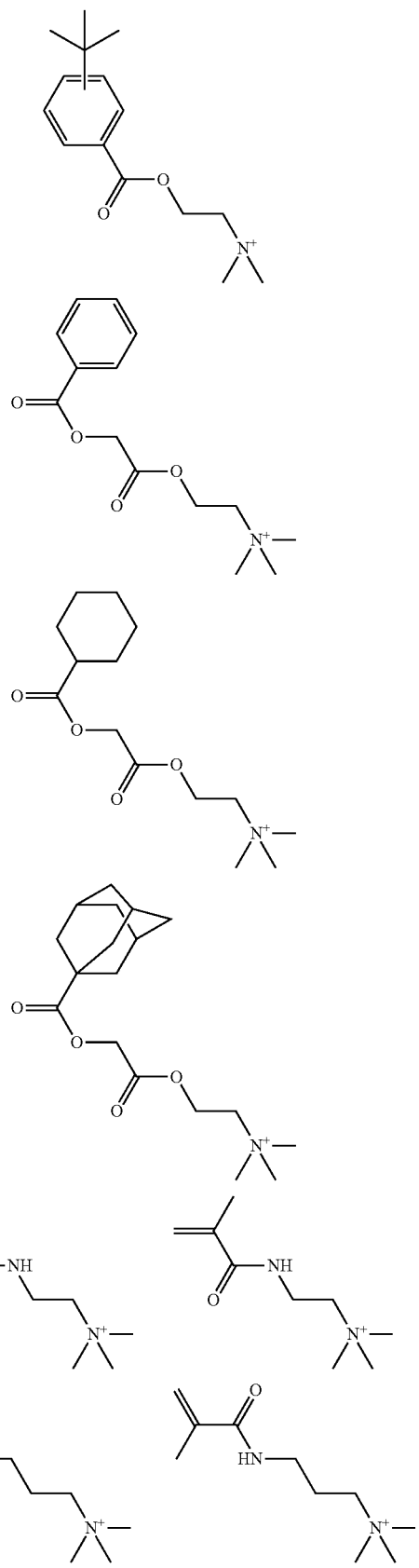

107
-continued
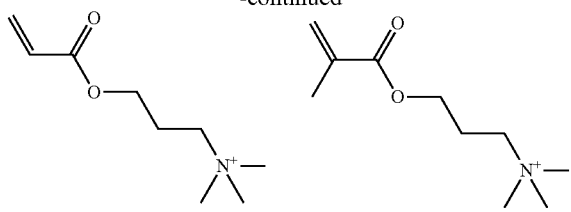
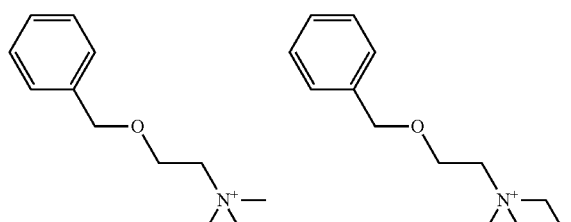
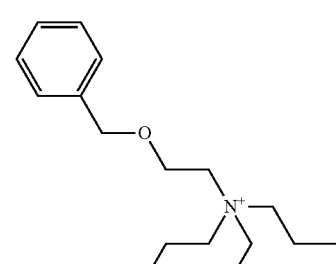
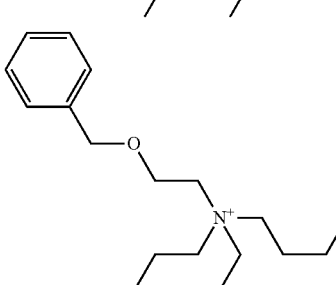
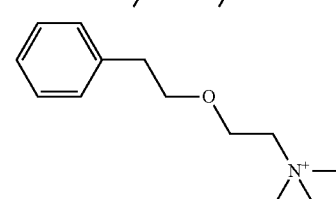
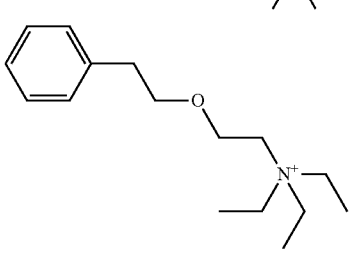
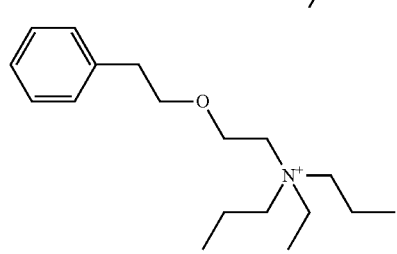
108
-continued
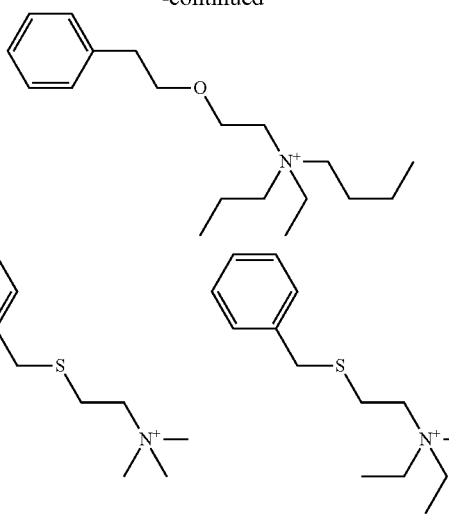
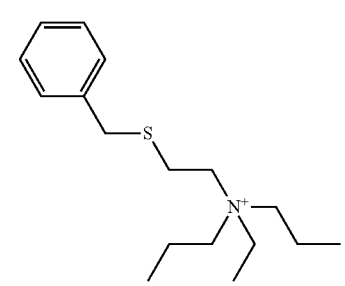
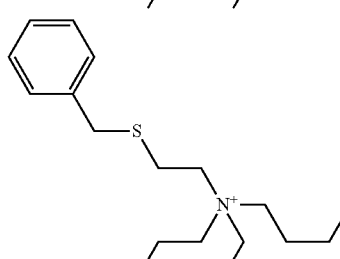
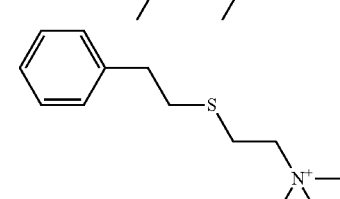
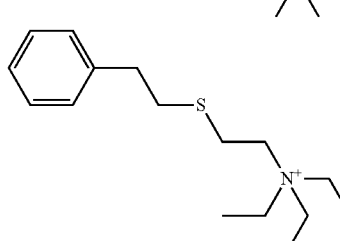
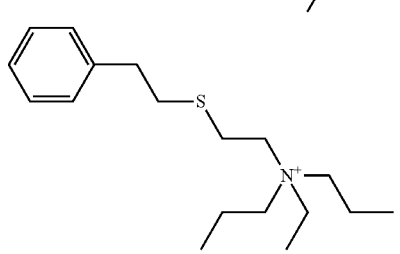

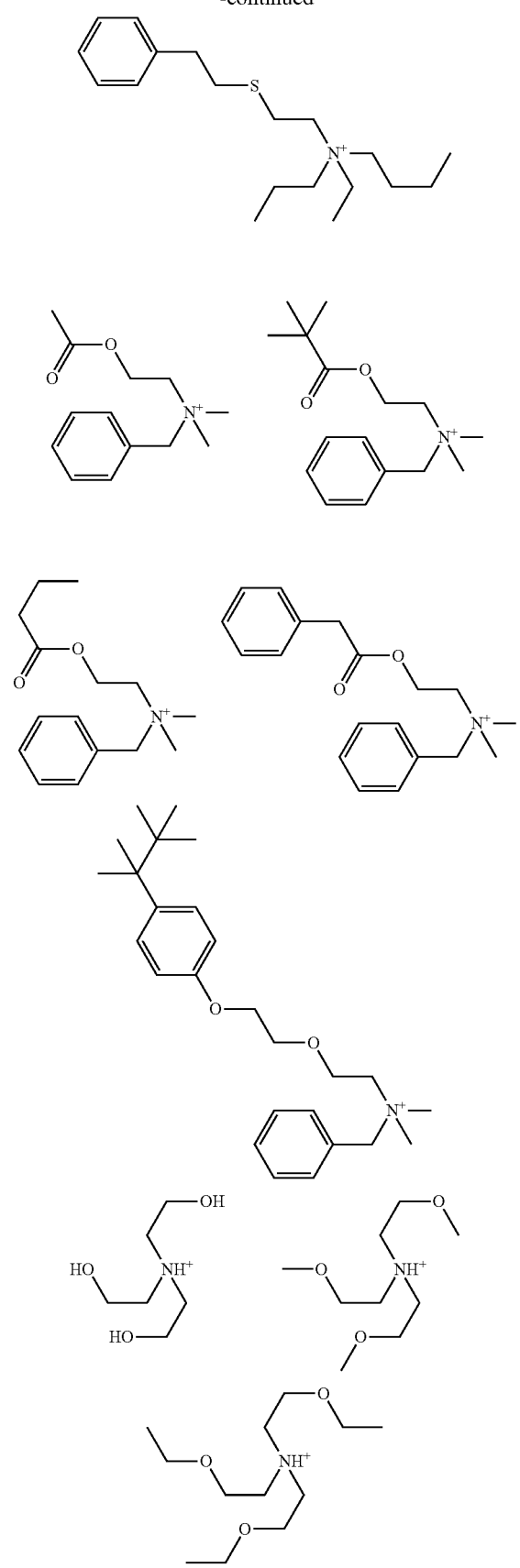
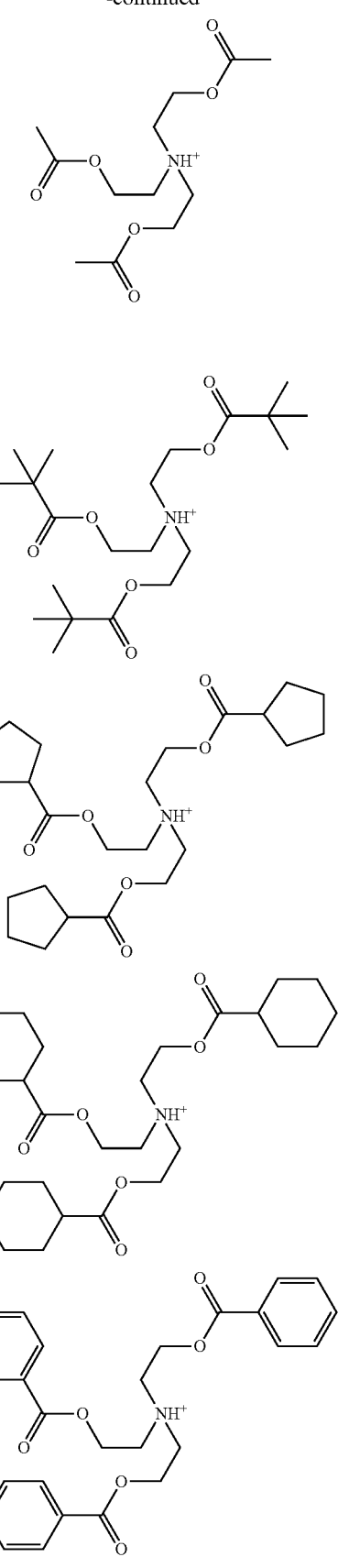

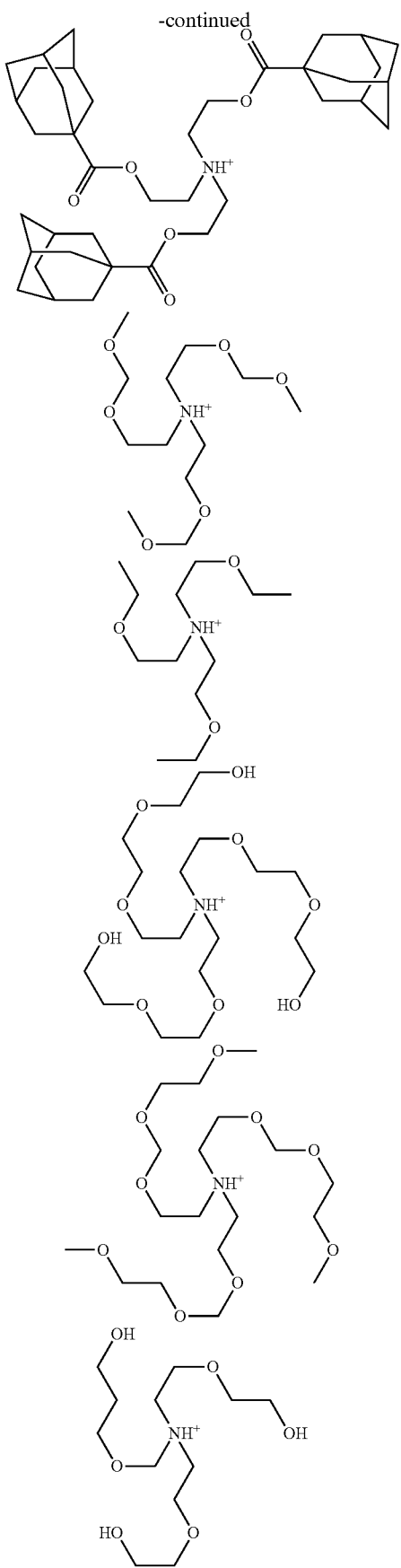
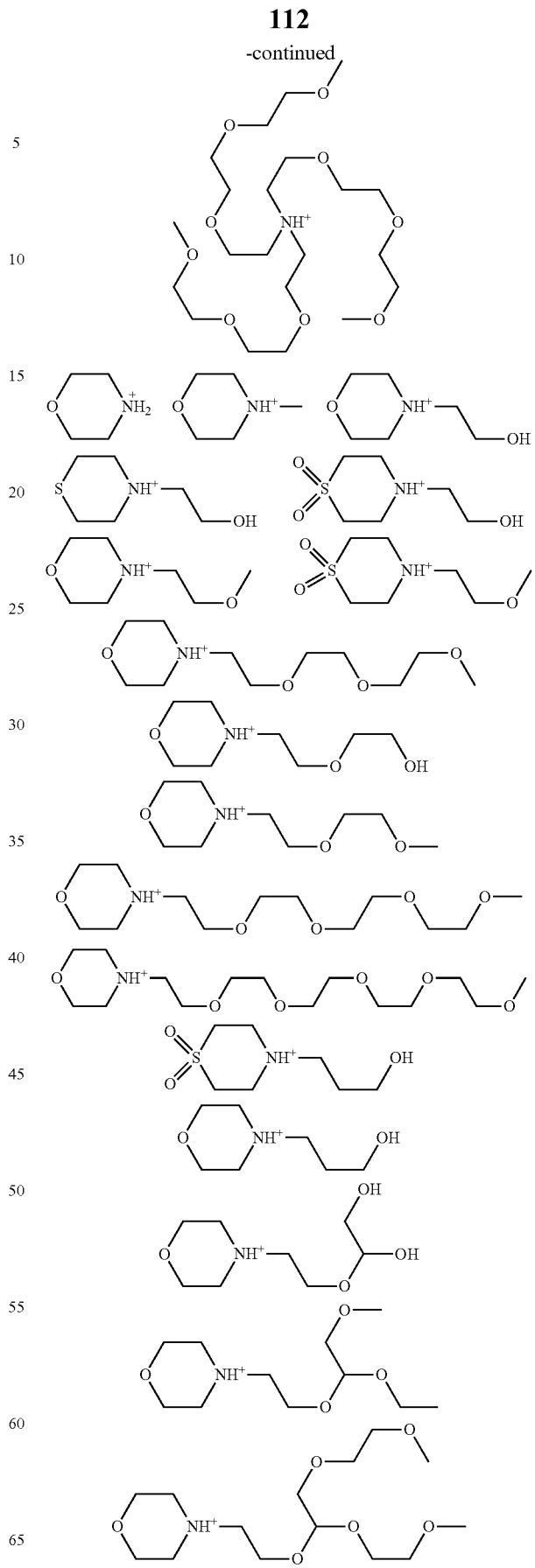

-continued

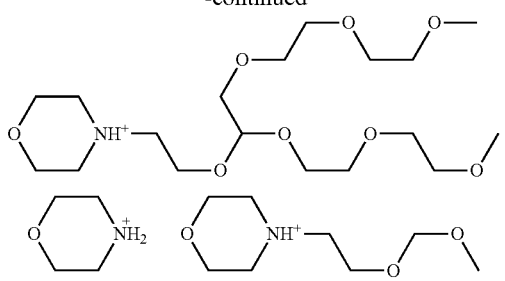
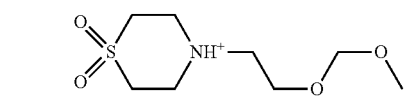
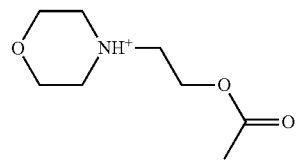
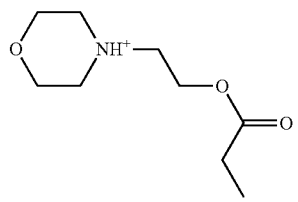
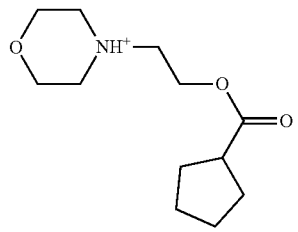
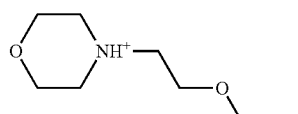
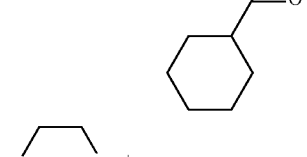
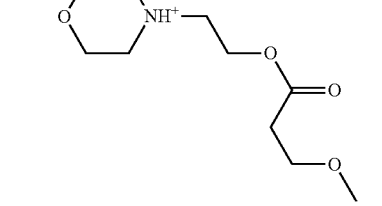
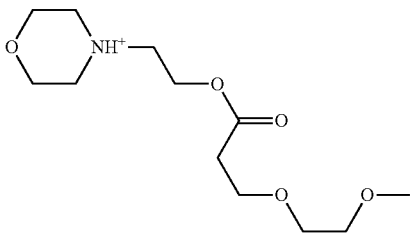

-continued

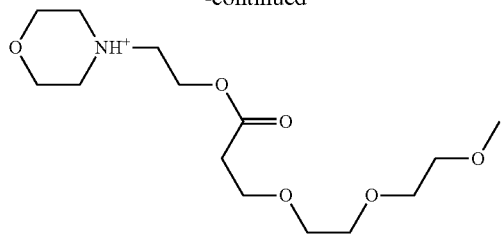

The ammonium ion shown by the general formula (2) is particularly preferably a tertiary or quaternary ammonium ion.

(Repeating Unit B)

In order to improve the electric conductivity, the polymer compound of the component (A) of the bio-electrode composition can also be copolymerized with a repeating unit B having a glyme chain, in addition to the repeating unit(s) A1 to A7. Specific examples of a monomer to give the repeating unit B having a glyme chain include the following. The copolymerization with a repeating unit having a glyme chain facilitates the movement of ions released from skin in the dry electrode film, and thus can increase the sensitivity of the dry electrode.

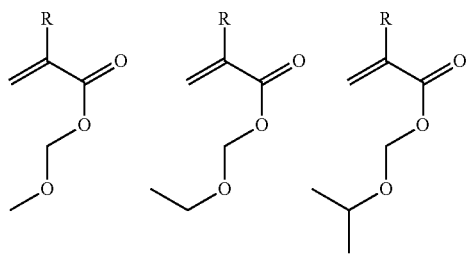
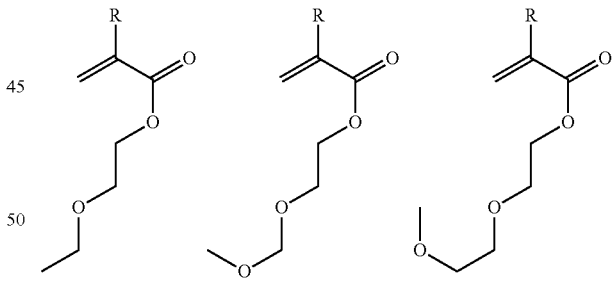
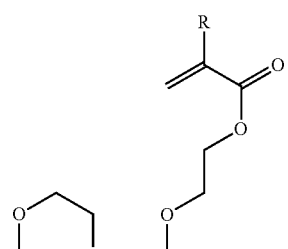

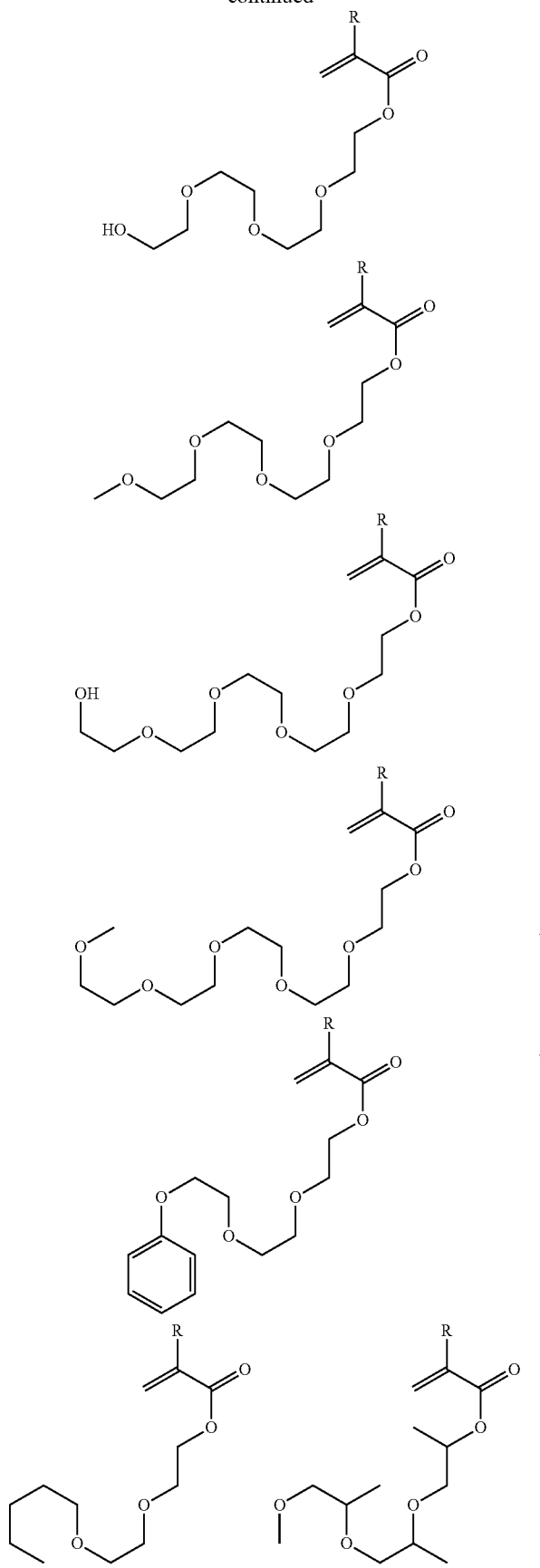
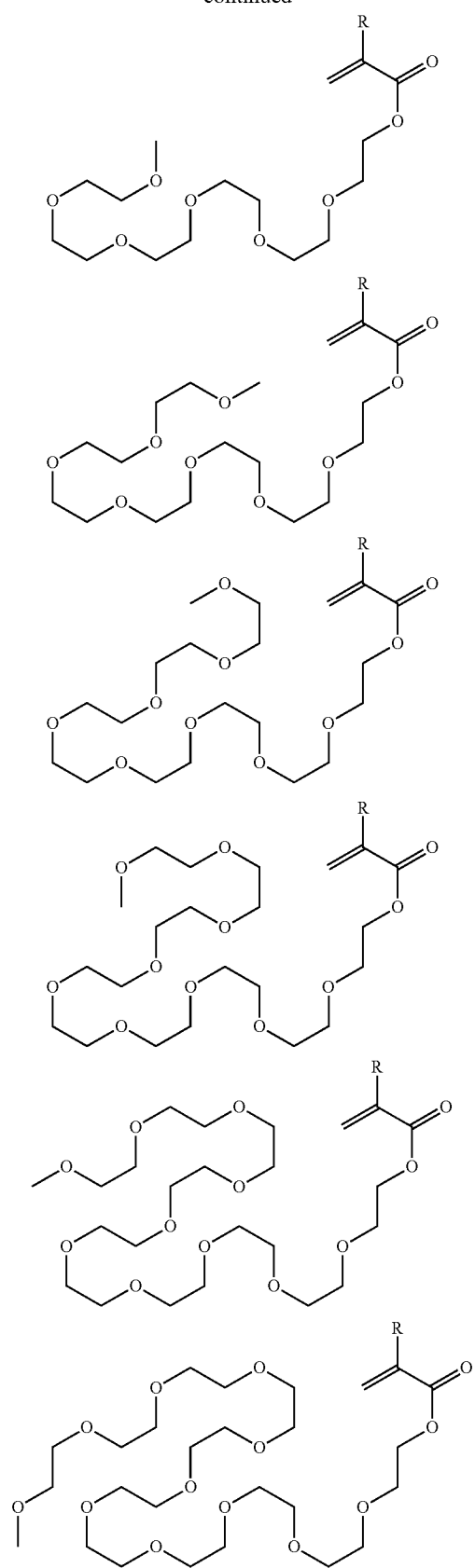

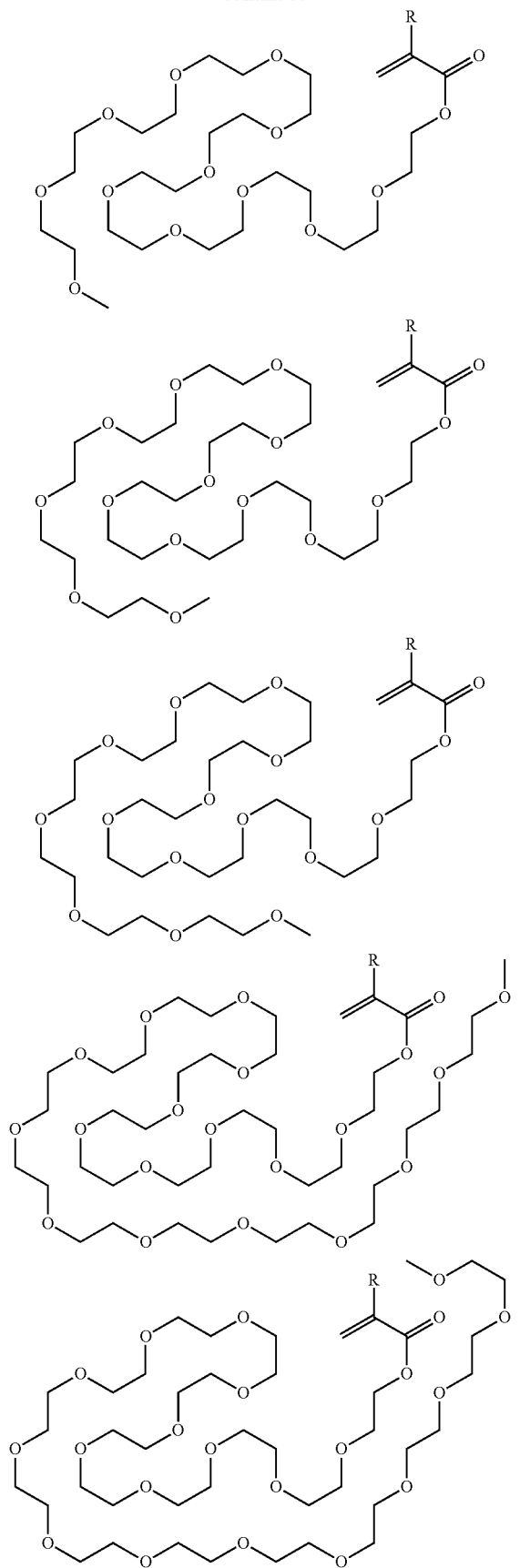
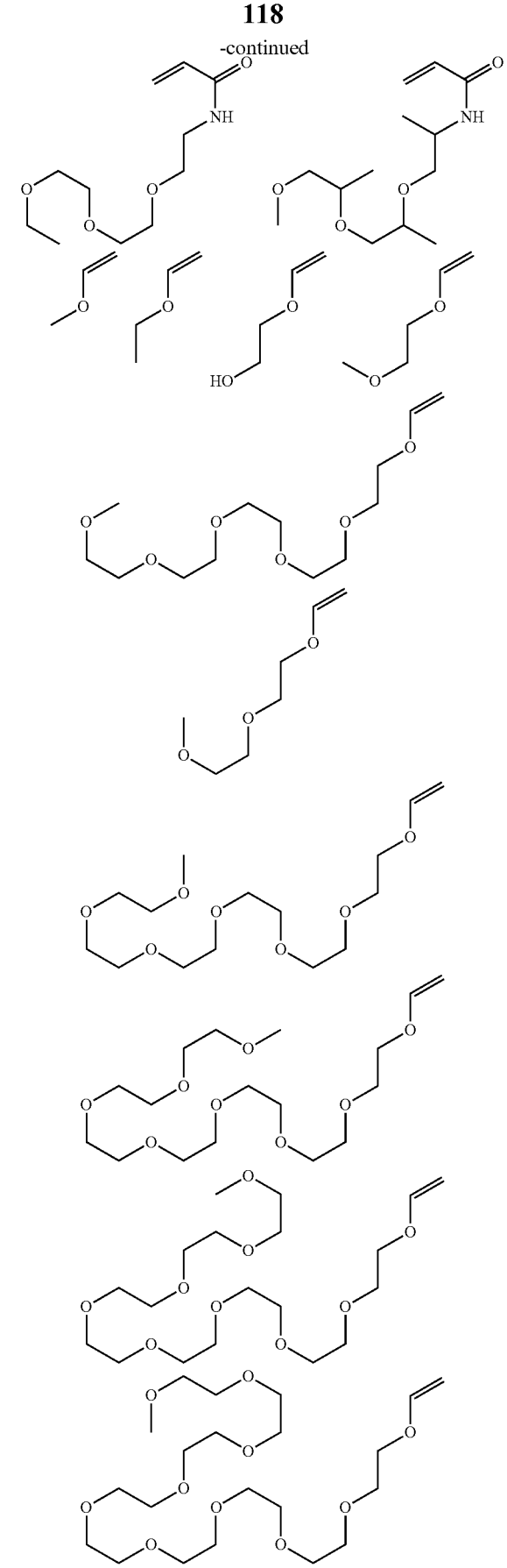

119
-continued
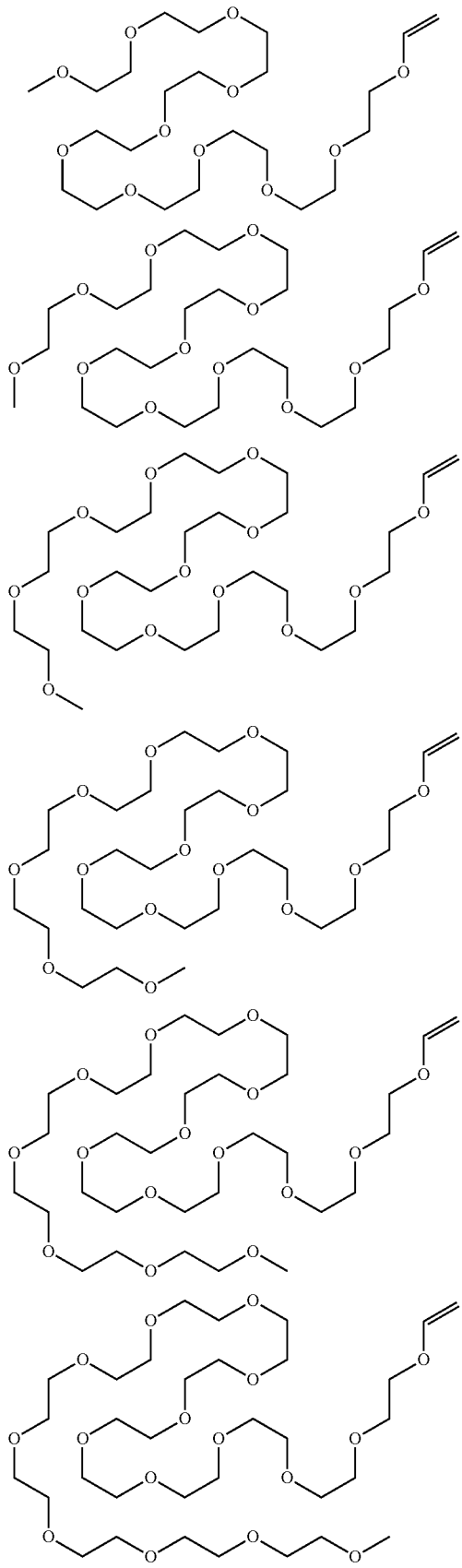
120
-continued
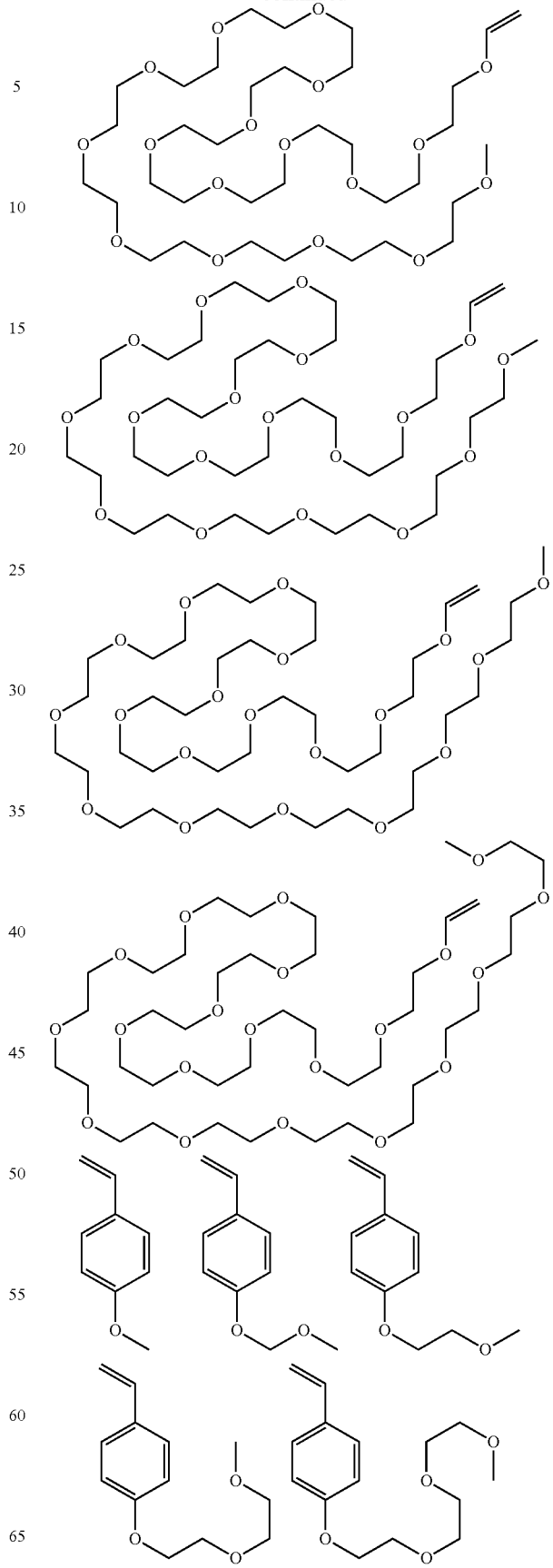

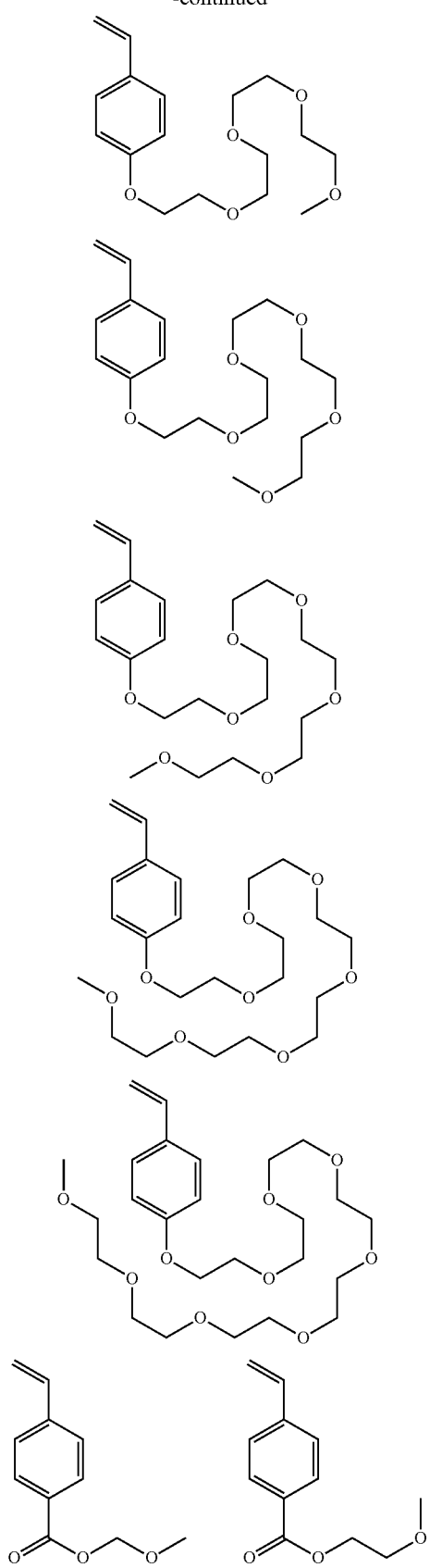
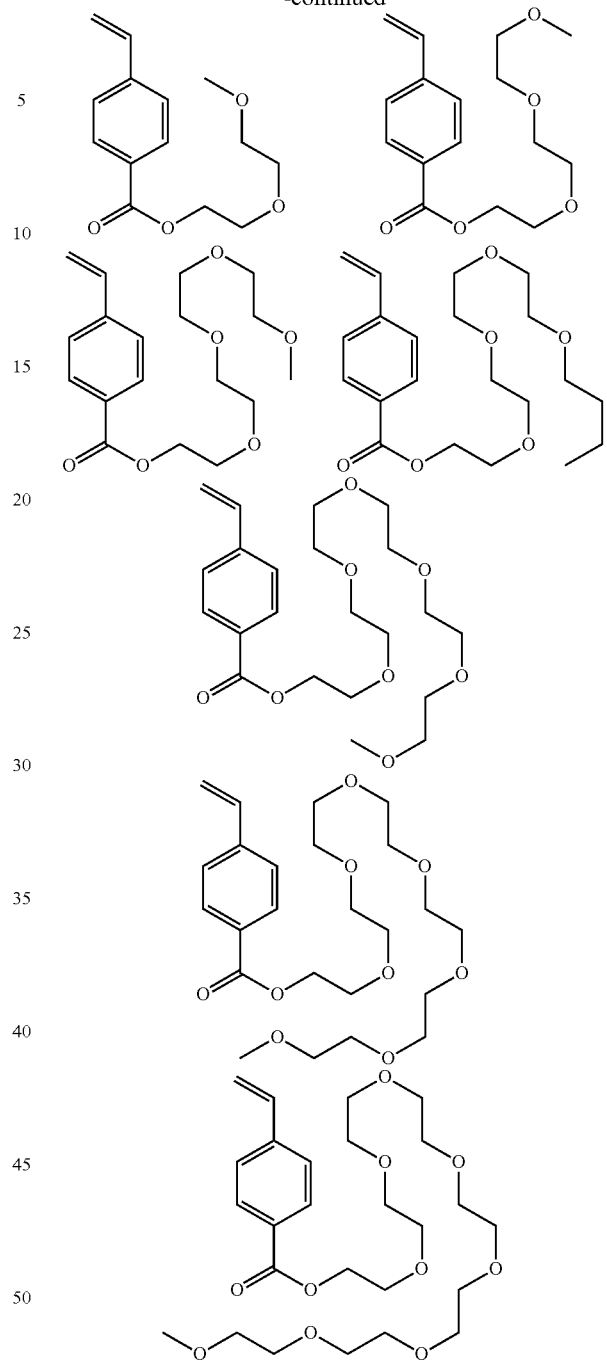

In the above formulae, R represents a hydrogen atom or a methyl group.

(Repeating Unit C)

In order to improve the electric conductivity, the polymer compound of the component (A) of the bio-electrode composition can also be copolymerized with, in addition to the repeating units A1 to A7 and B, a hydrophilic repeating unit C having a hydroxy group, a carboxyl group, an ammonium salt, a betaine, an amide group, pyrrolidone, a lactone ring, a lactam ring, a sultone ring, a sulfonic acid sodium salt, a phosphoric acid sodium salt, or a sulfonic acid potassium salt. Specific examples of a monomer to give the hydrophilic repeating unit C include the following. The copolymerization with repeating units containing such hydrophilic groups can increase the sensitivity of the dry electrode by increasing the sensitivity to ions released from skin.
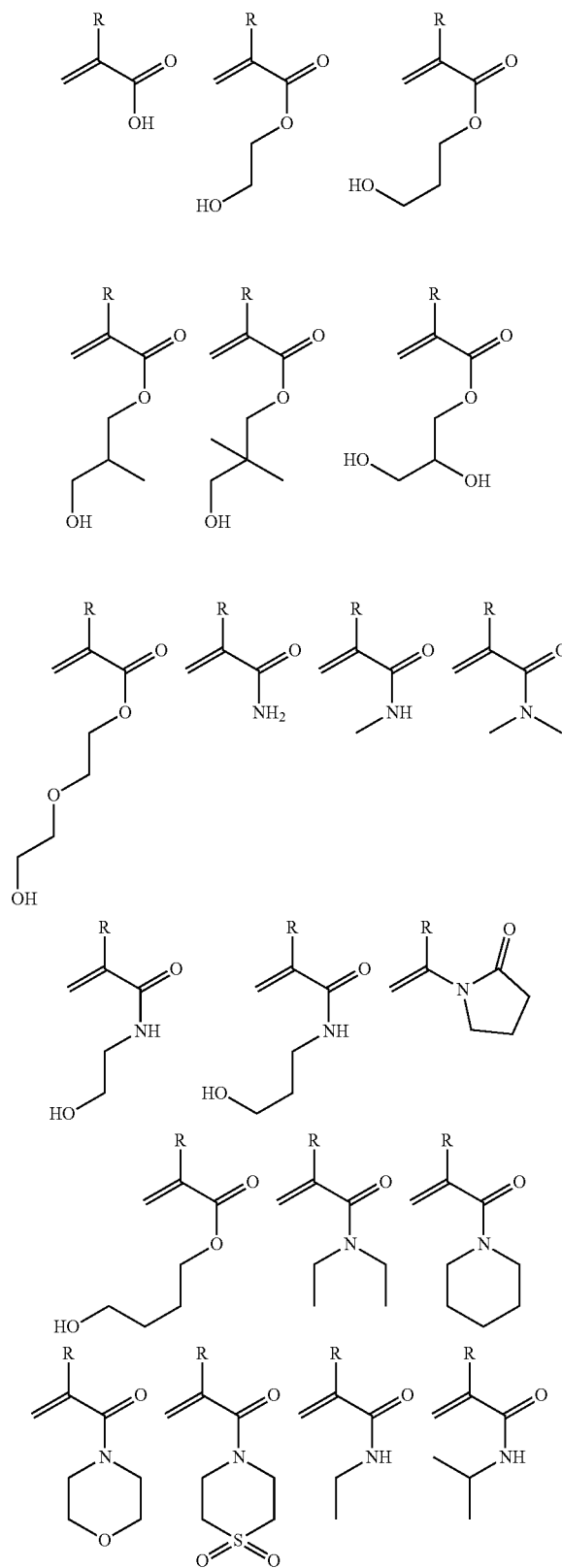
-continued
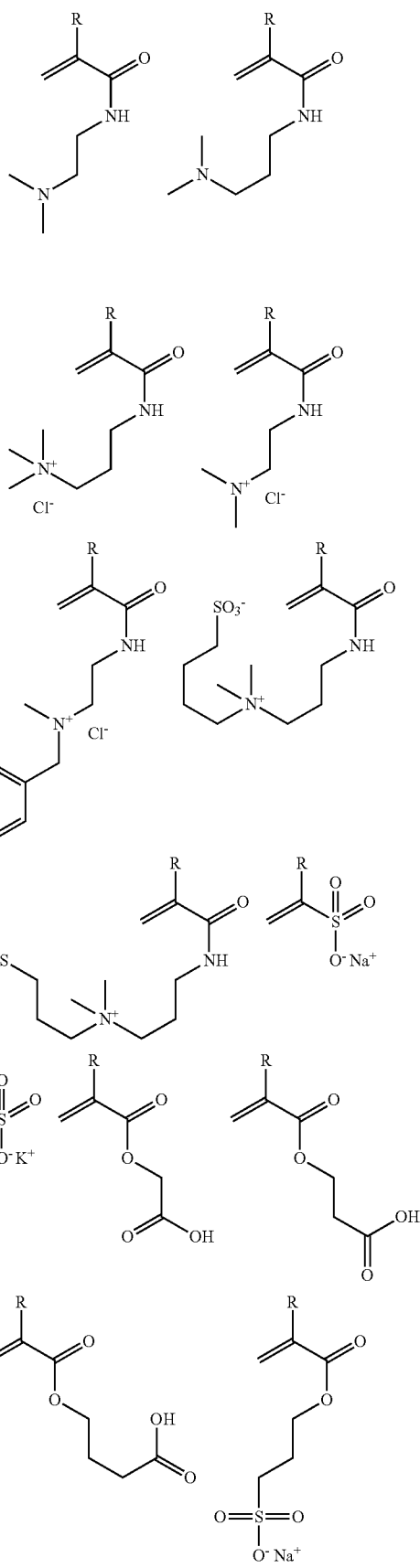

125
-continued
126
-continued
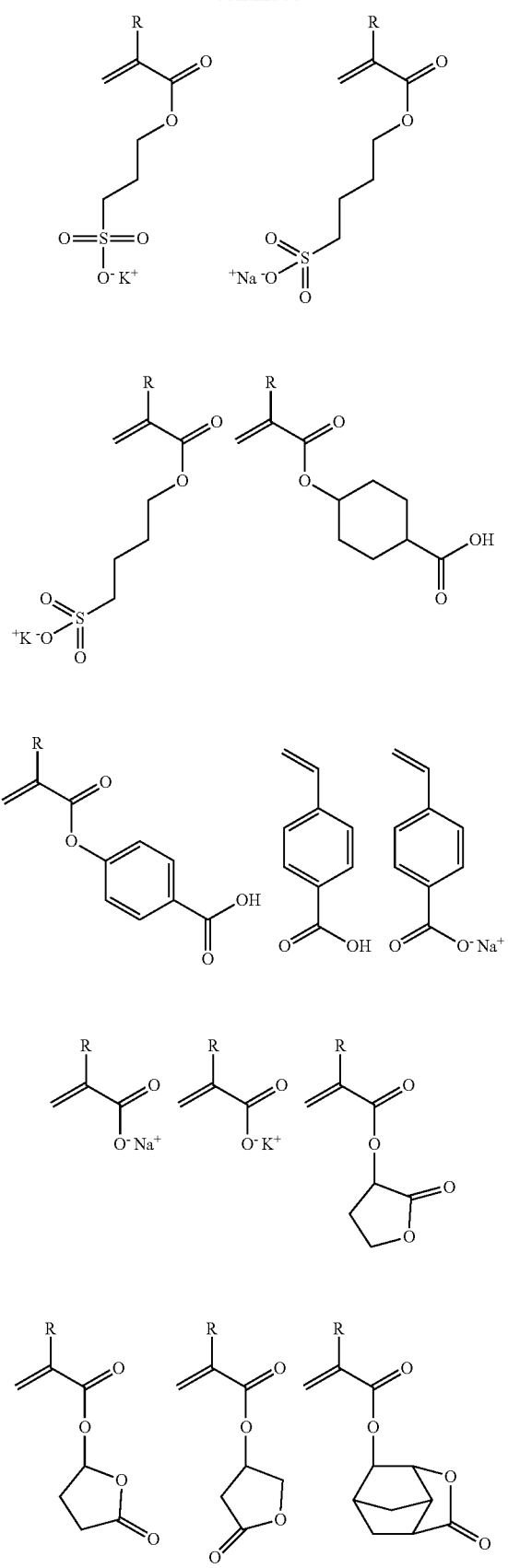

127
-continued
128
-continued
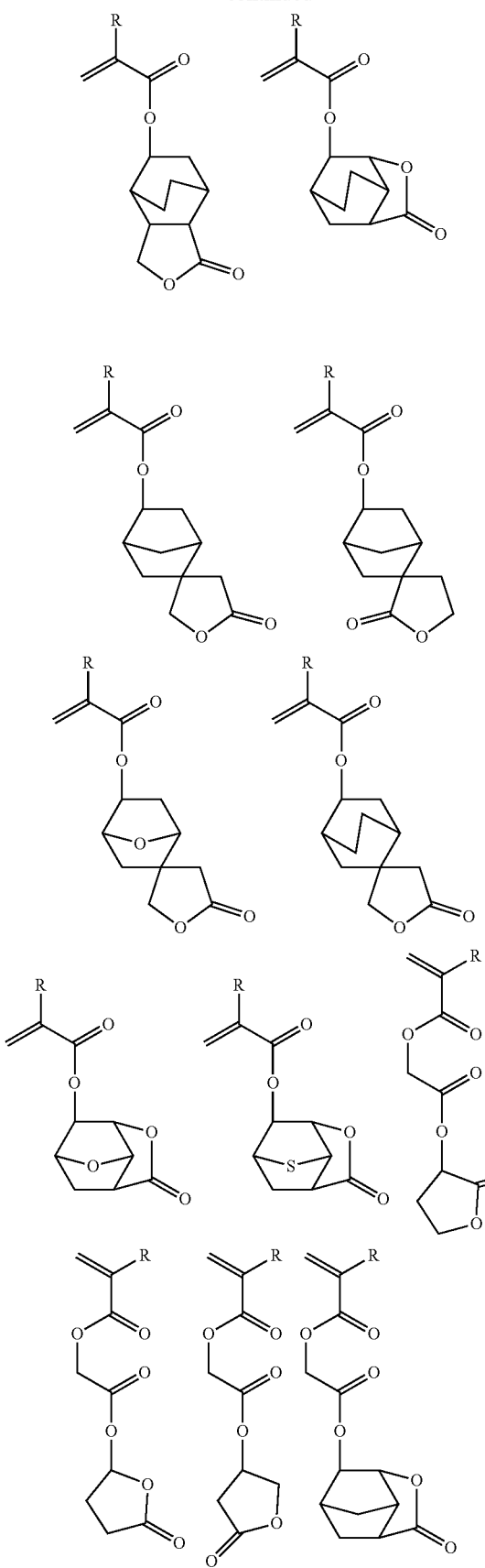
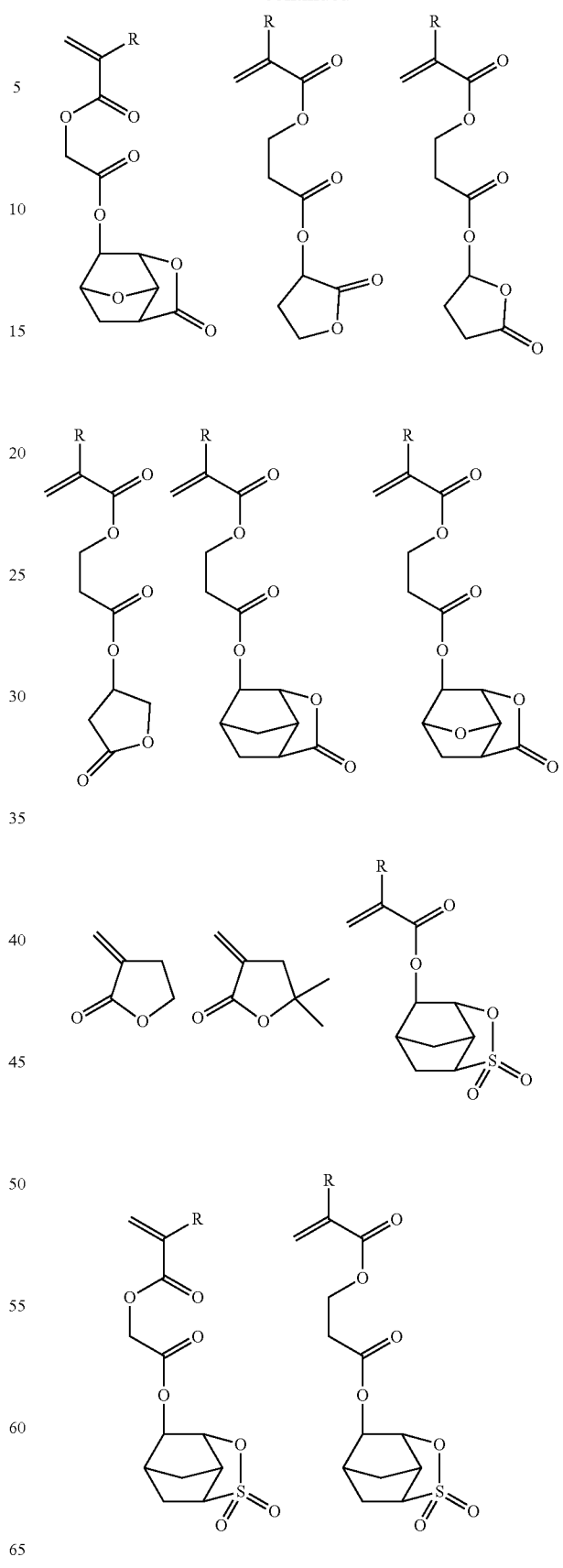

129
-continued
130
-continued
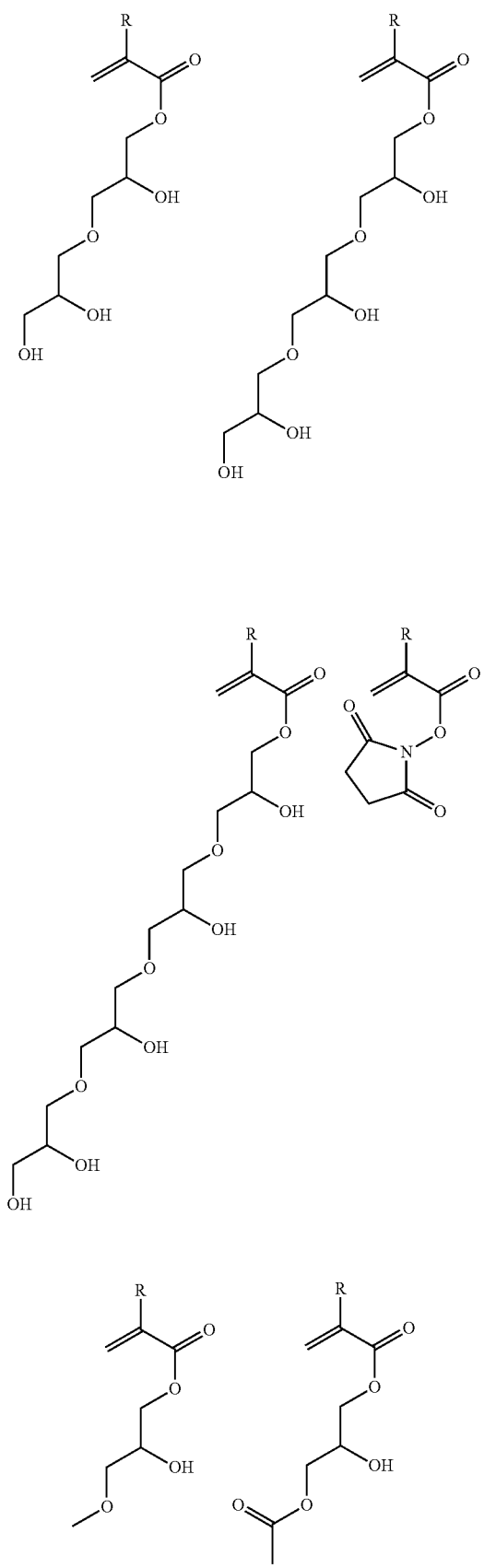
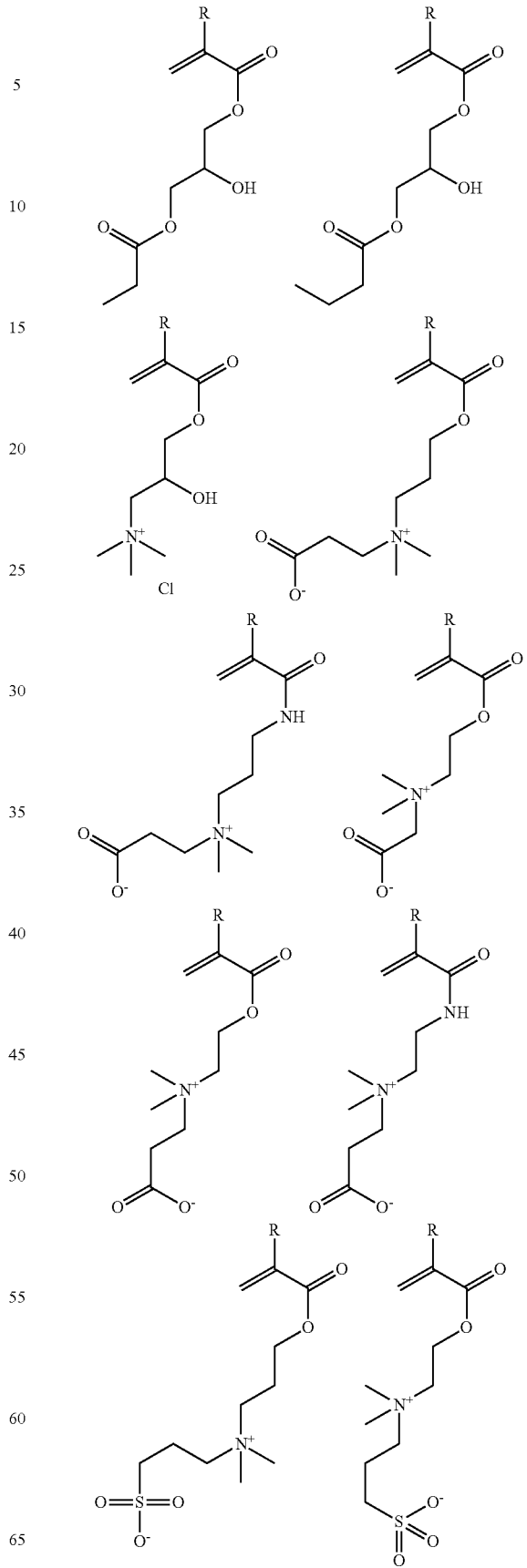

-continued

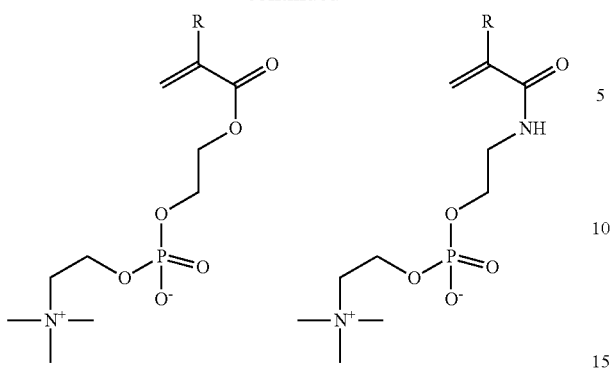

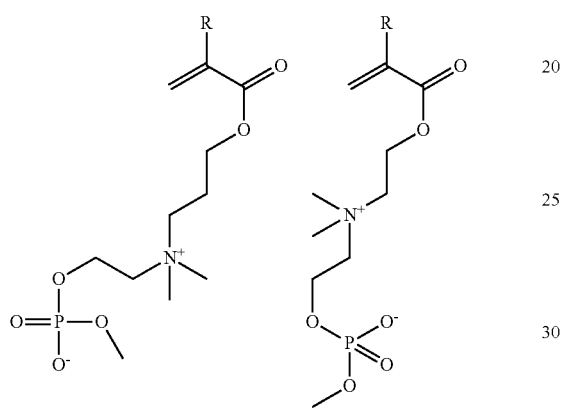

In these formulae, R represents a hydrogen atom or a methyl group.

(Repeating Unit D)

To impart adhesion properties, the polymer compound of the component (A) of the bio-electrode composition can also be copolymerized with a repeating unit D, in addition to the repeating units A1 to A7, B, and C. Specific examples of a monomer to give the repeating unit D include the following.

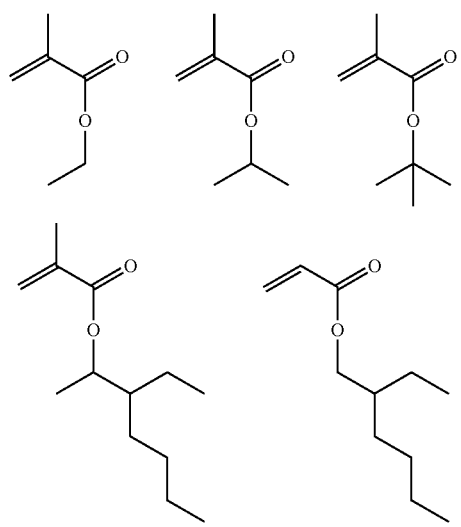

-continued

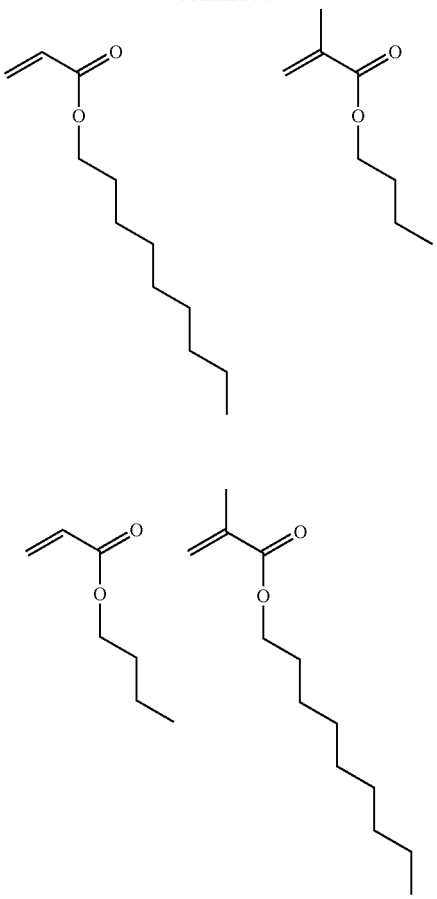

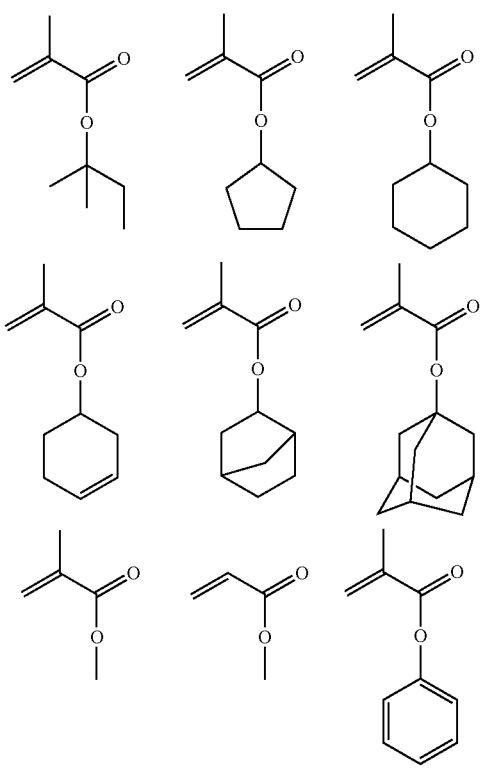

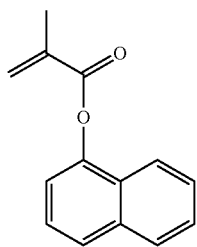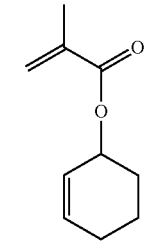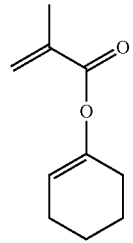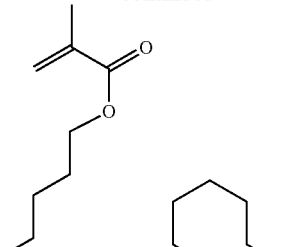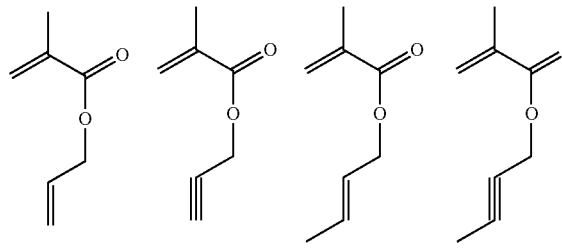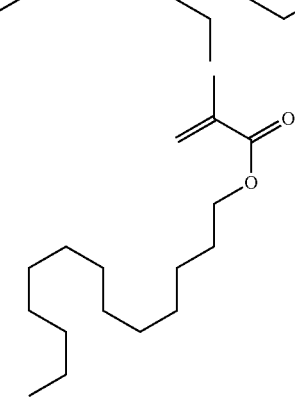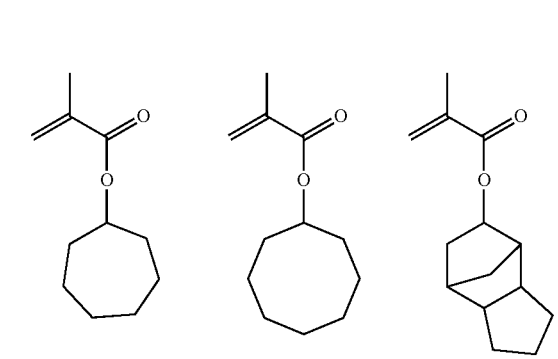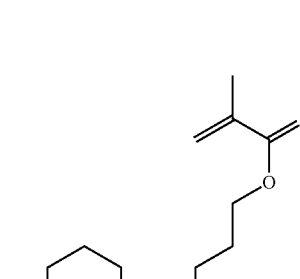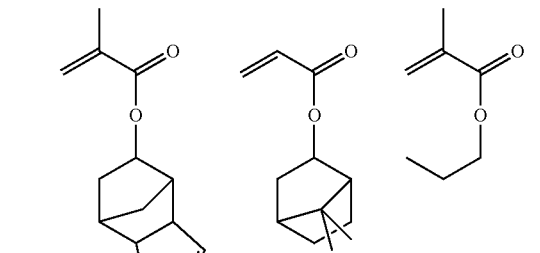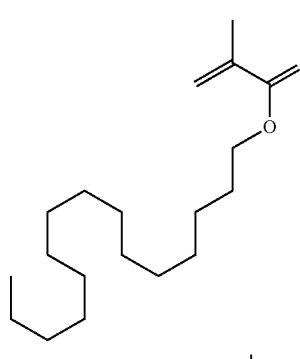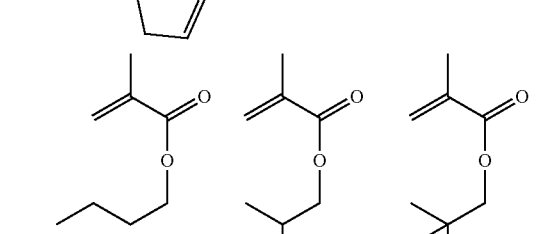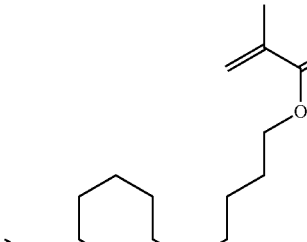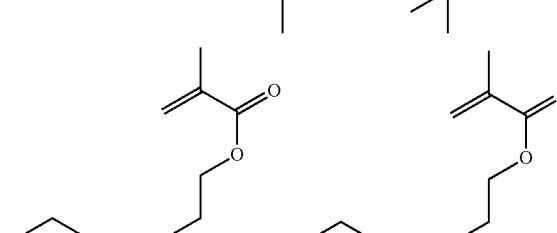

135
-continued
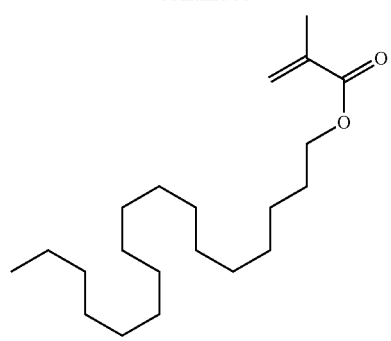
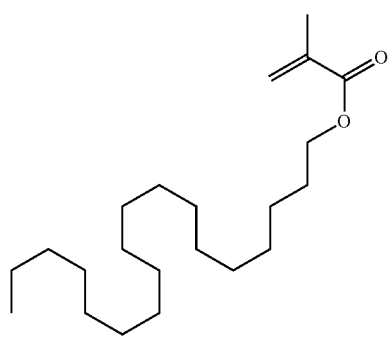
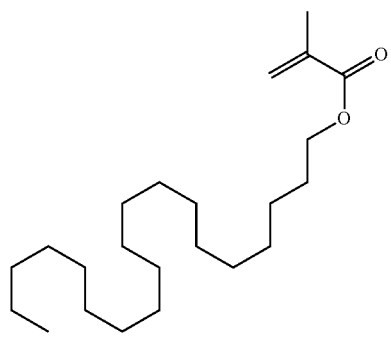
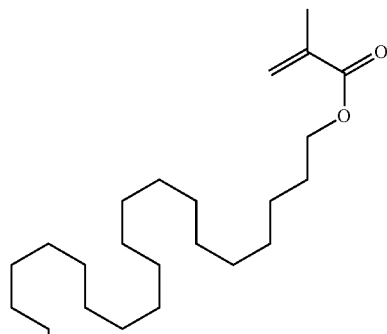
136
-continued
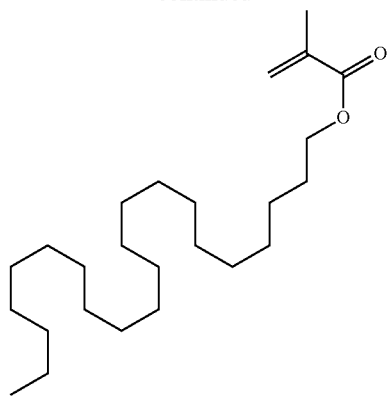
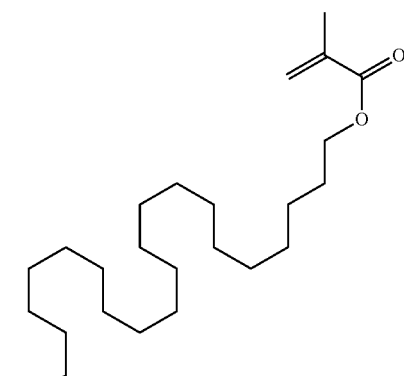
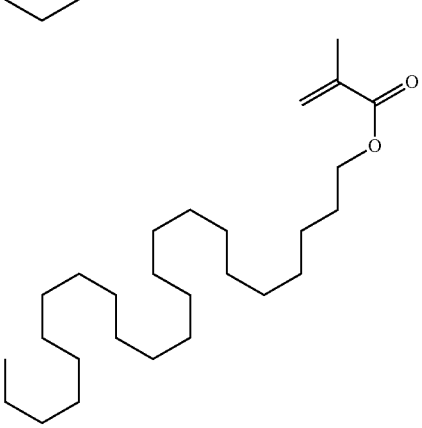
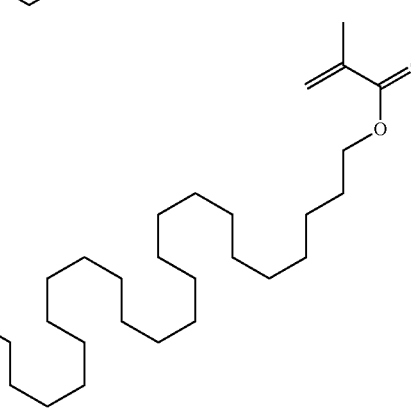

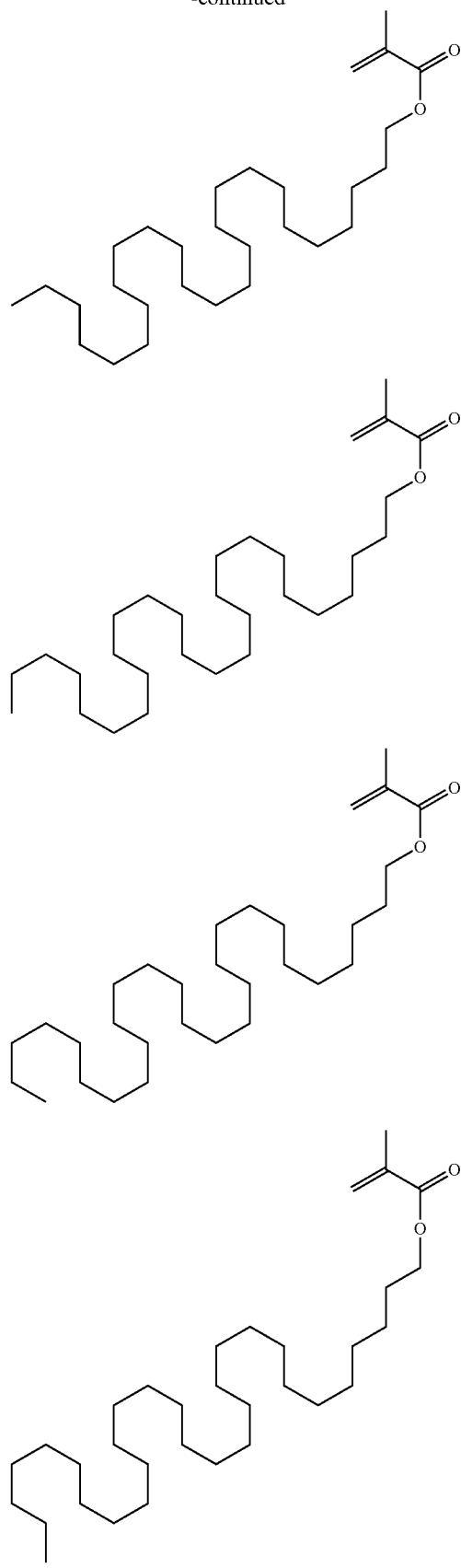
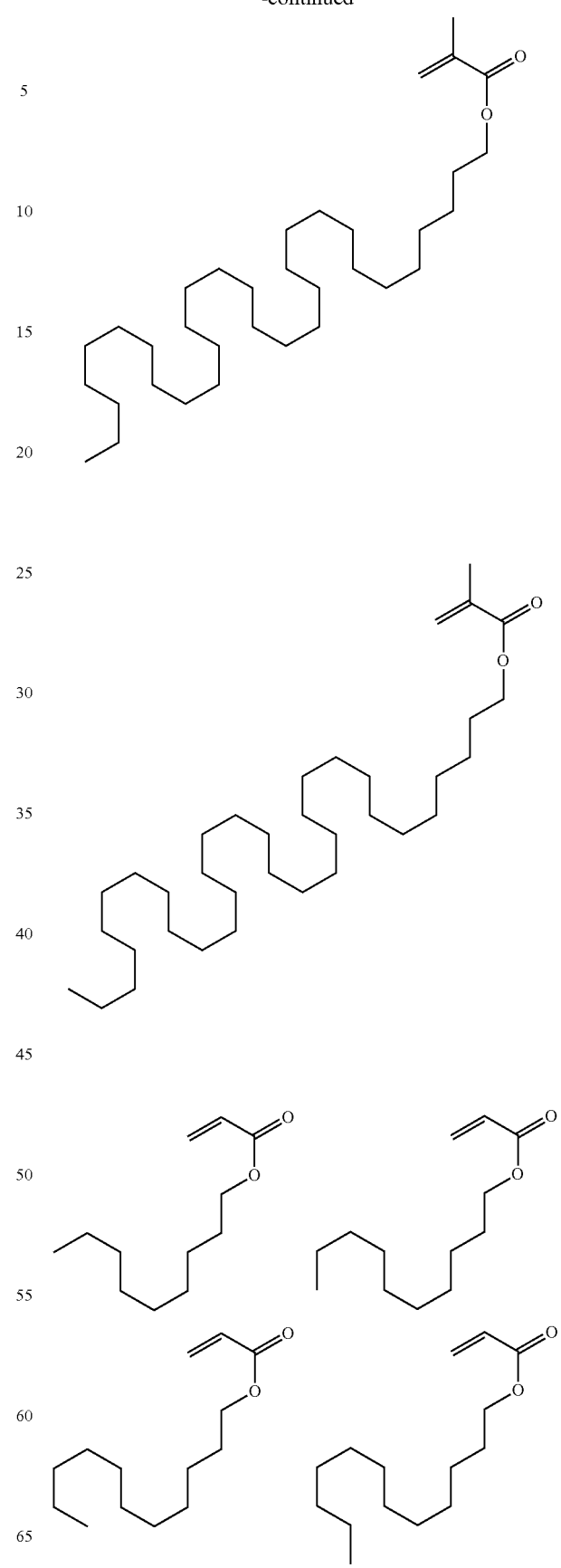

139
-continued
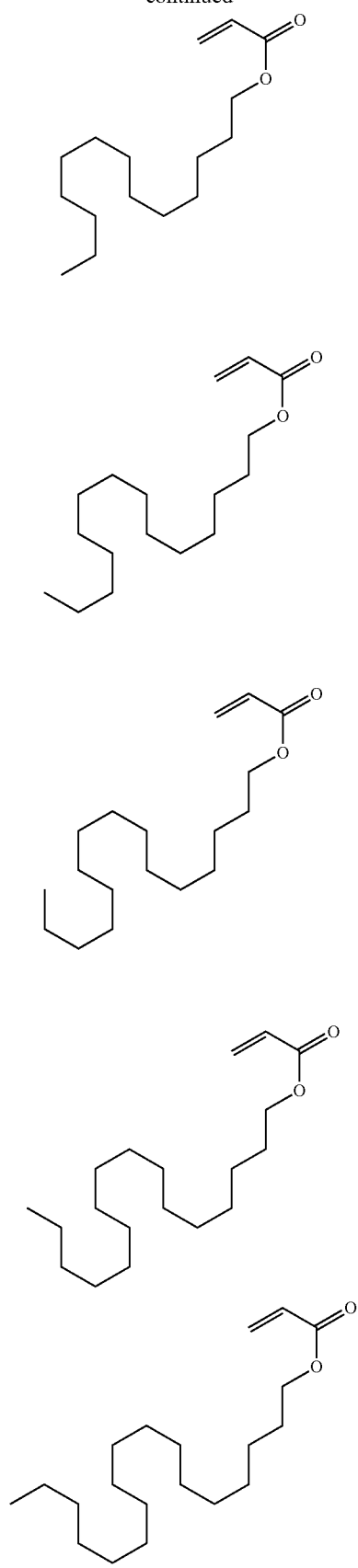
140
-continued
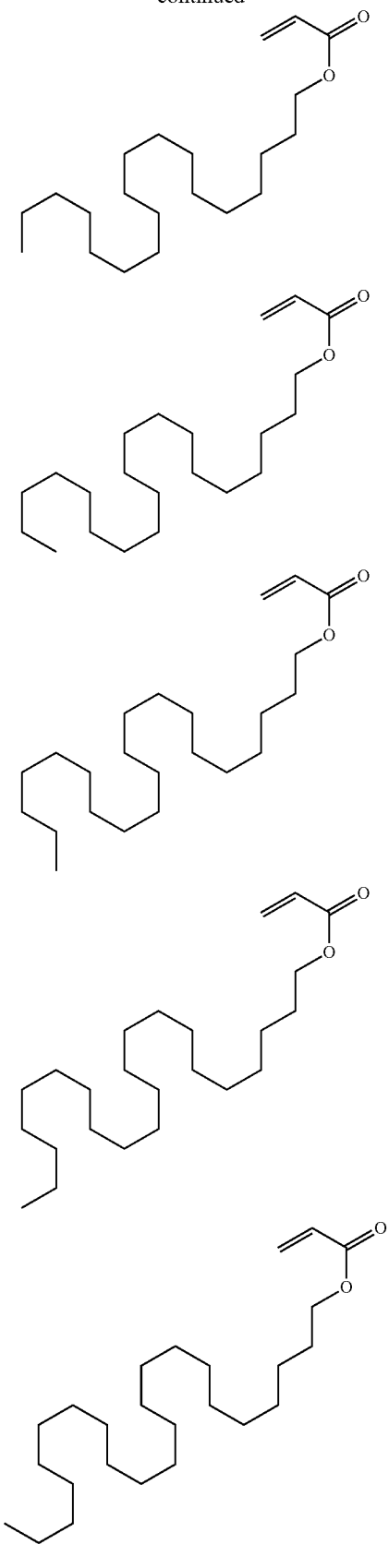

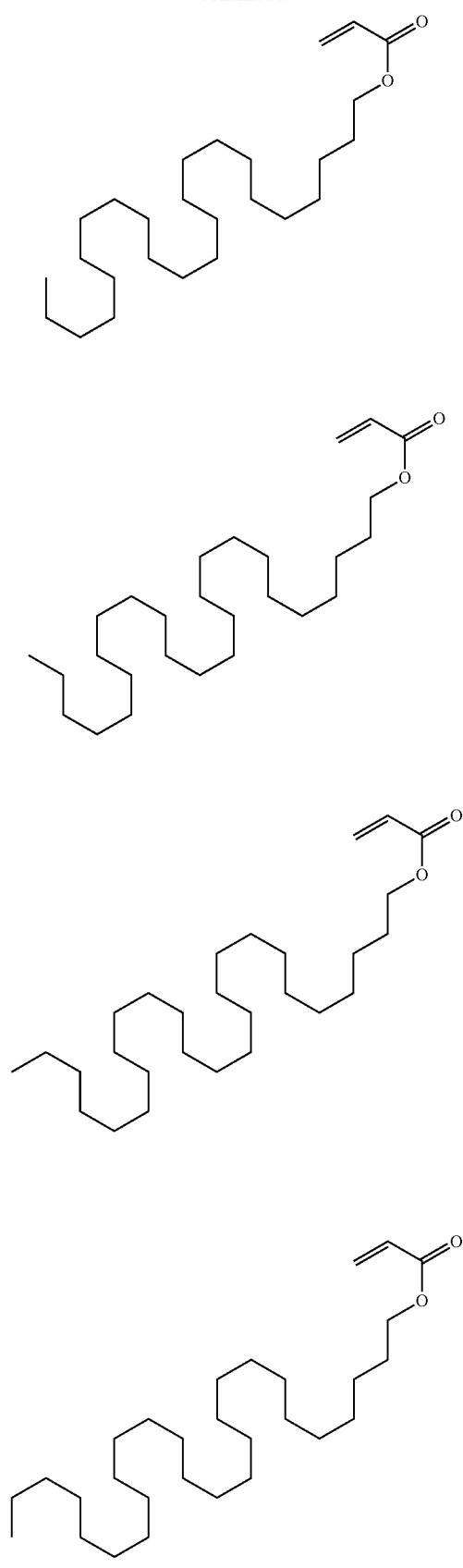

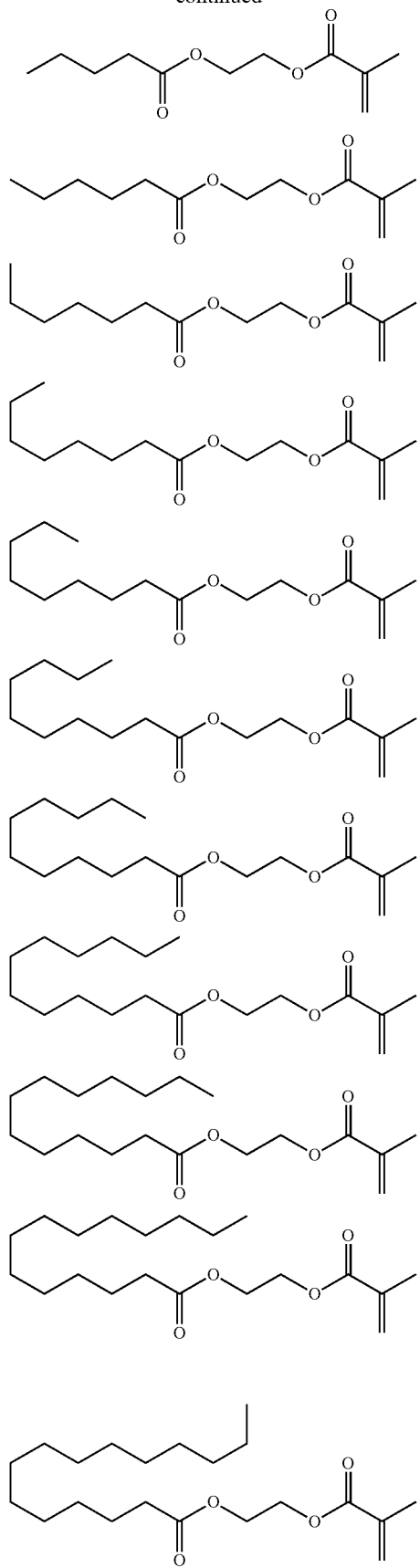
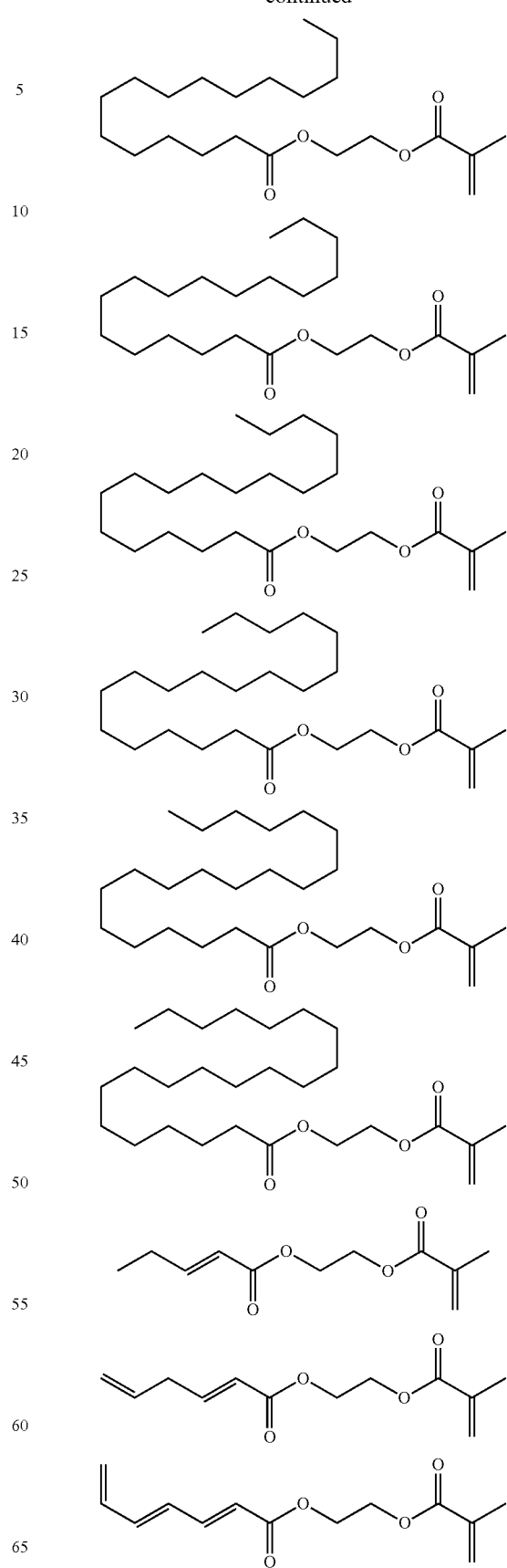

145
-continued
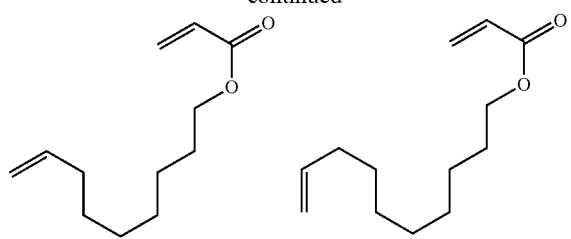
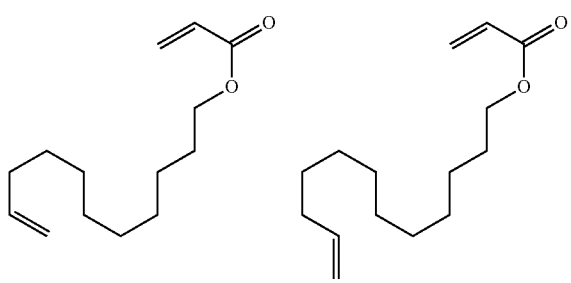
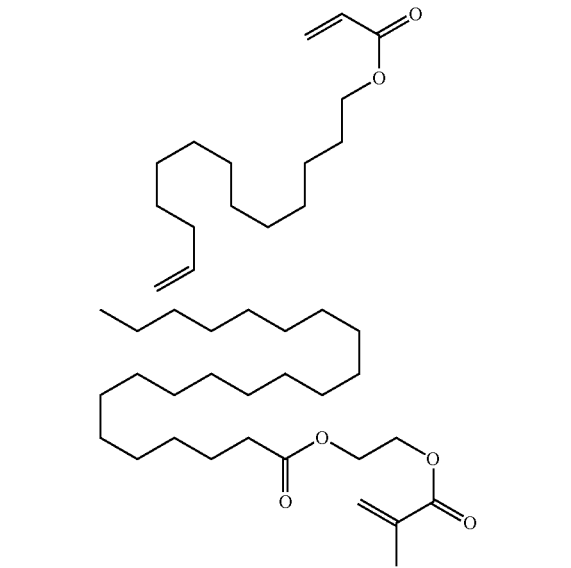
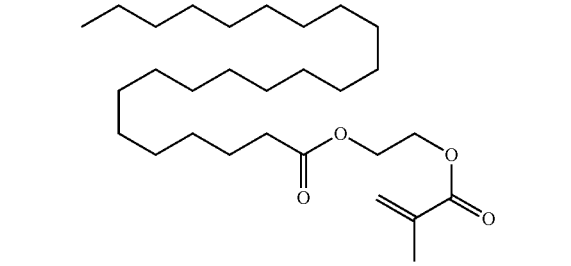
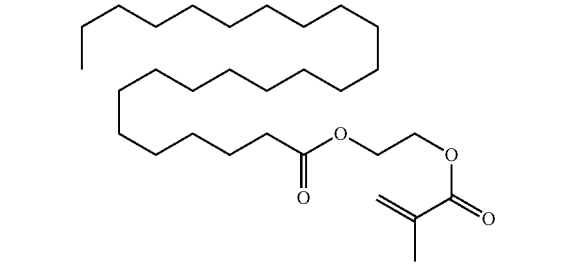
146
-continued
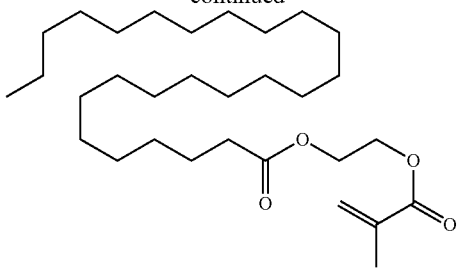
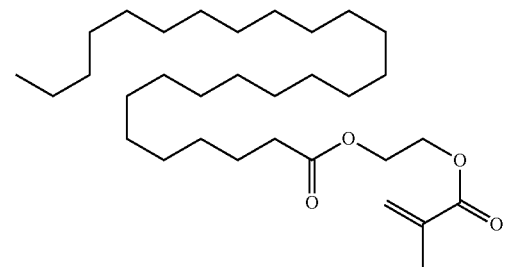
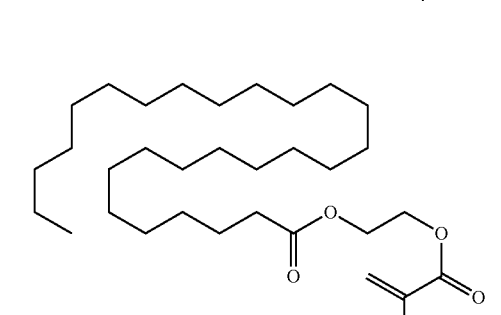
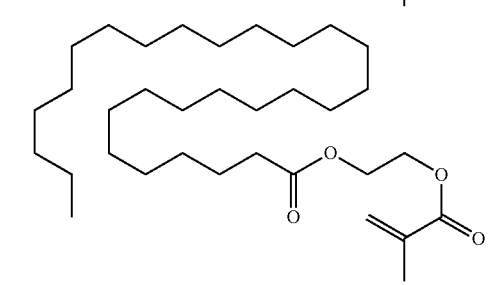
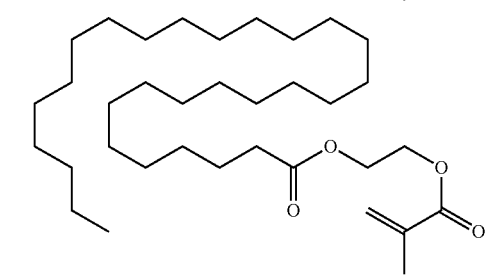
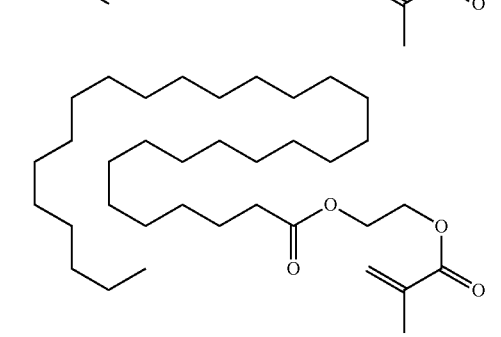

-continued

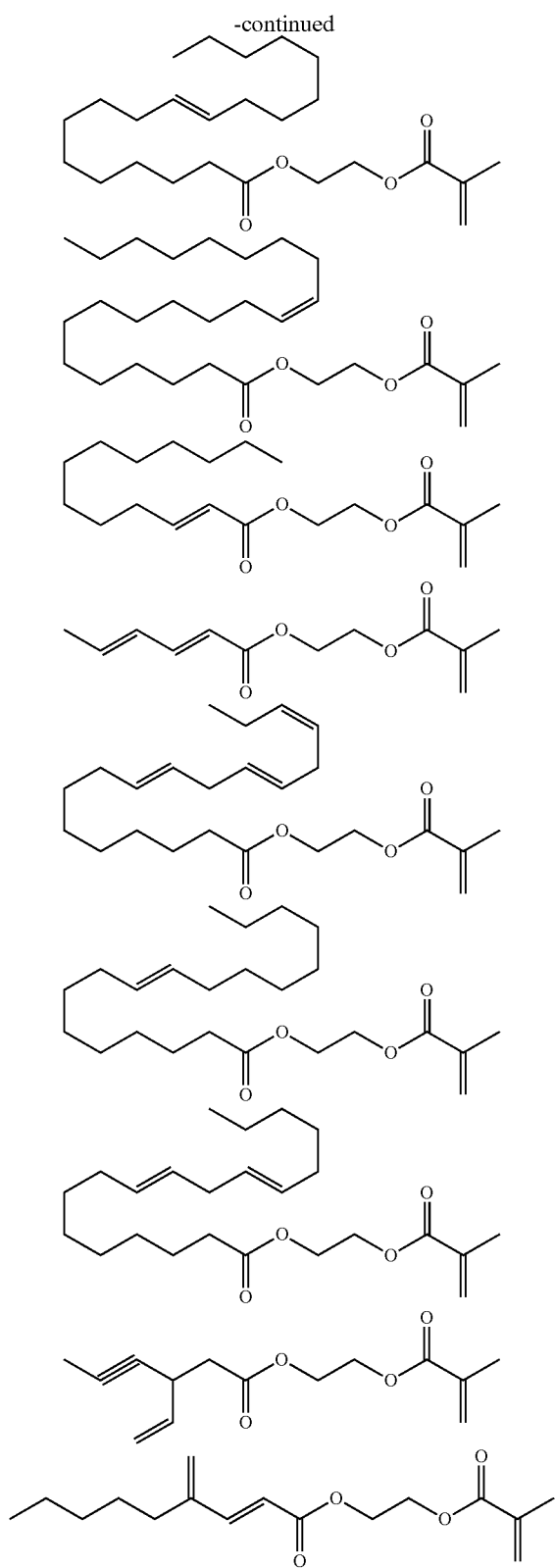

(Repeating Unit E)

Further, the polymer compound of the component (A) of the bio-electrode composition can also be copolymerized with a crosslinkable repeating unit E, in addition to the repeating units A1 to A7 and B to D. Examples of the crosslinkable repeating unit include repeating units having an oxirane ring or an oxetane ring. Specific examples of monomers to give the repeating unit E having an oxirane ring or an oxetane ring include the following.

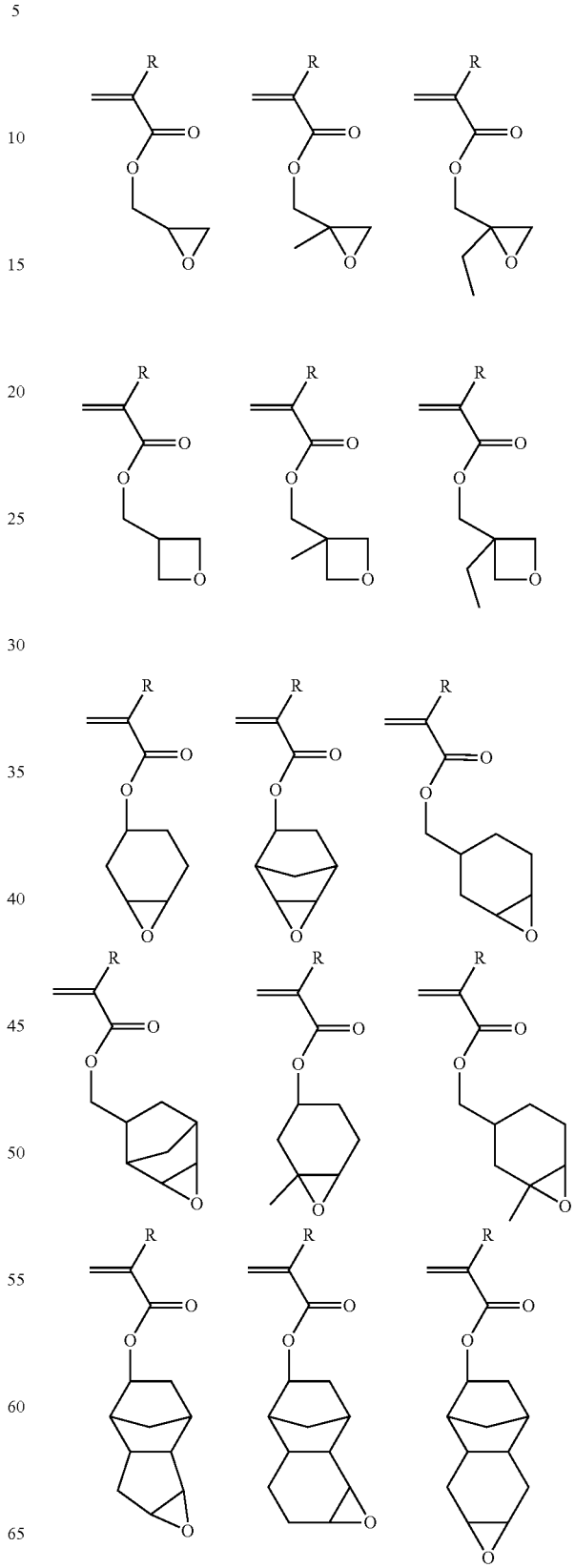

149
-continued
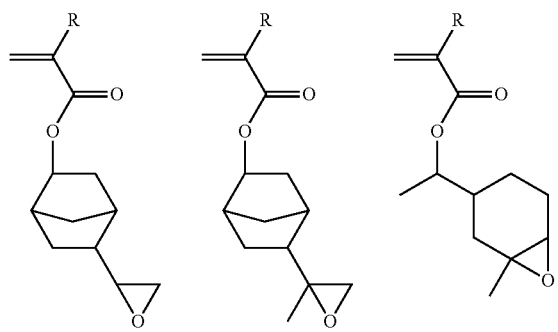
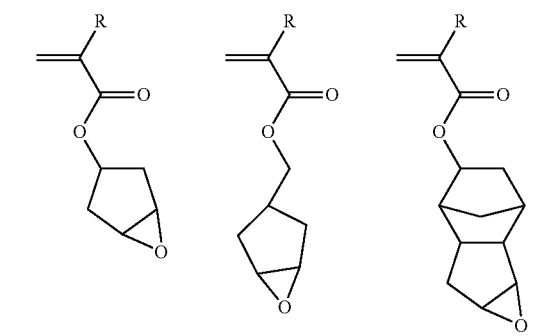
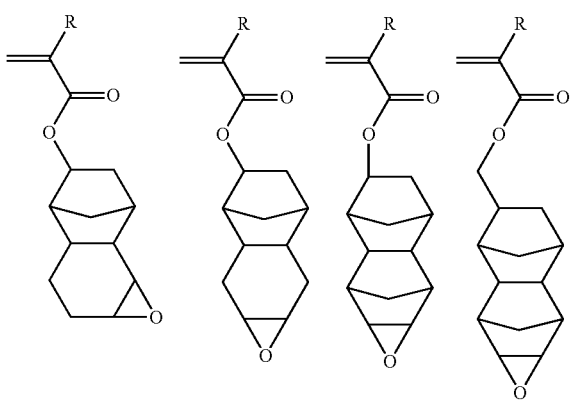
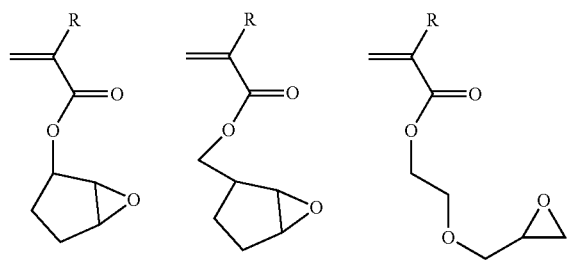
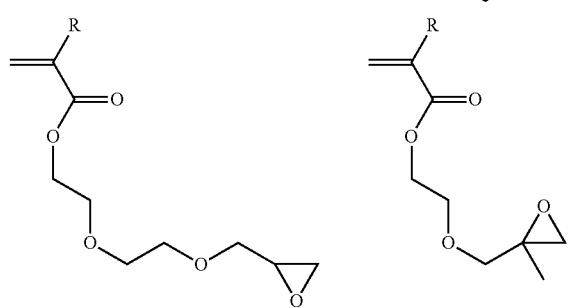
150
-continued
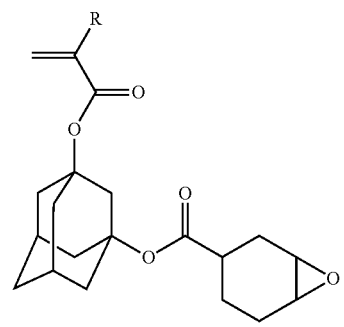
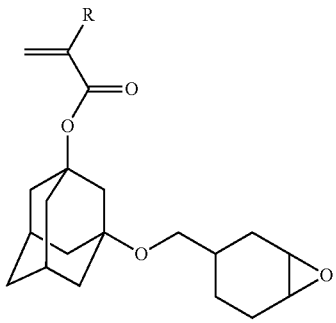
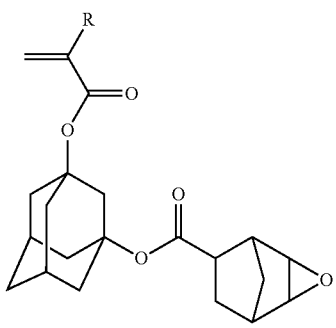
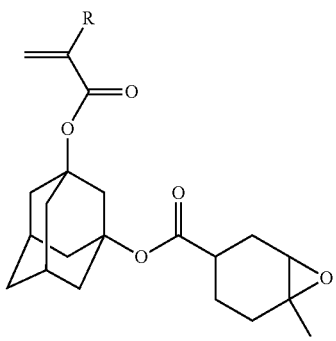
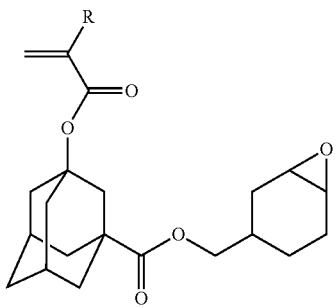

-continued
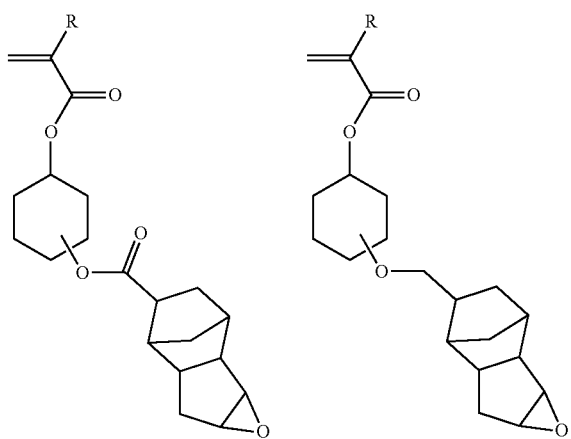
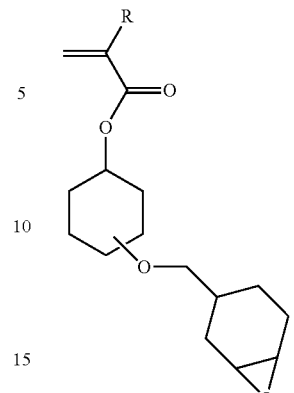
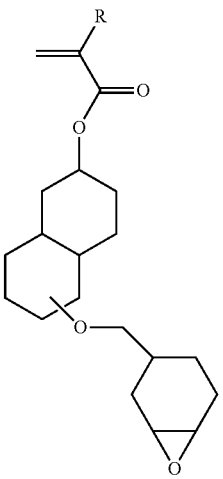
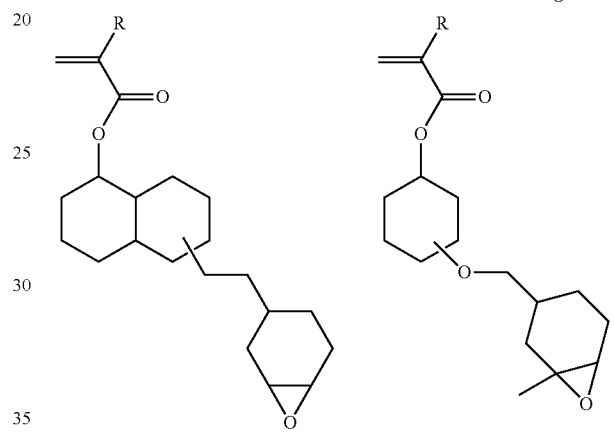
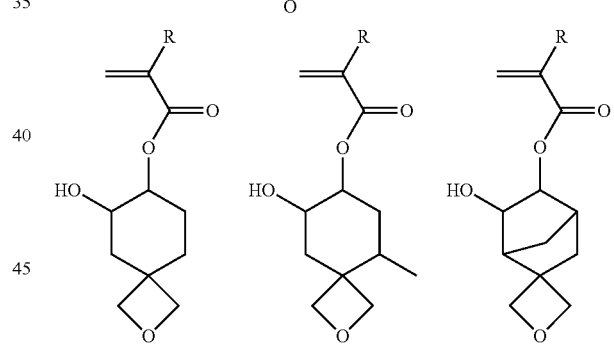
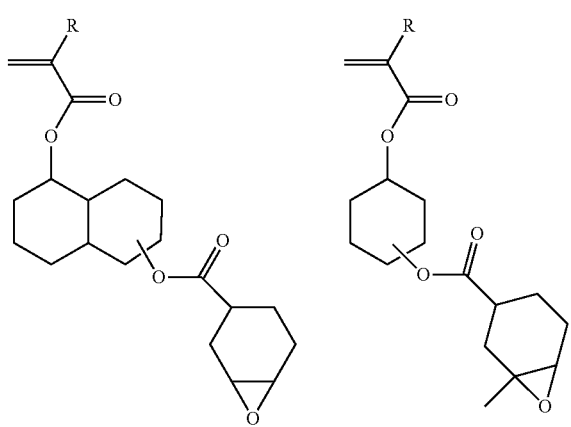
In these formulae, R represents a hydrogen atom or a methyl group.

(Repeating Unit F)
The polymer compound of the component (A) of the bio-electrode composition can also be copolymerized with a repeating unit F having silicon, in addition to the repeating units A1 to A7 and B to E. Specific examples of a monomer to give the repeating unit F having silicon include the following.
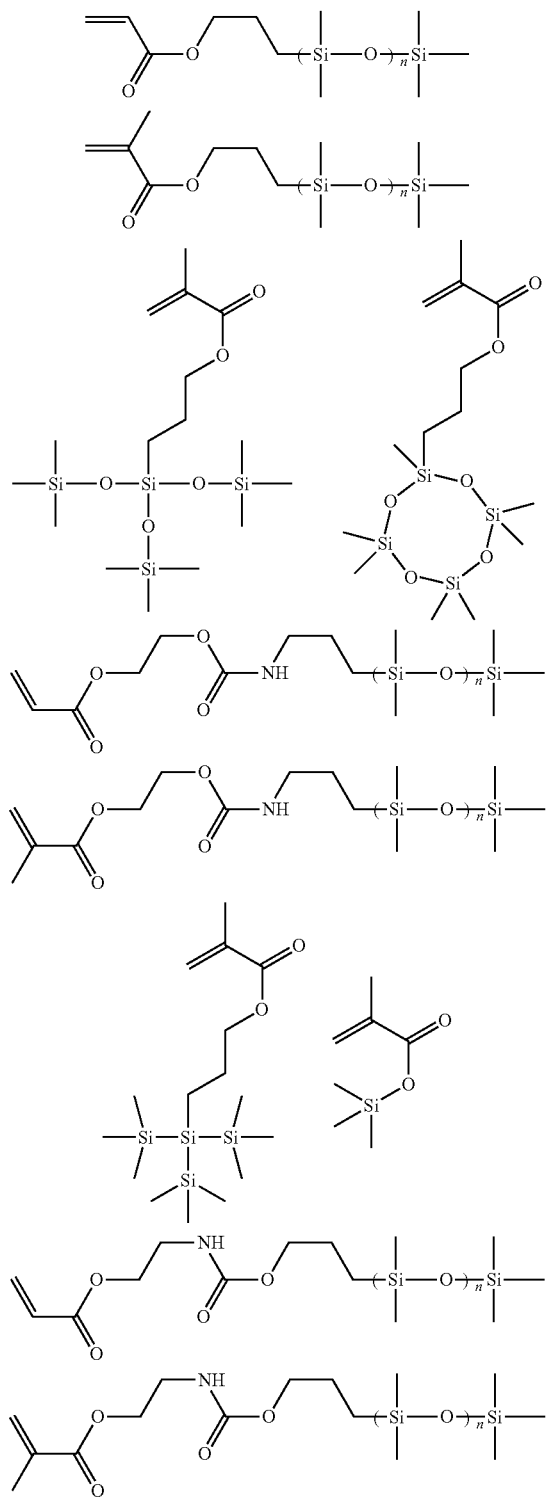
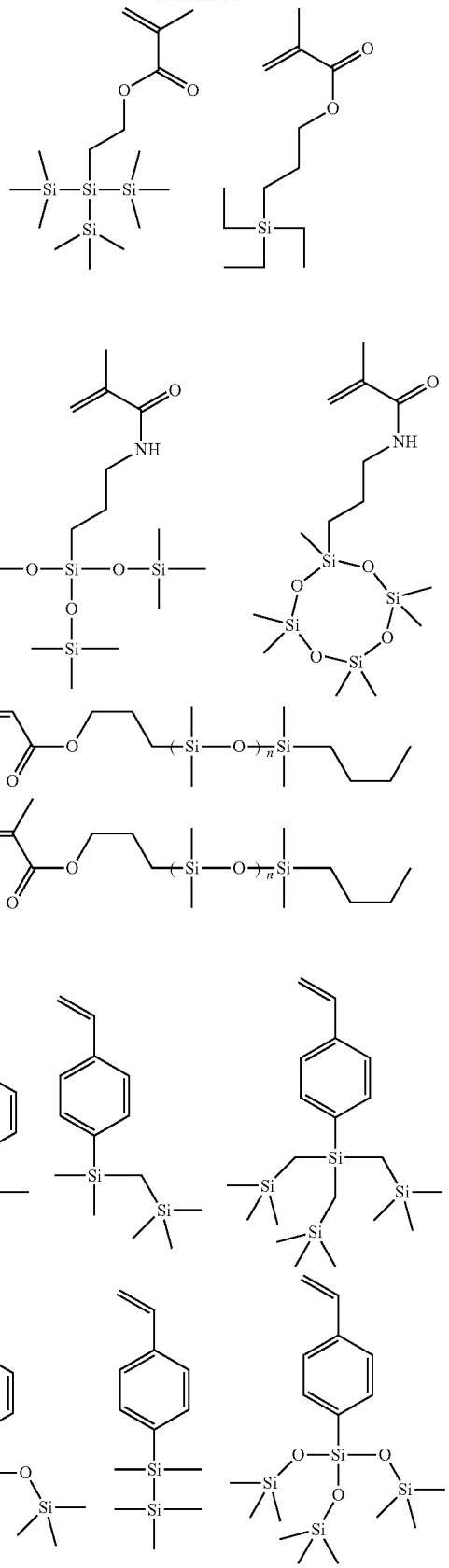
"n" represents the number in a range of 1 to 50.

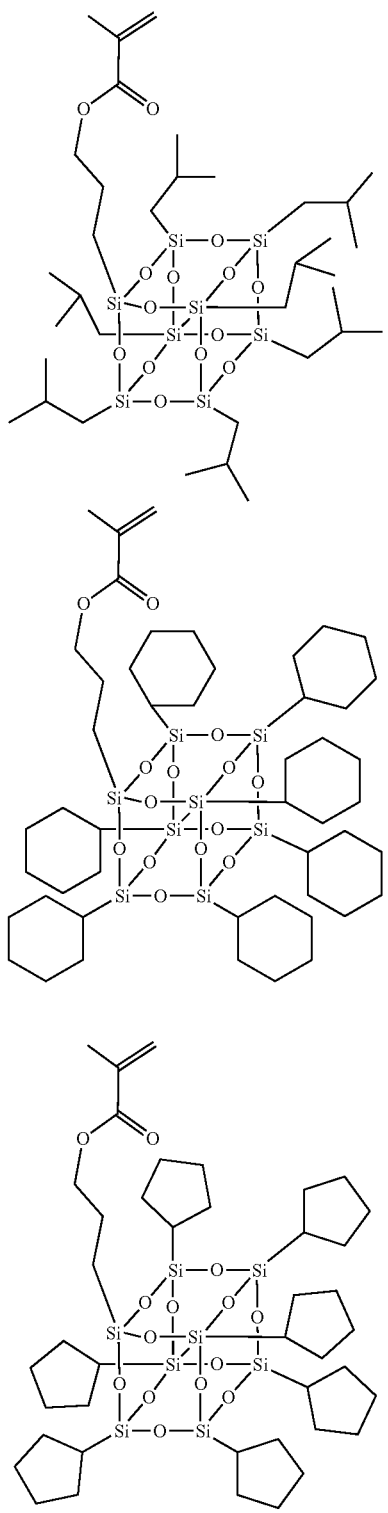
(Repeating Unit G)
The polymer compound of the component (A) of the bio-electrode composition can also be copolymerized with a repeating unit G having fluorine, in addition to the repeating units A1 to A7 and B to F. Specific examples of a monomer to give the repeating unit G having fluorine include the following.
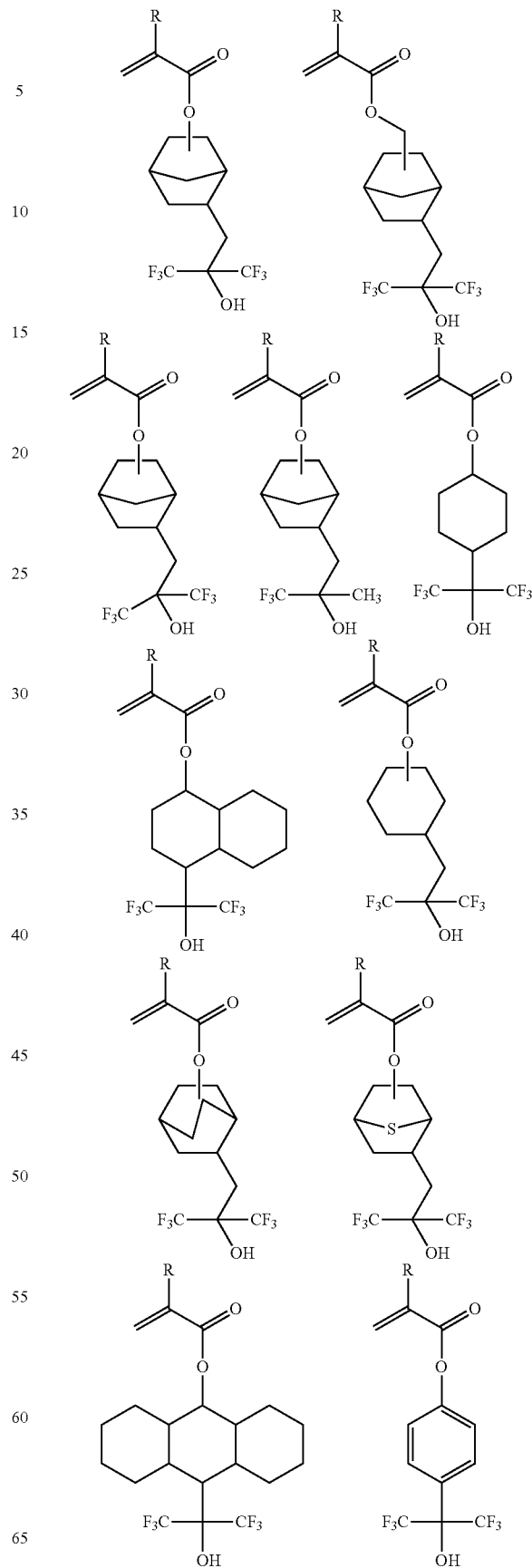

-continued
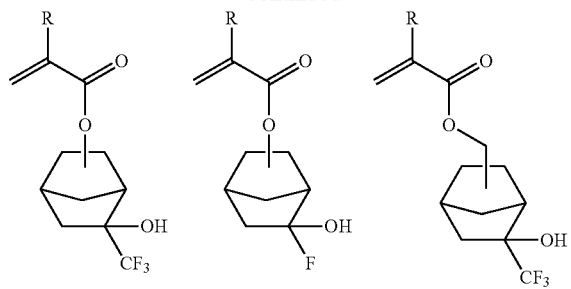
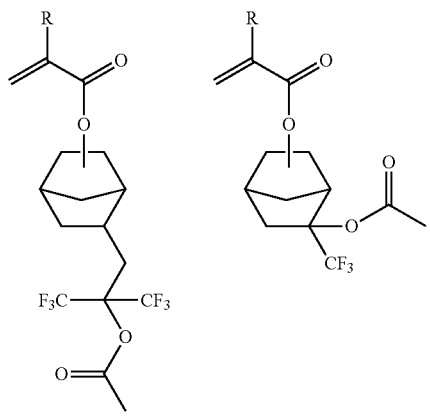
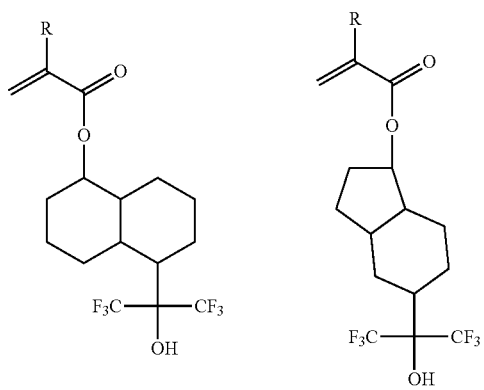
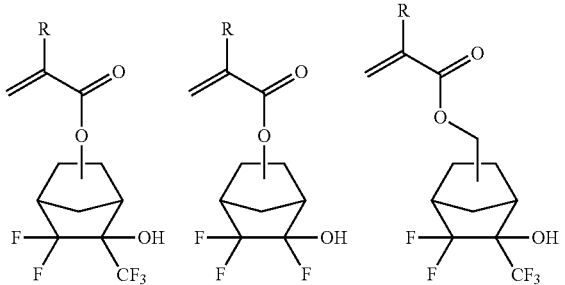
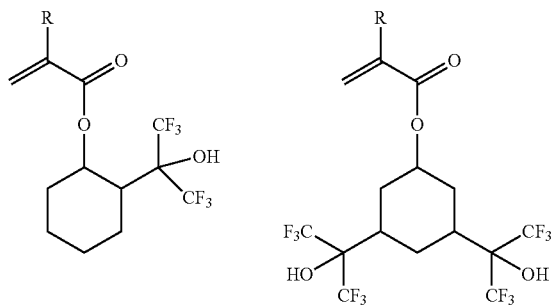
-continued
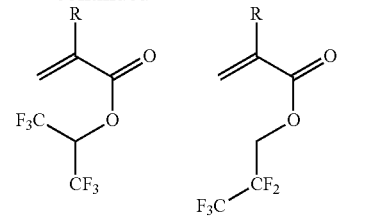
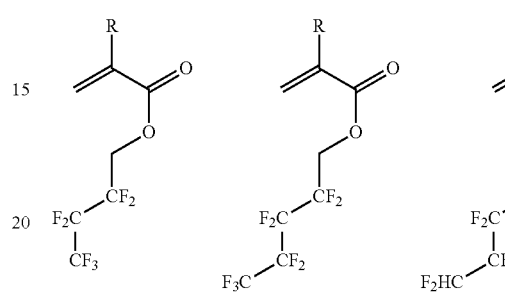
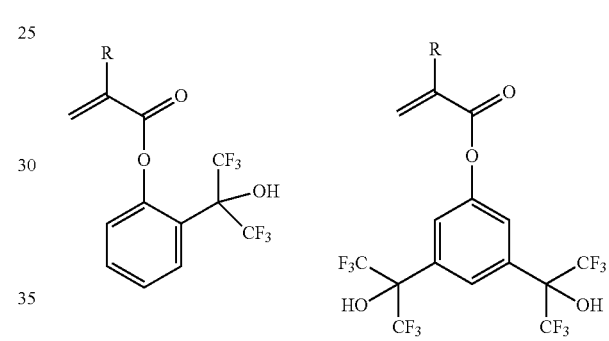
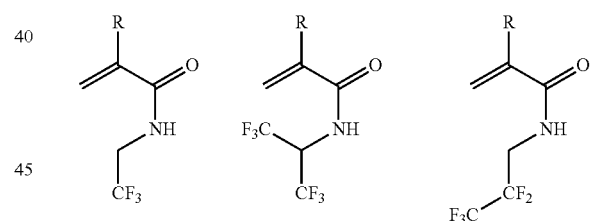
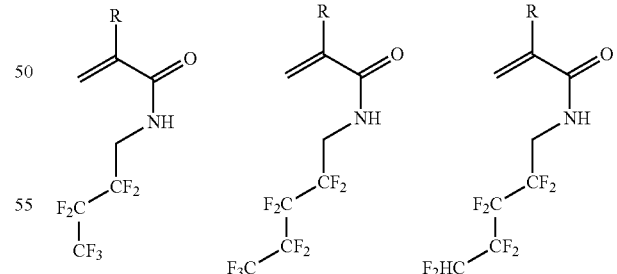
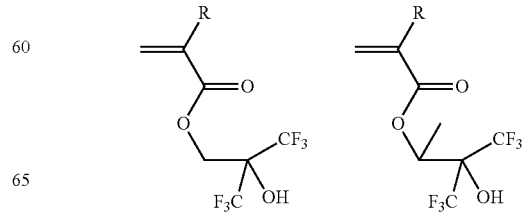

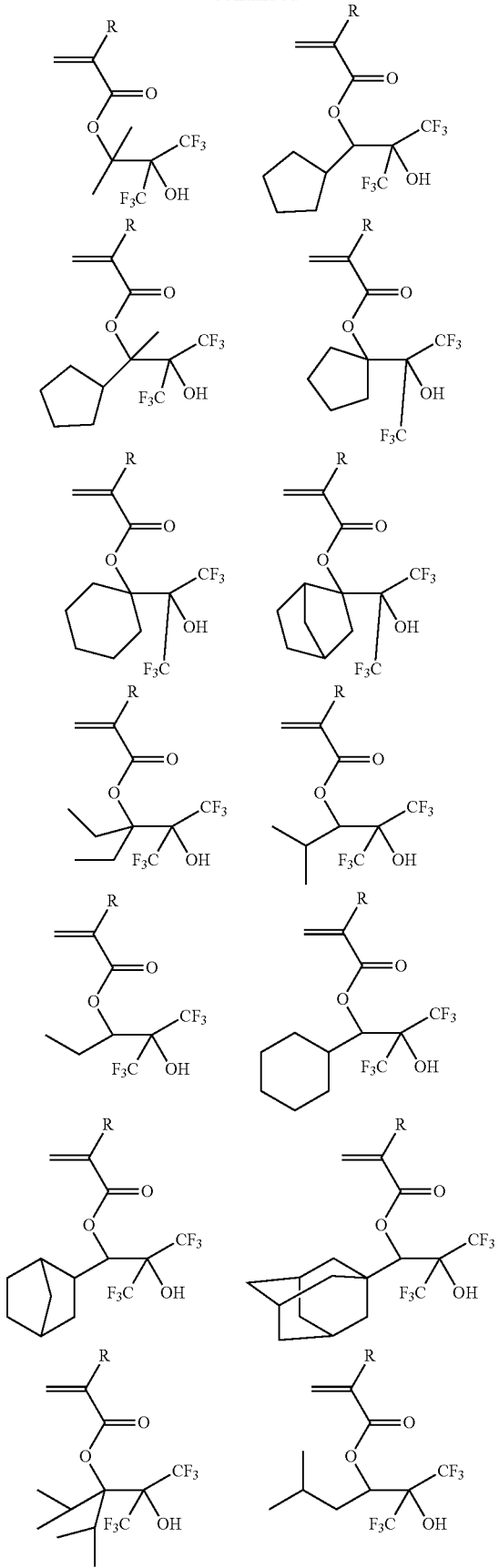
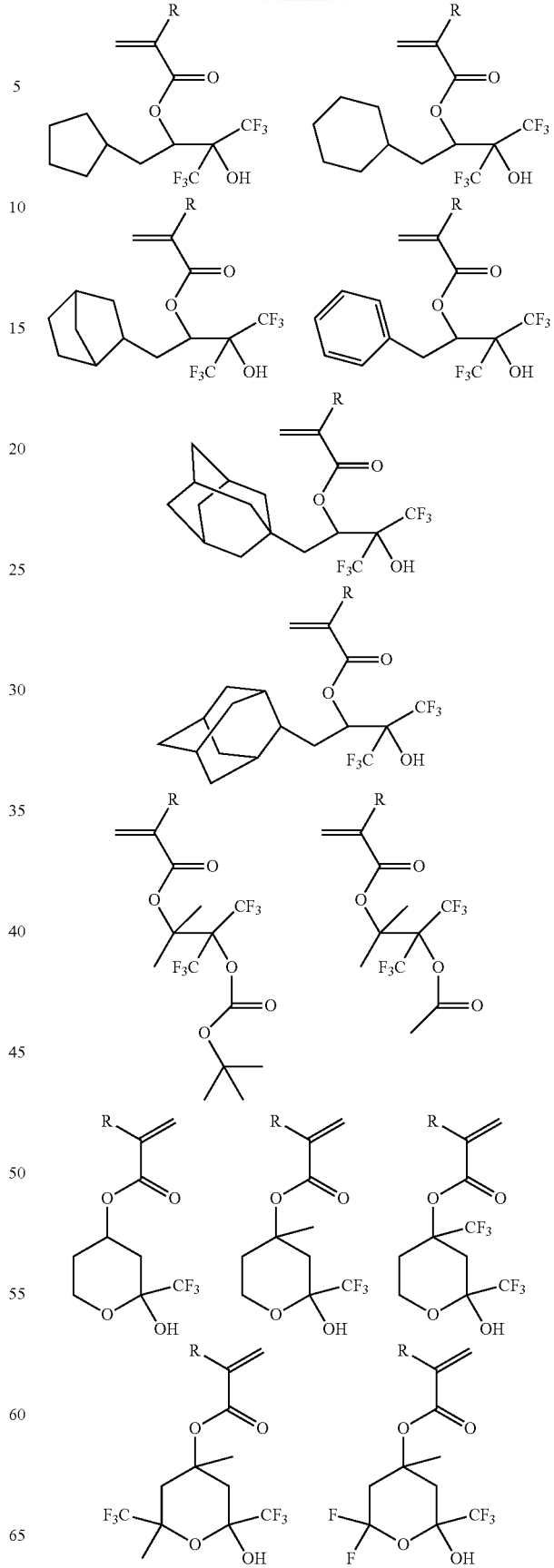

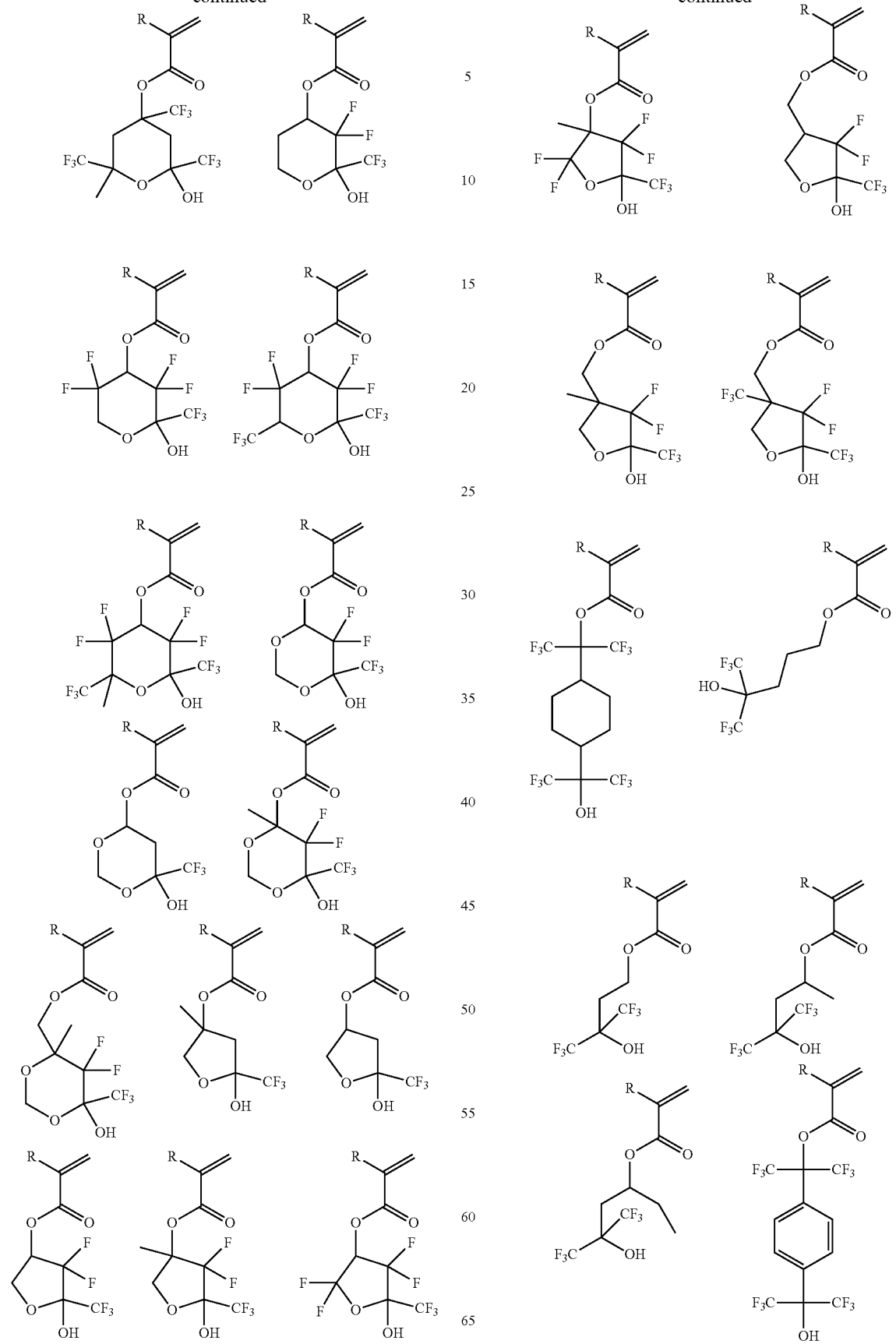

-continued
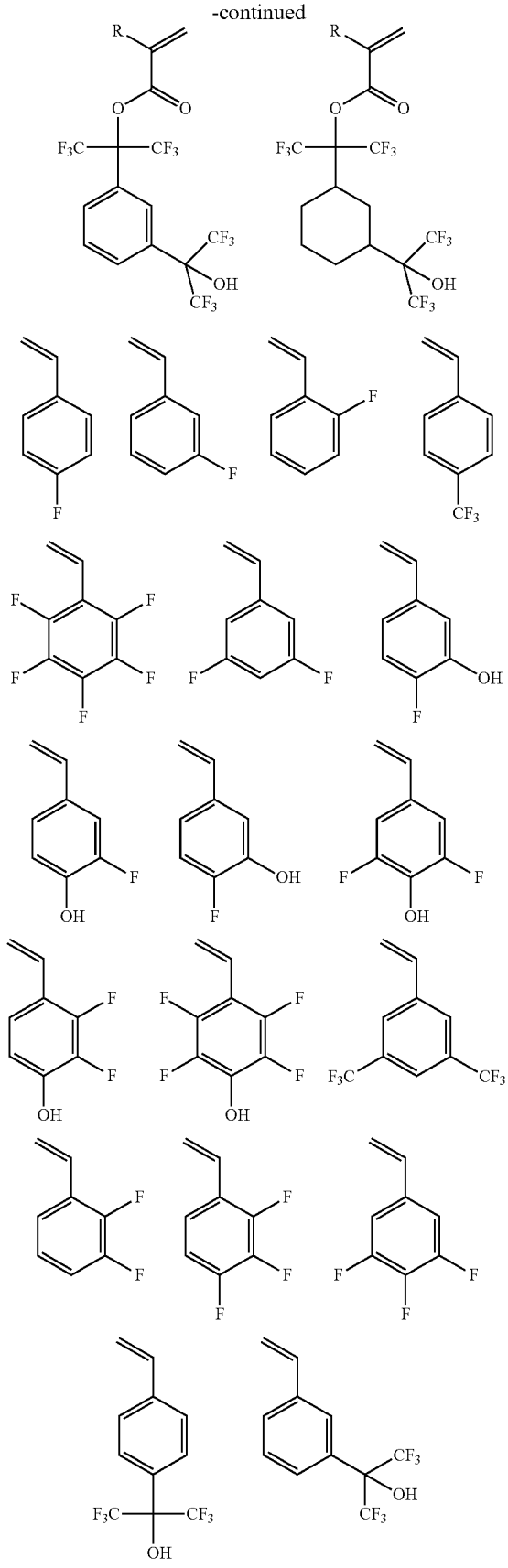
-continued
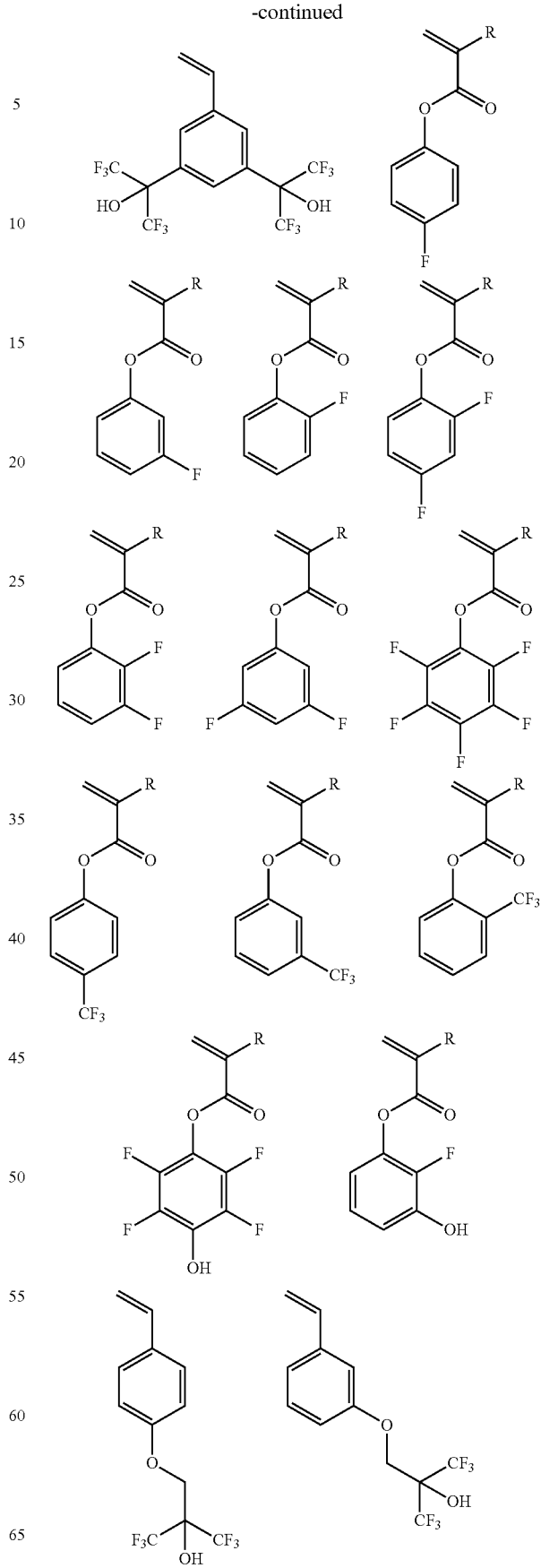

-continued
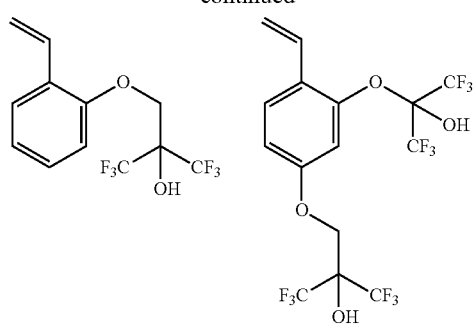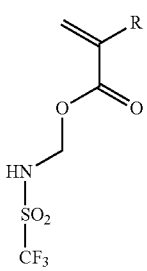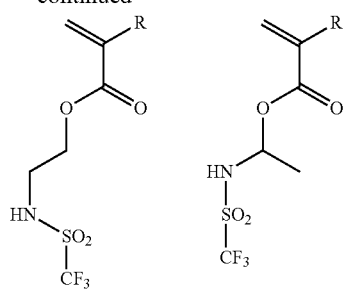
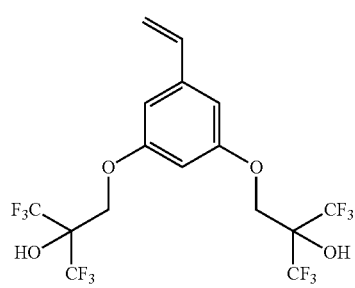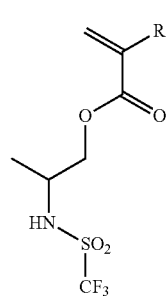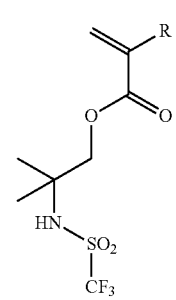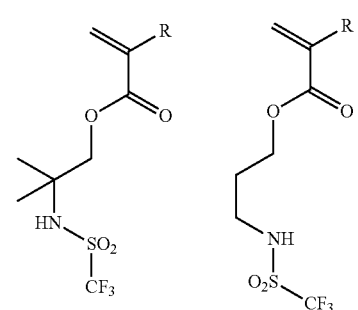
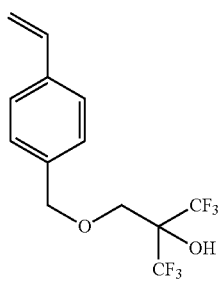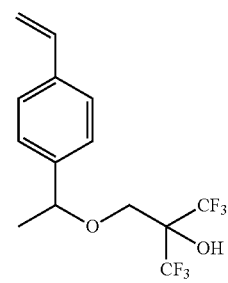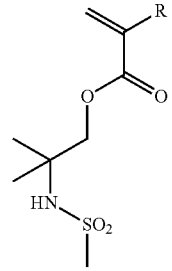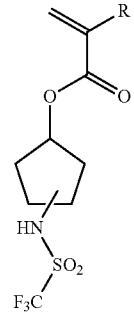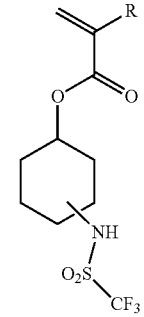
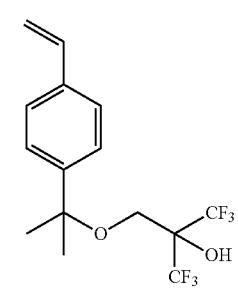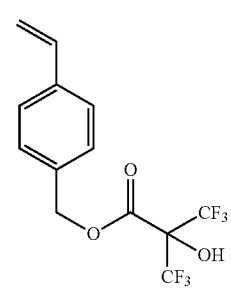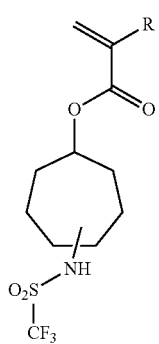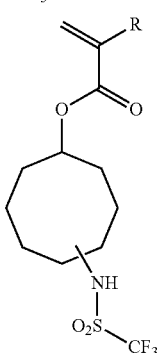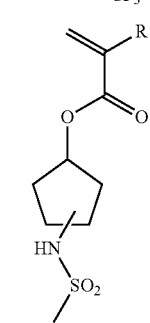
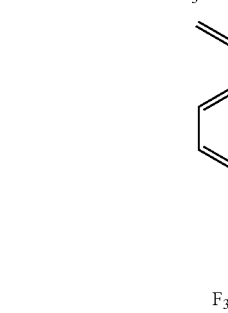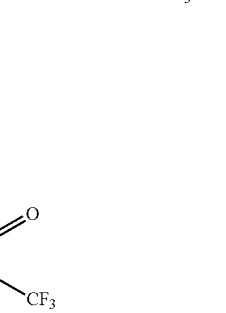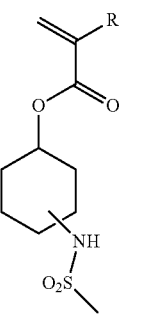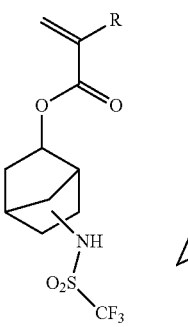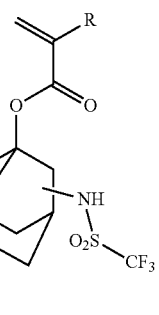

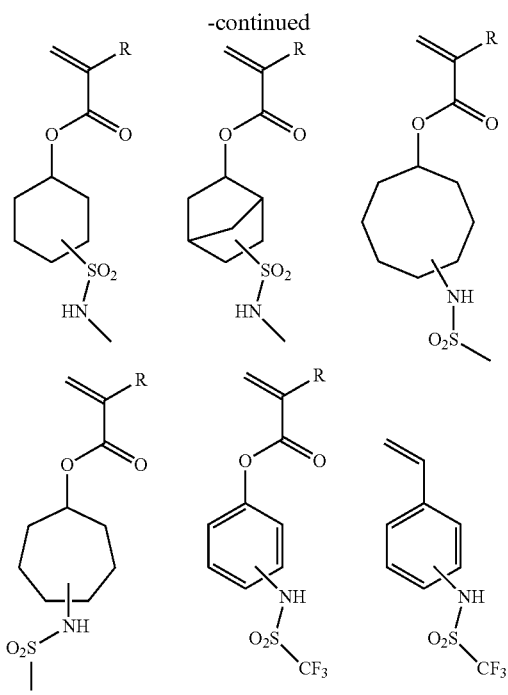

In these formulae, R represents a hydrogen atom or a methyl group.

As one of the method for synthesizing the polymer compound that is the component (A), a copolymer compound can be obtained, for example, by a method in which desired monomer(s) among the monomers to give the repeating units A1 to A7, B, C, D, E, F, and G undergo heat polymerization in an organic solvent to which a radical polymerization initiator is added.

Examples of the organic solvent used in the polymerization include toluene, benzene, tetrahydrofuran, diethyl ether, dioxane, etc. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, etc. The heating temperature is preferably 50 to 80° C., and the reaction time is preferably 2 to 100 hours, more preferably 5 to 20 hours.

Here, the ratios of the repeating units A1 to A7, B, C, D, E, F, and G in the polymer compound (A) are respectively expressed by a1 to a7, b1, c1, d1, e1, f1, and g1, and the ranges thereof can be respectively $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, $0 < a1+a2+a3+a4+a5+a6+a7 \leq 1.0$, $0 \leq b1 < 1.0$, $0 \leq c1 < 1.0$, $0 \leq d1 < 1.0$, $0 \leq e1 < 0.9$, $0 \leq f1 < 0.9$, and $0 \leq g1 < 0.9$; preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.9$, $0.03 \leq b1 \leq 0.9$, $0 c1 \leq 0.8$, $0 \leq d1 \leq 0.8$, $0 \leq e1 < 0.8$, $0 \leq f1 < 0.8$, and $0 \leq g1 < 0.8$; more preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.8$, $0.05 \leq b1 \leq 0.9$, $0 c1 \leq 0.7$, $0 \leq 1 \leq 0.5$, $0 \leq e1 < 0.3$, $0 \leq f1 < 0.7$, and $0 \leq g1 < 0.7$.

Incidentally, for example, $a1+a2+a3+a4+a5+a6+a7+b1+c1+d1+e1+f1+g1=1$ means that the total amount of the repeating units A1, A2, A3, A4, A5, A6, A7, B, C, D, E, F, and G is 100 mol % on the basis of the total amount of the whole repeating units in the polymer compound containing the repeating units A1, A2, A3, A4, A5, A6, A7, B, C, D, E, F, and G. $a1+a2+a3+a4+a5+a6+a7+b1+c1+d1+e1+f1+g1<1$ means that the total amount of the repeating units A1, A2, A3, A4, A5, A6, A7, B, C, D, E, F, and G is less than 100 mol % on the basis of the total amount of the whole repeating units, which indicates that the polymer compound contains another repeating unit(s) besides the repeating units A1, A2, A3, A4, A5, A6, A7, B, C, D, E, F, and G.

Regarding the molecular weight of the polymer compound of the component (A), the weight-average molecular weight is preferably 500 or more, more preferably 1,000 or more and 1,000,000 or less, further preferably 2,000 or more and 500,000 or less. Regarding the ionic monomer (residual monomer) that is not incorporated into the polymer compound of the component (A) after polymerization, if the amount is small, the residual monomer can be prevented from permeating to skin in a biocompatibility test to cause allergy. Accordingly, it is preferable to decrease the amount of residual monomer(s). The amount of residual monomer(s) is preferably 10 parts by mass or less on the basis of 100 parts by mass of the whole polymer compound of the component (A). As the component (A), one kind of the polymer compound may be used singly or in admixture of two or more kinds which differ in molecular weight, dispersity, and constitutive polymerizable monomer.

[(B) Resin]

A resin (B) (component (B)) blendable into the bio-electrode composition is a component for: preventing elution of the ionic material (salt) of the polymer compound (A) by being compatibilized with the salt, metal powder; holding an electric conductivity improver such as a carbon material, a silicon powder, or a lithium titanate powder; and for achieving adhesion. When the ionic material of the polymer compound (A) has adhesion, the resin (B) is not necessarily essential. It is to be noted that the resin may be any resin other than the polymer compound of the component (A), and is preferably either or both of a thermosetting resin and a photo-curable resin, particularly preferably one or more resins selected from the group consisting of silicone based, acrylic based, and urethane based resins.

The adherent (adhesive) silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having $R_3SiO_{0.5}$ and $SiO_2$ units, organohydrogenpolysiloxane having a plurality of SiH groups, a platinum catalyst, an addition reaction inhibitor, and an organic solvent, for example, described in JP 2015-193803A. As the radical curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols and improves adhesive strength by addition of it, but does not bind to the polysiloxane in molecular level because it is not crosslinkable. The adhesive strength can be increased by integrating the polysiloxane and the resin as described above.

The silicone resin may contain modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the polymer compound of the component (A) in the silicone resin. The modified siloxane may be modified at any part such as one terminal, both terminals, or a side chain of the siloxane.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the bio-electrode composition, the resin (B) preferably has high compatibility with the polymer compound of the component (A) to prevent lowering of the electric conductivity due to elution of the polymer compound of the component (A) from the living body contact layer. In the bio-electrode composition, the resin (B) preferably has high adhesion to the electro-conductive base material (substrate) to prevent peeling of the living body contact layer from the electro-conductive base material. In order to increase the compatibility of the resin with the electro-conductive base material and the salt, the use of a resin with high polarity is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin, etc. On the other hand, the living body contact layer comes into contact with a living body, thereby being susceptible to perspiration. Accordingly, in the bio-electrode composition, the resin (B) preferably has high repellency and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, silsesquioxane, siloxane having a (meth)acrylpropyl group, or the like can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating thereof. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s). Particularly, a polyurethane main chain having a silicone chain on a side chain as described in JP 2018-123304 A and JP 2019-70109A is preferable because of the properties of high strength and high stretchability.

The silicon atom-containing polythiourethane resin can be obtained by reaction of a compound having a thiol group(s) and a compound having an isocyanate group(s), provided that either of them contains a silicon atom(s). It can also be photo-cured if (meth)acrylate groups are contained at the terminals.

The compatibility of the silicone base resin with the foregoing salt is improved by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

In the bio-electrode composition, the amount of the component (B) blended is preferably 0 to 2000 parts by mass, more preferably 10 to 1000 parts by mass, on the basis of 100 parts by mass of the ion polymer of the polymer compound (A). One kind of the resin (B) may be used singly or in admixture of two or more kinds.

As described above, the living body contact layer of the inventive bio-electrode is a cured product of the bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou hannou handbook (handbook of crosslinking reaction)", Chapter 2, pages 51-371, Yasuharu Nakayama, Maruzen Publishing Co., Ltd. (2013).

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

The amount of the platinum catalyst added is preferably in a range of 5 to 2,000 ppm, particularly preferably 10 to 500 ppm, on the basis of 100 parts by mass of the resin including the polymer compound (A) and the resin (B).

When the addition curable silicone resin is used, an addition reaction inhibitor may be added. This addition reaction inhibitor is added as a quencher to prevent the action of the platinum catalyst in the solution and under a low temperature circumstance after forming the coating film and before heat curing. Specific examples of the addition reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The amount of the addition reaction inhibitor added is preferably in a range of 0 to 10 parts by mass, particularly preferably 0.05 to 3 parts by mass, on the basis of 100 parts by mass of the resin.

Examples of the photo-curing method include a method of adding a photoradical generator to generate radical by light, together with a resin having a (meth)acrylate terminal(s) or an olefin terminal(s), or a crosslinking agent with the terminal(s) being (meth)acrylate, olefin, or a thiol group(s); and a method of adding a photo-acid generator to generate acid by light, together with a resin or a crosslinking agent having an oxirane group(s), an oxetane group(s), or a vinyl ether group(s).

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

Examples of the photo-acid generator include sulfonium salt, iodonium salt, sulfonyldiazomethane, N-sulfonyloxyimide, oxime-O-sulfonate type acid generators, etc. Specific examples of the photo-acid generator include ones described in paragraphs to of JP 2008-111103A, and in JP 2009-080474A.

The amount of the radical generator or photo-acid generator added is preferably in a range of 0.1 to 50 parts by mass on the basis of 100 parts by mass of the resin.

Among them, the resin of the component (B) particularly preferably contains: a silicone resin having an $SiO_2$ unit and an $R_xSiO_{(4-x)/2}$ unit, where R represents a substituted or unsubstituted monovalent hydrocarbon group having 1 to 10 carbon atoms, and "x" is a number in a range of 2.5 to 3.5; diorganosiloxane having an alkenyl group; and organohydrogenpolysiloxane having an SiH group.

[Metal Powder]

The bio-electrode composition can also contain a metal powder selected from the group consisting of gold, silver, platinum, copper, tin, titanium, nickel, aluminum, tungsten, molybdenum, ruthenium, chromium, and indium in order to improve electron conductivity. The amount of the metal powder added is preferably in a range of 1 to 50 parts by mass on the basis of 100 parts by mass of the resin.

As the kind of the metal powder, gold, silver, and platinum are preferable in view of electric conductivity; and silver, copper, tin, titanium, nickel, aluminum, tungsten, molybdenum, ruthenium, and chromium are preferable in view of cost. In view of biocompatibility, noble metals are preferable. On the whole of these viewpoints, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of not more than 5 g/cm$^3$, and a specific surface area of not less than 0.5 m$^2$/g.

[Carbon Material]

A carbon material can be added as an electric conductivity improver. Examples of the carbon material include carbon black, graphite, carbon nanotube, carbon fiber, etc. The carbon nanotube may be either single layer or multilayer, and the surface may be modified with an organic group(s). The amount of the carbon material added is preferably in a range of 1 to 50 parts by mass on the basis of 100 parts by mass of the resin.

[Silicon Powder]

The bio-electrode composition may contain a silicon powder to enhance ion reception sensitivity. Examples of the silicon powder include powders of silicon, silicon monoxide, or silicon carbide. The particle diameter of the powder is preferably smaller than 100 μm, more preferably 1 μm or less. Since finer particles have a larger surface area, the resulting bio-electrode can receive a larger amount of ions and has higher sensitivity. The amount of the silicon powder added is preferably in a range of 1 to 50 parts by mass on the basis of 100 parts by mass of the resin.

[Lithium Titanate Powder]

The bio-electrode composition may contain a lithium titanate powder to enhance ion reception sensitivity. Examples of the lithium titanate powder include ones containing materials shown by molecular formulae $Li_2TiO_3$, $LiTiO_2$, and $Li_4Ti_5O_{12}$ with a spinel structure, preferably ones with a spinel structure. It is also possible to use carbon-incorporated lithium titanate particles. The particle diameter of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The amount of the lithium titanate powder added is preferably in a range of 1 to 50 parts by mass on the basis of 100 parts by mass of the resin.

[Tackifier]

The bio-electrode composition may also contain a tackifier in order to have adhesion to a living body. Examples of such a tackifier include silicone resin, non-crosslinkable siloxane, non-crosslinkable poly(meth)acrylate, non-crosslinkable polyether, etc.

[Crosslinking Agent]

The bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass on the basis of 100 parts by mass of the resin.

[Crosslinking Catalyst]

The bio-electrode composition may also contain a catalyst for crosslinking the epoxy groups or the oxetane groups. As this catalyst, ones described in paragraphs 0027 to 0029 of JP 2019-503406A can be used. The amount of the catalyst added is preferably 0.01 to 10 parts by mass on the basis of 100 parts by mass of the resin.

[Ionic Additive]

The bio-electrode composition may contain an ionic additive to increase ionic conductivity. In consideration of biocompatibility, examples of the ionic additive include sodium chloride, potassium chloride, calcium chloride, magnesium chloride, saccharin sodium salt, acesulfame potassium, and salts disclosed in JP 2018-44147A, JP 2018-59050A, JP 2018-59052A, and JP 2018-130534A.

The inventive bio-electrode composition can also contain a silicone compound (C) having a polyglycerin structure (component (C)). The component (C) is blended in an amount of preferably 0.01 to 100 parts by mass, more preferably 0.5 to 60 parts by mass, on the basis of 100 parts by mass of the component (A). One kind of the component (C) may be used singly or in admixture of two or more kinds.

The silicone compound (C) having a polyglycerin structure is preferably shown by the following general formula (3) or (4).

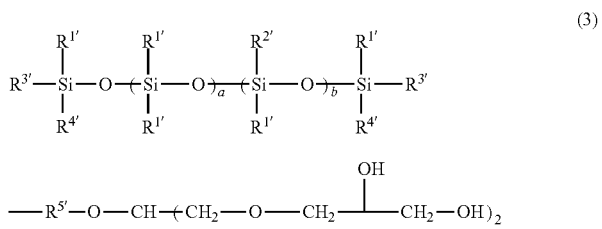

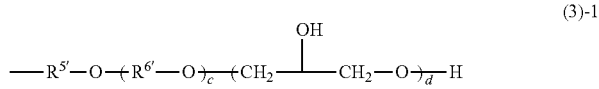

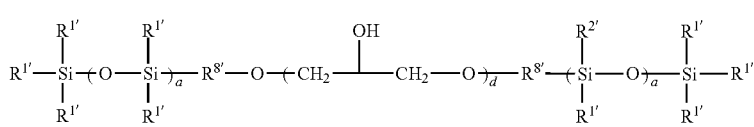

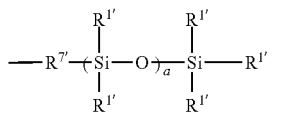

In the formulae (3) and (4), each $R^{1\prime}$ is identical to or different from each other and independently represents a linear alkyl group having 1 to 50 carbon atoms, a branched alkyl group having 3 to 50 carbon atoms, a phenyl group, or a silicone chain shown by a general formula (5), and optionally contains an ether group. $R^{2\prime}$ represents a group having a polyglycerin group structure shown by a general formula (3)-1 or (3)-2. Each $R^{3\prime}$ is identical to or different from each other and independently represents the $R^{1\prime}$ group or the $R^{2\prime}$ group. Each $R^{4\prime}$ is identical to or different from each other and independently represents the $R^{1\prime}$ group, the $R^{2\prime}$ group, or an oxygen atom. When $R^{4\prime}$ represents an oxygen atom, the two $R^{4\prime}$ moieties are integrated with each other and optionally constitute an ether group to form a ring together with silicon atoms. Each "a" is identical to or different from each other and represents 0 to 100, "b" represents 0 to 100, and a+b is 0 to 200. Nevertheless, when "b" is 0, at least one $R^{3\prime}$ is the $R^{2\prime}$ group. In the general formulae (3)-1 and (3)-2, $R^{5\prime}$ represents an alkylene group having 2 to 10 carbon atoms or an aralkylene group having 7 to 10 carbon atoms. $R^{6\prime}$, $R^{7\prime}$, and $R^{8\prime}$ each represent an alkylene group having 2 to 6 carbon atoms. "c" represents 0 to 20. "d" represents 1 to 20.

Examples of the silicone compound (C) having such a polyglycerin structure include the following.

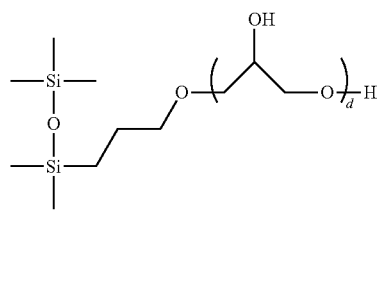
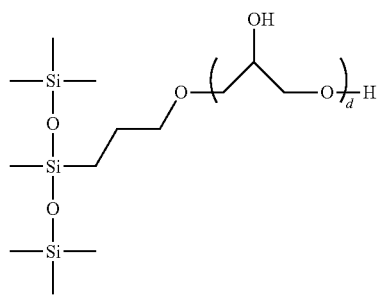
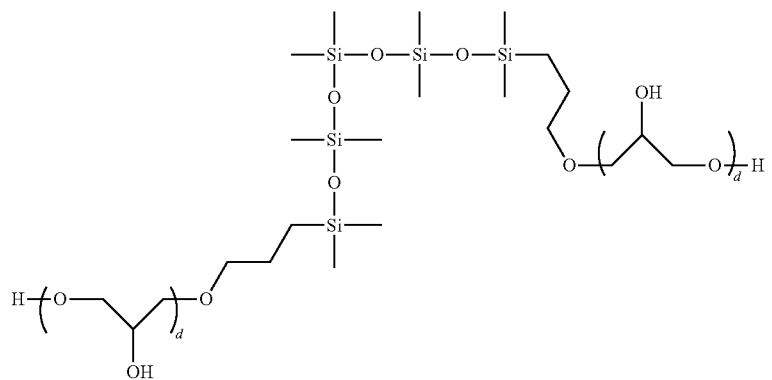
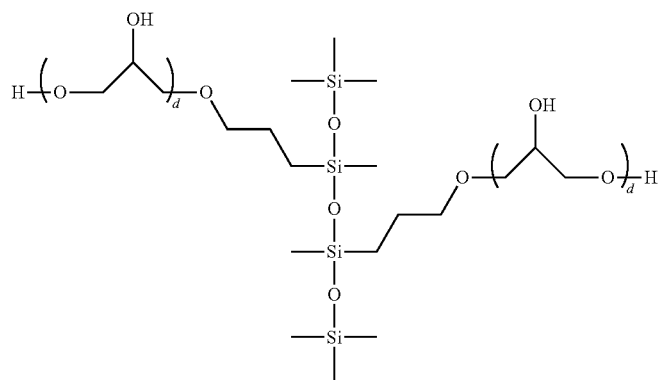
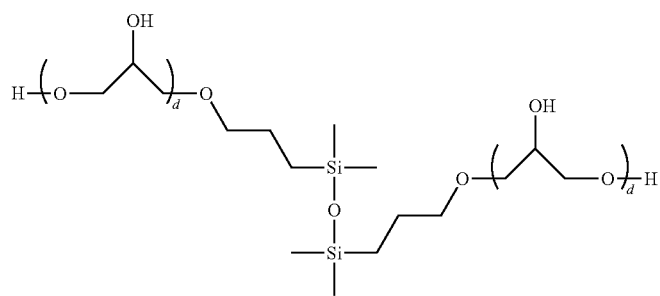

-continued
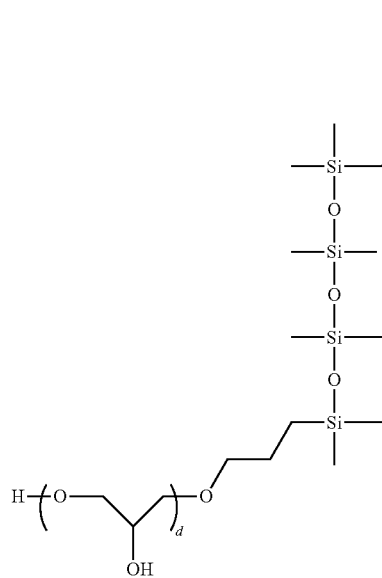
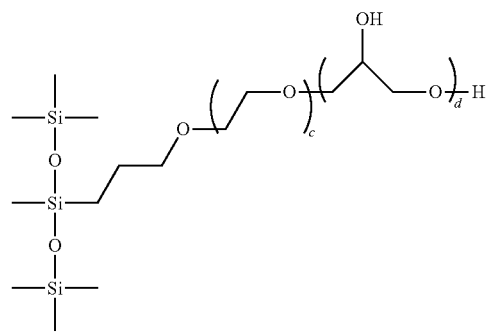
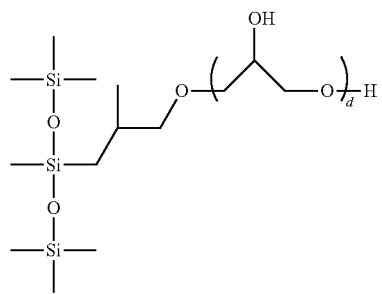
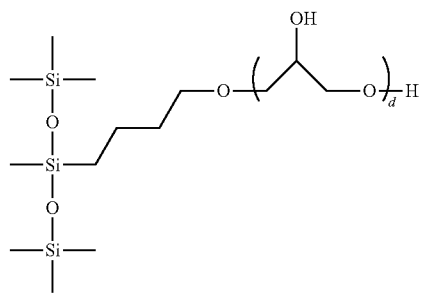
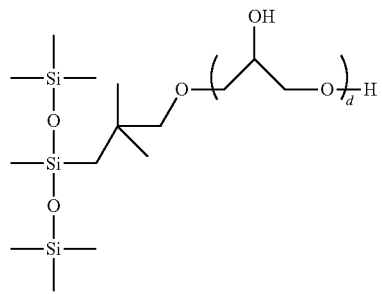
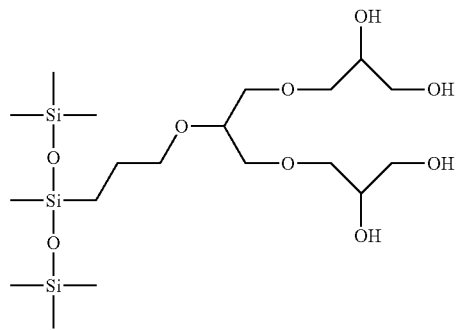
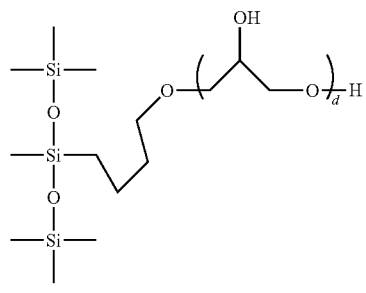
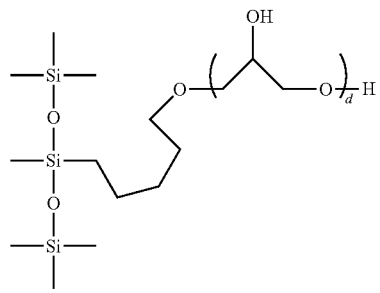

-continued
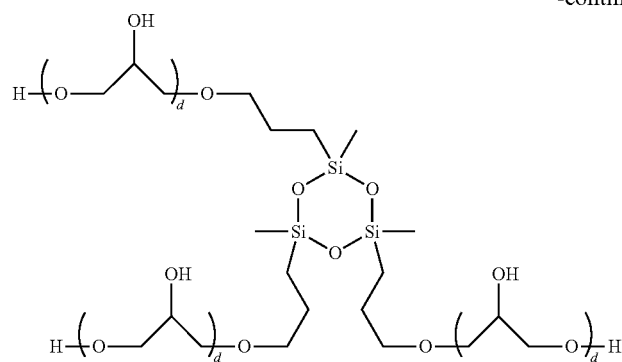
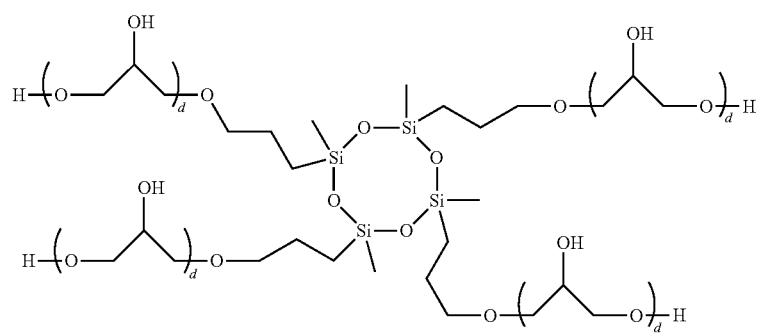
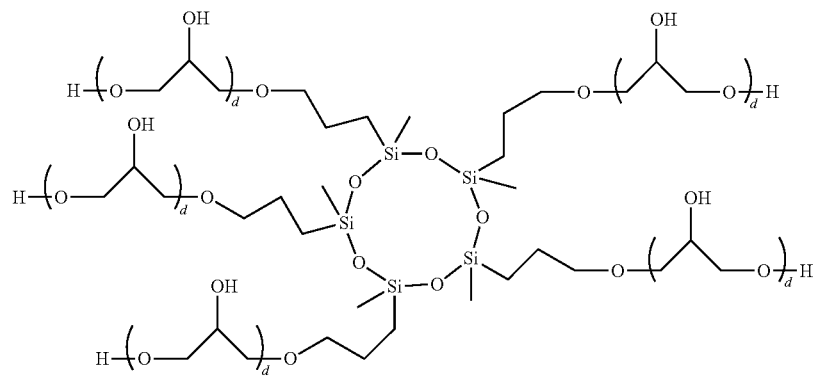
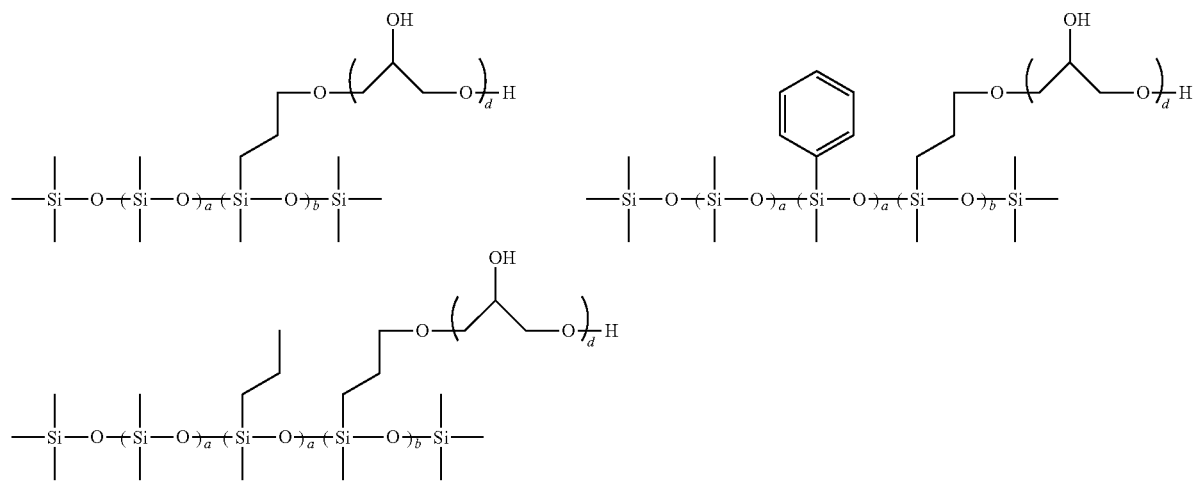

-continued
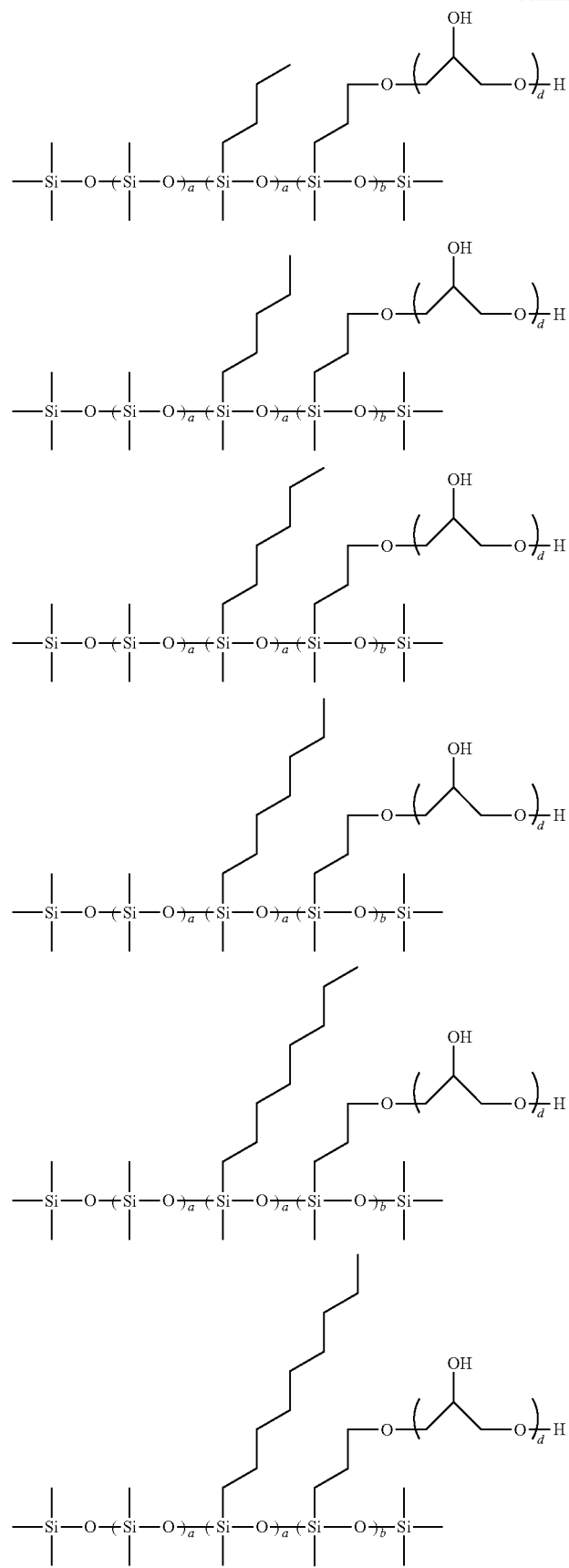

-continued
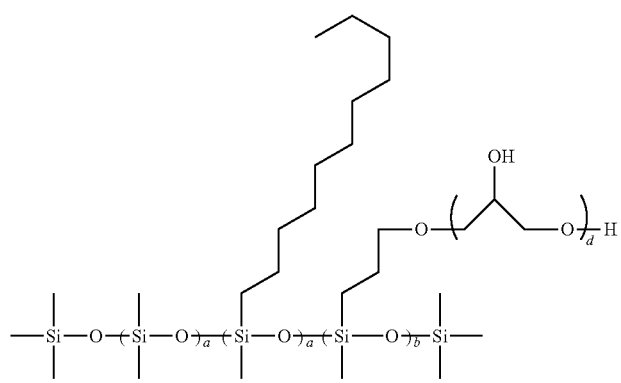
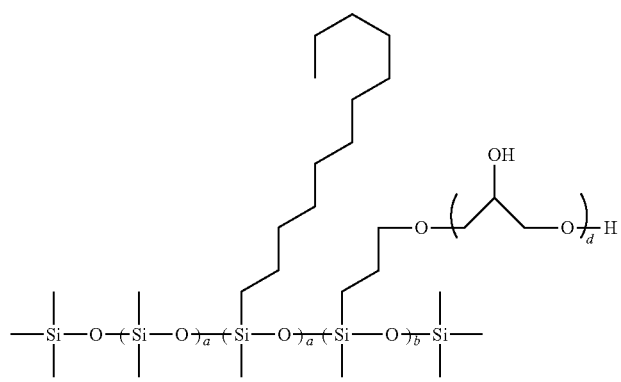
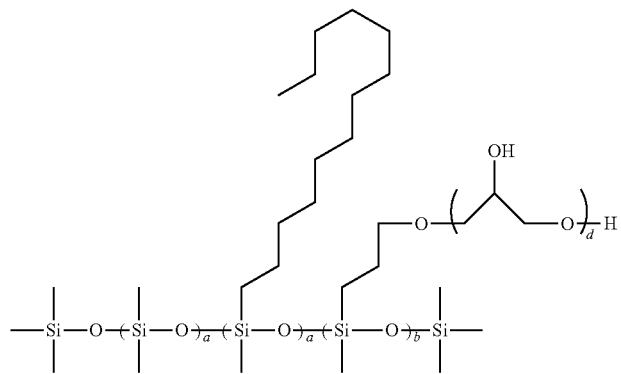
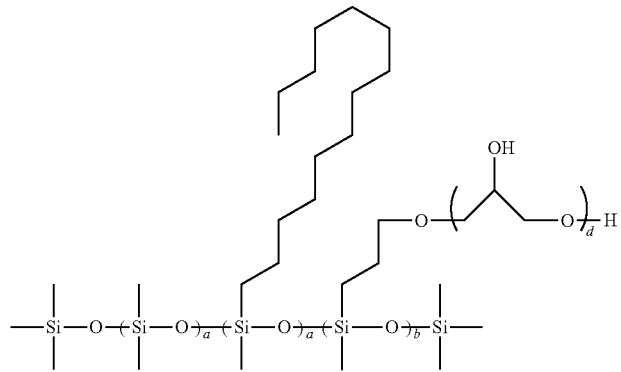

-continued
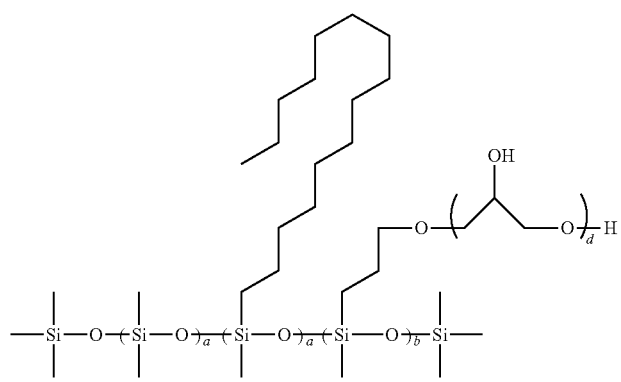
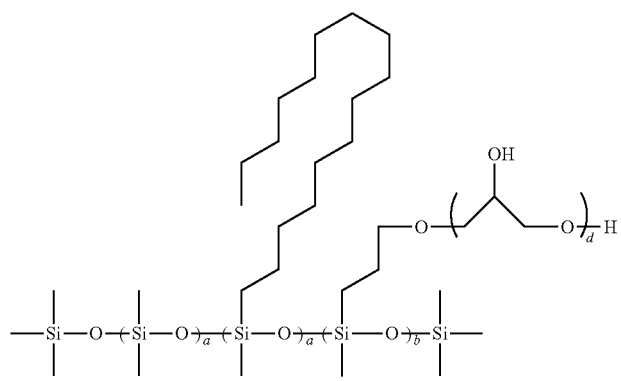
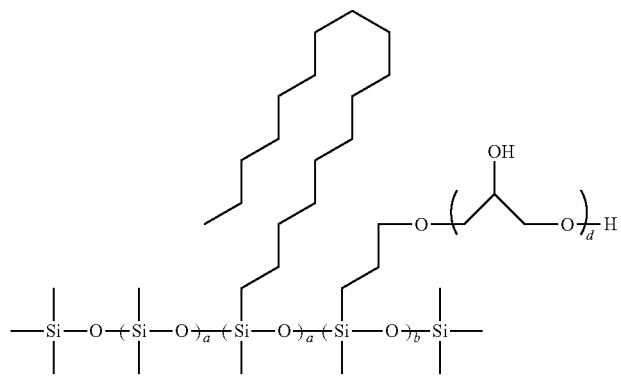
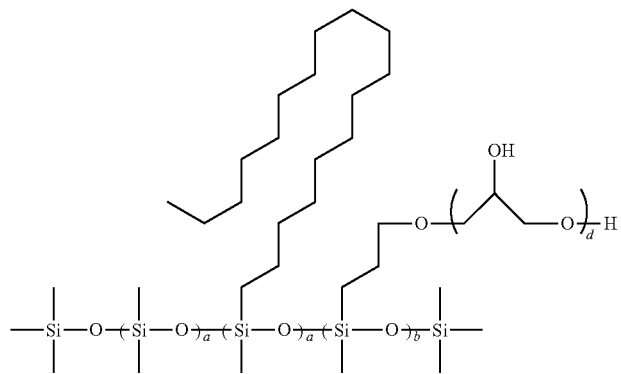

-continued
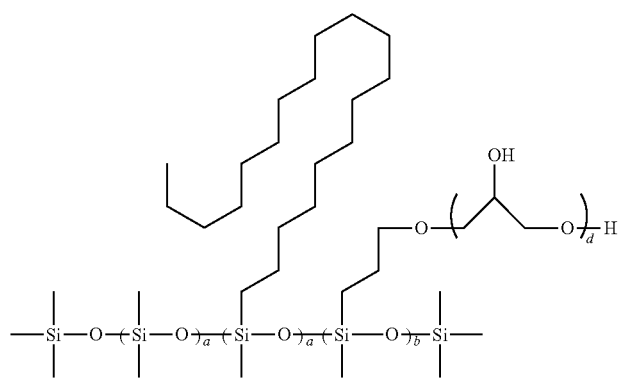
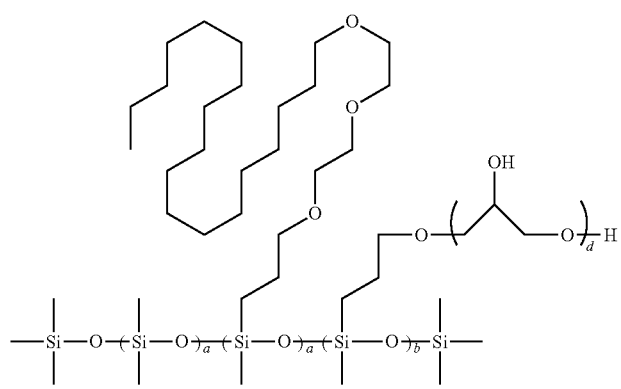
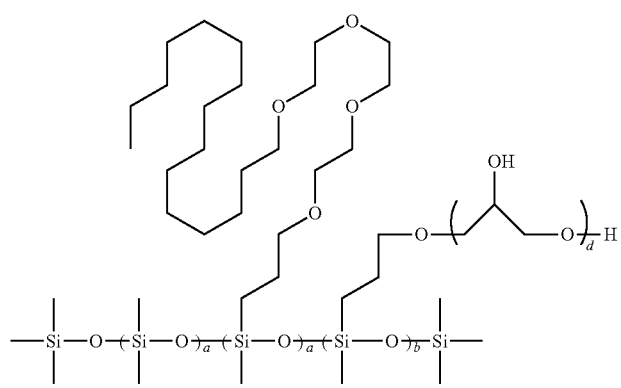
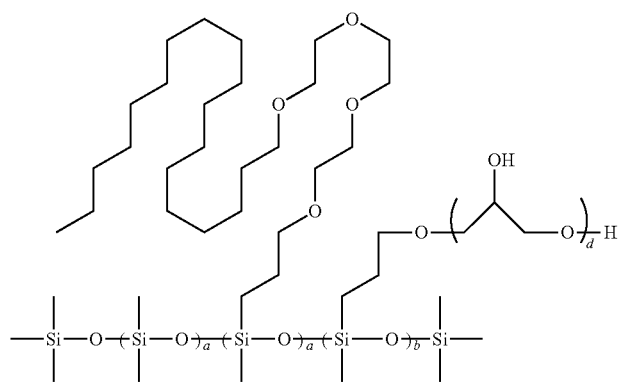

-continued
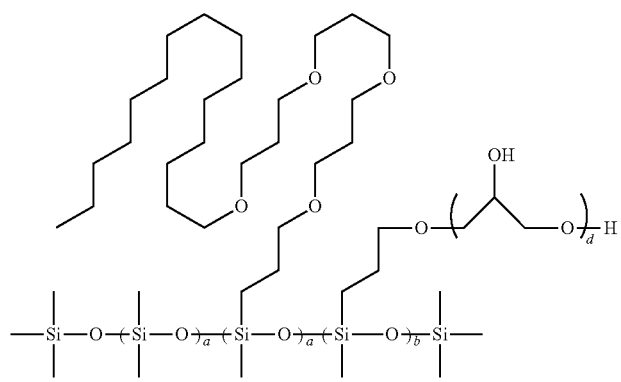
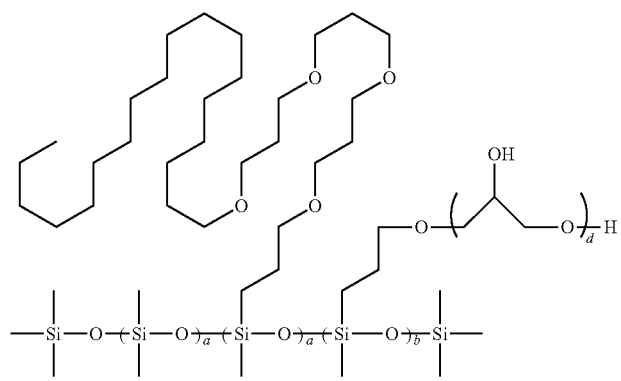
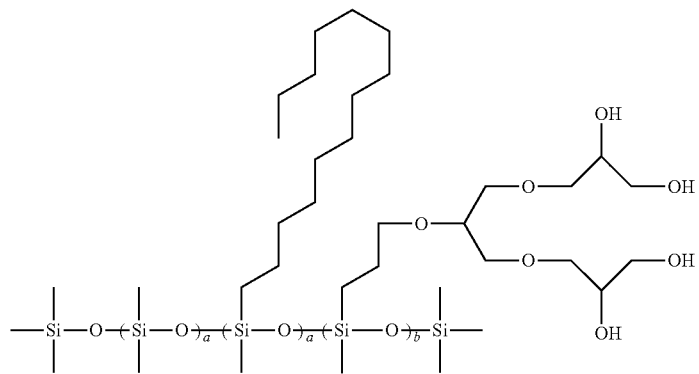
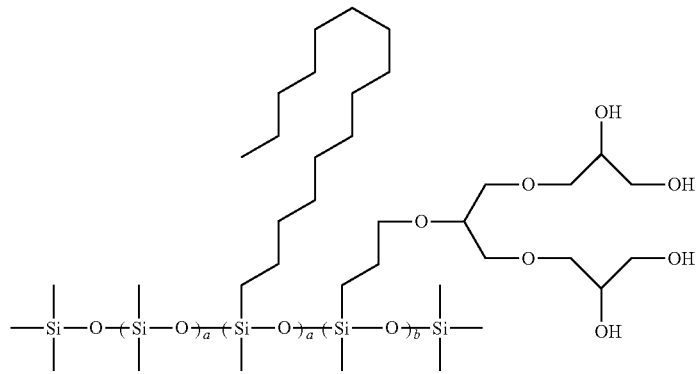

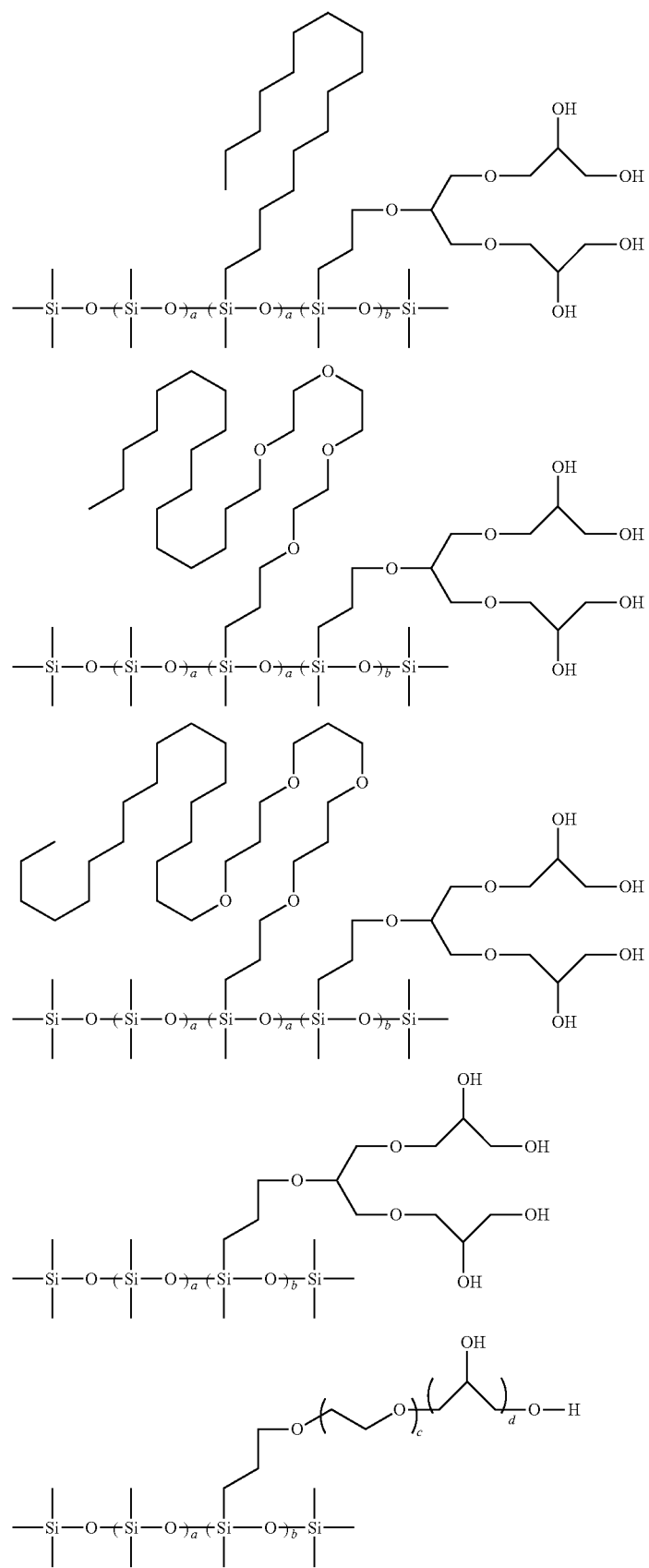

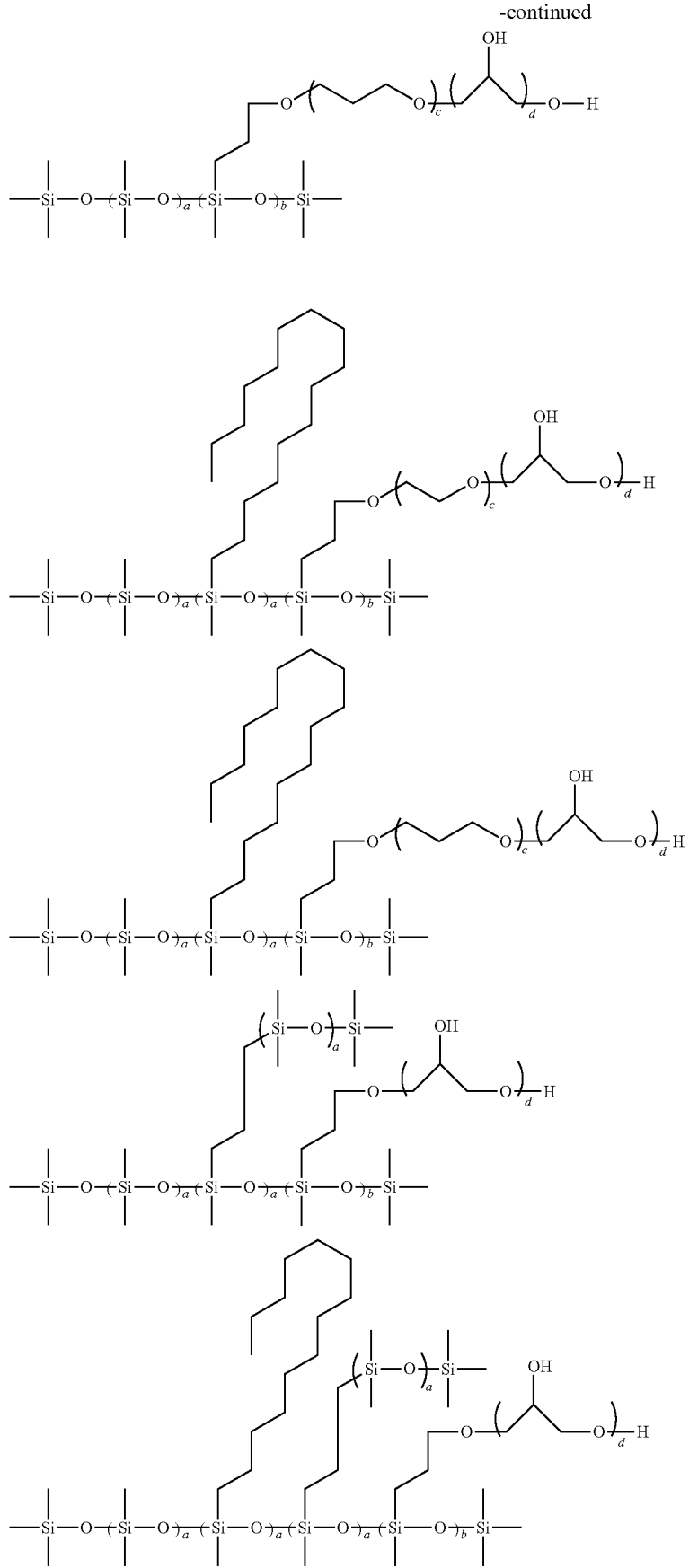

-continued
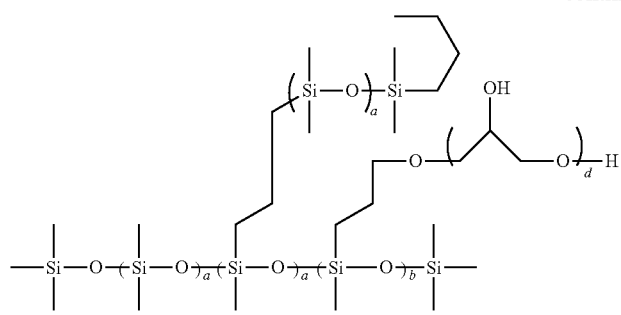
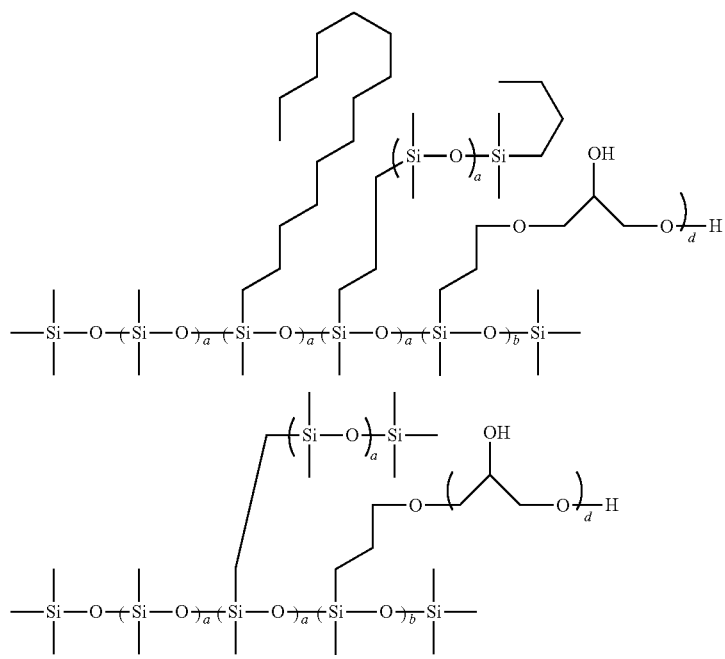
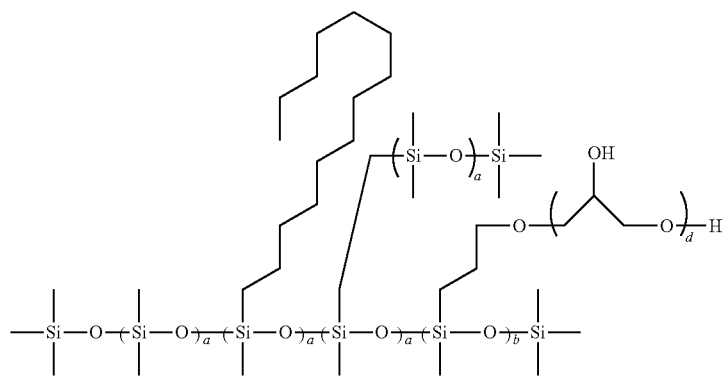
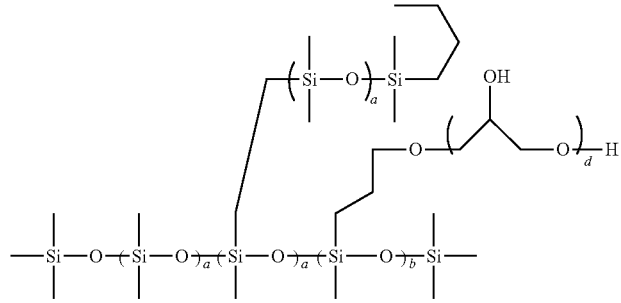

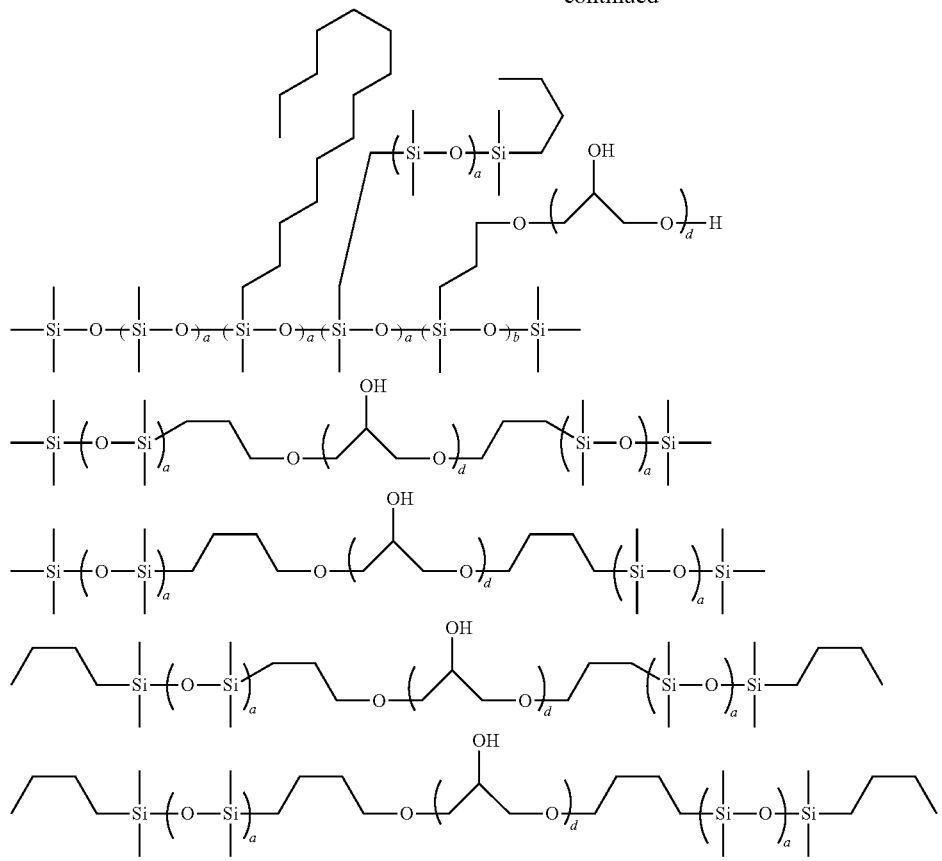

In the formulae, "a", "b", "c", and "d" are each independently as defined above.

[Organic Solvent]

The bio-electrode composition can further contain an organic solvent. Specific examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene.

Other examples of the organic solvent include aliphatic hydrocarbon solvent such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin.

Still other examples of the organic solvent include: ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone;

alcohol solvent such as 3-methoxybutanol, 3-methyl-3-methoxybutanol, 1-methoxy-2-propanol, and 1-ethoxy-2-propanol;

ether solvent such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, diisopentyl ether, di-sec-pentyl ether, di-tert-amyl ether, di-n-hexyl ether, and anisole;

ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate;

lactone solvent such as γ-butyrolactone; etc.

The amount of the organic solvent added is preferably in a range of 10 to 50,000 parts by mass on the basis of 100 parts by mass of the resin.

[Other Additives]

The bio-electrode composition can be mixed with silica particles, alumina particles, titania particles, and zirconia particles. These silica particles, alumina particles, titania particles, and zirconia particles have hydrophilic surfaces and favorable compatibility with the hydrophilic ion polymer and polyglycerin silicone, and can improve the dispersibility of the ion polymer in a hydrophobic silicone adhesive and that of the polyglycerin silicone in the silicone adhesive. The silica particles, alumina particles, titania particles, and zirconia particles may be either dry type or wet type both of which are preferably usable. The shape of the silica particles, alumina particles, titania particles, and zirconia particles may be any of spherical, elliptical, irregular, hollow, and porous shapes.

As has been described above, since the living body contact layer of the inventive bio-electrode is formed using a cured material of the above-described bio-electrode composition, this makes it possible to efficiently conduct electric signals from skin to a device (i.e., excellent electric conductivity) and prevent allergy even when the bio-electrode is worn on skin for a long time (i.e., excellent biocompatibility). Moreover, the bio-electrode is light-weight, manufacturable at low cost, and capable of preventing significant reduction in the electric conductivity even when wetted with water or dried. It is also possible to further improve the electric conductivity by adding a metal powder. In addition, combination with a resin having adhesion and stretchability enables manufacturing of a bio-electrode with particularly high adhesive strength and stretchability. Further, the stretchability and adhesion to skin can be improved by using an additive and so forth. Furthermore, the stretchability and adhesion can be controlled by appropriately adjusting the composition of the resin and the thickness of the living body contact layer. Accordingly, the inventive bio-electrode described above is particularly suitable as a bio-electrode used for a medical wearable device.

<Method for Manufacturing Bio-Electrode>

A method for manufacturing a bio-electrode according to the present invention is not particularly limited, as long as the method is for manufacturing a bio-electrode having an electro-conductive base material and a living body contact layer formed on the electro-conductive base material, the living body contact layer being configured to include a water-free resin layer and a permeation layer permeated with water and a water-soluble salt on a surface side of the resin layer where a body comes into contact. For example, the method can include: applying a bio-electrode composition onto the electro-conductive base material; curing the bio-electrode composition to form the living body contact layer; and then forming the permeation layer. The permeation layer can be formed using a solution (permeate solution) containing water and a water-soluble salt to permeate the surface side of the water-free resin layer toward which a body comes into contact. A permeate solution to be described below can be used.

The electro-conductive base material, the bio-electrode composition, etc. used for the inventive method for manufacturing a bio-electrode may be the same as those described above.

Specifically, the inventive method for manufacturing a bio-electrode may include:

coating an electro-conductive base material with a bio-electrode composition containing a polymer compound (A) containing a repeating unit having a salt structure selected from the group consisting of salts of ammonium, sodium, potassium, and silver formed with any of fluorosulfonic acid, fluorosulfonimide, and N-carbonyl-fluorosulfonamide;

curing the bio-electrode composition to form a living body contact layer; and bringing an aqueous solution containing a water-soluble salt selected from the group consisting of sodium salts, potassium salts, calcium salts, magnesium salts, and betaines (permeate solution) into contact with a surface of the living body contact layer where a living body comes into contact to form a permeation layer in the surface of the living body contact layer where a living body comes into contact, the permeation layer being permeated with the aqueous solution containing the water-soluble salt.

The method for coating the electro-conductive base material with the bio-electrode composition (the method for applying the bio-electrode composition onto the electro-conductive base material) is not particularly limited. Examples of the suitable method include dip coating, spray coating, spin coating, roll coating, flow coating, doctor coating, screen printing, flexographic printing, gravure printing, stencil printing, inkjet printing, etc.

The method for curing the resin is not particularly limited and can be appropriately selected based on the kind of the resin (B) used for the bio-electrode composition. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the resin (B) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

The living body contact layer preferably has fine uneven surface so as to facilitate the permeation with the aqueous solution containing the water-soluble salt. Such fine uneven surface can be formed by, for example, a method in which after the bio-electrode composition is applied and the solvent is evaporated, the resultant is pressed against an uneven substrate and cured; a method in which the bio-electrode composition is applied and cured on an uneven substrate such as electro-conductive fibers serving as the electro-conductive base material; a printing method such as screen printing or inkjet printing to make the surface uneven; etc.

The surface of the cured film may be sprayed with water droplets, water vapor, or mist each of which contain a water-soluble salt. Performing such pretreatments improves the compatibility with skin, and biological signals can be obtained quickly. The water-soluble salt mixed with water is selected from the group consisting of sodium salts, potassium salts, calcium salts, magnesium salts, and betaines.

[Permeation Layer]

The permeation layer incorporated in the living body contact layer of the inventive bio-electrode is formed by such a treatment that a surface of the water-free resin layer toward which a living body is brought into contact is permeated with a solution containing water and a water-soluble salt selected from the group consisting of sodium salts, potassium salts, calcium salts, magnesium salts, and betaines (permeate solution).

[Water-Soluble Salt]

The water-soluble salt contained in the permeate solution is not particularly limited, and can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the polymer compound (A) described above is excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl isethionate, sodium lauroyl methylalanine, sodium methyl cocoyl taurate, sodium cocoyl glutamate, sodium cocoyl sarcosinate, sodium lauroyl methyl taurate, lauramidopropyl, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

[Alcohol and Silicone Compound]

The permeate solution can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, pentaerythritol, sorbitan, sorbitol, polyethylene glycol, polypropylene glycol, diglycerin, polyglycerin, a silicone compound having a polyglycerin structure, monosaccharide, polysaccharide, and products obtained from any preceding materials by substituting hydroxy groups thereof. More preferably, the silicone compound having a polyglycerin structure is shown by the general formula (3).

In the pretreatment methods with the aqueous solution containing the water-soluble salt, the cured bio-electrode film can be wetted with the aqueous solution by a spraying method, a droplet-dispensing method, etc. The bio-electrode film can also be wetted under a high-temperature, high-humidity condition like sauna. To prevent drying after the wetting, a protective film can be further stacked on the permeation layer to cover the surface. Since the protective film needs to be removed immediately before the bio-electrode is attached to skin, the protective film may be coated with a release agent, or a peelable Teflon film may be used as the protective film. For long-time storage, the dry electrode covered with the peelable film is preferably sealed in a bag that is covered with aluminum or the like. To prevent drying in the bag covered with aluminum, it is preferable to include water therein, too.

The pretreatment methods of spraying the aqueous solution (permeate solution) containing the water-soluble salt are most effective for the dry electrode containing the ion polymer having the repeating unit(s) shown by the general formula (1'), and are also effective for dry electrodes including electro-conductive fibers containing PEDOT-PSS, silver chloride, carbon, or metal.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

<Method for Measuring Biological Signal>

A method for measuring a biological signal according to the present invention includes: treating a portion of skin with a solution containing water; and attaching the inventive bio-electrode to the treated portion to measure a biological signal. Immediately before the attachment, the skin portion where the bio-electrode is to be attached may be wiped with fabric containing water or a water-containing alcohol such as ethanol, glycerin, diglycerin, or polyglycerin; alternatively, the skin portion may be sprayed with such liquid. These treatments moisturize the skin surface, so that biological signals are effectively collected in shorter time with high sensitivity and high precision. Wiping with the water-containing fabric has effects of not only moisturizing skin but also removing the fat/oil content on the skin surface, thereby improving the sensitivity to biological signals.

EXAMPLE

Hereinafter, the present invention will be specifically described by giving Examples and Comparative Examples, but the present invention is not limited thereto. Incidentally, "Me" represents a methyl group, and "Vi" represents a vinyl group.

Ionic polymers 1 to 16 and Comparative ionic polymer 1, which were blended as the ionic material (conductive material) to bio-electrode composition solutions (also referred to as bio-electrode solutions), were synthesized as follows. Each 30 mass % monomer solution in cyclopentanone was introduced into a reaction vessel and mixed. The reaction vessel was cooled to $-70°$ C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.01 mole per 1 mole of the whole monomers. This was warmed to a temperature of $60°$ C. and then allowed to react for 15 hours. The composition of obtained polymer was identified by $^1$H-NMR after drying the solvent. The weight-average molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 16 and Comparative ionic polymer 1 are shown below.

Ionic Polymer 1
  Mw=38,100
  Mw/Mn=1.91

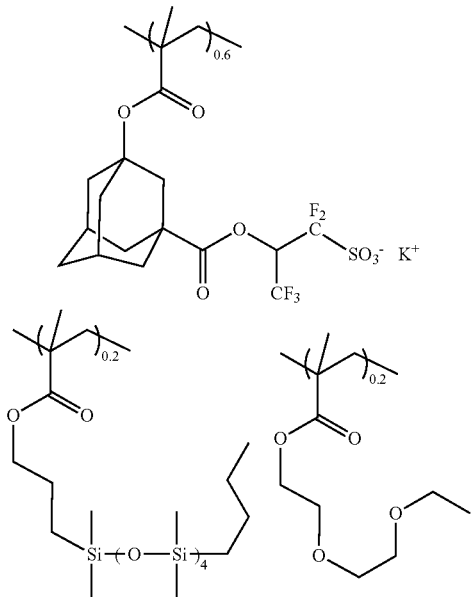

The repeating number in each formula shows the average value.

Ionic Polymer 2
  Mw=36,100
  Mw/Mn=1.93

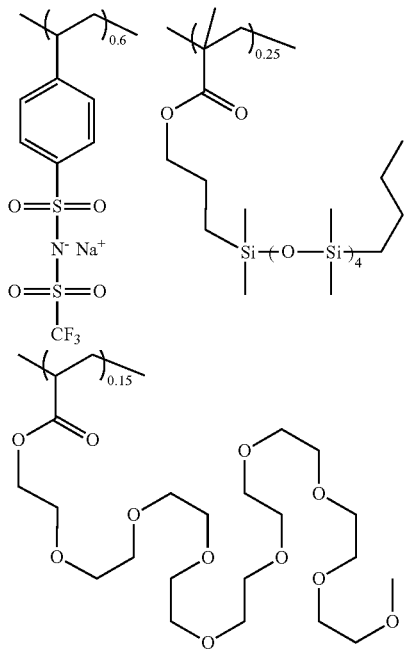

The repeating number in each formula shows the average value.

Ionic Polymer 3
  Mw=150,600
  Mw/Mn=1.85

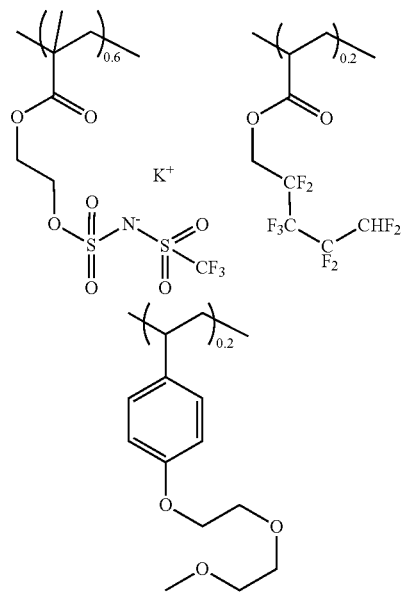

The repeating number in each formula shows the average value.

Ionic Polymer 4
  Mw=44,400
  Mw/Mn=1.94

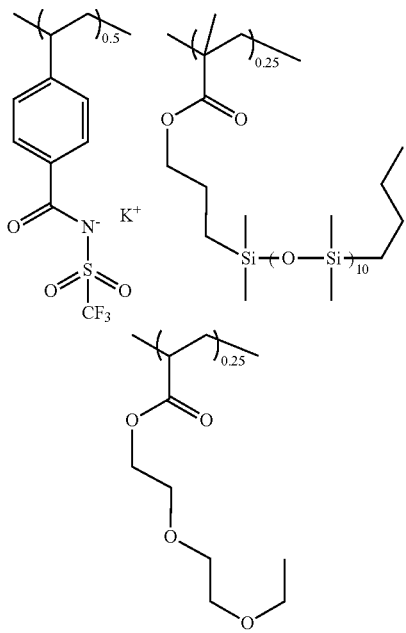

The repeating number in each formula shows the average value.

Ionic Polymer 5
  Mw=43,100
  Mw/Mn=1.88

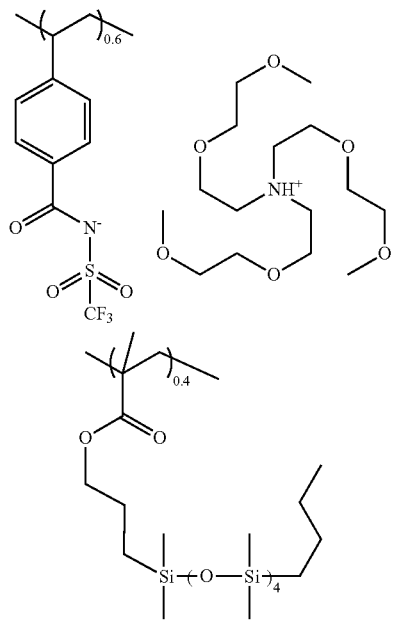

The repeating number in each formula shows the average value.

Ionic Polymer 6
  Mw=41,200
  Mw/Mn=1.72

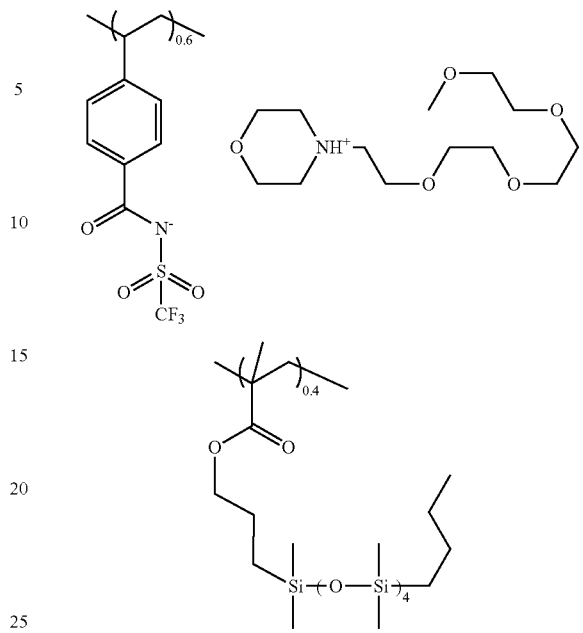

The repeating number in each formula shows the average value.

Ionic Polymer 7
  Mw=43,600
  Mw/Mn=1.93

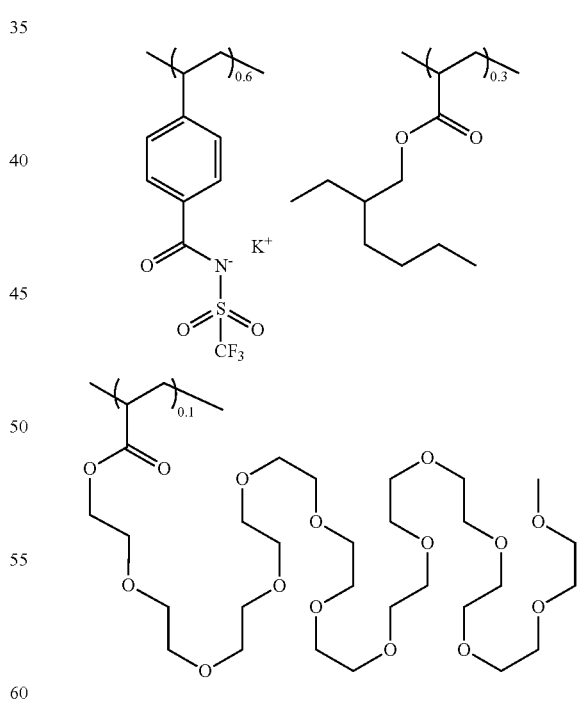

The repeating number in each formula shows the average value.

Ionic Polymer 8
  Mw=31,600
  Mw/Mn=2.10

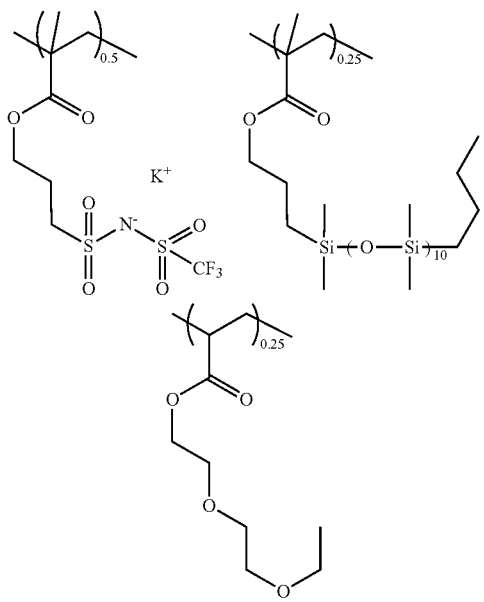
The repeating number in each formula shows the average value.
Ionic Polymer 9
  Mw=55,100
  Mw/Mn=2.02
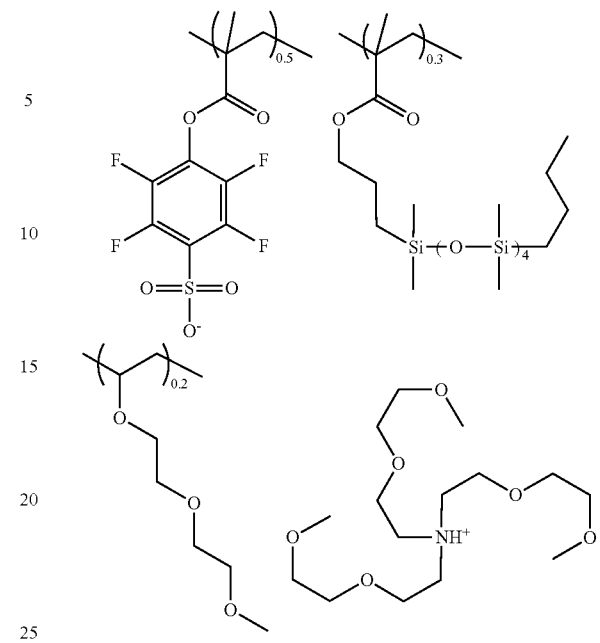
The repeating number in each formula shows the average value.
Ionic Polymer 11
  Mw=43,600
  Mw/Mn=1.91
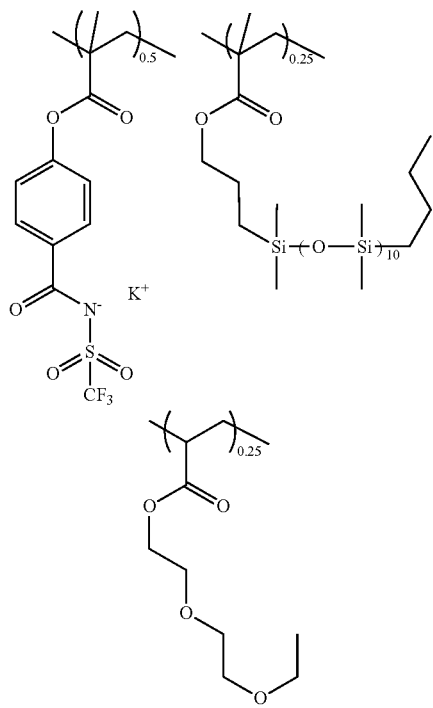
The repeating number in each formula shows the average value.
Ionic Polymer 10
  Mw=87,500
  Mw/Mn=2.01
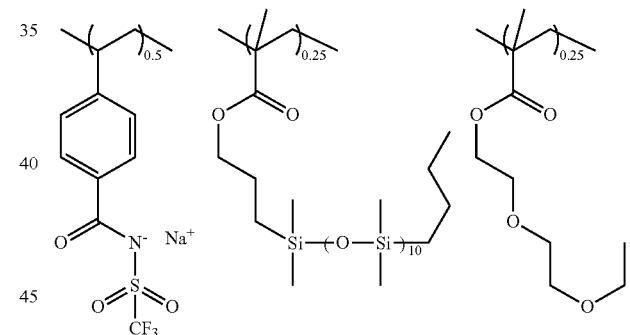
The repeating number in each formula shows the average value.
Ionic Polymer 12
  Mw=97,100
  Mw/Mn=2.20
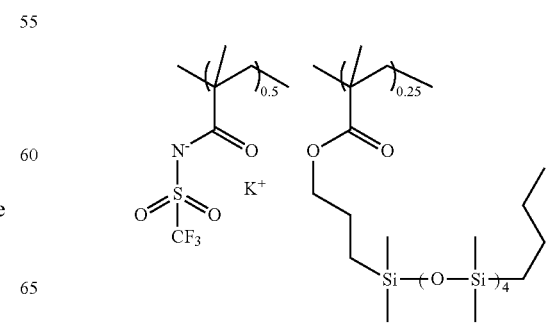

209
-continued

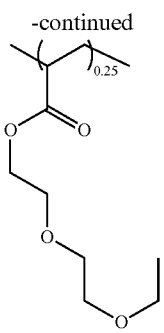

210
-continued

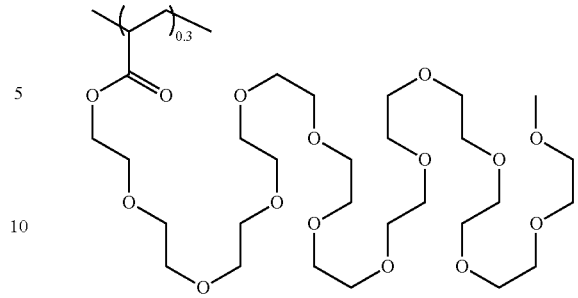

The repeating number in each formula shows the average value.

Ionic Polymer 13
  Mw=98,300
  Mw/Mn=2.05

The repeating number in each formula shows the average value.

Ionic Polymer 15
  Mw=67,100
  Mw/Mn=1.89

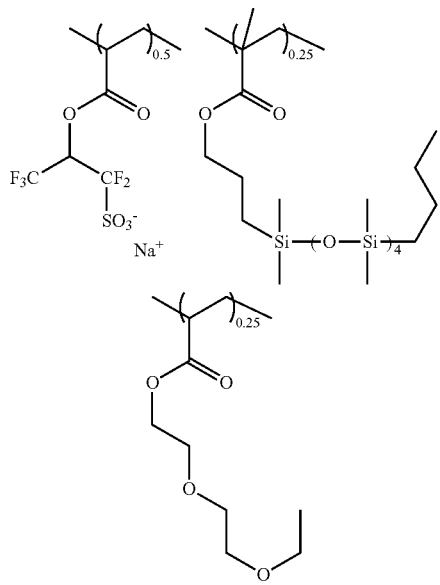

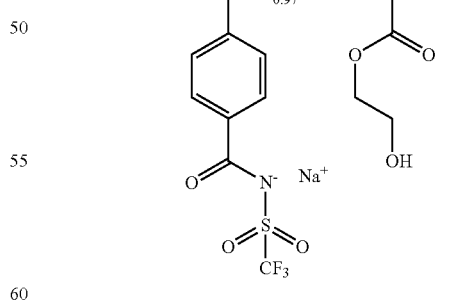

The repeating number in each formula shows the average value.

Ionic Polymer 16
  Mw=23,400
  Mw/Mn=1.77

The repeating number in each formula shows the average value.

Ionic Polymer 14
  Mw=68,900
  Mw/Mn=2.26

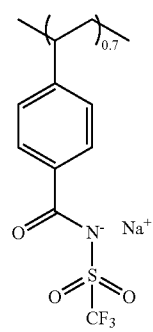

The repeating number in each formula shows the average value.

Comparative Ionic Polymer 1
  Mw=46,700
  Mw/Mn=2.25

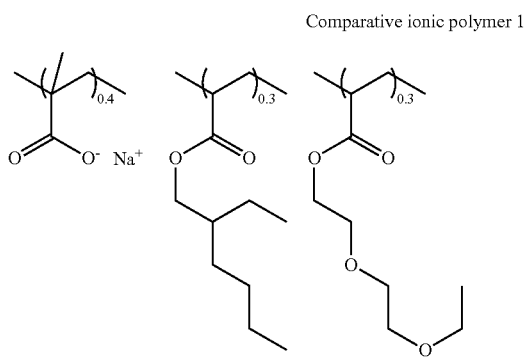

Comparative ionic polymer 1

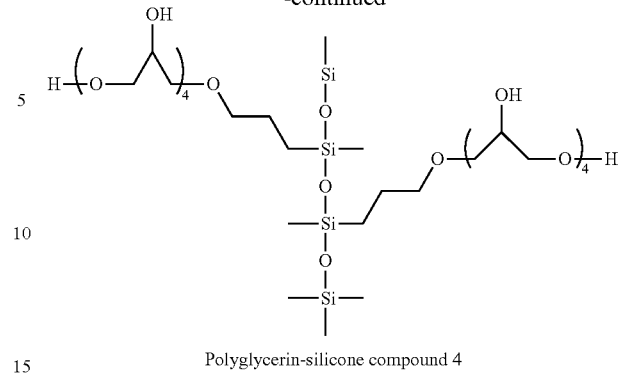

Polyglycerin-silicone compound 4

The repeating number in each formula shows the average value.

Polyglycerin-silicone compounds 1 to 6 are shown below. These compounds were synthesized through hydrosilylation reaction using a silicone compound having an SiH group and a polyglycerin compound having a double bond in the presence of a platinum catalyst according to JP 2019-99469A.

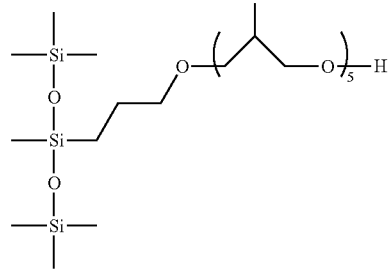

Polyglycerin-silicone compound 1

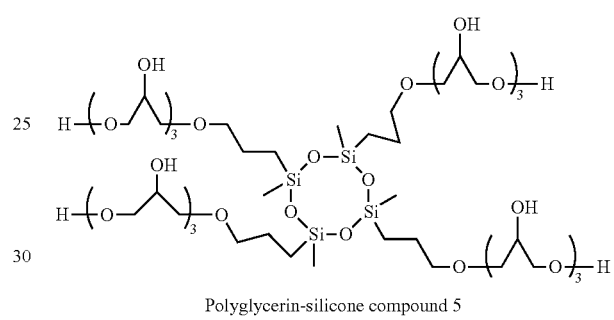

Polyglycerin-silicone compound 5

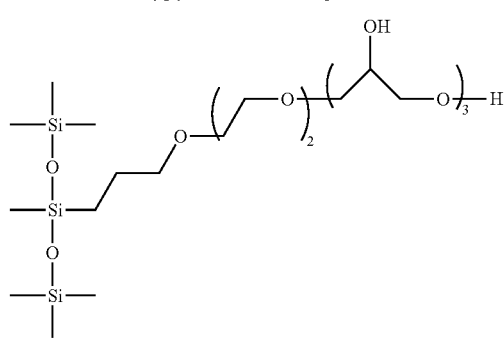

Polyglycerin-silicone compound 2

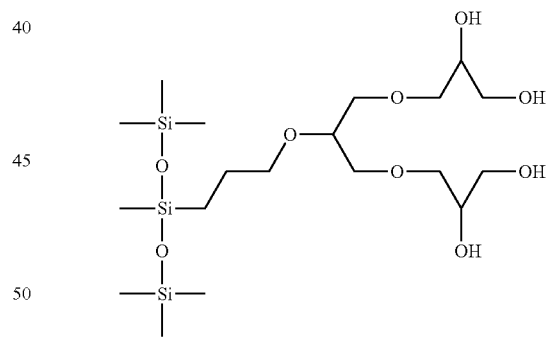

Polyglycerin-silicone compound 6

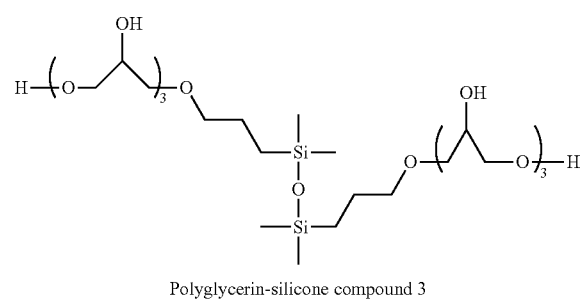

Polyglycerin-silicone compound 3

Siloxane compounds 1 to 4, which were blended to the bio-electrode composition solutions as a silicone based resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_3SiO_{0.5}$ unit/$SiO_2$ unit=0.8).

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were blocked with OH groups, with the 30% toluene solution having a viscosity of 42,000 mPa·s; 100 parts by mass of 60% toluene solution of polysiloxane of MQ resin composed of an $Me_3SiO_{0.5}$ unit and an $SiO_2$ unit ($Me_3SiO_{0.5}$ unit/$SiO_2$ unit=0.8); and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

Acrylic polymer blended as an acrylic based resin to the bio-electrode composition solutions is shown below.

Acrylic Polymer 1

Mw=108,000

Mw/Mn=2.32

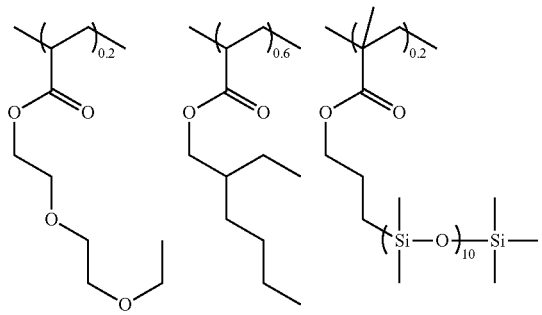

Acrylic polymer 1

The repeating number in each formula shows the average value.

Silicone pendant urethane (meth)acrylates 1 to 3 and Urethane (meth)acrylate 1, which were blended to the bio-electrode composition solutions as silicone, acrylic, or urethane based resins, are shown below.

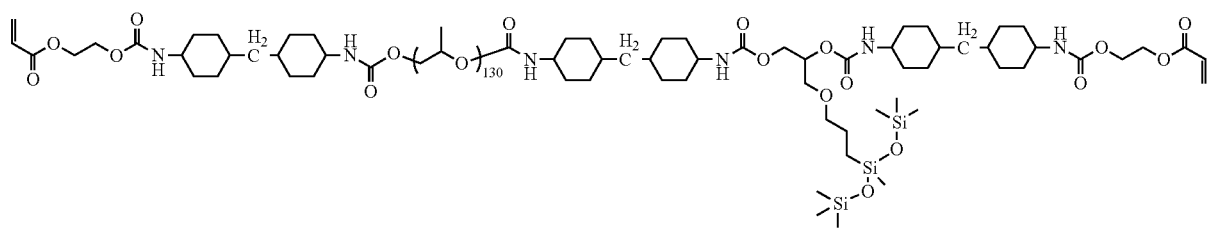

Silicone pendant urethane (meth)acrylate 1
Mw 24800 Mw/Mn 2.65

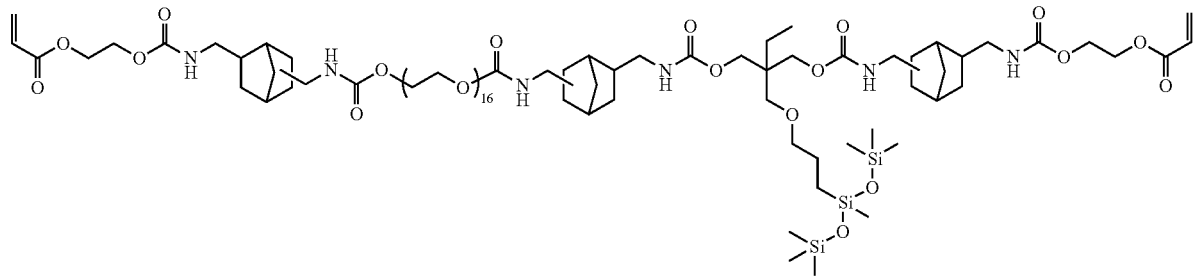

Silicone pendant urethane (meth)acrylate 2
Mw 8900 Mw/Mn 2.67

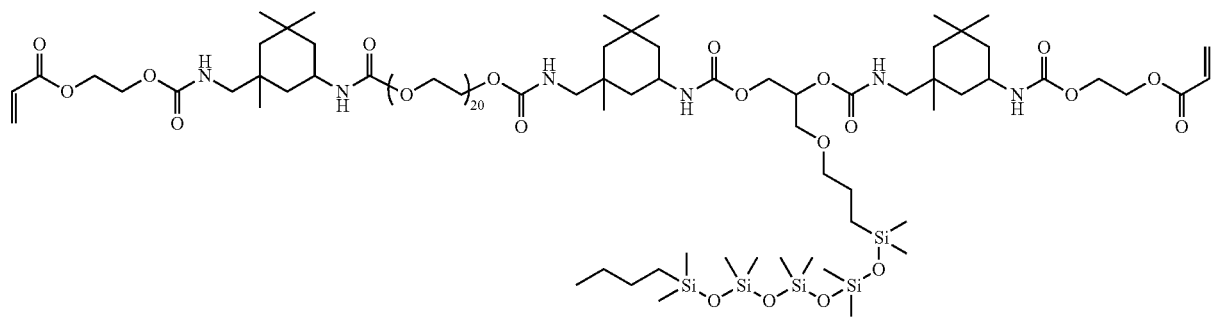

Silicone pendant urethane (meth)acrylate 3
Mw 8100 Mw/Mn 2.69

-continued

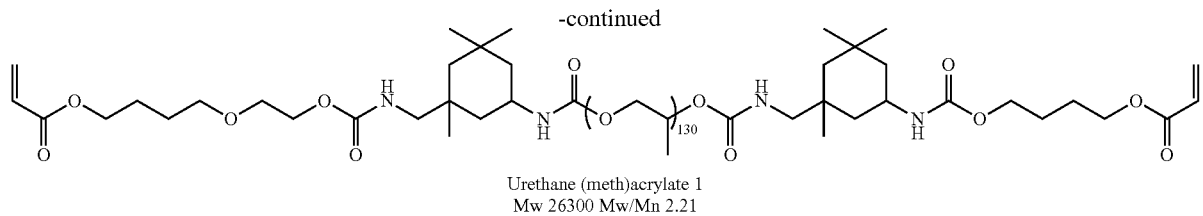

Urethane (meth)acrylate 1
Mw 26300 Mw/Mn 2.21

The repeating number in each formula shows the average value.

A crosslinking agent, which was blended to the bio-electrode composition solutions, is shown below.

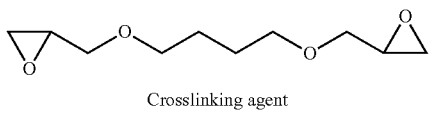 [SMILES: C(CCOCC1CO1)COCC1CO1]

Crosslinking agent

The abbreviations and so forth of organic solvents, which were blended to the bio-electrode composition solutions, are shown below.

EDE: diethylene glycol diethyl ether
BE: diethylene glycol butyl ether
ISOPAR G (manufactured by Exxon Mobile Corporation): isoparaffin A lithium titanate powder, silver flakes, a radical generator, a platinum catalyst, and electric conductivity improvers (carbon black, carbon nanotube), which were blended to the bio-electrode composition solutions as additives, are shown below.

Lithium titanate powder, spinel: manufactured by Sigma-Aldrich Co. LLC., with the size of 200 nm or less Silver flakes: manufactured by Sigma-Aldrich Co. LLC., with the average size of 10 μm Radical generator: IRGACURE TPO manufactured by BASF SE Platinum catalyst: CAT-PL-50T manufactured by Shin-Etsu Chemical Co., Ltd.

Carbon black: DENKA BLACK Li-400 manufactured by Denka Co., Ltd.

Multilayer carbon nanotube: manufactured by Sigma-Aldrich Co. LLC., with the diameter of 110 to 170 nm and length of 5 to 9 μm Examples 1 to 42, Comparative Examples 1 to 3

On the basis of the compositions shown in Tables 1 and 2, the ionic material (salt), the resin, the organic solvent, the additives (e.g., radical generator, platinum catalyst, electric conductivity improver), and the crosslinking agent were blended to prepare bio-electrode solutions (Bio-electrode solutions 1 to 17, Comparative bio-electrode solutions 1, 2).

On the basis of the compositions shown in Table 3, a water-soluble salt, a solvent (water), and an additive (alcohol) were blended to prepare Pretreatment aqueous solutions 1 to 25. Note that, as polyglycerin, Polyglycerin #310 manufactured by Sakamoto Yakuhin Kogyo Co., Ltd. was used.

TABLE 1

| Bio-electrode solution | Ionic material (parts by mass) | Resin (parts by mass) | Organic solvent (parts by mass) | Additive (parts by mass) |
|---|---|---|---|---|
| Bio-electrode solution 1 | Ionic polymer 1(30) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode solution 2 | Ionic polymer 2(30) | Siloxane compound 3(126) Siloxane compound 4(3) | ISOPAR G(60) cyclopentanone(70) | CAT-PL-50T(1.5) carbon black(14) |
| Bio-electrode solution 3 | Ionic polymer 3(25.0) | Siloxane compound 1(40) Siloxane compound 2(100) Siloxane compound 4(3) | ISOPAR G(60) cyclopentanone(70) | CAT-PL-50T(1.5) carbon black(14) |
| Bio-electrode solution 4 | Ionic polymer 4(30) | Siloxane compound 1(40) Siloxane compound 2(100) Siloxane compound 4(3) | ISOPAR G(60) cyclopentanone(70) | CAT-PL-50T(0.7) lithium titanate powder(12) silver flake(8) |
| Bio-electrode solution 5 | Ionic polymer 5(30) | Siloxane compound 3(126) Siloxane compound 4(3) | n-octane(60) cyclopentanone(70) | CAT-PL-50T(1.5) carbon black(14) |
| Bio-electrode solution 6 | Ionic polymer 6(30) | Siloxane compound 3(126) Siloxane compound 4(3) | n-nonane(60) 2-heptanone(14) | CAT-PL-50T(1.5) lithium titanate powder(5) carbon black(5) |
| Bio-electrode solution 7 | Ionic polymer 7(30) | Siloxane compound 3(126) Siloxane compound 4(3) | ISOPAR G(60) cyclopentanone(70) | CAT-PL-50T(1.5) carbon black(14) |
| Bio-electrode solution 8 | Ionic polymer 8(30) | Siloxane compound 3(126) Siloxane compound 4(3) | n-decane(30) n-octane(30) 2-heptanone(14) | CAT-PL-50T(1.5) lithium titanate powder(5) carbon black(5) |
| Bio-electrode solution 9 | Ionic polymer 9(30) | Siloxane compound 3(126) Siloxane compound 4(3) | ISOPAR G(60) cyclopentanone(70) | CAT-PL-50T(1.5) lithium titanate powder(5) multilayer carbon nanotube(3) |

TABLE 1-continued

| Bio-electrode solution | Ionic material (parts by mass) | Resin (parts by mass) | Organic solvent (parts by mass) | Additive (parts by mass) |
|---|---|---|---|---|
| Bio-electrode solution 10 | Ionic polymer 10(40) | Silicone pendant urethane (meth)acrylate 1(80) | EDE(60) cyclopentanone(70) | IRGACURE TPO(1) |
| Bio-electrode solution 11 | Ionic polymer 11(20) | Acrylic polymer 1(55) Silicone pendant urethane (meth)acrylate 1(25) | EDE(60) cyclopentanone(70) | IRGACURE TPO(1) |
| Bio-electrode solution 12 | Ionic polymer 12(20) | Acrylic polymer 1(20) Silicone pendant urethane (meth)acrylate 2(60) | EDE(60) cyclopentanone(70) | IRGACURE TPO(1) |
| Bio-electrode solution 13 | Ionic polymer 13(25) | Acrylic polymer 1(20) Silicone pendant urethane (meth)acrylate 3(60) | EDE(60) cyclopentanone(70) | IRGACURE TPO(1) |
| Bio-electrode solution 14 | Ionic polymer 14(25) | Silicone pendant urethane (meth)acrylate 1(80) | BE (120) water (10) | IRGACURE TPO(1) sodium chloride(2) |
| Bio-electrode solution 15 | Ionic polymer 15(26) | Silicone pendant urethane (meth)acrylate 1(80) | BE (120) water (10) | IRGACURE TPO(1) potassium chloride(2) |
| Bio-electrode solution 16 | Ionic polymer 16(16) | Silicone pendant urethane (meth)acrylate 1(80) | BE (120) water (10) | IRGACURE TPO(1) crosslinking agent(2) |
| Bio-electrode solution 17 | Ionic polymer 11(20) | Urethane (meth)acrylate 1(80) | EDE(60) cyclopentanone(70) | IRGACURE TPO(1) |

TABLE 2

| Bio-electrode solution | Ionic material (parts by mass) | Resin (parts by mass) | Organic solvent (parts by mass) | Additive (parts by mass) |
|---|---|---|---|---|
| Comparative bio-eletrode solution 1 | Comparative Ionic polymer 1(30) | Siloxane compound 1(40) Siloxane compound 2(100) Siloxane compound 4(3) | ISOPAR G(60) cyclopentanone(70) | CAT-PL-50T(1.5) carbon black(14) |
| Comparative bio-electrode solution 2 | Comparative Ionic polymer 1(30) | Siloxane compound 3(126) Siloxane compound 4(3) | ISOPAR G(60) cyclopentanone(70) | CAT-PL-50T(1.5) carbon black(14) |

TABLE 3

| Pretreatment aqueous solution No. | Salt (parts by mass) | Solvent (parts by mass) | Additive (parts by mass) |
|---|---|---|---|
| 1 | sodium chloride(3) | water(100) | — |
| 2 | potassium chloride(3) | water(100) | — |
| 3 | calcium chloride(3) | water(100) | diethylene glycol(10) |
| 4 | sodium chloride(3) | water(100) | glycerin(5) |
| 5 | saccharin(5) | water(100) | glycerin(5) |
| 6 | acesulfame K(5) | water(100) | glycerin(5) |
| 7 | sodium chloride(3) | water(100) | polyethylene glycol Mn:300(2) |
| 8 | sodium chloride(3) | water(100) | Polyglycerin-silicone 1(5) |
| 9 | sodium chloride(3) | water(100) | Polyglycerin-silicone 2(5) |
| 10 | sodium acetate(3) | water(100) | Polyglycerin-silicone 3(5) |
| 11 | sodium benzoate(3) | water(100) | Polyglycerin-silicone 4(5) |
| 12 | sodium glycolate(3) | water(100) | Polyglycerin-silicone 5(5) |
| 13 | sodium methanesulfonate(3) | water(100) | Polyglycerin-silicone 6(5) |
| 14 | magnesium chloride(3) | water(100) | — |
| 15 | sodium phosphate(3) | water(100) | — |
| 16 | sodium laurate(3) | water(100) | glycerin(5) |
| 17 | sodium lauryl phosphate(3) | water(100) | glycerin(5) |

TABLE 3-continued

| Pretreatment aqueous solution No. | Salt (parts by mass) | Solvent (parts by mass) | Additive (parts by mass) |
|---|---|---|---|
| 18 | trimethylglycine (betaine)(2) | water(100) | — |
| 19 | sodium cocoyl isethionate (3) | water(100) | glycerin(5) |
| 20 | sodium cocoyl sarcosinate(3) | water(100) | glycerin(5) |
| 21 | sodium methyl lauroyl taurate(3) | water(100) | glycerin(5) |
| 22 | sodium chloride(1) | water(100) | polyglycerin(5) |
| 23 | sodium chloride(1) | water(100) | polyglycerin(2) pentaerythritol(1) |
| 24 | sodium chloride(1) | water(100) | polyglycerin(2) sorbitan(1) |
| 25 | sodium chloride(1) | water(100) | polyglycerin(2) sorbitol(1) |

(Preparation of Bio-Electrodes)

A thermoplastic urethane (TPU) film ST-604 (manufactured by Bemis Associates Inc.) was coated with an electro-conductive paste DOTITE FA-333 (manufactured by Fujikura Kasei Co., Ltd.) by screen printing. The resultant was baked in an oven at 120° C. for 10 minutes to print a keyhole-shaped electro-conductive pattern including a circular portion with a diameter of 2 cm. Then, one of the bio-electrode solutions shown in Tables 1 and 2 was applied onto the circular portion by screen printing. After air-dried at room temperature for 10 minutes, the resultant was baked using an oven at 125° C. for 10 minutes to evaporate the solvent. In this manner, cured bio-electrodes were prepared (Bio-Electrodes 1 to 9, Comparative Bio-Electrodes 1, 2). Bio-Electrodes 10 to 17 were further cured by irradiation with a xenon lamp at 200 mJ/cm$^2$ under a nitrogen atmosphere. FIG. 4 shows a cured bio-electrode 9 prepared on an electro-conductive pattern 8 printed on a urethane film 7. FIG. 5 shows the bio-electrode 9 having a double-sided tape 10 pasted on the cured urethane film 7 on which the electro-conductive pattern 8 was printed, the urethane film 7 having been cut out.

(Thickness Measurement of Living Body Contact Layer)

The thickness of the living body contact layer of each bio-electrode prepared as described above was measured with a micrometer. Table 4 shows the result.

(Pretreatment)

Onto each of Bio-Electrodes 1 to 17 prepared as described above, droplets of one of Pretreatment aqueous solutions 1 to 25 were discharged from a spray nozzle for 20 seconds in a spraying method and then dried for 20 minutes. Subsequently, a Teflon film was attached. In a dispensing method, approximately 100 µL of one of the pretreatment aqueous solutions was spilled onto the bio-electrode, and a Teflon film was attached.

(Biological Signal Measurement)

The electro-conductive wiring pattern formed from the electro-conductive paste of each bio-electrode was connected to a portable electrocardiograph HCG-901 (manufactured by OMRON HEALTHCARE Co., Ltd.) through an electro-conductive wire. A positive electrode of the electrocardiograph was attached to a location LA in FIG. 6 on a human body, a negative electrode was attached to a location LL, and an earth was attached to a location RA. In Example 30, immediately before the attachments, the skin surface was wiped with an absorbent cotton containing water. The Teflon film was peeled off, and the bio-electrode was quickly attached on the chest. Immediately thereafter, the electrocardiogram measurement was started to measure the time until an electrocardiogram waveform (ECG signal) including P, Q, R, S, and T waves appeared as shown in FIG. 7. Table 4 shows the result.

TABLE 4

| Example | Bio-Electrode | Resin thickness (µm) | Pretreatment aqueous solution No. | Pretreatment method | Time (min.) until ECG signal appeared |
|---|---|---|---|---|---|
| Example 1 | Bio-Electrode 1 | 20 | 1 | spraying | 0 |
| Example 2 | Bio-Electrode 1 | 20 | 2 | spraying | 0 |
| Example 3 | Bio-Electrode 1 | 20 | 3 | spraying | 0 |
| Example 4 | Bio-Electrode 1 | 20 | 4 | spraying | 0 |
| Example 5 | Bio-Electrode 1 | 20 | 5 | spraying | 0 |
| Example 6 | Bio-Electrode 1 | 20 | 6 | spraying | 0 |
| Example 7 | Bio-Electrode 1 | 20 | 7 | spraying | 0 |
| Example 8 | Bio-Electrode 1 | 20 | 8 | spraying | 0 |
| Example 9 | Bio-Electrode 1 | 20 | 9 | spraying | 0 |
| Example 10 | Bio-Electrode 1 | 20 | 10 | spraying | 0 |
| Example 11 | Bio-Electrode 1 | 20 | 11 | spraying | 0 |
| Example 12 | Bio-Electrode 1 | 20 | 12 | spraying | 0 |
| Example 13 | Bio-Electrode 1 | 20 | 13 | spraying | 0 |
| Example 14 | Bio-Electrode 1 | 20 | 1 | dispensing | 0 |
| Example 15 | Bio-Electrode 2 | 18 | 1 | spraying | 0 |
| Example 16 | Bio-Electrode 3 | 22 | 1 | spraying | 0 |
| Example 17 | Bio-Electrode 4 | 28 | 1 | spraying | 0 |

TABLE 4-continued

| Example | Bio-Electrode | Resin thickness (μm) | Pretreatment aqueous solution No. | Pretreatment method | Time (min.) until ECG signal appeared |
|---|---|---|---|---|---|
| Example 18 | Bio-Electrode 5 | 27 | 1 | spraying | 0 |
| Example 19 | Bio-Electrode 6 | 31 | 1 | spraying | 0 |
| Example 20 | Bio-Electrode 7 | 33 | 1 | spraying | 0 |
| Example 21 | Bio-Electrode 8 | 29 | 1 | spraying | 0 |
| Example 22 | Bio-Electrode 9 | 28 | 1 | spraying | 0 |
| Example 23 | Bio-Electrode 10 | 31 | 1 | spraying | 0 |
| Example 24 | Bio-Electrode 11 | 41 | 1 | spraying | 0 |
| Example 25 | Bio-Electrode 12 | 33 | 1 | spraying | 0 |
| Example 26 | Bio-Electrode 13 | 25 | 1 | spraying | 0 |
| Example 27 | Bio-Electrode 14 | 21 | 1 | spraying | 0 |
| Example 28 | Bio-Electrode 15 | 26 | 1 | spraying | 0 |
| Example 29 | Bio-Electrode 16 | 20 | 1 | spraying | 0 |
| Example 30 | Bio-Electrode 17 | 23 | 1 | spraying | 0 |
| Example 31 | Bio-Electrode 1 | 20 | 14 | spraying | 0 |
| Example 32 | Bio-Electrode 1 | 20 | 15 | spraying | 0 |
| Example 33 | Bio-Electrode 1 | 20 | 16 | spraying | 0 |
| Example 34 | Bio-Electrode 1 | 20 | 17 | spraying | 0 |
| Example 35 | Bio-Electrode 1 | 20 | 18 | spraying | 0 |
| Example 36 | Bio-Electrode 1 | 20 | 19 | spraying | 0 |
| Example 37 | Bio-Electrode 1 | 20 | 20 | spraying | 0 |
| Example 38 | Bio-Electrode 1 | 20 | 21 | spraying | 0 |
| Example 39 | Bio-Electrode 1 | 20 | 22 | spraying | 0 |
| Example 40 | Bio-Electrode 1 | 20 | 23 | spraying | 0 |
| Example 41 | Bio-Electrode 1 | 20 | 24 | spraying | 0 |
| Example 42 | Bio-Electrode 1 | 20 | 25 | spraying | 0 |
| Comparative Example 1 | Bio-Electrode 1 | 21 | — | — | 10 |
| Comparative Example 2 | Comparative Bio-Electrode 1 | 29 | — | — | N/A |
| Comparative Example 3 | Comparative Bio-Electrode 2 | 29 | — | — | N/A |

As shown in Table 4, in Examples 1 to 42 in each of which the inventive bio-electrode was formed using the living body contact layer pretreated with water containing a particular salt, biological signals were detected immediately after the attachment to the body. In contrast, in the case where no pretreatment was performed to include the permeation layer (Comparative Example 1), or where the ionic component having a particular structure was not incorporated (Comparative Examples 2, 3), it took longer time to obtain a biological signal, or no signal was obtained at all.

Moreover, such bio-electrodes of Examples 1 to 42 had high initial electric conductivity, and the electric conductivity was not significantly reduced even when the bio-electrodes were wetted with water or dried. The bio-electrodes were light-weight, excellent in biocompatibility, and manufacturable at low cost.

The above results have revealed that the inventive bio-electrode including the living body contact layer formed to have a permeation layer in the surface by the pretreatment enables quick signal collection after attachment to skin, and that the inventive bio-electrode is excellent in electric conductivity and biocompatibility, light-weight, manufacturable at low cost, and prevents significant reduction in the electric conductivity even when wetted with water or dried prevents.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A bio-electrode comprising an electro-conductive base material and a living body contact layer, wherein the living body contact layer comprises a water-free resin layer and a permeation layer on a surface side of the resin layer where a living body comes into contact, and the permeation layer comprises water and a water-soluble salt selected from the group consisting of sodium salts, potassium salts, calcium salts, magnesium salts, and betaines, wherein the resin layer comprises a polymer compound (A) comprising a repeating unit having a salt structure selected from the group consisting of salts of ammonium, sodium, potassium, and silver formed with any of fluorosulfonic acid, fluorosulfonimide, and N-carbonyl-fluorosulfonamide.

2. The bio-electrode according to claim 1, wherein the water-soluble salt is a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines.

3. The bio-electrode according to claim 1, wherein the salt structure is shown by any of the following general formulae (1)-1 to (1)-4,

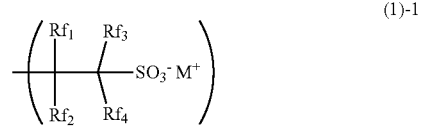

-continued (1)-2

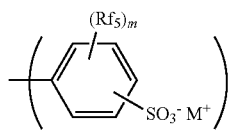

(1)-3

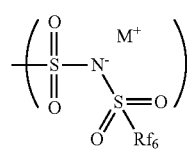

(1)-4

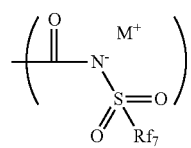

wherein at least one of $Rf_1$ to $Rf_4$ is a fluorine atom or a trifluoromethyl group, and $Rf_1$ and $Rf_2$ optionally bond to a carbon atom bonded therewith to form a carbonyl group; $Rf_5$, $Rf_6$, and $Rf_7$ each represent a fluorine atom, a linear alkyl group having 1 to 4 carbon atoms, or a branched alkyl group having 3 or 4 carbon atoms, and have at least one or more fluorine atoms; "m" represents an integer of 1 to 4; and M represents ammonium, sodium, potassium, or silver.

4. The bio-electrode according to claim 3, wherein one or more repeating units selected from the group consisting of salts of ammonium, sodium, potassium, and silver formed with any of fluorosulfonic acid as shown by the general formula (1)-1 or (1)-2, sulfonimide as shown by the general formula (1)-3, and sulfonamide as shown by the general formula (1)-4 comprise at least one repeating unit selected from the group consisting of repeating units A1 to A7 shown by the following general formula (1'), (1')

(A1)

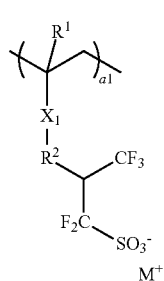

(A2)

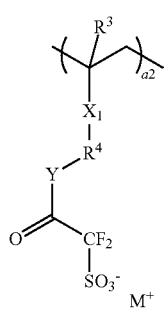

(A3)

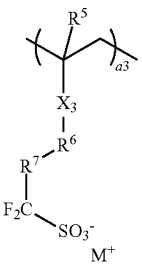

(A4)

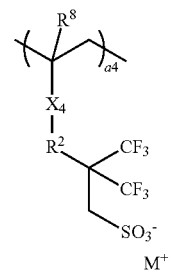

(A5)

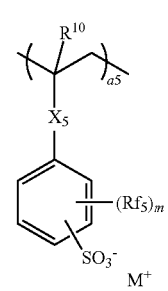

(A6)

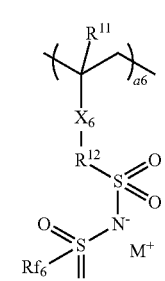

(A7)

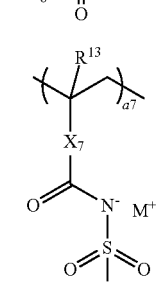

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, a linear hydrocarbon group having 1 to 12 carbon atoms, and a branched or cyclic hydrocarbon group having 3 to 12 carbon atoms, the hydrocarbon groups optionally having either or both of an ester group and an ether group; $R^7$ represents a linear alkylene group having 1 to 4 carbon atoms, or a branched alkylene group having 3 or 4 carbon atoms, and one or two hydrogen atoms in $R^7$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a —$NR^{14}$— group; $R^{14}$ represents a hydrogen atom, a linear alkyl group having 1 to 4 carbon atoms, or a branched alkyl group having 3 or 4 carbon atoms, and optionally forms a ring together with $R^4$; "m" represents an integer of 1 to 4; a1, a2, a3, a4, a5, a6, and a7 satisfy 0≤a1≤1.0, 0≤a2≤1.0, 0≤a3≤1.0, 0≤a4≤1.0, 0≤a5≤1.0, 0≤a6≤1.0, 0≤a7≤1.0, and 0<a1+a2+a3+a4+a5+a6+a7<1.0; and M, $Rf_5$, $Rf_6$, and $Rf_7$ are as defined above.

5. The bio-electrode according to claim 3, wherein the salt structure shown by any of the general formulae (1)-1 to (1)-4 comprises an ammonium ion shown by the following general formula (2) as $M^+$,

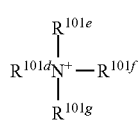

(2)

wherein $R^{101d}$, $R^{101d}$, $R^{101f}$, and $R^{101g}$ each represent a hydrogen atom, a linear alkyl group having 1 to 12 carbon atoms, a branched or cyclic alkyl group having 3 to 12 carbon atoms, a linear alkenyl group or alkynyl group having 2 to 12 carbon atoms, a branched or cyclic alkenyl group or alkynyl group having 3 to 12 carbon atoms, or an aromatic group having 4 to 20 carbon atoms, and optionally have at least one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

6. The bio-electrode according to claim 1, wherein the permeation layer further comprises a monohydric alcohol or polyhydric alcohol having 1 to 4 carbon atoms.

7. The bio-electrode according to claim 6, wherein the polyhydric alcohol is selected from the group consisting of glycerin, pentaerythritol, sorbitan, sorbitol, polyethylene glycol, polypropylene glycol, diglycerin, polyglycerin, a silicone compound having a polyglycerin structure, monosaccharide, polysaccharide, and products obtained from any preceding materials by substituting hydroxy groups thereof.

8. The bio-electrode according to claim 7, wherein the silicone compound having a polyglycerin structure is shown by the following general formula (3) or (4),

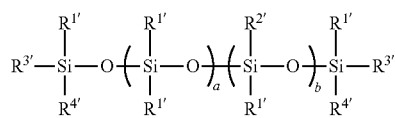

(3)

-continued

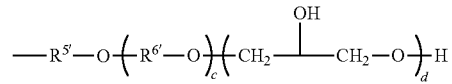

(3)-1

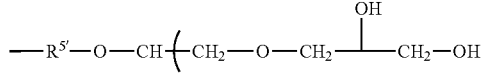

(3)-2

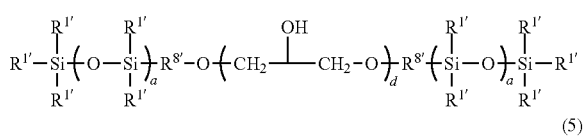

(4)

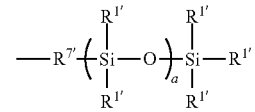

(5)

wherein each $R^{1'}$ is identical to or different from each other and independently represents a linear alkyl group having 1 to 50 carbon atoms, a branched alkyl group having 3 to 50 carbon atoms, a phenyl group, or a silicone chain shown by a general formula (5), and optionally contains an ether group; $R^{2'}$ represents a group having a polyglycerin group structure shown by a general formula (3)-1 or (3)-2; each $R^{3'}$ is identical to or different from each other and independently represents the $R^{1'}$ group or the $R^{2'}$ group; each $R^{4'}$ is identical to or different from each other and independently represents the $R^{1'}$ group, the $R^{2'}$ group, or an oxygen atom, provided that when $R^{4'}$ represents an oxygen atom, the two $R^{4'}$ moieties are integrated with each other and optionally constitute an ether group to form a ring together with silicon atoms; and each "a" is identical to or different from each other and represents 0 to 100, "b" represents 0 to 100, and a+b is 0 to 200, provided that when "b" is 0, at least one $R^{3'}$ is the $R^{2'}$ group; and $R^{5'}$ represents an alkylene group having 2 to 10 carbon atoms or an aralkylene group having 7 to 10 carbon atoms; $R^{6'}$, $R^{7'}$, and $R^{8'}$ each represent an alkylene group having 2 to 6 carbon atoms; "c" represents 0 to 20; and "d" represents 1 to 20.

9. The bio-electrode according to claim 1, wherein the resin layer further comprises a component (B) which is one or more selected from the group consisting of silicone based, acrylic based, and urethane based resins.

10. The bio-electrode according to claim 9, wherein the silicone based resin of the component (B) comprises:
a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" is a number in a range of 2.5 to 3.5;
diorganosiloxane having an alkenyl group; and
organohydrogenpolysiloxane having an SiH group.

11. The bio-electrode according to claim 1, wherein the resin layer further comprises a carbon material, a silver powder, a silicon powder, or a lithium titanate powder.

12. The bio-electrode according to claim 11, wherein the carbon material is one or both of carbon black and carbon nanotube.

13. The bio-electrode according to claim 1, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

14. The bio-electrode according to claim 1, further comprising a protective film on the permeation layer.

15. A method for manufacturing a bio-electrode, comprising:
   coating an electro-conductive base material with a bio-electrode composition comprising a polymer compound (A) containing a repeating unit having a salt structure selected from the group consisting of salts of ammonium, sodium, potassium, and silver formed with any of fluorosulfonic acid, fluorosulfonimide, and N-carbonyl-fluorosulfonamide;
   curing the bio-electrode composition to form a living body contact layer; and
   bringing an aqueous solution containing a water-soluble salt selected from the group consisting of sodium salts, potassium salts, calcium salts, magnesium salts, and betaines into contact with a surface of the living body contact layer where a living body comes into contact to form a permeation layer in the surface of the living body contact layer where a living body comes into contact, the permeation layer being permeated with the aqueous solution containing the water-soluble salt.

16. The method for manufacturing a bio-electrode according to claim 15, wherein a solution containing the water-soluble salt, a monohydric alcohol or polyhydric alcohol having 1 to 4 carbon atoms, and water is brought, by a spraying method, into contact with the surface of the living body contact layer where a living body comes into contact.

17. The method for manufacturing a bio-electrode according to claim 15, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

18. The method for manufacturing a bio-electrode according to claim 15, further comprising stacking a protective film on the permeation layer.

19. A method for measuring a biological signal, comprising:
   treating a portion of skin with a solution containing water; and
   attaching the bio-electrode according to claim 1 to the treated portion to measure a biological signal.

* * * * *